United States Patent
Ju et al.

(10) Patent No.: US 10,246,479 B2
(45) Date of Patent: Apr. 2, 2019

(54) METHOD OF PREPARATION OF NANOPORE AND USES THEREOF

(71) Applicants: Jingyue Ju, Englewood Cliffs, NJ (US); Shiv Kumar, Belle Mead, NJ (US); Chuanjuan Tao, New York, NY (US); Minchen Chien, Tenafly, NJ (US); James J. Russo, New York, NY (US); John J. Kasianowicz, Darnestown, MD (US); Joseph W. F. Robertson, Washington, DC (US)

(72) Inventors: Jingyue Ju, Englewood Cliffs, NJ (US); Shiv Kumar, Belle Mead, NJ (US); Chuanjuan Tao, New York, NY (US); Minchen Chien, Tenafly, NJ (US); James J. Russo, New York, NY (US); John J. Kasianowicz, Darnestown, MD (US); Joseph W. F. Robertson, Washington, DC (US)

(73) Assignees: THE TRUSTEES OF COLUMBIA UNIVERSITY IN THE CITY OF NEW YORK, New York, NY (US); THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 782 days.

(21) Appl. No.: 14/391,320

(22) PCT Filed: Apr. 8, 2013

(86) PCT No.: PCT/US2013/035635
§ 371 (c)(1),
(2) Date: Oct. 8, 2014

(87) PCT Pub. No.: WO2013/154999
PCT Pub. Date: Oct. 17, 2013

(65) Prior Publication Data
US 2015/0111759 A1    Apr. 23, 2015

Related U.S. Application Data

(60) Provisional application No. 61/781,353, filed on Mar. 14, 2013, provisional application No. 61/662,334, (Continued)

(51) Int. Cl.
*C07H 19/00* (2006.01)
*C12Q 1/42* (2006.01)
(Continued)

(52) U.S. Cl.
CPC .............. *C07H 19/00* (2013.01); *C07H 19/06* (2013.01); *C07H 19/16* (2013.01); *C12Q 1/42* (2013.01);
(Continued)

(58) Field of Classification Search
CPC ............................. C07H 19/00; C12Q 1/6869
(Continued)

(56) References Cited

U.S. PATENT DOCUMENTS 5,547,839 A * 8/1996 Dower .................. B01J 19/0046
435/6.11
5,756,355 A   5/1998 Lang et al.
(Continued)

FOREIGN PATENT DOCUMENTS

WO    WO 2001/048235 A2    7/2001
WO    WO2001/094609    12/2001
(Continued)

OTHER PUBLICATIONS

Jun. 23, 2011 Restriction Requirement issued in connection with U.S. Appl. No. 12/308,091.
(Continued)

*Primary Examiner* — Jezia Riley
(74) *Attorney, Agent, or Firm* — John P. White; Gary J. Gershik; Cooper & Dunham LLP

(57) ABSTRACT

This disclosure provides systems and methods for sequencing nucleic acids using nucleotide analogues and translocation of tags from incorporated nucleotide analogues through
(Continued)

a nanopore. In aspects, this disclosure is related to composition, method, and system for sequencing a nucleic acid using tag molecules and detection of translocation through a nanopore of tags released from incorporation of the molecule.

17 Claims, 65 Drawing Sheets

Specification includes a Sequence Listing.

Related U.S. Application Data filed on Jun. 20, 2012, provisional application No. 61/662,330, filed on Jun. 20, 2012, provisional application No. 61/662,329, filed on Jun. 20, 2012, provisional application No. 61/621,981, filed on Apr. 9, 2012.

(51) Int. Cl.

| | | |
|---|---|---|
| C12Q 1/48 | (2006.01) | |
| C12Q 1/6869 | (2018.01) | |
| C07H 19/06 | (2006.01) | |
| C07H 19/16 | (2006.01) | |
| C12Q 1/6883 | (2018.01) | |
| G01N 33/487 | (2006.01) | |
| C12Q 1/68 | (2018.01) | |
| B82Y 5/00 | (2011.01) | |

(52) U.S. Cl.
CPC ............ *C12Q 1/48* (2013.01); *C12Q 1/6869* (2013.01); *C12Q 1/6883* (2013.01); *G01N 33/48721* (2013.01); *B82Y 5/00* (2013.01); *C12Q 2600/158* (2013.01); *G01N 2333/9125* (2013.01)

(58) Field of Classification Search
USPC .............................................. 435/6.1; 536/4.1
See application file for complete search history.

(56) References Cited

U.S. PATENT DOCUMENTS

| | | | |
|---|---|---|---|
| 5,770,367 | A | 6/1998 | Southern et al. |
| 5,795,782 | A | 8/1998 | Church et al. |
| 5,804,386 | A | 9/1998 | Ju et al. |
| 5,814,454 | A | 9/1998 | Ju |
| 5,876,936 | A | 3/1999 | Ju |
| 5,952,180 | A | 9/1999 | Ju et al. |
| 6,015,714 | A | 1/2000 | Baldarelli et al. |
| 6,046,005 | A | 4/2000 | Ju et al. |
| 6,362,002 | B1 | 3/2002 | Denison et al. |
| 6,383,749 | B2 | 5/2002 | Bochkariov et al. |
| 6,399,335 | B1 | 6/2002 | Kao et al. |
| 6,413,792 | B1 | 7/2002 | Sauer et al. |
| 6,485,703 | B1 | 11/2002 | Cote et al. |
| 6,616,895 | B2 | 9/2003 | Dugas et al. |
| 6,627,748 | B1 | 9/2003 | Ju et al. |
| 6,664,079 | B2 | 12/2003 | Ju et al. |
| 6,746,594 | B2 | 6/2004 | Akeson et al. |
| 6,916,665 | B2 | 7/2005 | Bayley et al. |
| 7,074,597 | B2 | 7/2006 | Ju et al. |
| 7,189,503 | B2 | 3/2007 | Akeson et al. |
| 7,238,485 | B2 | 7/2007 | Akeson et al. |
| 7,279,337 | B2 | 10/2007 | Zhu |
| 7,345,159 | B2 | 3/2008 | Ju et al. |
| 7,622,279 | B2 | 11/2009 | Ju et al. |
| 7,622,934 | B2 | 11/2009 | Hibbs et al. |
| 7,625,701 | B2 | 12/2009 | Williams et al. |
| 7,635,578 | B2 | 12/2009 | Ju et al. |
| 7,713,698 | B2 | 5/2010 | Ju et al. |
| 7,745,116 | B2 | 6/2010 | Williams |
| 7,777,505 | B2 | 8/2010 | White et al. |
| 7,790,869 | B2 | 9/2010 | Ju et al. |
| 7,883,869 | B2 | 2/2011 | Ju et al. |
| 7,939,270 | B2 | 5/2011 | Holden et al. |
| 7,947,454 | B2 | 5/2011 | Akeson et al. |
| 7,982,029 | B2 | 7/2011 | Ju et al. |
| 8,058,414 | B2 | 11/2011 | Menchen et al. |
| 8,088,575 | B2 | 1/2012 | Ju et al. |
| 8,133,672 | B2 | 3/2012 | Bjornson et al. |
| 8,137,569 | B2 | 3/2012 | Harnack et al. |
| 8,148,516 | B2 | 4/2012 | Williams et al. |
| 8,298,792 | B2 | 10/2012 | Ju et al. |
| 8,541,849 | B2 | 9/2013 | Chen et al. |
| 8,652,779 | B2 | 2/2014 | Turner et al. |
| 8,796,432 | B2 | 8/2014 | Ju et al. |
| 8,889,348 | B2 | 11/2014 | Ju |
| 9,115,163 | B2 | 8/2015 | Ju et al. |
| 9,133,511 | B2 | 9/2015 | Ju et al. |
| 9,175,342 | B2 | 11/2015 | Ju et al. |
| 9,255,292 | B2 | 2/2016 | Ju et al. |
| 9,297,042 | B2 | 3/2016 | Ju et al. |
| 9,528,151 | B2 | 12/2016 | Ju et al. |
| 9,605,309 | B2 | 3/2017 | Davis et al. |
| 9,624,539 | B2 | 4/2017 | Ju et al. |
| 9,890,426 | B2 | 2/2018 | Ju et al. |
| 2003/0027140 | A1 | 2/2003 | Ju et al. |
| 2003/0054360 | A1 | 3/2003 | Gold et al. |
| 2003/0166282 | A1 | 9/2003 | Brown et al. |
| 2003/0198982 | A1 | 10/2003 | Seela et al. |
| 2005/0208574 | A1 | 9/2005 | Bayley et al. |
| 2005/0239134 | A1 | 10/2005 | Gorenstein et al. |
| 2006/0057565 | A1 | 3/2006 | Ju et al. |
| 2006/0105461 | A1 | 5/2006 | Tom-Moy et al. |
| 2006/0115951 | A1 | 6/2006 | Mosley |
| 2006/0252037 | A1 | 11/2006 | Ju et al. |
| 2007/0190542 | A1 | 8/2007 | Ling et al. |
| 2007/0275387 | A1 | 11/2007 | Ju et al. |
| 2008/0101988 | A1 | 5/2008 | Kang et al. |
| 2008/0199932 | A1 | 8/2008 | Hanzel et al. |
| 2008/0218184 | A1 | 9/2008 | White et al. |
| 2009/0029477 | A1 | 1/2009 | Meller et al. |
| 2009/0066315 | A1 | 3/2009 | Hu et al. |
| 2009/0073293 | A1 | 3/2009 | Yaffe et al. |
| 2009/0099786 | A1 | 4/2009 | Oliver et al. |
| 2009/0136958 | A1 | 5/2009 | Gershow et al. |
| 2009/0167288 | A1 | 7/2009 | Reid et al. |
| 2009/0240030 | A1 | 9/2009 | Ju et al. |
| 2009/0263791 | A1 | 10/2009 | Ju et al. |
| 2009/0325154 | A1 | 12/2009 | Ju |
| 2010/0025249 | A1 | 2/2010 | Polonsky et al. |
| 2010/0035260 | A1 | 2/2010 | Olasagasti et al. |
| 2010/0072080 | A1 | 3/2010 | Karhanek et al. |
| 2010/0148126 | A1 | 6/2010 | Guan et al. |
| 2010/0227414 | A1 | 9/2010 | Ervin |
| 2010/0320094 | A1 | 12/2010 | White et al. |
| 2010/0331194 | A1 | 12/2010 | Turner et al. |
| 2011/0005918 | A1 | 1/2011 | Akeson et al. |
| 2011/0014611 | A1 | 1/2011 | Ju et al. |
| 2011/0039259 | A1 | 2/2011 | Ju et al. |
| 2011/0160093 | A1 | 6/2011 | Van den Boom et al. |
| 2011/0168968 | A1 | 7/2011 | Yang et al. |
| 2011/0174625 | A1 | 7/2011 | Akeson et al. |
| 2011/0192723 | A1 | 8/2011 | Chen et al. |
| 2011/0193249 | A1 | 8/2011 | Chen et al. |
| 2011/0193570 | A1 | 8/2011 | Chen et al. |
| 2011/0287414 | A1 | 11/2011 | Chen et al. |
| 2012/0052188 | A1 | 3/2012 | Chen et al. |
| 2012/0094278 | A1 | 4/2012 | Akeson et al. |
| 2012/0115736 | A1 | 5/2012 | Bjornson et al. |
| 2012/0142006 | A1 | 6/2012 | Ju et al. |
| 2012/0156680 | A1 | 6/2012 | Ju et al. |
| 2012/0160681 | A1 | 6/2012 | Davis et al. |
| 2012/0160687 | A1 | 6/2012 | Akeson et al. |
| 2012/0160688 | A1 | 6/2012 | Davis et al. |
| 2012/0187963 | A1 | 7/2012 | Chen |
| 2012/0188092 | A1 | 7/2012 | Chen |
| 2012/0196759 | A1 | 8/2012 | Chen |
| 2012/0214162 | A1 | 8/2012 | Oliver |
| 2012/0261261 | A1 | 10/2012 | Huber |

(56) References Cited

U.S. PATENT DOCUMENTS

| | | | |
|---|---|---|---|
| 2013/0264207 A1 | 10/2013 | Ju et al. | |
| 2013/0280700 A1 | 10/2013 | Ju et al. | |
| 2014/0034497 A1 | 2/2014 | Davis et al. | |
| 2014/0093869 A1 | 4/2014 | Ju et al. | |
| 2014/0206553 A1 | 7/2014 | Ju et al. | |
| 2014/0309144 A1* | 10/2014 | Turner | G01N 27/447 506/16 |
| 2015/0037788 A1 | 2/2015 | Ju | |
| 2015/0119259 A1 | 4/2015 | Ju et al. | |
| 2015/0197800 A1 | 7/2015 | Ju et al. | |
| 2015/0368710 A1 | 12/2015 | Fuller et al. | |
| 2016/0024570 A1 | 1/2016 | Ju et al. | |
| 2016/0024574 A1 | 1/2016 | Ju et al. | |
| 2016/0041179 A1 | 2/2016 | Ju et al. | |
| 2016/0076092 A1* | 3/2016 | Jayasinghe | C12N 9/127 435/6.1 |
| 2016/0090621 A1 | 3/2016 | Ju et al. | |
| 2016/0208313 A1 | 7/2016 | Ju et al. | |
| 2016/0264612 A1 | 9/2016 | Ju et al. | |
| 2016/0265048 A1 | 9/2016 | Ju et al. | |
| 2016/0312279 A1 | 10/2016 | Ju et al. | |
| 2017/0058335 A1 | 3/2017 | Tao et al. | |
| 2017/0096704 A1 | 4/2017 | Ju | |
| 2017/0101675 A1 | 4/2017 | Ju et al. | |

FOREIGN PATENT DOCUMENTS

| | | |
|---|---|---|
| WO | WO 02/22883 A1 | 3/2002 |
| WO | WO 02/29003 | 4/2002 |
| WO | WO 02/79519 A1 | 10/2002 |
| WO | WO 04/07773 | 1/2004 |
| WO | WO 2004/071155 A2 | 8/2004 |
| WO | WO 2004/072238 A2 | 8/2004 |
| WO | WO 05/84367 | 9/2005 |
| WO | WO 07/02204 | 1/2007 |
| WO | WO 07/53702 | 5/2007 |
| WO | WO 07/53719 | 5/2007 |
| WO | WO2007/127327 | 11/2007 |
| WO | WO2008/102120 | 8/2008 |
| WO | WO2008/124107 | 10/2008 |
| WO | WO2009/007743 | 1/2009 |
| WO | WO 2009/020682 A2 | 2/2009 |
| WO | WO2009/054922 | 4/2009 |
| WO | WO 2010/109197 A2 | 9/2010 |
| WO | WO 2011/038241 A1 | 3/2011 |
| WO | WO 2011/097028 A1 | 8/2011 |
| WO | WO2011/106459 | 9/2011 |
| WO | WO2012/009578 | 1/2012 |
| WO | WO2012/083249 | 6/2012 |
| WO | WO 2012/162429 | 11/2012 |
| WO | WO 2013/016486 A1 | 1/2013 |
| WO | WO 2003/020734 A2 | 3/2013 |
| WO | WO2013/123450 | 8/2013 |
| WO | WO 2013/154999 | 10/2013 |
| WO | WO2013/188841 | 12/2013 |
| WO | WO 2013/191793 | 12/2013 |
| WO | WO 2014/144883 | 9/2014 |
| WO | WO 2014/144898 | 9/2014 |
| WO | WO2015/123430 | 8/2015 |
| WO | WO2015/148402 | 10/2015 |
| WO | WO2015/179284 | 11/2015 |
| WO | WO2016/144973 | 9/2016 |
| WO | WO2016/154215 | 9/2016 |

OTHER PUBLICATIONS

Oct. 24, 2011 Response to Restriction Requirement dated Jun. 23, 2011 in connection with U.S. Appl. No. 12/308,091.
Office Action dated Nov. 29, 2011 in connection with U.S. Appl. No. 12/308,091.
Apr. 30, 2012 Amendment in Response to Office Action dated Nov. 29, 2011 in connection with U.S. Appl. No. 12/308,091.
Office Action dated Jun. 28, 2012 in connection with U.S. Appl. No. 12/308,091.
Dec. 28, 2012 Amendment in response to Office Action dated Jun. 28, 2012 in connection with U.S. Appl. No. 12/308,091.
Jul. 17, 2014 Notice of Allowance dated Jun. 28, 2012 in connection with U.S. Appl. No. 12/308,091.
International Search Report and Written Opinion of the International Searching Authority issued by the International Searching Authority (ISA/US) dated Oct. 29, 2007 in connection with International Application No. PCT/US2007/013559.
International Preliminary Report on Patentability, dated Dec. 10, 2008 in connection with International Application No. PCT/US07/13559.
Jun. 22, 2011 Office Action in connection with Chinese Patent Application No. 200780028545.1 (with English translation of cover page only).
Jan. 6, 2012 Response to First Office Action filed in connection with Chinese Patent Application No. 200780028545.1.
Jul. 2, 2012 Second Office Action in connection with Chinese Patent Application No. 200780028545.1.
Nov. 19, 2012 Response to Second Office Action filed in connection with Chinese Patent Application No. 200780028545.1.
Apr. 9, 2013 Third Office Action in connection with Chinese Patent Application No. 200780028545.1.
Jun. 21, 2013 Response to Third Office Action filed in connection with Chinese Patent Application No. 200780028545.1.
Oct. 12, 2013 Decision of Rejection issued in connection with Chinese Patent Application No. 200780028545.1.
Jan. 26, 2014 Request for Reexamination filed in connection with Chinese Patent Application No. 200780028545.1.
International Search Report and the Written Opinion of the International Searching Authority, or the Declaration, including an International Search Report and Written Opinion of the International Searching Authority, dated Feb. 4, 2013 in connection with PCT International Application No. PCT/US2011/065640, filed Dec. 16, 2011.
Apr. 16, 2014 Communication transmitting Supplementary European Search Report and European Search Opinion in connection with European Patent Application No. EP 11848220.
Mar. 27, 2014 Office Action in connection with Chinese Patent Application No. 201180063978.7.
Aug. 11, 2014 Response to Mar. 27, 2014 Office Action in connection with Chinese Patent Application No. 201180063978.7 (with English translation of cover page only).
International Search Report and Written Opinion of the International Searching Authority dated Sep. 24, 2013 in connection with PCT International Application No. PCT/US2013/035630.
Invitation to Pay Additional Fees mailed by the International Searching Authority dated Aug. 19, 2013 connection with PCT International Application No. PCT/US2013/035635.
International Search Report and Written Opinion of the International Searching Authority dated Jul. 30, 2014 in connection with PCT International Application No. PCT/US2014/029495.
Eid et al. (2008) "Real-Time DNA Sequencing from Single Polymerase Molecules", Science, 23(5910):133-138.
Guranowski et al., (2000) "Selective Degradation of 2'-Adenlyated Diadenosine Tri- and Tetraphosphates, $Ap_3A$ and $Ap_4A$, by Two Specific Human Dinucleoside Polyphosphate Hydrolases", Archives of Biochemistry and Biophysics, 373(1):218-224.
Ju et al., "Four-color DNA Sequencing by Synthesis using Cleavable Fluorescent Nucleotide Reversible Terminators", PNAS, 103(52):19635-19640 (2006).
Kumar et al. (2005) "Terminal phosphate labeled nucleotides: Synthesis, applications, and linker effect on incorporation by DNA polymerases", Nucleosides, Nucleotides, and Nucleic Acids, 24(5-7):401-108.
Mulder et al. (2005) "Nucleotide modification at the γ-phosphate leads to the improved fidelity of HIV-1 reverse transcriptase", Nucleic Acids Research, 33(15):4865-4873.
Reynolds et al. (2008) "Synthesis and Stability of Novel Terminal Phosphate-labeled Nucleotides", Nucleosides, Nucleotides, and Nucleic Acids, 27(1):18-30.

(56) References Cited

OTHER PUBLICATIONS

Sood et al. (2005) "Terminal phosphate-labeled nucleotides with improved substrate properties for homogenous nucleic acid assays", JACS, 127(8):2394-2395.
Wei et al., "Stochastic sensing of proteins with receptor-modified solid-state nanopores" Nature Nanotechnology, 7(4):257-263 (2012).
Nov. 14, 2014 Response to Apr. 16, 2014 Communication transmitting Supplementary European Search Report and European Search Opinionn in connection with European Patent Application No. EP 11848220.
Mar. 4, 2016 Office Action issued in connection with U.S. Appl. No. 14/516,785, Ju et al.
Jan. 26, 2014 Request for Reexamination filed in connection with Chinese Patent Application No. 200780028545.1 (with English translation).
Mar. 24, 2015 Office Action issued in connection with Chinese Patent Application No. 200780028545.1.
Sep. 8, 2015 Response to Mar. 24, 2015 Office Action issued in connection with Chinese Patent Application No. 200780028545.1.
Nov. 13, 2015 Decision on Reexamination issued in connection with Chinese Patent Application No. 200780028545.1.
Feb. 3, 2016 Office Action issued in connection with Chinese Patent Application No. 200780028545.1.
Apr. 18, 2016 Response to Feb. 3, 2016 Office Action issued in connection with Chinese Patent Application No. 200780028545.1.
Jun. 29, 2016 Office Action issued in connection with Chinese Patent Application No. 200780028545.1.
Sep. 13, 2016 Amendment in Response to the Jun. 29, 2016 Office Action issued in connection with Chinese Patent Application No. 200780028545.1.
Notice on Grant of Patent Right for Invention dated Oct. 10, 2016 by the Chinese Patent Office in connection with Chinese Patent Application No. 200780028545.1, English translation.
Oct. 22, 2014 Amendment in response to May 22, 2014 Notice of Missing Requirements in connection with U.S. Appl. No. 13/994,431.
Preliminary Amendment filed Feb. 17, 2015 in connection with U.S. Appl. No. 13/994,431.
Restriction Requirement dated Feb. 9, 2017 in connection with U.S. Appl. No. 13/994,431, Ju et al.
Dec. 23, 2014 Communication pursuant to Article 94(3) EPC in connection with European Patent Application No. EP 11848220.7.
May 4, 2015 Amendment in response to Dec. 23, 2014 Communication pursuant to Article 94(3) EPC in connection with European Patent Application No. EP 11848220.7.
Jul. 15, 2015 Communication pursuant to Article 94(3) EPC in connection with European Patent Application No. EP 11848220.7.
Jan. 15, 2016 Communication Pursuant to Article 94(3) EPC in connection with European Patent Application No. EP 11848220.7.
May 12, 2016 Amendment in Response to Communication Pursuant to Article 94(3) in connection with European Patent Application No. EP 11848220.7, Ju et al.
Aug. 5, 2016 Communication Under Rule 71(3) EPC issued by the European Patent Office in connection with European Patent Application No. EP11848220.7, Ju et al.
Second Communication Under Rule 71(3) EPC, issued by the European Patent Office in connection with European Patent Application No. EP11848220.7 dated Feb. 7, 2017, Ju et al.
Dec. 22, 2014 Second Office Action in connection with Chinese Patent Application No. 201180063978.7 (with English translation of cover page only).
Mar. 6, 2015 Response to Dec. 22, 2014 Second Office Action in connection with Chinese Patent Application No. 201180063978.7.
Jul. 13, 2015 Third Office Action in connection with Chinese Patent Application No. 201180063978.7 (with English translation of cover page only).
Sep. 28, 2015 Response to Jul. 13, 2015 Office Action issued in connection with Chinese Patent Application No. 201180063978.7.
Jan. 29, 2016 Office Action issued in connection with Chinese Patent Application No. 201180063978.7.
Mar. 31, 2016 Response to the Jan. 29, 2016 Office Action issued in connection with Chinese Patent Application No. 201180063978. 7.
Jul. 29, 2016 Notice on Grant of Patent Right for Invention, issued in connection with Chinese Patent Application No. 201180063978.7 (English Translation).
Office Action dated Jul. 15, 2015 by the Chinese State Intellectual Property Office in connection with Chinese Patent Application No. 201380025837.5.
Response to the Jul. 15, 2015 Office Action, filed Jan. 29, 2016 in connection with Chinese Patent Application No. 201380025837.5.
May 4, 2016 Office Action issued by the Chinese State Intellectual Property Office in connection with Chinese Patent Application No. 201380025837.5.
Jul. 19, 2016 Amendment filed in Response to the May 4, 2016 Office Action issued by the State Intellectual Property Office of the People's Republic of China in connection with Chinese Patent Application No. 201380025837.5.
Communication pursuant to Rule 164(1) EPC dated Dec. 7, 2015 by the EPO in connection with EP 13775787.8.
Extended European Search Report dated Mar. 11, 2016 by the EPO in connection with EP 13775787.8.
Oct. 10, 2016 Amendment in Response to the Extended European Search Report dated Mar. 11, 2016 by the EPO in connection with EP 13775787.8.
Feb. 9, 2017 Communication Pursuant to Article 94(3) EPC, issued by the European Patent Office in connection with EP 13775787.8.
Mar. 16, 2016 Restriction Requirement issued in connection with U.S. Appl. No. 14/391,337.
Sep. 16, 2016 Response to the Mar. 16, 2016 Restriction Requirement issued in connection with U.S. Appl. No. 14/391,337.
Office Action dated Oct. 26, 2016 in connection with U.S. Appl. No. 14/391,337, Ju et al.
Apr. 25, 2017 Amendment in Response to the Oct. 26, 2016 Office Action issued in connection with U.S. Appl. No. 14/391,337, Ju et al.
Communication pursuant to Rule 164(1) EPC dated by Dec. 2, 2015 by the EPO in connection with EP 13807639.3.
Extended European Search Report dated Mar. 11, 2016 by the EPO in connection with EP 13807639.3.
Oct. 10, 2016 Amendment in Response to the Extended European Search Report dated Mar. 11, 2016 by the EPO in connection with EP 13807639.3.
Communication Pursuant to Article 94(3), dated Feb. 9, 2017 by the European Patent Office in connection with EP 13807639.3.
Aug. 5, 2015 Applicant Statement in connection with U.S. Appl. No. 14/666,124 regarding Amendments to p. 40 Regarding Tagged Nucleotides.
International Search Report and Written Opinion of the International Searching Authority dated Jun. 29, 2015 in connection with PCT International Application No. PCT/US2015/022063.
International Preliminary Report on Patentability (Chapter II of the Patent Cooperation Treaty), dated Mar. 6, 2016 in connection with PCT International Application No. PCT/US2015/022063.
International Search Report and Written Opinion of the International Searching Authority dated Aug. 25, 2015 in connection with PCT International Application No. PCT/US2015/015647.
International Search Report dated May 20, 2016 in connection with WO2016/154215, The Trustees of Columbia University in the City of New York, Ju et al.
International Search Report, dated Feb. 16, 2017 in connection with PCT Application No. PCT/US2016/062917, The Trustees of Columbia University in the City of New York, Ju et al.
Roberston, J. W. F. et al. (2007). Single-molecule mass spectrometry in solution using a solitary nanopore. *Proceedings of the National Academy of Sciences*, 104(20), 8207-8211.
Notification of Transmittal of the International Search Report and the Written Opinion of the International Searching Authority, or the Declaration, including an International Search Report and Written Opinion of the International Searching Authority, dated Oct. 25, 2013 in connection with PCT International Application No. PCT/US2013/035635, filed Apr. 8, 2013.

(56) References Cited

OTHER PUBLICATIONS

Anderson, Sequencing and the single channel. Biophys J. Dec. 1999; 77(6):2899-901.
Ashkenasy et al. Recognizing a single base in an individual DNA strand: a step toward DNA sequencing in nanopores. Angew Chem Int Ed Engl. Feb. 18, 2005; 44(9):1401-4.
Atanasnov et al. Membrane on a chip: a functional tethered lipid bilayer membrane on silicon oxide surfaces. Biophys J. Sep. 2005; 89(3):1780-8.
Benner, et al. Sequence-specific detection of individual DNA polymerase complexes in real time using a nanopore. Nat Nanotechnol. Nov. 2007; 2(11):718-24. Epub Oct. 28, 2007.
Bokhari, S.H. et al. (2005) "A Parallel Graph Decomposition Algorithm for DNA Sequencing with Nanopores" Bioinformatics 21(7):889-896.
Buchmann, et al. Electrochemical release from gold-thiolate electrodes for controlled insertion of ion channels into bilayer membranes. Bioorg Med Chem. Mar. 15, 2004; 12(6):1315-24.
Butler, et al. Determination of RNA orientation during translocation through a biological nanopore. Biophys J. Jan. 1, 2006; 90(1):190-9. Epub Oct. 7, 2005.
Butler, et al. Ionic current blockades from DNA and RNA molecules in the alpha-hemolysin nanopore. Biophys J. Nov. 1, 2007; 93(9):3229-40. Epub Aug. 3, 2007.
Cockroft, et al. A single-molecule nanopore device detects DNA polymerase activity with single-nucleotide resolution. J Am Chem Soc. Jan. 23, 2008; 130(3):818-20. Epub Jan. 1, 2008.
Danleon, et al. Cell membranes suspended across nanoaperture arrays. Langmuir. Jan. 3, 2006; 22(1):22-5.
Ervin, et al. Simultaneous alternating and direct current readout of protein ion channel blocking events using glass nanopore membranes. Anal Chem. Mar. 15, 2008; 80(6):2069-76.
Fologea, D. et al. (2005) "Slowing DNA Translocation in a Solid State Nanopore" Nano Letters 5(9), 1734-1737.
Fologea, D. et al. (2005) "Detecting Single Stranded DNA with a Solid State Nanopore" Nano Letters 5(10):1905-1909.
Fuller et al., "Real-time single-molecule electronic DNA sequencing by synthesis using polymer-tagged nucleotides on a nanopore array", PNAS, vol. 113, No. 19, pp. 5233-5238, published May 10, 2016; doi/10.1073.
Guo et al., "An Integrated System for DNA Seqeuncing by Synthesis Using Novel Nucleotide Analogues", Accounts of Chem. Res. vol. 43, No. 4, Apr. 20, 2010, pp. 551-563, XP55032473, ISSN: 0001-4842, DOI: 10.1021/ar900255c.
Heng, J.B. et al. (2005) "Stretching DNA Using the Electric Field in a Synthetic Nanopore" Nano Letters 5(9):1734-1737.
Heng, J.B. et al. (2006) "The Electromechanics of DNA in a synthetic nanopore" Biophysical Journal 90:1098-1106.
Holden, et al. Direct introduction of single protein channels and pores into lipid bilayers. J Am Chem Soc. May 11, 2005; 127(18):6502-3.
Holden, et al. Direct transfer of membrane proteins from bacteria to planar bilayers for rapid screening by single-channel recording. Nat Chem Biol. Jun. 2006; 2(6):314-8. Epub May 7, 2006.
Hromada, et al. Single molecule measurements within individual membrane-bound ion channels using a polymer-based bilayer lipid membrane chip. Lab Chip. Apr. 2008; 8(4):602-8. Epub Feb. 29, 2008.
Kang et al. A storable encapsulated bilayer chip containing a single protein nanopore. J Am Chem Soc. Apr. 18, 2007; 129(15):4701-5. Epub Mar. 22, 2007.
Kawano et al. Controlling the translocation of single-stranded DNA through alpha-hemolysin ion channels using viscosity. Langmuir. Jan. 20, 2009; 25(2):1233-7.
Kumar et al. PEG-labeled nucleotides and nanopore detection for single molecule DNA sequencing by synthesis. Sci Rep. 2012; 2:684. Epub Sep. 21, 2012.
Kutik et al. Dissecting membrane insertion of mitochondrial beta-barrel proteins. Cell. Mar. 21, 2008; 132(6):1011-24.
Li. L. et al. (2001) "Ion-beam sculpting at nanometre length scales" Nature 412:166-169.
Lieberman et al. "Processive Replication of Single DNA Molecules in a Nanopore Catalyzed by phi29 DNA Polymerase", Jol. ACS, vol. 132, No. 50, Dec. 22, 2010, pp. 17961-17972.
Madampage, et al. Nanopore detection of antibody prion interactions. Anal Biochem. Jan. 1, 2010; 396(1):36-41. Epub Aug. 21, 2009.
Mauer et al. Reconstitution of ion channels in agarose-supported silicon orifices. Biosens Bioelectron. May 15, 2007; 22(11):2577-84. Epub Nov. 13, 2006.
McNally et al. Optical recognition of converted DNA nucleotides for single-molecule DNA sequencing using nanopore arrays. Nano Lett. Jun. 9, 2010; 10(6):2237-44.
Meller, A. et al. (2002) "Single Molecule Measurements of DNA Transport Through a Nanopore" Electrophoresis 23:2583-2591.
Mohammad et al. Controlling a single protein in a nanopore through electrostatic traps. J Am Chem Soc. Mar. 26, 2008; 130(12):4081-8. Epub Mar. 6, 2008.
Nakane et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Park et al. DNA hybridization sensors based on electrochemical impedance spectroscopy as a detection tool. Sensors (Basel). 2009; 9(12):9513-32. Epub Nov. 26, 2009.
Purnell et al. Discrimination of single base substitutions in a DNA strand immobilized in a biological nanopore. ACS Nano. Sep. 22, 2009; 3(9):2533-8.
Sanchez-Magraner, et al. Membrane insertion of *Escherichia coli* alpha-hemolysin is independent from membrane lysis. J Biol Chem. Mar. 3, 2006; 281(9):5461-7. Epub Dec. 22, 2005.
Sauer-Budge, A. F. et al. (2003) "Unzipping Kinetics of Double Stranded DNA in a Nanopore" Physical Review Letters 90(23):238101-1-238101-4.
Seo et al., (2004) "Photocleavable Fluorescent Nucleotides for DNA Sequencing on a Chip Constructed by Site-Specific Coupling Chemistry," PNAS 101(15):5488-5493.
Shim et al., Encapsulating a single G-quadruplex aptamer in a protein nanocavity. J Phys Chem B. Jul. 17, 2008; 112(28):8354-60. Epub Jun. 19, 2008.
Simon et al., Formation and stability of a suspended biomimetic lipid bilayer on silicon submicrometer-sized pores. J Colloid Interface Sci. Apr. 15, 2007; 308(2):337-43. Epub Jan. 31, 2007.
Singer et al. Nanopore Based Sequence Specific Detection of Duplex DNA for Genomic Profiling, Jan. 8, 2010, published Jan. 20, 2010, pp. 738-742.
Sterfureac et al. Transport of alpha-helical peptides through alpha-hemolysin and aerolysin pores. Biochemistry. Aug. 1, 2006; 45(30):9172-9.
Stefureac et al. Nanopore analysis of the interaction of metal ions with prion proteins and peptides. Biochem Cell Biol. Apr. 2010; 88(2):347-58.
Stoddart et al. Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.
Stoddart et al. Nucleobase recognition in ssDNA at the central constriction of the alpha-hemolysin pore. Nano Lett. Sep. 8, 2010; 10(9):3633-7.
Studer et al., Formation of individual protein channels in lipid bilayers suspended in nanopores. Colloids Surf B Biointerfaces., Oct. 15, 2009; 73(2):325-31. Epub Jun. 10, 2009.
Suzuki et al., Highly reproducible method of planar lipid bilayer reconstitution in polymethyl methacrylate microfluidic chip. , Feb. 2006, Langmuir. 22(4):1937-42.
Thomson et al., Preliminary nanopore cheminformatics analysis of aptamer-target binding strength, Nov. 2007, BMC Bioinformatics. 1; 8 Suppl 7:S11.
Viasnoff et al., Probing DNA base pairing energy profiles using a nanopore. Eur Biophys J., Feb. 2009, 38(2):263-9. Epub Oct. 3, 2008.
Walker et al., "Key Residues for Membrane Binding, Oligomerization, and Pore Forming Activity of Staphylococcal alpha-hemolysin

(56) References Cited

OTHER PUBLICATIONS

Identified by Cysteine Scanning Mutagenesis and Targeted Chemical Modification", J. Biol. Chem. 1995, doe: 10.1074/jbc.270.39.23065.
Wanunu et al., DNA profiling using solid-state nanopores: detection of DNA-binding molecules. Nano Lett. Oct. 2009; 9(10):3498-502.
Weng et al., Fluid biomembranes supported on nanoporous aerogel/xerogel substrates. Langmuir. Aug. 17, 2004; 20(17):7232-9.
Wilson et al., Feedback control of a DNA molecule tethered in a nanopore to repeatedly probe DNA-binding enzymes. Conf Proc IEEE Eng Med Biol Soc. 2008; 2008:5745-8.
Winters-Hilt et al., Nanopore-based kinetics analysis of individual antibody-channel and antibody-antigen interactions. BMC Bioinformatics. Nov. 1, 2007; 8 Suppl 7:S20.
Wu et al., Single-molecule detection of nitrogen mustards by covalent reaction within a protein nanopore. J Am Chem Soc. May 28, 2008; 130(21):6813-9. Epub Apr. 30, 2008.
Zeineldin et al., Using bicellar mixtures to form supported and suspended lipid bilayers on silicon chips. Langmuir. Sep. 12, 2006; 22(19):8163-8.
Zwolak, et al. Electronic signature of DNA nucleotides via transverse transport. Nano Lett. Mar. 2005; 5(3):421-4.
Sep. 25, 2017 Non-Final Office Action issued in connection with U.S. Appl. No. 13/994,431, Ju et al.
Dec. 22, 2017 Amendment in Response to Sep. 25, 2017 Non-Final Office Action issued in connection with U.S. Appl. No. 13/994,431, Ju et al.
Feb. 26, 2018 Non-Final Office Action issued in connection with U.S. Appl. No. 13/994,431, Ju et al.
Aug. 18, 2017 Amendment in Response to Communication Pursuant to Article 94(3) EPC, issued by the European Patent Office in connection with EP 13775787.8, Ju et al.
Apr. 13, 2018 Communication Pursuant to Article 94(3) EPC, issued by the European Patent Office in connection with EP 13775787.8, Ju et al.
Aug. 18, 2017 Amendment in Response to Communication Pursuant to Article 94(3), dated Feb. 9, 2017 by the European Patent Office in connection with EP 13807639.3, Ju et al.
Communication Pursuant to Article 94(3), dated Feb. 23, 2018 by the European Patent Office in connection with EP 13807639.3, Ju et al.
Jul. 7, 2018 Restriction Requirement issued in connection with U.S. Appl. No. 14/666,124, Fuller et al.
Nov. 20, 2017 Amendment in Response to Restriction Requirement issued in connection with U.S. Appl. No. 14/666,124, Fuller et al.
Mar. 7, 2018 Non-Final Office Action issued in connection with U.S. Appl. No. 14/666,124, Fuller et al.
Nov. 9, 2017 Extended European Search Report issued in by the European Patent Office in connection with EP 15768383.0, Fuller et al.

Akeson, M. et al. (1999) "Microsecond time-scale discrimination between polycytidylic acid and polyadenylic acid segments wtihin single RNA molecules" Biophys. J. 77:3227-3233.
Bezrukov, S.M. et al. (2001) "Neutral Polymers in the nanopores of alamethicin and alpha-hemolysin." Biologicheskie Membrany 18:451-455.
Chandler, E.L. et al. (2004) "Membrane Surface Dynamics of DNA-Threaded Nanopores Revealed by Simultaneous Single-Molecule Optical and Ensemble Electrical Recording." Langmuir 20:898-905.
Clarke, et al. "Continuous base identification for single-molecule nanopore DNA sequencing" Nat Nanotechnol. Apr. 2009; 4(4):265-70. Epub Feb. 22, 2009.
Deamer, D.W. et al (2002) "Characterization of nucleic acids by nanopore analysis." Acc. Chem. Res. 35(10):817-825.
Henrickson, S.E. et al (2000) "Driven DNA Transport into an Asymmetric Nanometer-scale Pore" Physical Review Letters 85:3057-3060.
Kasianowicz, J.J. et al. (1996) "Characterization of Individual Polynucleotide Molecules Using a Membrane Channel," Proc. Natl. Acad. Sci. USA 93:13770-13773.
Kasianowicz, J.J. (2003) "Nanometer-scale pores: potential applications for DNA characterization and analyte detection." Disease Markers 18:185-191.
Kasianowicz, J.J. (2004) "Nanopore. Flossing with DNA" Nature Materials 3:355-356.
Meller, A. et al. (2000) "Rapid nanopore discrimination between single polynucleotide molecules." Proc. Natl. Acad. Sci. USA 97:1079-1084.
Perkins, T.T. et al. (1994) "Relaxation of a single DNA molecule observed by optical microscopy" Science 264:822-826.
Rief, M. (1999) "Sequence-dependent mechanics of single DNA molecules" Mat. Struct. Biol. 6:346-349.
Rothberg, J.M. et al. (2011) "An integrated semiconductor device enabling non-optical genome sequencing" Nature 475:348-352.
Smith, S.B. et al. (1996) "Overstretching B-DNA: the elastic response of individual double-stranded and single-stranded DNA molecules." Science 271:795-799.
Vercoutere, W. et al. (2001) "Rapid discrimination among individual DNA hairpin molecules at single-nucleotide resolution using an ion channel." Nat. Biotech 19:248-252.
Pending claims in U.S. Appl. No. 11/922,385, Ju et al. (published as 2009/0325154 A1, Dec. 31, 2009).
Pending claims in U.S. Appl. No. 12/734,229, Ju et al. (published as 2011/0039259 A1, published Feb. 17, 2011).
Pending claims in U.S. Appl. No. 13/186,353, Ju et al. (published as 2012/0156680 A1, Jun. 21, 2012).
Pending claims in U.S. Appl. No. 13/959,660, Ju et al. (published as 2014/0206553 A1, Jul. 24, 2014).
Pending claims in U.S. Appl. No. 13/994,431, Ju et al. (published as 2013/0264207 A1, Oct. 10, 2013).
Pending claims in U.S. Appl. No. 14/242,487, Ju et al. (published as 2014/0315191 A1, Oct. 23, 2014).

\* cited by examiner

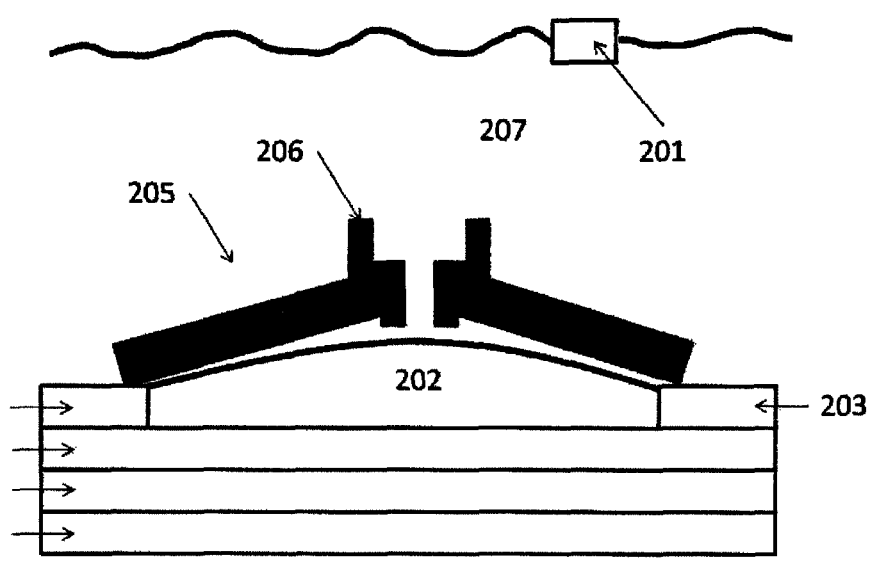

BASE= A, C, T, U, G, 7-deaza-A, 7-deaza-G or derivatives thereof
$R_1$ and $R_2$ = H or OH
TAG-OH= detectable moiety in the hydroxy form, such as, aliphatic or aromatic alcohols
TAG-COR= detectable moiety to react with the amino group, such as NHS esters, acid chloride etc BASE= A, C, T, U, G, 7-deaza-A, 7-deaza-G or derivatives thereof
$R_1$ and $R_2$= H or OH
X= O, NH, S or $CH_2$
TAG= detectable moiety, such as, aliphatic or aromatic alcohols, aminoacids, dyes, carbohydrates, oligos etc
TAG-COR= detectable moiety to react with the amino group, such as NHS esters, acid chloride etc Array of Nanopores for Sequencing by Synthesis Synthesis of first generation PEG tag-nucleotides Extension Reaction with dG4P-PEG24

Extension Reaction with dG4P-PEG37

Linear PEGs n= 27-33 n=27; dPEG$_{30}$: 30 ethylene glycol units    For T
n=29; dPEG$_{32}$: 32 ethylene glycol units    For G
n=31; dPEG$_{34}$: 34 ethylene glycol units    For C
n=33; dPEG$_{36}$: 36 ethylene glycol units    For A

Branched PEGs

R= NH$_2$, OH, COOH, COOR', CHO, SH, N$_3$

Synthesis of phosphate-tagged nucleoside-5'-triphosphates

Synthesis of phosphate-tagged nucleoside-5'-tetraphosphates

Synthesis of terminal phosphate-tagged nucleoside-5'-pentaphosphates

Synthesis of 3'-O-blocked-PEG-nucleotides

D. MALDI-TOF mass spectrum of Coumarin-PEG36-dG4P

METHOD OF PREPARATION OF NANOPORE AND USES THEREOF

CROSS-REFERENCE TO RELATED APPLICATIONS

This application is a § 371 national stage of PCT International Application No. PCT/US2013/035635, filed Apr. 8, 2013, claiming the benefit of U.S. Provisional Applications Nos. 61/781,353, filed Mar. 14, 2013, 61/662,334, filed Jun. 20, 2012, 61/662,330, filed Jun. 20, 2012, 61/662,329, filed Jun. 20, 2012, and 61/621,981, filed Apr. 9, 2012, the contents of each of which are hereby incorporated by reference in their entirety.

STATEMENT AS TO FEDERALLY SPONSORED RESEARCH

This invention was made with government support under Grant number HG005109 awarded by the National Institutes of Health. The government has certain rights in the invention.

REFERENCE TO A SEQUENCE LISTING

This application incorporates-by-reference nucleotide and/or amino acid sequences which are present in the file named "141008_0575_84043_A_PCT_US_Substitute_Sequence_Listing_JR.txt," which is 803 bytes in size, and which was created Sep. 19, 2014 in the IBM-PC machine format, having an operating system compatibility with MS-Windows, which is contained in the text file filed Oct. 8, 2014 as part of this application.

BACKGROUND

Nucleic acid sequencing is the process for determining the nucleic acid basis of a nucleic acid. Such sequence information may be helpful in diagnosing and/or treating a subject. For example, the nucleic acid sequence of a subject may be used to identify, diagnose and potentially develop treatments for genetic diseases. As another example, research into pathogens may lead to treatment for contagious diseases.

There are methods available which may be used to sequence a nucleic acid. Such methods, however, are expensive and may not provide sequence information within a time period and at an accuracy that may be necessary to diagnose and/or treat a subject.

SUMMARY

Methods of nucleic acid sequencing that involve a single stranded nucleic acid molecule passing through a nanopore may have insufficient sensitivity. Nucleic acid bases comprising the nucleic acid molecule (e.g., adenine (A), cytosine (C), guanine (G), thymine (T) and/or uracil (U)) may not provide a sufficiently distinct signal from each other. In particular, the purines (i.e., A and G) are of a similar size, shape and charge to each other and provide an insufficiently distinct signal in some instances. Also, the pyrimidines (i.e., C, T and U) are of a similar size, shape and charge to each other and provide an insufficiently distinct signal in some instances. Recognized herein is the need for improved methods for nucleic acid molecule identification and nucleic acid sequencing.

An aspect of the present disclosure provides a method for sequencing a nucleic acid molecule, the method comprising: (a) providing a chip comprising a plurality of individually addressable nanopores, wherein an individually addressable nanopore of said plurality of individually addressable nanopores comprises a nanopore in a membrane that is disposed adjacent to an electrode, wherein said nanopore is linked to a nucleic acid polymerase, and wherein each individually addressable nanopore is adapted to detect a tag that is released from a tagged nucleotide upon the polymerization of said tagged nucleotide; (b) directing said nucleic acid molecule adjacent to or in proximity to said nanopore; (c) with the aid of said polymerase, polymerizing nucleotides along said nucleic acid molecule to generate a strand that is complementary to at least a portion of said nucleic acid molecule, wherein during polymerization a tag is released from an individual nucleotide of said nucleotides, and wherein said released tag flows through or in proximity to said nanopore; and (d) detecting the tag with the aid of said electrode, wherein the tag is detected subsequent to being released from said individual nucleotide. In some embodiments, said detecting of (d) further comprises identifying said tag. In some cases, the method further comprises correlating said identified tag with a type of said individual nucleotide. In some cases, the method further comprises generating, with the aid of a computer processor, a nucleic acid sequence of the nucleic acid molecule based upon an assessment of the tags detected during polymerization.

Another aspect of the present disclosure provides a method for nucleic acid sequencing, the method comprising: (a) ligating a nucleic acid hairpin onto an end of a double stranded nucleic acid molecule; (b) dissociating the double stranded nucleic acid molecule and hairpin to form a single stranded nucleic acid template; (c) extending a primer hybridized to the single stranded nucleic acid template using tagged nucleotides, wherein a tag associated with an individual nucleotide is released upon extension; and (d) detecting the released tag with the aid of a nanopore, thereby determining the nucleic acid sequence of double stranded nucleic acid molecule. In some cases, the method further comprises directing the tag released from the individual nucleotide through the nanopore. In some cases, the method further comprises directing the tag released from the individual nucleotide to a location adjacent to the nanopore.

Another aspect of the present disclosure provides a method for nucleic acid sequencing, the method comprising: (a) polymerizing tagged nucleotides at a first rate, wherein a tag associated with an individual nucleotide is released upon polymerization; and (b) detecting the released tag by passing the tag through a nanopore at a second rate, where the second rate is greater than or equal to the first rate.

Another aspect of the present disclosure provides a method for nucleic acid sequencing, the method comprising: (a) polymerizing tagged nucleotides, wherein a tag associated with an individual nucleotide is released upon polymerization; and (b) detecting the released tag with the aid of a nanopore. In some cases, the method further comprises directing the tag released from the individual nucleotide through the nanopore. In some cases, the method further comprises directing the tag released from the individual nucleotide to a location adjacent to the nanopore.

Another aspect of the present disclosure provides a method for nucleic acid sequencing, comprising detecting, with the aid of a nanopore, the incorporation of a nucleotide into a nucleic acid molecule, wherein the nucleic acid molecule does not pass through the nanopore.

Another aspect of the present disclosure provides a method for nucleic acid sequencing, comprising detecting a byproduct of an individual nucleotide incorporation event with the aid of a nanopore.

A method for sequencing a nucleic acid molecule, comprising distinguishing between individual nucleotide incorporation events with an accuracy of greater than 4σ.

Another aspect of the present disclosure provides a method for nucleic acid sequencing, the method comprising: (a) providing an array of nanopores, wherein an individual nanopore in said array is coupled to a nucleic acid polymerase; and (b) polymerizing tagged nucleotides with the polymerase, wherein an individual tagged nucleotide comprises a tag, and wherein the tag is released and detected with the aid of the nanopore.

Another aspect of the present disclosure provides a tagged nucleotide, wherein the nucleotide comprises a tag capable of being cleaved in a nucleotide polymerization event and detected with the aid of a nanopore in a chip comprising an array of nanopores.

Another aspect of the present disclosure provides a system for sequencing a nucleic acid molecule, comprising: (a) a chip comprising a plurality of individually addressable nanopores, wherein an individually addressable nanopore of said plurality of individually addressable nanopores comprises at least one nanopore in a membrane disposed adjacent to an electrode, wherein each individually addressable nanopore is adapted to aid in the detection of a tag released from a tagged nucleotide upon the incorporation of said tagged nucleotide in a nucleic acid strand that is complementary to said nucleic acid molecule; and (b) a computer processor coupled to said individually addressable nanopores, wherein said computer processor is programmed to aid in characterizing a nucleic acid sequence of said nucleic acid molecule based upon electrical signals received from said plurality of individually addressable nanopores, wherein an individual electrical signal is associated with a tag that is released from a tagged nucleotide subsequent to the incorporation of said tagged nucleotide in a nucleic acid strand that is complementary to said nucleic acid molecule.

Another aspect of the present disclosure provides a method for sequencing a nucleic acid molecule, the method comprising providing an array of individually addressable sites at a density of at least about 500 sites per mm$^2$, each site having a nanopore attached to a nucleic acid polymerase, and, at a given site of the array, polymerizing tagged nucleotides with a polymerase, wherein upon polymerization a tag is released and detected by a nanopore at the given site. In some cases, the method further comprises directing generating, with the aid of a processor, a nucleic acid sequence of the nucleic acid molecule based upon the detected tags.

Another aspect of the present disclosure provides a conductance measurement system comprising: (a) a first and a second compartment with a first and a second electrolyte solution separated by a physical barrier, which barrier has at least one pore with diameter on nanometer scale; (b) a means for applying an electric field across the barrier; (c) a means for measuring change in the electric field; (d) at least one polymerase attached to the pore; and (e) more than one phosphatase enzyme attached to the pore.

Another aspect of the present disclosure provides a compound having the structure:

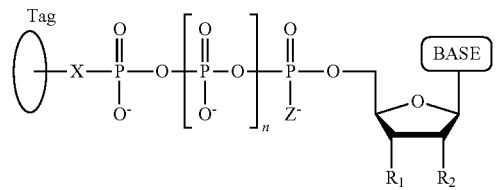

wherein the tag comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or $BH_3$, wherein the base is adenine, guanine, cytosine, thymine, uracil, or a derivative of one of these bases, wherein n is 1, 2, 3, or 4, and wherein the tag has a charge which is reverse in sign relative to the charge on the rest of the compound.

Another aspect of the present disclosure provides a composition comprising four different types of a compound having the structure:

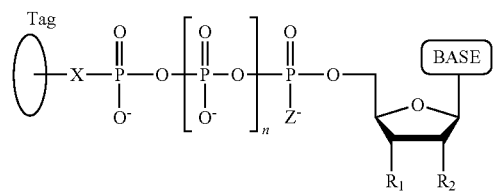

wherein the tag comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or $BH_3$, wherein n is 1, 2, 3, or 4, wherein the tag has a charge which is reverse in sign relative to the charge on the rest of the compound, wherein the base of a first type of compound is adenine or a derivative thereof, the base of a second type of compound is guanine or a derivative thereof, the base of a third type of compound is cytosine or a derivative thereof, and the base of a fourth type of compound is thymine or a derivative thereof or uracil or a derivative thereof, and wherein the tag on each type of compound is different from the tag on each of the other three types of compound.

In some cases, the composition further comprises a fifth type of compound which differs from each of the four types of compound in the base and in the tag, wherein the base of the fifth type of compound is uracil or a derivative thereof if the base of the fourth type of compound is thymine or a derivative thereof, or wherein the base of the fifth type of compound is thymine or a derivative thereof if the base of the fourth type of compound is uracil or a derivative thereof.

Another aspect of the present disclosure provides a method for determining the identity of a compound comprising: (a) contacting the compound with a conductance measurement system comprising: (i) a first and a second compartment with a first and a second electrolyte solution separated by a physical barrier, which barrier has at least one pore with diameter on nanometer scale; (ii) a means for applying an electric field across the barrier; (iii) a means for measuring change in the electric field; and (b) recording the change in the electric field when the compound translocates through the pore wherein the change in the electric field is the result of interaction between the compound, the electrolyte, and the pore, and is indicative of the size, charge, and composition of the compound, thereby allowing correlation between the change and predetermined values to determine the identity of the compound. In some cases, the method further comprises a step of treating the compound with a phosphatase enzyme before step (a).

Another aspect of the present disclosure provides a method for determining whether a compound is a tag or a precursor of the tag comprising: (a) contacting the compound with a conductance measurement system comprising: (i) a first and a second compartment with a first and a second electrolyte solution separated by a physical barrier, which barrier has at least one pore with diameter on nanometer scale; (ii) a means for applying an electric field across the barrier; (iii) a means for measuring change in the electric field; (b) recording the change in the electric field when the compound translocates through the pore; and (c) comparing the change in the electric field with pre-determined values corresponding to the tag and the precursor of the tag, thereby determining whether the compound is the tag or the precursor thereof. In some cases, the method further comprises a step of adjusting current bias of the electric field in step (a).

Another aspect of the present disclosure provides a method for determining the nucleotide sequence of a single-stranded DNA, which method comprising: (a) contacting the single-stranded DNA with a conductance measurement system comprising: (i) a first and a second compartment with a first and a second electrolyte solution separated by a physical barrier, which barrier has at least one pore with diameter on nanometer scale; (ii) a means for applying an electric field across the barrier; (iii) a means for measuring change in the electric field; (iv) at least one polymerase attached to the pore; and (v) more than one phosphatase enzyme attached to the pore, and a composition comprising four different types of a compound having the structure:

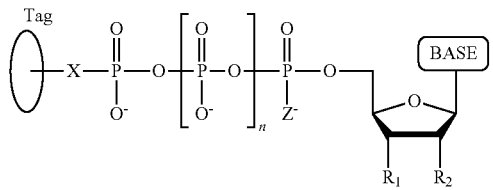

wherein the tag comprises one or more of ethylene glycol, an amino acid, a carbohydrate, a peptide, a dye, a chemiluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or $BH_3$, wherein n is 1, 2, 3, or 4, wherein the tag has a charge which is reverse in sign relative to the charge on the rest of the compound, wherein the base of a first type of compound is adenine or a derivative thereof, the base of a second type of compound is guanine or a derivative thereof, the base of a third type of compound is cytosine or a derivative thereof, and the base of a fourth type of compound is thymine or a derivative thereof, and wherein the tag on each type of compound is different from the tag on each of the other three types of compound, wherein the single-stranded DNA is in an electrolyte solution in contact with the polymerase attached to the pore and wherein the single-stranded DNA has a primer hybridized to a portion thereof, under conditions permitting the polymerase to catalyze incorporation of one of the compounds into the primer if the compound is complementary to the nucleotide residue of the single-stranded DNA immediately 5' to a nucleotide residue of the single-stranded DNA hybridized to the 3' terminal nucleotide residue of the primer, so as to form a DNA extension product, wherein incorporation of the compound results in release of a polyphosphate having the tag attached thereto, wherein the phosphatase enzyme attached to the pore cleaves the tag from the polyphosphate to release the tag; (b) determining which compound has been incorporated into the primer to form the DNA extension product in step (a) by applying an electric field across the barrier and measuring an electronic change across the pore resulting from the tag generated in step (a) translocating through the pore, wherein the electronic change is different for each type of tag, thereby identifying the nucleotide residue in the single-stranded DNA complementary to the incorporated compound; and (c) repeatedly performing step (b) for each nucleotide residue of the single-stranded DNA being sequenced, thereby determining the nucleotide sequence of the single-stranded DNA.

Another aspect of the present disclosure provides a method for determining the nucleotide sequence of a single-stranded DNA, the method comprising: (a) contacting the single-stranded DNA with a conductance measurement system comprising: (i) a first and a second compartment with a first and a second electrolyte solution separated by a physical barrier, which barrier has at least one pore with diameter on nanometer scale; (ii) a means for applying an electric field across the barrier; (iii) a means for measuring change in the electric field; (iv) at least one polymerase attached to the pore; and (v) more than one phosphatase enzyme attached to the pore, and a compound having the structure:

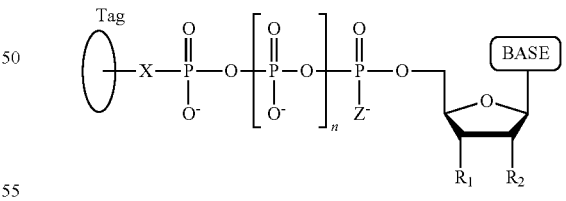

wherein the tag comprises one or more of ethylene glycol, an amino acid, a carbohydrate, a peptide, a dye, a chemiluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or $BH_3$, wherein the base is adenine, guanine, cytosine, thymine, or a derivative of one of these bases, wherein n is 1, 2, 3, or 4, and wherein the tag has a charge which is reverse in sign relative to the charge on the rest of the compound, wherein the single-stranded DNA is in an electrolyte solution in contact with the polymerase attached to the pore and wherein the single-stranded DNA has a primer hybridized to a portion thereof, under conditions permitting the polymerase to catalyze incorporation of the compound into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein if the compound is not incorporated, iteratively repeating the contacting with different compounds until a compound is incorporated, with the proviso that (1) the type of base on the compound is different from the type of base on each of the previous compounds, and (2) the type of tag on the compound is different from the type of tag on each of the previous compounds, wherein incorporation of the compound results in release of a polyphosphate having the tag attached thereto, wherein the phosphatase enzyme attached to the pore cleaves the tag from the polyphosphate to release the tag; (b) determining which compound has been incorporated into the primer to form the DNA extension product in step (a) by applying an electric field across the barrier and measuring an electronic change across the pore resulting from the tag generated in step (a) translocating through the pore, wherein the electronic change is different for each type of tag, thereby identifying the nucleotide residue in the single-stranded DNA complementary to the incorporated compound; and (c) iteratively performing steps (a) and (b) for each nucleotide residue of the single-stranded DNA being sequenced, thereby determining the nucleotide sequence of the single-stranded DNA.

Another aspect of the present disclosure provides a method for determining the nucleotide sequence of a single-stranded RNA, which method comprising: (a) contacting the single-stranded RNA with a conductance measurement system comprising: (i) a first and a second compartment with a first and a second electrolyte solution separated by a physical barrier, which barrier has at least one pore with diameter on nanometer scale; (ii) a means for applying an electric field across the barrier; (iii) a means for measuring change in the electric field; (iv) at least one polymerase attached to the pore; and (v) more than one phosphatase enzyme attached to the pore, and a composition comprising four different types of a compound having the structure:

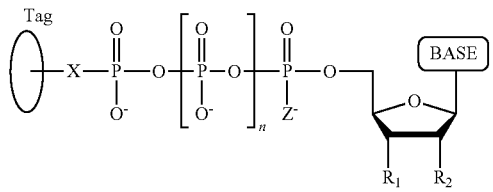

wherein the tag comprises one or more of ethylene glycol, an amino acid, a carbohydrate, a peptide, a dye, a chemilluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or $BH_3$, wherein n is 1, 2, 3, or 4, wherein the tag has a charge which is reverse in sign relative to the charge on the rest of the compound, wherein the base of a first type of compound is adenine or a derivative thereof, the base of a second type of compound is guanine or a derivative thereof, the base of a third type of compound is cytosine or a derivative thereof, and the base of a fourth type of the compound is uracil or a derivative thereof, and wherein the tag on each type of compound is different from the tag on each of the other three types of compound, wherein the single-stranded RNA is in an electrolyte solution in contact with the polymerase attached to the pore and wherein the single-stranded RNA has a primer hybridized to a portion thereof, under conditions permitting the polymerase to catalyze incorporation of one of the compounds into the primer if the compound is complementary to the nucleotide residue of the single-stranded RNA immediately 5' to a nucleotide residue of the single-stranded RNA hybridized to the 3' terminal nucleotide residue of the primer, so as to form an RNA extension product, wherein incorporation of the compound results in release of a polyphosphate having the tag attached thereto, wherein the phosphatase enzyme attached to the pore cleaves the tag from the polyphosphate to release the tag; (b) determining which compound has been incorporated into the pruner to form the RNA extension product in step (a) by applying an electric field across the barrier and measuring an electronic change across the pore resulting from the tag generated in step (a) translocating through the pore, wherein the electronic change is different for each type of tag, thereby identifying the nucleotide residue in the single-stranded RNA complementary to the incorporated compound; and (c) repeatedly performing step (b) for each nucleotide residue of the single-stranded RNA being sequenced, thereby determining the nucleotide sequence of the single-stranded RNA.

Another aspect of the present disclosure provides a method for determining the nucleotide sequence of a single-stranded RNA, the method comprising: (a) contacting the single-stranded RNA with a conductance measurement system comprising: (i) a first and a second compartment with a first and a second electrolyte solution separated by a physical barrier, which barrier has at least one pore with diameter on nanometer scale; (ii) a means for applying an electric field across the barrier; (iii) a means for measuring change in the electric field; (iv) at least one polymerase attached to the pore; and (v) more than one phosphatase enzyme attached to the pore, and a compound having the structure:

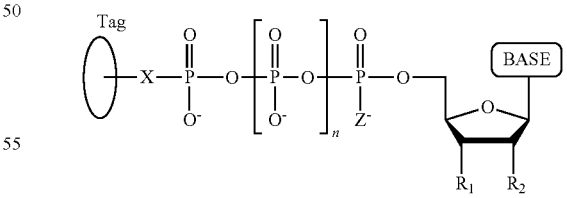

wherein the tag comprises one or more of ethylene glycol, an amino acid, a carbohydrate, a peptide, a dye, a chemilluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or BH$_3$, wherein the base is adenine, guanine, cytosine, uracil, or a derivative of one of these bases, wherein n is 1, 2, 3, or 4, and wherein the tag has a charge which is reverse in sign relative to the charge on the rest of the compound, wherein the single-stranded RNA is in an electrolyte solution in contact with the polymerase attached to the pore and wherein the single-stranded RNA has a primer hybridized to a portion thereof, under conditions permitting the polymerase to catalyze incorporation of the compound into the primer if it is complementary to the nucleotide residue of the single-stranded RNA which is immediately 5' to a nucleotide residue of the single-stranded DNA hybridized to the 3' terminal nucleotide residue of the primer, so as to form an RNA extension product, wherein if the compound is not incorporated, iteratively repeating the contacting with different compounds until a compound is incorporated, with the proviso that (1) the type of base on the compound is different from the type of base on each of the previous compounds, and (2) the type of tag on the compound is different from the type of tag on each of the previous compounds, wherein incorporation of the compound results in release of a polyphosphate having the tag attached thereto, wherein the phosphatase enzyme attached to the pore cleaves the tag from the polyphosphate to release the tag; (b) determining which compound has been incorporated into the primer to form the RNA extension product in step (a) by applying an electric field across the barrier and measuring an electronic change across the pore resulting from the tag generated in step (a) translocating through the pore, wherein the electronic change is different for each type of tag, thereby identifying the nucleotide residue in the single-stranded RNA complementary to the incorporated compound; and (c) iteratively performing steps (a) and (b) for each nucleotide residue of the single-stranded RNA being sequenced, thereby determining the nucleotide sequence of the single-stranded RNA.

Another aspect of the present disclosure provides a conductance measurement system comprising: (a) an electrically resistive barrier separating at least a first and a second electrolyte solution; (b) said electrically resistive barrier comprises at least one pore with a diameter on nanometer scale; (c) at least one compound with a tag in at least one of said first and second electrolyte solutions; (d) said at least one pore being configured to allow an ionic current to be driven across said first and second electrolyte solutions by an applied potential; (e) said at least one pore comprising a feature configured to cleave the tag from the compound to release the tag; and (f) a means of measuring the ionic current and a means of recording its time course as a time series, including time periods when the at least one pore is unobstructed by the tag and also time periods when the tag causes pulses of reduced-conductance. In some cases, the tag has a residence time in the pore which is greater than limitations of ionic current bandwidth and current shot noise of said means of measuring the ionic current.

Another aspect of the present disclosure provides a method to delineate segments of a conductance time series into regions statistically consistent with the unobstructed pore conductance level, and pulses of reduced-conductance, and also statistically stationary segments within individual pulses of reduced-conductance, said conductance time series being generated with a conductance measurement system comprising: an electrically resistive barrier separating at least a first and a second electrolyte solution; said electrically resistive bather comprises at least one pore with a diameter on nanometer scale; at least one compound with a tag in at least one of said first and second electrolyte solutions; said at least one pore being configured to allow an ionic current to be driven across said first and second electrolyte solutions by an applied potential; said at least one pore comprising a feature configured to cleave the tag from the compound to release the tag; and a means of measuring the ionic current and a means of recording said conductance time series, including time periods when the at least one pore is unobstructed by said tag and also time periods when said tag causes pulses of reduced-conductance; said method to delineate segments of a conductance time series being selected from the group consisting of: (a) a Viterbi decoding of the maximum likelihood state sequence of a Continuous Density of a Hidden Markov Model estimated from the raw conductance time series; (b) a delineation of the regions of pulses of reduced-conductance via comparison to a threshold for deviation from the open-pore conductance level; and (c) a means to characterize pulses of reduced-conductance by estimating the central tendencies of the ionic current levels for each segment, or by measure of central tendencies and segment duration together, the measure of segment central tendency being selected from the group consisting of: (i) a mean parameter of a Gaussian component of a first GMM estimated from the conductance time series as part of a Continuous Density Hidden Markov Model; (ii) an arithmetic mean; (iii) a trimmed mean; (iv) a median; and (v) a Maximum A Posteriori estimator of sample location, or a maximum likelihood estimator of sample location.

In some cases, the method further comprises at least one: (a) a maximum likelihood estimate of a second Gaussian Mixture Model based upon the measures of central tendency of conductance segments; (b) a peak finding by means of interpolation and smoothing of the empirical probability density of the estimates of central tendencies of segments of the conductance times series and finding roots of the derivatives of the interpolating functions; and (c) another means of locating the modes of multimodal distribution estimator.

Another aspect of the present disclosure provides a method for determining at least one parameter of a compound in a solution comprising the steps of: placing a first fluid in a first reservoir; placing a second fluid in a second reservoir; at least one of said first and said second fluid comprising at least one compound, wherein the compound is a tagged nucleotide or a tag cleaved from a tagged nucleotide; said first fluid in said first reservoir being separated from said second fluid in said second reservoir with an electrically resistive barrier; said electrically resistive barrier comprising at least one pore; passing an ionic current through said first fluid, said at least one pore, and said second fluid with an electrical potential between said first and said second fluid; measuring the ionic current passing through said at least one pore and the duration of changes in the ionic current; the measuring of the ionic current being carried out for a period of time sufficient to measure a reduction in the ionic current caused by the compound interacting with said at least one pore; and determining at least one parameter of the compound by mathematically analyzing the changes in the ionic current and the duration of the changes in the ionic current over the period of time; said mathematical analysis comprising at least one step selected from the group consisting of: (a) a mean parameter of a Gaussian component of a first GMM estimated from the conductance time series as part of a Continuous Density Hidden Markov Model; (b) an Event-Mean Extraction; (c) Maximum Likelihood Event State Assignment; (d) threshold detection and averaging; (e) sliding window analysis; (f) an arithmetic mean; (g) a trimmed mean; (h) a median; and (i)

a Maximum A Posteriori estimator of sample location, or a maximum likelihood estimator of sample location.

Another aspect of the present disclosure provides a tagged nucleotide, wherein the nucleotide comprises a tag capable of being cleaved in a nucleotide polymerization event and detected with the aid of a nanopore.

A further aspect of the present disclosure provides a method for nucleic acid sequencing, the method comprising providing an array of individually addressable sites, each site having a nanopore attached to a nucleic acid polymerase, and, at a given site of said array, polymerizing tagged nucleotides with a polymerase, wherein a tag is released and detected by a nanopore at said given site.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A, 2B and 2C show examples of nanopore detectors, where FIG. 2A has the nanopore disposed upon the electrode, FIG. 2B has the nanopore inserted in a membrane over a well and FIG. 2C has the nanopore over a protruding electrode.

DETAILED DESCRIPTION

Figure 1:
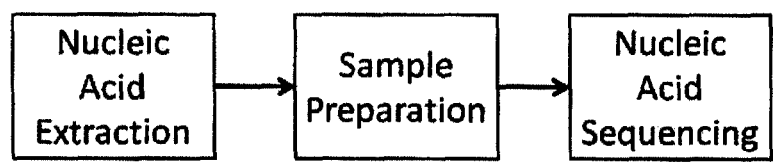
FIG. 1 schematically shows the steps of the method.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nanopore," as used herein, generally refers to a pore, channel or passage formed or otherwise provided in a membrane. A nanopore can be defined by a molecule (e.g., protein) in a membrane. A membrane can be an organic membrane, such as a lipid bilayer, or a synthetic membrane, such as a membrane formed of a polymeric material. The nanopore may be disposed adjacent or in proximity to a sensing circuit, such as, for example, a complementary metal-oxide semiconductor (CMOS) or field effect transistor (FET) circuit. A nanopore may have a characteristic width or diameter on the order of 0.1 nanometers (nm) to about 1000 nm. Some nanopores are proteins. Alpha hemolysin is an example of a protein nanopore, The term "nucleic acid," as used herein, generally refers to a molecule comprising one or more nucleic acid subunits. A nucleic acid can include one or more subunits selected from adenosine (A), cytosine (C), guanine (G), thymine (T) and uracil (U). In some examples, a nucleic acid is deoxyribonucleic acid (DNA) or ribonucleic acid (RNA), or derivatives thereof. A nucleic acid may be single-stranded or double stranded.

The articles "a", "an" and "the" are non-limiting. For example, "the method" includes the broadest definition of the meaning of the phrase, which can be more than one method.

A "derivative" of adenine, guanine, cytosine, thymine or uracil, includes a 7-deaza-purine and a 5-methyl pyrimidine. Other examples include 7-deaza adenine, 7-deaza-guanine, and 5-methyl-cytosine.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" is defined to include groups having 1, 2 . . . n−1, or n carbons in a linear or branched arrangement. For example, a "C1-C5 alkyl" is defined to include groups having 1, 2, 3, 4, or 5 carbons in a linear or branched arrangement, and specifically includes methyl, ethyl, n-propyl, isopropyl, n-butyl, t-butyl, and pentyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl radical having 2, 3, 4, or 5, carbon atoms, and up to 1, 2, 3 or 4, carbon-carbon double bonds respectively. Alkenyl groups include ethenyl, propenyl, and butenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl radical having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

It is understood that substituents and substitution patterns on the compounds of the instant invention can be selected by one of ordinary skill in the art to provide compounds that are chemically stable and that can be readily synthesized, using, for example, the methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with principles of chemical structure connectivity.

In the compound structures depicted herein, hydrogen atoms, except on ribose and deoxyribose sugars, are generally not shown. However, it is understood that sufficient hydrogen atoms exist on the represented carbon atoms to satisfy the octet rule.

As used herein, and unless stated otherwise, each of the following terms shall have the definition set forth: A—Adenine; C—Cytosine; DNA—Deoxyribonucleic acid; G—Guanine; RNA—Ribonucleic acid; T—Thymine; U—Uracil; dNPP—deoxyribonucleotide polyphosphate; and rNPP—ribonucleotide polyphosphate.

A nucleic acid can include any nucleic acid molecule, including, without limitation, DNA, RNA and hybrids or variants thereof. A nucleic acid may be single-stranded or double stranded. In an embodiment, the nucleic acid bases that form nucleic acid molecules can be the bases A, C, G, T and U, as well as derivatives thereof. Derivatives of these bases are exemplified in PCR Systems, Reagents and Consumables (Perkin Elmer Catalogue 1996-1997, Roche Molecular Systems, Inc., Branchburg, N.J., USA), which is entirely incorporated herein by reference.

A nucleotide polyphosphate, such as a deoxyribonucleotide polyphosphate ("dNPP") or a ribonucleotide polyphosphate "(rNPP"), is a nucleotide comprising multiple, i.e. three, four, five, six, or more phosphates in a linear fashion bonded to its 5' sugar carbon atom. A nucleotide polyphosphate analogue is an analogue of such a deoxyribonucleotide polyphosphate or of such a ribonucleotide polyphosphate as defined herein, differing thereform by having a tag attached thereto at a specified position. Such analogues are incorporable into a primer or nucleic acid extension strand, such as a DNA extension strand, by contacting with an appropriate nucleic acid polymerase under the appropriate nucleic acid polymerization conditions.

In an embodiment, the dNPP is a deoxynucleotide triphosphate.

As used herein a tetranucleotide, a pentanucleotide, or a hexanucleotide, encompasses 4, 5 or 6, respectively, nucleic acid monomer residues joined by phosphodiester bonds, wherein the free terminal residue can be a nucleotide or a nucleoside. In an embodiment, the free terminal residue is a nucleoside and the other residues are nucleotides.

"Solid substrate" shall mean any suitable medium present in the solid phase to which a nucleic acid may be affixed. Non-limiting examples include chips, wells, beads, nanopore structures and columns. In a non-limiting embodiment the solid substrate can be present in a solution, including an aqueous electrolyte solution.

"Hybridize" shall mean the annealing of one single-stranded nucleic acid to another nucleic acid (such as primer) based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is described in, for example, Sambrook J, Fritsch E F, Maniatis T., Molecular cloning: a laboratory manual, Cold Spring Harbor Laboratory Press, New York (1989). As used herein, hybridization of a primer sequence, or of a DNA extension product, to another nucleic acid shall mean annealing sufficient such that the primer, or DNA extension product, respectively, is extendable by creation of a phosphodiester bond with an available nucleotide or nucleotide analogue capable of forming a phosphodiester bond, therewith.

As used herein, unless otherwise specified, a base which is "different from" another base or a recited list of bases shall mean that the base has a different structure than the other base or bases. For example, a base that is "different from" adenine, thymine, and cytosine can include a base that is guanine or a base that is uracil.

"Primer" as used herein (a primer sequence) is a short, usiuslly chemically synthesized oligonucleotide, of appropriate length, for example about 18-24 bases, sufficient to hybridize to a target DNA (e.g. a single stranded DNA) and permit the addition of a nucleotide residue thereto, or oligonucleotide or polynucleotide synthesis therefrom, under suitable conditions. In an embodiment the primer is a DNA primer, i.e. a primer consisting of, or largely consisting of, deoxyribonucleotide residues. The primers are designed to have a sequence which is the reverse complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product.

Methods and Systems for Nucleic Acid Identification and Sequencing

Described herein are methods, devices and systems for sequencing nucleic acids using a nanopore. The methods may accurately detect individual nucleotide incorporation events, such as upon the incorporation of a nucleotide into a growing strand that is complementary to a template. An enzyme (e.g., DNA polymerase) may incorporate nucleotides to a growing polynucleotide chain, wherein the added nucleotide is complimentary to the corresponding template nucleic acid strand, which is hybridized to the growing strand (e.g., polymerase chain reaction (PCR)). These nucleotide incorporation events release tags from the nucleotides, which pass through a nanopore and are detected. In this way, the incorporated base may be identified (i.e., A, C, G, T or U) because a unique tag is released from each type of nucleotide (i.e., A, C, G, T or U).

Nucleotide incorporation events may be detected in real-time (i.e., as they occur) and with the aid of a nanopore. In some instances, an enzyme (e.g., DNA polymerase) attached to or in proximity to the nanopore may facilitate the flow of a nucleic acid molecule through or adjacent to a nanopore. A nucleotide incorporation event, or the incorporation of a plurality of nucleotides, may release one or more tag molecules (also "tags" herein), which may be detected by a nanopore as the tags flow through or adjacent to the nanopore. In some cases, an enzyme attached to or in proximity to the nanopore may aid in detecting tags or other by-products released upon the incorporation of one or more nucleotides.

Methods described herein may be single-molecule methods. That is, the signal that is detected is generated by a single molecule (i.e., single nucleotide incorporation) and is not generated from a plurality of clonal molecules. The method may not require DNA amplification.

Nucleotide incorporation events may occur from a mixture comprising a plurality of nucleotides (e.g., deoxyribonucleotide triphosphate (dNTP where N is adenosine (A), cytidine (C), thymidine (T), guanosine (G), or uridine (U)). Nucleotide incorporation events do not necessarily occur from a solution comprising a single type of nucleotide (e.g., dATP). Nucleotide incorporation events do not necessarily occur from alternating solutions of a plurality of nucleotides (e.g., dATP, followed by dCTP, followed by dGTP, followed by dTTP, followed by dATP).

DNA sequencing is a fundamental technology for biology. Several analytical methods have been developed to detect DNA or RNA at single molecule level using chemical or physical microscopic technologies (Perkins et al. 1994, Rief et al. 1999, Smith et al. 1996, and Vercoutere et al. 2001).

In the past few years, ion-sensing technologies such as ion channel, which relies on the detection of hydrogen ion ($H^+$) released when a nucleotide is incorporated into a strand of DNA by a polymerase (Rothberg et al. 2011), have been explored to detect individual DNA or RNA strands (Kasianowicz 2003 & 2004, Chandler et al. 2004, Deemer et al. 2002, Berzukov et al. 2001, and Henrickson et al. 2000).

Figure 21:
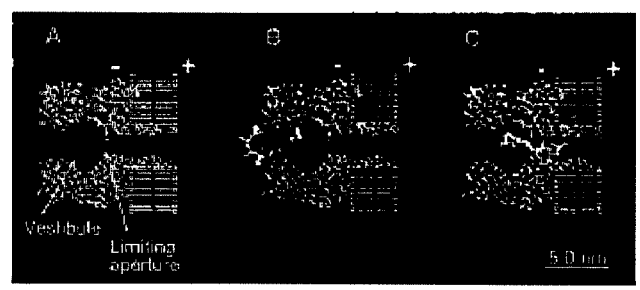
FIG. 21 shows α-Hemolysin protein self-assembling in a lipid bilayer to form an ion channel and a nucleic acid stretch passes through it (top), with the corresponding electronic signatures generated (bottom) (Vercoutere et al. 2001 and Deamer et al. 2002).
Figure 21:
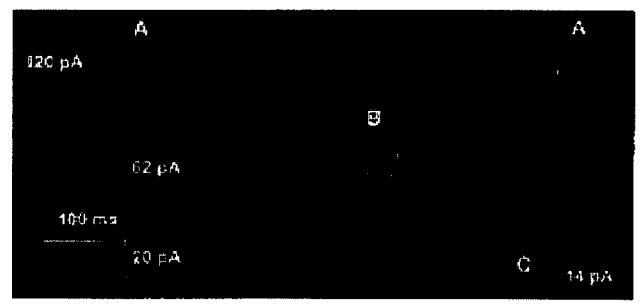

In some cases, an α-hemolysin channel, an exotoxin secreted by a bacterium, can be used to detect nucleic acids at the single molecule level (Kasianowicz et al. 1996). An α-hemolysin protein is a monomeric polypeptide which self-assembles in a lipid bilayer membrane to form a heptameric pore, with a 2.6 nm-diameter vestibule and 1.5 nm-diameter limiting aperture (the narrowest point of the pore) (Meller et al. 2000, Akeson et al. 1999, and Deamer et al. 2002). The limiting aperture of the nanopore allows linear single-stranded but not double-stranded, nucleic acid molecules (diameter ~2.0 nm) to pass through. In an aqueous ionic salt solution such as KCl, when an appropriate voltage is applied across the membrane, the pore formed by an α-hemolysin channel conducts a sufficiently strong and steady ionic current. The polyanionic nucleic acids are driven through the pore by the applied electric field, thus blocking or reducing the ionic current that can be otherwise unimpeded. This process of passage generates an electronic signature (FIG. 21) (Vercoutere et al. 2001 and Deamer et al.

2002). A particular nucleic acid molecule, when entering and passing through the nanopore generates a characteristic signature that distinguishes it from other nucleic acid molecules. The duration of the blockade is proportional to the length of nucleic acid, and the signal strength is related to the steric and electronic properties of the nucleotides, namely the identity of the four bases (A, C, G and T). Thus a specific event diagram, which is a plot of translocation time versus blockade current, is obtained and used to distinguish the length and the composition of polynucleotides by single-channel recording techniques based on characteristic parameters such as translocation current, translocation duration, and their corresponding dispersion in the diagram (Meller et al, 2000).

It has also been shown that a protein nanopore with a covalently attached adaptor can accurately identify unlabeled nucleoside 5'-monophosphates (dAMP, dGMP, dCMP & dTMP) with high accuracy (Clarke et al. 2009). For example, aminocyclodextrin adaptor has been covalently attached within the a-hemolysin pore successfully. When a dNMP is captured and driven through the pore in a lipid bilayer membrane, the ionic current through the pore is reduced to one of four levels, each representing one of the four dNMP's (A, G, C, or T). Moreover, Robertson et al. (2007) have recently demonstrated that when a poly(ethylene glycol) (PEG) molecule enters a single a-hemolysin pore, it causes distinct mass-dependent conductance states with characteristic mean residence times. The conductance-based mass spectrum clearly resolves the repeat units of ethylene glycol, and the residence time increases with the mass of the PEG.

Although the current nanopore approach shows promise as a DNA detection method, the more demanding goal of accurate base-to-base sequencing has not yet been achieved.

Methods for sequencing nucleic acids may include retrieving a biological sample having the nucleic acid to be sequenced, extracting or otherwise isolating the nucleic acid sample from the biological sample, and in some cases preparing the nucleic acid sample for sequencing.

FIG. 1 schematically illustrates a method for sequencing a nucleic acid sample. The method comprises isolating the nucleic acid molecule from a biological sample (e.g., tissue sample, fluid sample), and preparing the nucleic acid sample for sequencing. In some instances, the nucleic acid sample is extracted from a cell. Some exemplary techniques for extracting nucleic acids are using lysozyme, sonication, extraction, high pressures or any combination thereof. The nucleic acid is cell-free nucleic acid in some cases and does not require extraction from a cell.

In some cases, a nucleic acid sample may be prepared for sequencing by a process that involves removing proteins, cell wall debris and other components from the nucleic acid sample. There are many commercial products available for accomplishing this, such as, for example, spin columns. Ethanol precipitation and centrifugation may also be used.

The nucleic acid sample may be partitioned (or fractured) into a plurality of fragments, which may facilitate nucleic acid sequencing, such as with the aid of a device that includes a plurality of nanopores in an array. However, fracturing the nucleic acid molecule(s) to be sequenced may not be necessary.

In some instances, long sequences are determined (i.e., "shotgun sequencing" methods may not be required). Any suitable length of nucleic acid sequence may be determined. For instance, at least about 400, about 500, about 600, about 700, about 800, about 800, about 1000, about 1500, about 2000, about 2500, about 3000, about 3500, about 4000, about 4500, about 5000, about 6000, about 7000, about 8000, about 9000, about 10000, about 20000, about 40000, about 60000, about 80000, about 100000, and the like bases may be sequenced. In some instances, at least 400, at least 500, at least 600, at least 700, at least 800, at least 800, at least 1000, at least 1500, at least 2000, at least 2500, at least 3000, at least 3500, at least 4000, at least 4500, at least 5000, at least 6000, at least 7000, at least 8000, at least 9000, at least 10000, at least 20000, at least 40000, at least 60000, at least 80000, at least 100000, and the like bases are sequenced. In some instances the sequenced bases are contiguous. In some cases, the nucleic acid sample may be partitioned prior to sequencing.

Nanopore Sequencing and Molecular Detection

Provided herein are systems and methods for sequencing a nucleic acid molecule with the aid of a nanopore. The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide).

In some cases, as a nucleic acid or tag flows through the nanopore, the sensing circuit detects an electrical signal associated with the nucleic acid or tag. The nucleic acid may be a subunit of a larger strand. The tag may be a byproduct of a nucleotide incorporation event. A detected signal may be collected and stored in a memory location, and later used to construct a sequence of the nucleic acid. The collected signal may be processed to account for any abnormalities in the detected signal, such as errors.

Figure 2A:
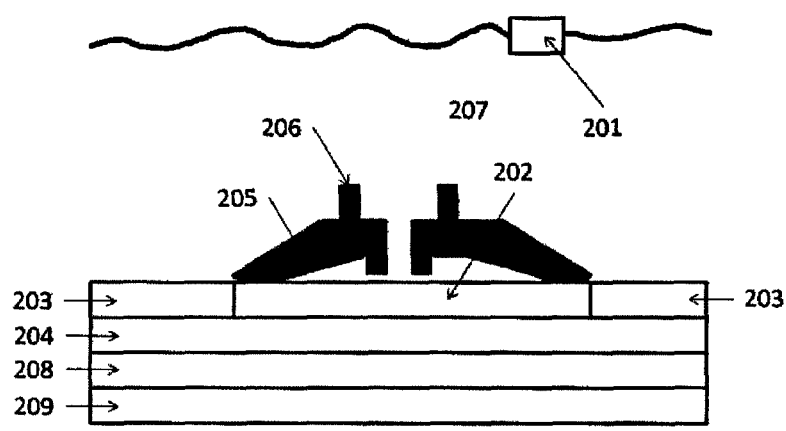

FIG. 2 shows an examples of a nanopore detector (or sensor) having temperature control, as may be prepared according to methods described in U.S. Patent Application Publication No. 2011/0193570, which is entirely incorporated herein by reference. With reference to FIG. 2A, the nanopore detector comprises a top electrode 201 in contact with a conductive solution (e.g., salt solution) 207. A bottom conductive electrode 202 is near, adjacent, or in proximity to a nanopore 206, which is inserted in a membrane 205. In some instances, the bottom conductive electrode 202 is embedded in a semiconductor 203 in which is embedded electrical circuitry in a semiconductor substrate 204. A surface of the semiconductor 203 may be treated to be hydrophobic. A sample being detected goes through the pore in the nanopore 206. The semiconductor chip sensor is placed in package 208 and this, in turn, is in the vicinity of a temperature control element 209. The temperature control element 209 may be a thermoelectric heating and/or cooling device (e.g., Peltier device). Multiple nanopore detectors may form a nanopore array.

Figure 2B:
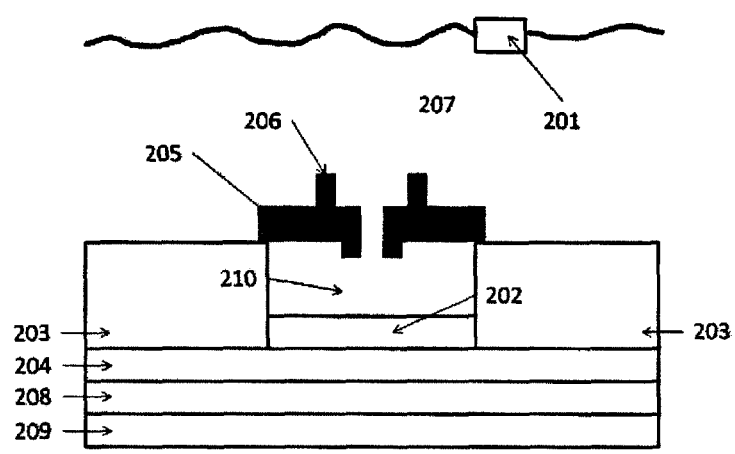

With reference to FIG. 2B, where like numerals represent like elements, the membrane 205 can be disposed over a well 210, where the sensor 202 forms part of the surface of the well. FIG. 2C shows an example in which the electrode 202 protrudes from the treated semiconductor surface 203.

In some examples, the membrane 205 forms on the bottom conductive electrode 202 and not on the semiconductor 203. The membrane 205 in such a case may form coupling interactions with the bottom conductive electrode 202. In some cases, however, the membrane 205 forms on the bottom conductive electrode 202 and the semiconductor 203. As an alternative, the membrane 205 can form on the semiconductor 203 and not on the bottom conductive electrode 202, but may extend over the bottom conductive electrode 202.

Indirect Sequencing with Nanopores

Nanopores may be used to sequence nucleic acid molecules indirectly, optionally with electrical detection. Indirect sequencing may be any method where a polymerized nucleic acid molecule such as DNA or RNA does not pass through the nanopore. The nucleic acid molecule may be at least partially located in the vestibule of the nanopore, but not in the pore (i.e., narrowest portion) of the nanopore. The nucleic acid molecule may pass within any suitable distance from and/or proximity to the nanopore, optionally within a distance such that tags released from nucleotide incorporation events are detected in the nanopore.

Byproducts of nucleotide incorporation events may be detected by the nanopore. "Nucleotide incorporation events" are the incorporation of a nucleotide into a growing polynucleotide chain. A byproduct may be correlated with the incorporation of a given type nucleotide. The nucleotide incorporation events are generally catalyzed by an enzyme, such as DNA polymerase, and use base pair interactions with a template molecule to choose amongst the available nucleotides for incorporation at each location.

In some cases, the byproduct passes through the nanopore and/or generates a signal detectable in the nanopore. Released tag molecules are an example of byproducts. In some cases, the byproducts are protons (i.e., a pH change). In other cases, the byproducts are phosphates (e.g., phosphates released during nucleotide incorporation events). For example, each of the different types of nucleotides may comprise a different number of phosphates, and detection of the released phosphates allows one to determine the identity of the incorporated nucleotide.

Figure 3:
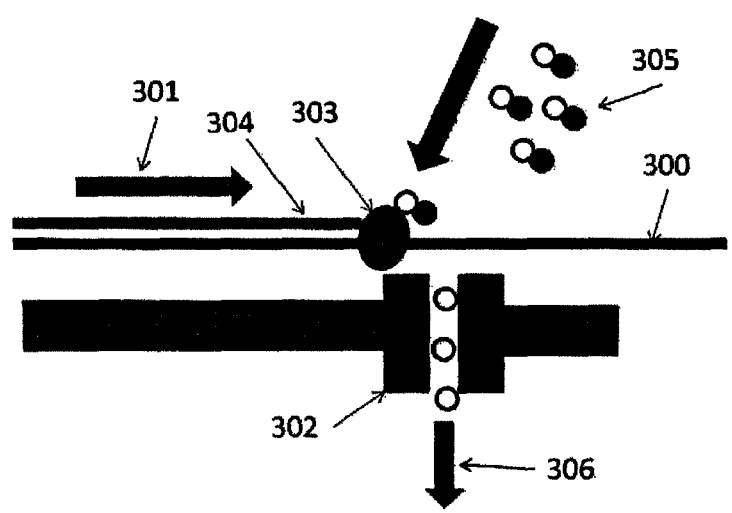
FIG. 3 illustrates a method for nucleic acid sequencing.

An example of the method is depicted in FIG. 3. Here, the nucleic acid strand 300 passes across or in proximity to (but not through as indicated by the arrow at 301) the nanopore 302. An enzyme 303 (e.g., DNA polymerase) extends a growing nucleic acid strand 304 by incorporating one nucleotide at a time using a first nucleic acid molecule as a template 300 (i.e., the enzyme catalyzes nucleotide incorporation events).

The enzyme 303 may be attached to the nanopore 302. Suitable methods for attaching the enzyme to the nanopore include cross-linking such as the formation of intra-molecular disulfide bonds. The nanopore and the enzyme may also be a fusion protein, that is encoded by a single polypeptide chain. Methods for producing fusion proteins can include fusing the coding sequence for the enzyme in frame and adjacent to the coding sequence for the nanopore (without a stop codon in between) and expressing this fusion sequence from a single promoter. In some cases, phosphatase enzymes are also attached to the nanopore.

In some cases, the DNA polymerase is 9° N polymerase or a variant thereof, E. Coli DNA polymerase I, Bacteriophage T4 DNA polymerase, Sequenase, Taq DNA polymerase, 9° N polymerase (exo-) A485L/Y409V or Phi29 DNA Polymerase (φ29 DNA Polymerase).

Nanopores Sequencing of Tag Molecules

A nucleic acid sample may be sequenced using tagged nucleotides or nucleotide analogs. In some examples, a method for sequencing a nucleic acid molecule comprises (a) polymerizing tagged nucleotides, wherein a tag associated with an individual nucleotide is released upon polymerization, and (b) detecting the released tag with the aid of a nanopore.

In some instances, the method further comprises directing the tag released from an individual nucleotide through the nanopore. The released tag may be directed by any suitable technique, in some cases with the aid of an enzyme (or molecular motor). Alternative, the released tag may be directed through the nanopore without the use of an enzyme. For example, the tag may be directed by a voltage difference across the nanopore as described herein.

With continued reference to FIG. 3, the enzyme draws from a pool of nucleotides (filled circles at indication 305) attached to tag molecules (open circles at indication 305). Each type of nucleotide is attached to a different tag molecule so that when the tags are released and pass through the nanopore 306, they may be differentiated from each other based on the signal that is generated in the nanopore.

Figure 4:
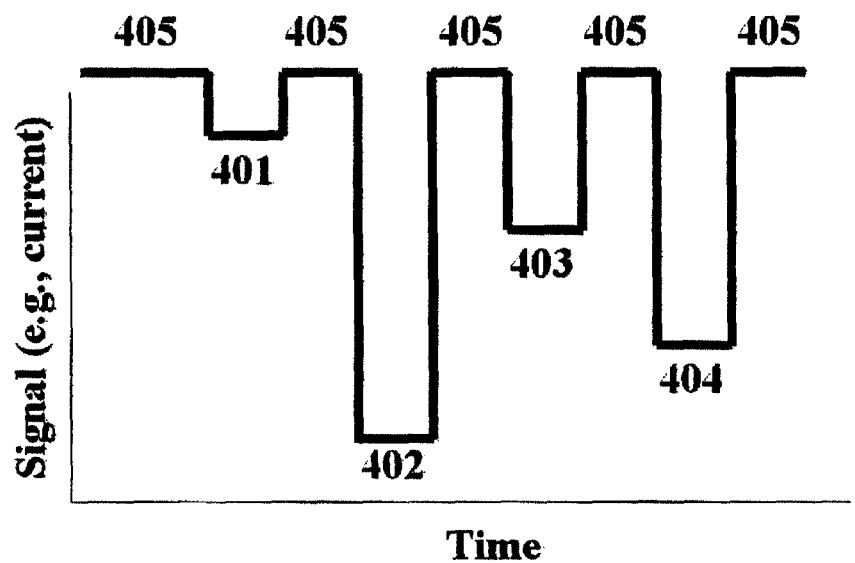
FIG. 4 shows an example of a signal generated by the passage of tags through a nanopore.

FIG. 4 shows an example of different signals being generated by different tags as they are detected by the nanopore. Four different signal intensities (401, 402, 403 and 404) are detected. These may correspond to four different tags. For example, the tag presented to the nanopore and/or released by incorporation of adenosine (A) may generate a signal with an amplitude 401. A tag presented to the nanopore and/or released by incorporation of cytosine (C) may generate a signal with a higher amplitude 403; a tag presented to the nanopore and/or released by incorporation of guanine (G) may generate a signal with an even higher amplitude 404; and a tag presented to the nanopore and/or released by incorporation of thymine (T) may generate a signal with a yet higher amplitude 402. The signal may return to a baseline level 405 between detections in some cases.

The rate of nucleotide incorporation events is generally slower than (or equal to) the rate at which tags molecules released during the nucleotide incorporation events pass through and/or are detected by the nanopore. Generally, the rate of nucleotide incorporation events is not greater than the rate at which tags molecules released during the nucleotide incorporation events pass through and/or are detected by the nanopore (i.e., otherwise the nucleotide incorporation events are not detected accurately and/or in the correct sequence).

Arrays of Nanopores for Sequencing

Figure 5:
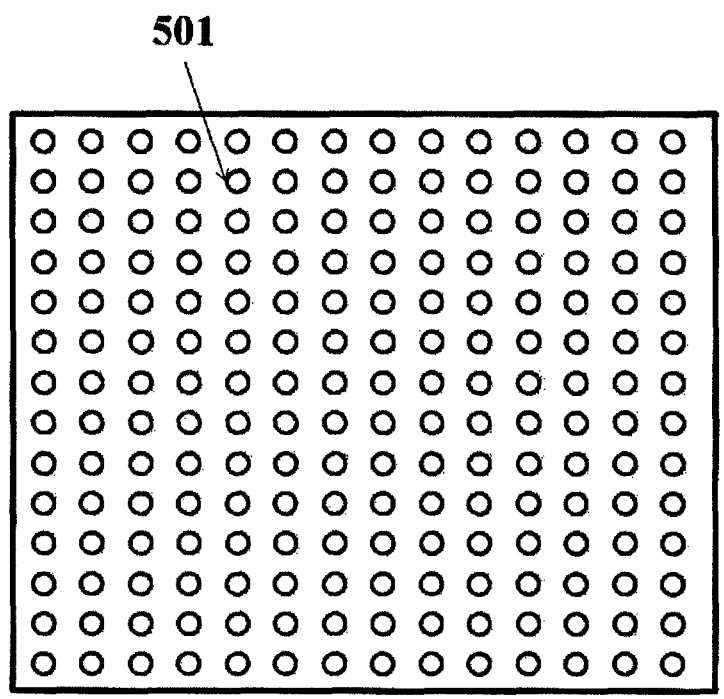
FIG. 5 shows an array of nanopore detectors.

FIG. 5 shows that a plurality of nucleic acid molecules may be sequenced on an array of nanopore detectors. Here, each nanopore location (e.g., 501) comprises a nanopore, optionally attached to a polymerase enzyme and/or phosphatase enzymes. There is also generally a sensor at each array location as described elsewhere herein.

In some examples, an array of nanopores attached to a nucleic acid polymerase is provided, and tagged nucleotides are polymerized with the polymerase. During polymerization, a tag is released and detected by the nanopore. The array of nanopores may have any suitable number of nanopores. In some instances, the array comprises about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, and the like nanopores. In some instances, the array comprises at least 200, at least 400, at least 600, at least 800, at least 1000, at least 1500, at least 2000, at least 3000, at least 4000, at least 5000, at least 10000, at least 15000, at least 20000, at least 40000, at least 60000, at least 80000, at least 100000, at least 200000, at least 400000, at least 600000, at least 800000, at least 1000000, and the like nanopores. The nanopores can be individually addressable. In some cases, the array can include individually addressable nanopores at a density of at least about 500, 600, 700, 800, 900, 1000, 10,000, 100,000, or 1,000,000 individually addressable nanopores per mm$^2$.

In some cases, a single tag is released upon incorporation of a single nucleotide and detected by a nanopore. In other cases, a plurality of tags is released upon incorporation of a plurality of nucleotides. A nanopore sensor adjacent to a nanopore may detect an individual released tag, or a plurality of released tag. One or more signals associated with plurality of released tags may be detected and processed to yield an averaged signal.

Tags may be detected by the sensor as a function of time. Tags detected with time may be used to determine the nucleic acid sequence of the nucleic acid sample, such as with the aid of a computer system (see, e.g., FIG. 18) that is programmed to record sensor data and generate sequence information from the data.

Sequencing Accuracy

Methods provided herein may accurately distinguish between individual nucleotide incorporation events (e.g., single-molecule events). The methods may accurately distinguish between individual nucleotide incorporation events in a single pass—i.e., without having to re-sequence a given nucleic acid molecule.

A method for nucleic acid sequencing comprises distinguishing between individual nucleotide incorporation events with an accuracy of greater than about 4σ. In some cases, the nucleotide incorporation events are detected with aid of a nanopore. Tags associated with the nucleotides may be released upon incorporation and the tags pass through the nanopore. A different tag may be associated with and/or released from each type of nucleotide (e.g., A, C, T, G) and is detected as it passes through the nanopore. Errors include, but are not limited to, (a) failing to detect a tag, (b) mis-identifying a tag, (c) detecting a tag where there is no tag, (d) detecting tags in the incorrect order (e.g., two tags are released in a first order, but pass each other and are detected in a second order), (e) a tag that has not been released from a nucleotide is detected as being released, or any combination thereof. In some embodiments, the accuracy of distinguishing between individual nucleotide incorporation events is 100% subtracted by the rate at which errors occur (i.e., error rate).

The accuracy of distinguishing between individual nucleotide incorporation events is any suitable percentage. The accuracy of distinguishing between individual nucleotide incorporation events may be about 93%, about 94%, about 95%, about 96%, about 97%, about 98%, about 99%, about 99.5%, about 99.9%, about 99.99%, about 99.999%, about 99.9999%, and the like. In some cases, the accuracy of distinguishing between individual nucleotide incorporation events is at least 93%, at least 94%, at least 95%, at least 96%, at least 97%, at least 98%, at least 99%, at least 99.5%, at least 99.9%, at least 99.99%, at least 99.999%, at least 99.9999%, and the like. In some instances, the accuracy of distinguishing between individual nucleotide incorporation events is reported in sigma (σ) units. Sigma is a statistical variable that is sometimes used in business management and manufacturing strategy to report error rates such as the percentage of defect-free products, Here, sigma values may be used interchangeably with accuracy according to the relationship as follows: 4σ is 99.38% accuracy, 5σ is 99.977% accuracy, and 6σ is 99.99966% accuracy.

Distinguishing between individual nucleotide incorporation events, according to methods described herein, may be used to accurately determine a nucleic acid sequence. In some instances, the determination of the nucleic acid sequence of a nucleic acid (e.g., DNA and RNA) includes errors. Exemplary errors include, but are not limited to deletions (failing to detect a nucleic acid) insertions (detecting a nucleic acid where none are truly present) and substitutions (detecting the incorrect nucleic acid). The accuracy of nucleic acid sequencing may be determined by lining up the measured nucleic acid sequence with the true nucleic acid sequence (e.g., according to bioinformatics techniques) and determining the percentage of nucleic acid positions that are deletions, insertions and/or substitutions. The errors are any combination of deletions, insertions and substitutions. The accuracy ranges from 0% to 100%, with 100% being a completely correct determination of the sequence of the nucleic acid. Similarly, the error rate is 100%—the accuracy and ranges from 0% to 100%, with 0% error rate being a completely correct determination of the sequence of the nucleic acid.

The accuracy of nucleic acid sequencing as performed according to the methods and/or using the devices described herein is high. The accuracy is any suitably high value. In some instances, the accuracy is about 95%, about 95.5%, about 96%, about 96.5%, about 97%, about 97.5%, about 98%, about 98.5%, about 99%, about 99.5%, about 99.9%, about 99.99%, about 99.999%, about 99.9999%, and the like. In some instances, the accuracy is at least 95%, at least 95.5%, at least 96%, at least 96.5%, at least 97%, at least 97.5%, at least 98%, at least 98.5%, at least 99%, at least 99.5%, at least 99.9%, at least 99.99%, at least 99.999%, at least 99.9999%, and the like. In some instances, the accuracy is between about 95% and 99.9999%, between about 97% and 99.9999%, between about 99% and 99.9999%, between about 99.5% and 99.9999%, between about 99.9% and 99.9999%, and the like.

High accuracy may be achieved by performing multiple passes (i.e., sequencing a nucleic acid molecule a plurality of times, e.g., by passing the nucleic acid through or in proximity to a nanopore and sequencing nucleic acid bases of the nucleic acid molecule). The data from multiple passes may be combined (e.g., deletions, insertions and/or substitutions in a first pass are corrected using data from other repeated passes). The method provides high accuracy with few passes (also referred to as reads, multiplicity of sequencing coverage). The number of passes is any suitable number, and need not be an integer. In some embodiments, the nucleic acid molecule is sequenced 1 time, 2 times, 3 times, 4 times, 5 times, 6 times, 7 times, 8 times, 9 times, 10 times, 12 times, 14 times, 16 times, 18 times, 20 times, 25 times, 30 times, 35 times, 40 times, 45 times, 50 times, and the like. In some embodiments, the nucleic acid molecule is sequenced at most 1 time, at most 2 times, at most 3 times, at most 4 times, at most 5 times, at most 6 times, at most 7 times, at most 8 times, at most 9 times, at most 10 times, at most 12 times, at most 14 times, at most 16 times, at most 18 times, at most 20 times, at most 25 times, at most 30 times, at most 35 times, at most 40 times, at most 45 times, at most 50 times, and the like. In some embodiments, the nucleic acid molecule is sequenced between about 1 time and 10 times, between about 1 time and 5 times, between about 1 time and 3 times, and the like. The level of accuracy may be achieved by combining data collected from at most 20 passes. In some embodiments, the level of accuracy is achieved by combining data collected from at most 10 passes. In some embodiments, the level of accuracy is achieved by combining data collected from at most 5 passes. In some cases, the level of accuracy is achieved in a single pass.

The error rate is any suitably low rate. In some instances, the error rate is about 10%, about 5%, about 4%, about 3%, about 2%, about 1%, about 0.5%, about 0.1%, about 0.01%, about 0.001%, about 0.0001%, and the like. In some instances, the error rate is at most 10%, at most 5%, at most 4%, at most 3%, at most 2%, at most 1%, at most 0.5%, at most 0.1%, at most 0.01%, at most 0.001%, at most 0.0001%, and the like. In some instances, the error rate is between 10% and 0.0001%, between 3% and 0.0001%, between 1% and 0.0001%, between 0.01% and 0.0001%, and the like.

Template Preparation

The method may involve sequencing a template nucleic acid strand by adding tagged nucleotides to a strand complimentary to the template strand and detecting released tag molecules in a nanopore.

Figure 10:
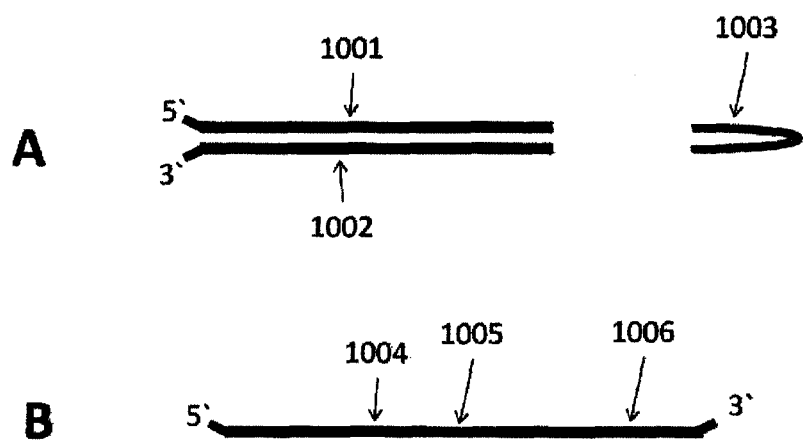
FIG. 10 shows a method for preparing a template strand.

FIG. 10 shows a method for preparing the nucleic acid template. In this case, the nucleic acid molecule to be sequenced is double stranded and comprises a sense strand 1001 and an anti-sense strand 1002. A nucleic acid hairpin 1003 may be ligated onto the 3' end of the sense strand and the 5' end of the anti-sense strand.

The strands of the nucleic acid molecule may be dissociated to form a single stranded template molecule that comprises the sense strand 1004, the hairpin 1005 and the anti-sense strand 1006. This single stranded nucleic acid may be sequenced as described herein.

In some cases, the present method for preparing the nucleic acid template allows one to sequence both the sense strand and the anti-sense strand in a single sequencing run. This may produce two redundant data sets (i.e., each nucleic acid base pair position is sequenced twice) that may result in a more accurate determination of the sequence than sequencing only one strand of the original double stranded nucleic acid molecule.

Device Set-Up

Figure 11:
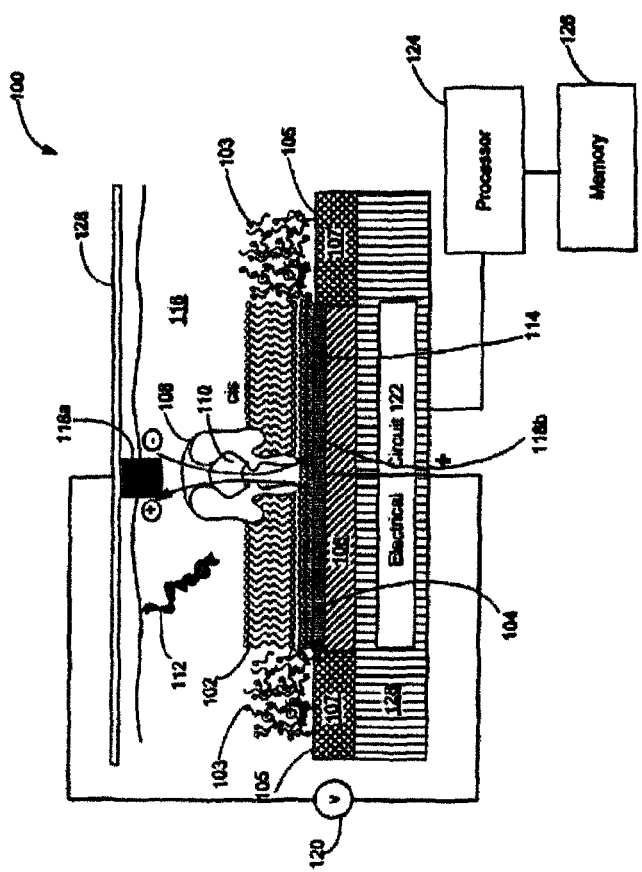
FIG. 11 shows an exemplary chip set-up comprising a nanopore.

FIG. 11 is a schematic diagram of a nanopore device 100 (or sensor) that may be used to sequence a nucleic acid and/or detect a tag molecule as described herein. The nanopore containing lipid bilayer may be characterized by a resistance and capacitance. The nanopore device 100 includes a lipid bilayer 102 formed on a lipid bilayer compatible surface 104 of a conductive solid substrate 106, where the lipid bilayer compatible surface 104 may be isolated by lipid bilayer incompatible surfaces 105 and the conductive solid substrate 106 may be electrically isolated by insulating materials 107, and where the lipid bilayer 102 may be surrounded by amorphous lipid 103 formed on the lipid bilayer incompatible surface 105. The lipid bilayer 102 may be embedded with a single nanopore structure 108 having a nanopore 110 large enough for passing of the tag molecules being characterized and/or small ions (e.g., $Na^+$, $K^+$, $Ca^{2+}$, $Cl^-$) between the two sides of the lipid bilayer 102. A layer of water molecules 114 may be adsorbed on the lipid bilayer compatible surface 104 and sandwiched between the lipid bilayer 102 and the lipid bilayer compatible surface 104. The aqueous film 114 adsorbed on the hydrophilic lipid bilayer compatible surface 104 may promote the ordering of lipid molecules and facilitate the formation of lipid bilayer on the lipid bilayer compatible surface 104. A sample chamber 116 containing a solution of the nucleic acid molecule 112 and tagged nucleotides may be provided over the lipid bilayer 102. The solution may be an aqueous solution containing electrolytes and buffered to an optimum ion concentration and maintained at an optimum pH to keep the nanopore 110 open. The device includes a pair of electrodes 118 (including a negative node 118a and a positive node 118b) coupled to a variable voltage source 120 for providing electrical stimulus (e.g., voltage bias) across the lipid bilayer and for sensing electrical characteristics of the lipid bilayer (e.g., resistance, capacitance, and ionic current flow). The surface of the positive electrode 118b is or forms a part of the lipid bilayer compatible surface 104. The conductive solid substrate 106 may be coupled to or forms a part of one of the electrodes 118. The device 100 may also include an electrical circuit 122 for controlling electrical stimulation and for processing the signal detected. In some embodiments, the variable voltage source 120 is included as a part of the electrical circuit 122. The electrical circuitry 122 may include amplifier, integrator, noise filter, feedback control logic, and/or various other components. The electrical circuitry 122 may be integrated electrical circuitry integrated within a silicon substrate 128 and may be further coupled to a computer processor 124 coupled to a memory 126.

The lipid bilayer compatible surface 104 may be formed from various materials that are suitable for ion transduction and gas formation to facilitate lipid bilayer formation. In some embodiments, conductive or semi-conductive hydrophilic materials may be used because they may allow better detection of a change in the lipid bilayer electrical characteristics. Example materials include Ag—AgCl, Au, Pt, or doped silicon or other semiconductor materials. In some cases, the electrode is not a sacrificial electrode.

The lipid bilayer incompatible surface 105 may be formed from various materials that are not suitable for lipid bilayer formation and they are typically hydrophobic. In some embodiments, non-conductive hydrophobic materials are preferred, since it electrically insulates the lipid bilayer regions in addition to separate the lipid bilayer regions from each other. Example lipid bilayer incompatible materials include for example silicon nitride (e.g., $Si_3N_4$) and Teflon.

In an example, the nanopore device 100 of FIG. 11 is a alpha hemolysin (aHL) nanopore device having a single alpha hemolysin (aHL) protein 108 embedded in a diphytanoylphosphatidylcholine (DPhPC) lipid bilayer 102 formed over a lipid bilayer compatible Pt surface 104 coated on an aluminum material 106. The lipid bilayer compatible Pt surface 104 is isolated by lipid bilayer incompatible silicon nitride surfaces 105, and the aluminum material 106 is electrically insulated by silicon nitride materials 107. The aluminum 106 is coupled to electrical circuitry 122 that is integrated in a silicon substrate 128. A silver-silver chloride electrode placed on-chip or extending down from a cover plate 128 contacts an aqueous solution containing nucleic acid molecules.

The aHL nanopore is an assembly of seven individual peptides. The entrance or vestibule of the aHL nanopore is approximately 26 Angstroms in diameter, which is wide enough to accommodate a portion of a dsDNA molecule. From the vestible, the aHL nanopore first widens and then narrows to a barrel having a diameter of approximately 15 Angstroms, which is wide enough to allow a single ssDNA molecule (or the released tag molecules) to pass through but not wide enough to allow a dsDNA molecule to pass through.

In addition to DPhPC, the lipid bilayer of the nanopore device may be assembled from various other suitable amphiphilic materials, selected based on various considerations, such as the type of nanopore used, the type of molecule being characterized, and various physical, chemical and/or electrical characteristics of the lipid bilayer formed, such as stability and permeability, resistance, and capacitance of the lipid bilayer formed. Example amphiphilic materials include various phospholipids such as palmitoyl-oleoyl-phosphatidyl-choline (POPC) and dioleoyl-phosphatidyl-methylester (DOPME), diphytanoylphosphatidylcholine (DPhPC) dipalmitoylphosphatidylcholine (DPPC), phosphatidylcholine, phosphatidylethanolamine, phosphatidylserine, phosphatidic acid, phosphatidylinositol, phosphatidylglycerol, and sphingomyelin.

In addition to the aHL nanopore shown above, the nanopore may be of various other types of nanopores. Examples include γ-hemolysin, leukocidin, melittin, and various other naturally occurring, modified natural, and synthetic nanopores. A suitable nanopore may be selected based on various characteristics of the analyte molecule such as the size of the analyte molecule in relation to the pore size of the nanopore. For example, the aHL nanopore that has a restrictive pore size of approximately 15 Angstroms.

High Array Densities

The array of nanopore detectors may have a high density of discrete sites. For example, a large number of sites per unit area (i.e., density) allows for the construction of smaller devices, which are portable, low-cost, or have other advantageous features. A large number of sites comprising a nanopore and a sensing circuit may allow for a large number of nucleic acid molecules to be sequenced at once. Such a system may increase the through-put and/or decrease the cost of sequencing a nucleic acid sample.

A nucleic acid sample may be sequenced using a sensor (or detector) having a substrate with a surface comprising discrete sites, each individual site having a nanopore, a polymerase and optionally at least one phosphatase enzyme attached to the nanopore and a sensing circuit adjacent to the nanopore. The system may further comprise a flow cell in fluid communication with the substrate, the flow cell adapted to deliver one or more reagents to said substrate.

The surface comprises any suitable density of discrete sites (e.g., a density suitable for sequencing a nucleic acid sample in a given amount of time or for a given cost). The surface may have a density of discrete sites greater than or equal to about 500 sites per 1 mm$^2$. In some embodiments, the surface has a density of discrete sites of about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 mm$^2$. In some cases, the surface has a density of discrete sites of at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 20000, at least 40000, at least 60000, at least 80000, at least 100000, or at least 500000 sites per 1 mm$^2$.

Current Measurement

A nanopore based sequencing chip may incorporate a large number of autonomously operating or individually addressable cells configured as an array. A nanopore device can include an array of individually addressable nanopores. Each individually addressable nanopore can include an individually addressable electrode. For example an array of one million cells can be constructed of 1000 rows of cells by 1000 columns of cells. This array can enable the parallel sequencing of nucleic acid molecules by measuring the conductance difference when tags released upon nucleotide incorporation events pass through the nanopore for example. Moreover this circuitry implementation allows the conductance characteristics of the pore-molecular complex to be determined which may be extremely valuable in distinguishing specific tags.

In some cases, current may be measured at an applied voltage. In order to accomplish this, a desired potential may be applied to the electrode, and the applied potential may be subsequently maintained throughout the measurement. In an implementation, an opamp integrator topology may be used for this purpose as described herein. The integrator maintains the voltage potential at the electrode by means of capacitive feedback. The integrator circuit may provide outstanding linearity, cell-to-cell matching, and offset characteristics. The opamp integrator typically requires a large size in order to achieve the required performance. A more compact integrator topology is described herein.

In some cases, a voltage potential "Vliquid" may be applied to the chamber which provides a common electrical potential (e.g., 350 mV) for all of the cells on the chip. The integrator circuit may initialize the electrode (which is electrically the top plate of the integrating capacitor) to a potential greater than the common liquid potential. For example, biasing at 450 mV may give a positive 100 mV potential between electrode and liquid. This positive voltage potential may cause a current to flow from the electrode to the liquid chamber contact. In this instance, the carriers are: (a) K+ ions which flow through the pore from the electrode (trans) side of the bi-layer to the liquid reservoir (cis) side of the bi-layer and (b) chlorine (Cl—) ions on the trans side which reacts with the silver electrode according to the following electro-chemical reaction: Ag+Cl—→AgCl+e−.

In some cases, K+ flows out of the enclosed cell (from trans to cis side of bi-layer) while Cl— is converted to silver chloride. The electrode side of the bilayer may become desalinated as a result of the current flow. In some cases, a silver/silver-chloride liquid spongy material or matrix may serve as a reservoir to supply Cl— ions in the reverse reaction which occur at the electrical chamber contact to complete the circuit.

In some cases, electrons ultimately flow onto the top side of the integrating capacitor which creates the electrical current that is measured. The electrochemical reaction converts silver to silver chloride and current will continue to flow only as long as there is available silver to be converted. The limited supply of silver leads to a current dependent electrode life in some cases. In some embodiments, electrode materials that are not depleted (e.g., platinum) are used.

Cell Circuitry

Figure 14A:
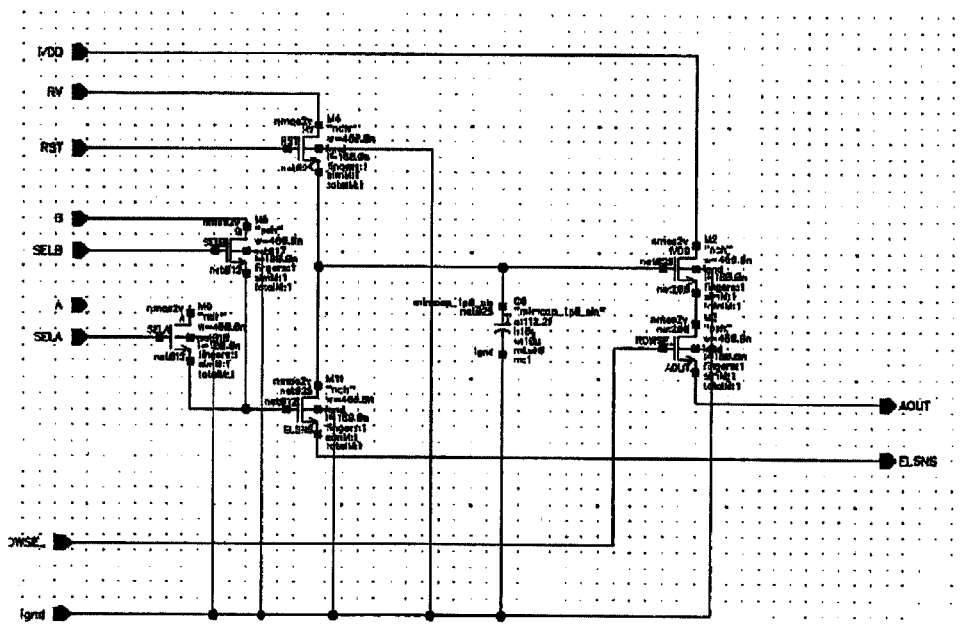
FIGS. 14A and 14B show examples of ultra compact circuits.
Figure 14B:
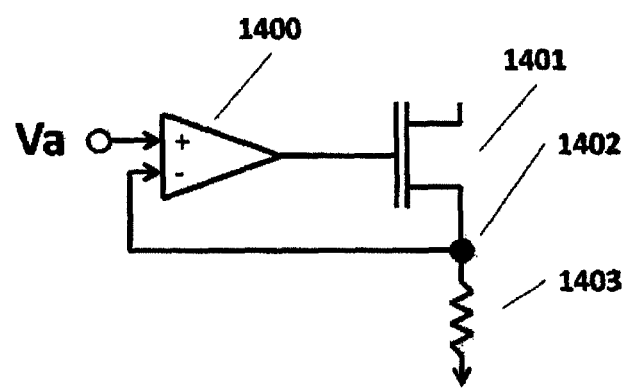

An example of cell circuitry is shown in FIG. 14B. An applied voltage Va is applied to an opamp 1400 ahead of a MOSFET current conveyor gate 1401. Also shown here are an electrode 1402 and the resistance of the nucleic acid and/or tag detected by the device 1403.

An applied voltage Va can drive the current conveyor gate 1401. The resulting voltage on the electrode sis then Va-Vt where Vt is the threshold voltage of the MOSFET. In some instances, this results in limited control of the actual voltage applied to the electrode as a MOSFET threshold voltage can vary considerably over process, voltage, temperature, and even between devices within a chip. This Vt variation can be greater at low current levels where sub-threshold leakage effects can come into play. Therefore, in order to provide better control of the applied voltage, an opamp can be used in a follower feedback configuration with the current conveyor device. This ensures that the voltage applied to the electrode is Va, independent of variation of the MOSFET threshold voltage.

Figure 13:
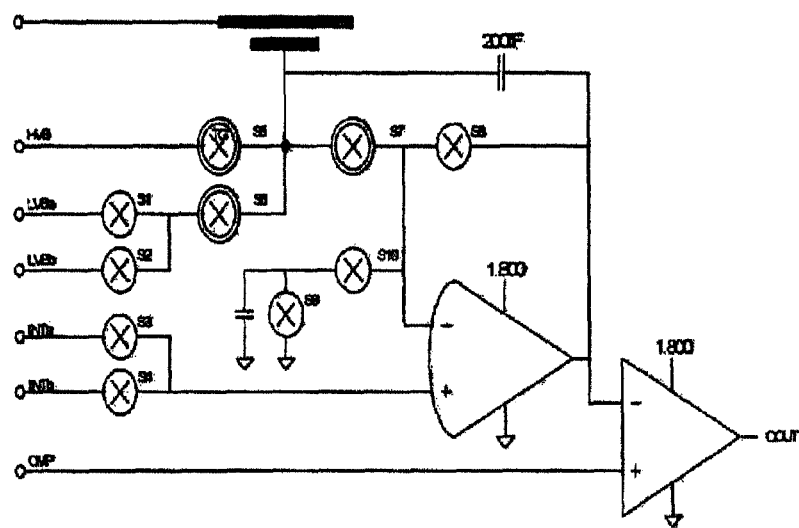
FIG. 13 shows an exemplary cell analog circuitry.
Figure 13:
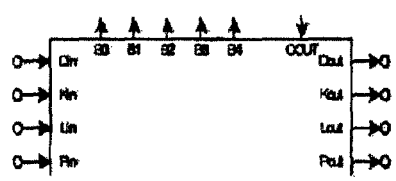

Another example of cell circuitry is shown in FIG. 13 and includes an integrator, comparator, and digital logic to shift in control bits and simultaneously shift out the state of the comparator output. The cell circuitry may be adapted for use with systems and methods provided herein. The B0 through B1 lines may come out of the shift register. The analog signals are shared by all cells within a bank while digital lines may be daisy-chained from cell to cell.

The cell digital logics comprises the 5 bit data shift register (DSR), 5 bit parallel load registers (PLR), control logic, and analog integrator circuit. Using the LIN signal, the control data shifted into the DSR is parallel loaded into the PLR. These 5 bits control digital "break-before-make" timing logic which controls the switches in the cell. In addition the digital logic has a set-reset (SR) latch to record the switching of the comparator output.

The architecture delivers a variable sample rate that is proportional to the individual cell current. A higher current may result in more samples per second than a lower current. The resolution of the current measurement is related to the current being measured. A small current may be measured with finer resolution than a large current, which may be a benefit over fixed resolution measurement systems. There is an analog input which allows the user to adjust sample rates by changing the voltage swing of the integrator. It may be possible to increase the sample rate in order to analyze biologically fast processes or to slow the sample rate (and thereby gain precision) in order to analyze biologically slow processes.

The output of the integrator is initialized to the voltage LVB (low voltage bias) and integrates up to the voltage CMP. A sample is generated every time the integrator output swings between these two levels. Thus the greater the current the faster the integrator output swings and therefore the faster the sample rate. Similarly if CMP voltage is reduced the output swing of the integrator needed to generate a new sample is reduced and therefore the sample rate is increased. Thus simply reducing the voltage difference between LVB and CMP provides a mechanism to increase the sample rate.

A nanopore based sequencing chip may incorporate a large number of autonomously operating or individually addressable cells configured as an array. For example an array of one million cells can be constructed of 1000 rows of cells by 1000 columns of cells. This array enables the parallel sequencing of nucleic acid molecules by measuring the conductance difference when tags released upon nucleotide incorporation events are detected by the nanopore for example. Moreover this circuitry implementation allows the conductance characteristics of the pore-molecular complex to be determined which may be valuable in distinguishing between tags.

The integrated nanopore/bilayer electronic cell structures may apply appropriate voltages in order to perform current measurements. For example, it may be necessary to both (a) control electrode voltage potential and (b) monitor electrode current simultaneously in order to perform correctly.

Moreover it may be necessary to control cells independently from one another. The independent control of a cell may be required in order to manage a large number of cells that may be in different physical states. Precise control of the piecewise linear voltage waveform stimulus applied to the electrode may be used to transition between the physical states of the cell.

In order to reduce the circuit size and complexity it may be sufficient to provide logic to apply two separate voltages. This allows two independent grouping of cells and corresponding state transition stimulus to be applied. The state transitions are stochastic in nature with a relatively low probability of occurrence. Thus it may be highly useful to be able to assert the appropriate control voltage and subsequently perform a measurement to determine if the desired state transition has occurred. For example the appropriate voltage may be applied to a cell and then the current measured to determine whether a bilayer has formed. The cells are divided into two groups: (a) those which have had a bilayer form and no longer need to have the voltage applied. These cells may have a 0V bias applied in order to effect the null operation (NOP)—that is stay in the same state and (b) those which do not have a bilayer formed. These cells will again have the bilayer formation electric voltage applied.

A substantial simplification and circuit size reduction may be achieved by constraining the allowable applied voltages to two and iteratively transitioning cells in batches between the physical states. For example, a reduction by at least a factor of 1.1, 2, 3, 4, 5, 6, 7, 8, 9, 10, 20, 30, 40, 50, or 100 may be achieved by constraining the allowable applied voltages.

Yet another implementation of the invention using a compact measurement circuit is shown in FIG. 14A. In some instances, the compact measurement circuit may be used to achieve the high array densities described herein. This circuit is also designed to apply a voltage to the electrode while simultaneously measuring low level currents.

The cell operates as an Ultra Compact Integrator (UCI) and the basic operation is described here. The cell is electrically connected to an electrochemically active electrode (e.g., AgCl) through the Electrod-Sense (ELSNS) connection. NMOS transistor M11 performs two independent functions: (1) operates as a source follower to apply a voltage to the ELSNS node given by (Vg1-Vt1) and (2) operates as a current conveyer to move electrons from the capacitor C1 to the ELSNS node (and vice versa).

In some instances, a controlled voltage potential may be applied to the ELSNS electrode and this may be varied simply by changing the voltage on the gate of the electrode source follower M11. Furthermore any current from M11 source pin is directly and accurately propagated to the M11 drain pin where it may accumulate on capacitor C0. Thus M11 and C0 act together as an ultra-compact integrator. This integrator may be used to determine the current sourced/sunk to/from the electrode by measuring the change in voltage integrated onto the capacitor according to the following: $I*t=C*V$, where I is current, t is time, C is capacitance and V is voltage change.

In some cases, the voltage change is measured at a fixed interval t (e.g., every 1 ms).

Transistor M2 may be configured as a source follower in order to buffer the capacitor voltage and provide a low impedance representation of the integrated voltage. This prevents charge sharing from changing the voltage on the capacitor.

Transistor M3 may be used as a row access device with the analog voltage output AOUT connected as a column shared with many other cells. Only a single row of the column connected AOUT signal is enabled so that a single cell's voltage is measured.

In an alternative implementation transistor M3 may be omitted by connecting transistor M2's drain to a row selectable "switched rail".

Transistor M4 may be used to reset the cell to a predetermined starting voltage from which the voltage is integrated. For example applying a high voltage (ex: to VDD=1.8V) to both RST and RV will pull the capacitor up to a pre-charged value of (VDD−Vt5). The exact starting value may vary both cell to cell (due to Vt variation of M4 and M2) as well as from measurement to measurement due to the reset switch thermal noise (sqrt(KTC) noise). As a result a correlated double sampling (CDS) technique is used to measure the integrator starting voltage and the ending voltage to determine the actual voltage change during the integration period.

Note also that the drain of transistor M4 may be connected to a controlled voltage RV (reset voltage). In normal operation this may be driven to VDD, however it may also be driven to a low voltage. If the "drain" of M4 is in fact driven to ground than the current flow may be reversed (i.e., current may flow from the electrode into the circuit through M1 and M4 and the notion of source and drain may be swapped). In some cases, when operating the circuit in this mode the negative voltage applied to the electrode (with respect to the liquid reference) is controlled by this RV voltage (assuming that Vg1 and Vg5 are at least a threshold greater than RV). Thus a ground voltage on RV may be used to apply a negative voltage to the electrode (for example to accomplish electro-poration or bi-layer formation).

An analog to digital converter (ADC, not shown) measures the AOUT voltage immediately after reset and again after the integration period (performs CDS measurement) in order to determine the current integrated during a fixed period of time. And ADC may be implemented per column or a separate transistor used for each column as an analog mux to share a single ADC between multiple columns. This column mux factor may be varied depending on the requirements for noise, accuracy, and throughput.

At any given time, each cell may be in one of four different physical states: (1) short-circuit to liquid (2) bi-layer formed (3) bi-layer+pore (4) bi-layer+pore+nucleic acid and/or tag molecules.

In some instances, a voltage is applied in order to move cells between states. The NOP operation is used to leave a cell in a particular desired state while other cells are stimulated with an applied potential to move from one state to another.

This may be accomplished by having two (or more) different voltages which may be applied to the gate voltage of the M1 source follower which is indirectly used to control the voltage applied to the electrode with respect to the liquid potential. Thus transistor M5 is used to apply voltage A while transistor M6 is used to apply voltage B. Thus together M5 and M6 operate as an analog mux with either SELA or SELB being driven high to select the voltage.

Since every cell can be in a possible different state and because SELA and SELB are complementary a memory element can be used in each cell to select between voltage A or B. This memory element can be a dynamic element (capacitor) that was refreshed on every cycle or a simple cheater-latch memory element (cross-coupled inverter).

Opamp Test Chip Structure

In some examples, a test chip includes an array of 264 sensors arranged in four separate groups (aka banks) of 66 sensor cells each. Each group is in turn divided into three "columns" with 22 sensors "cells" in each column. The "cell" name is apropos given that ideally a virtual cell consisting of a bi-lipid layer and inserted nanopore is formed above each of the 264 sensors in the array (although the device may operate successfully with only a fraction of the sensor cells so populated).

There is a single analog I/O pad which applies a voltage potential to the liquid contained within a conductive cylinder mounted to the surface of the die. This "liquid" potential is applied to the top side of the pore and is common to all cells in a detector array. The bottom side of the pore has an exposed electrode and each sensor cell may apply a distinct bottom side potential to its electrode. The current is then measured between the top liquid connection and each cell's electrode connection on the bottom side of the pore. The sensor cell measures the current traveling through the pore as modulated by the tag molecule passing within the pore.

Figure 12:
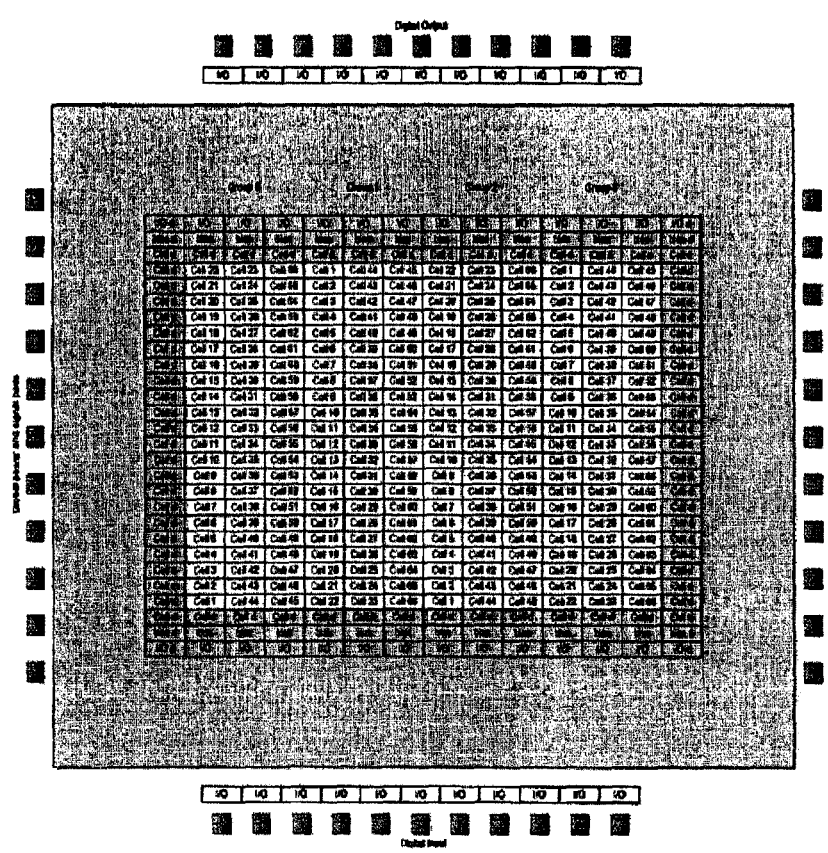
FIG. 12 shows an exemplary test chip cell array configuration.

In some cases, five bits control the mode of each sensor cell. With continued reference to FIG. 12, each of the 264 cells in the array may be controlled individually. Values are applied separately to a group of 66 cells. The mode of each of the 66 cells in a group is controlled by serially shifting in 330 (66*5 bits/cell) digital values into a DataShiftRegister (DSR). These values are shifted into the array using the KIN (clock), and DIN (dat in) pins with a separate pin pair for each group of 66 cells.

Thus 330 clocks are used to shift 330 bits into the DSR shift register. A second 330 bit Parallel Load Register (PLR) is parallel loaded from this shift register when the corresponding LIN<i> (Load Input) is asserted high. At the same time as the PLR is parallel loaded the status value of the cell is loaded into the DSR.

A complete operation may consist of 330 clocks to shift in 330 data bits into the DSR, a single clock cycle with LIN signal asserted high, followed by 330 clock cycles to read the captured status data shifted out of the DSR. The operation is pipelined so that a new 330 bits may be shifted into the DSR simultaneously while the 330 bits are being read out of the array. Thus at 50 MHz clock frequency the cycle time for a read is 331/50 MHz=6.62 us.

Tagged Nucleotides

In some cases a tagged nucleotide comprises a tag capable of being cleaved in a nucleotide polymerization event and detected with the aid of a nanopore. The tag may be attached to the 5'-phosphate of the nucleotide. In some instances, the tag is not a fluorophore. The tag may be detectable by its charge, shape, size, or any combination thereof. Exemplary tags include various polymers. Each type of nucleotide (i.e., A, C, G, T) generally comprises a unique tag.

Figure 6:
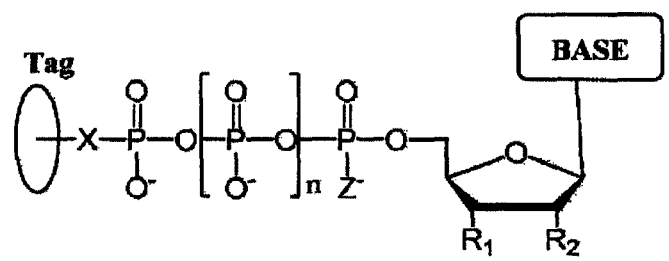
FIG. 6 shows an example of a tag molecule attached to the phosphate of a nucleotide.

Tags may be located on any suitable position on the nucleotide. FIG. 6 provides an example of a tagged nucleotide. Here, $R_1$ is generally OH and $R_2$ is H (i.e., for DNA) or OH (i.e., for RNA), although other modifications are acceptable. In FIG. 6, X is any suitable linker. In some cases, the linker is cleavable. Examples of linkers include without limitation, O, NH, S or $CH_2$. Examples of suitable chemical groups for the position Z include O, S, or $BH_3$. The base is any base suitable for incorporation into a nucleic acid including adenine, guanine, cytosine, thymine, uracil, or a derivative thereof. Universal bases are also acceptable in some cases.

The number of phosphates (n) is any suitable integer value (e.g., a number of phosphates such that the nucleotide may be incorporated into a nucleic acid molecule). In some instances, all types of tagged nucleotides have the same number of phosphates, but this is not required. In some applications, there is a different tag for each type of nucleotide and the number of phosphates is not necessarily used to distinguish the various tags. However, in some cases more than one type of nucleotide (e.g., A, C, T, G or U) have the same tag molecule and the ability to distinguish one nucleotide from another is determined at least in part by the number of phosphates (with various types of nucleotides having a different value for n). In various embodiments, the value for n is 1, 2, 3, 4, 5, 6, 7, 8, 9, 10, or greater.

Suitable tags are described below. In some instances, the tag has a charge which is reverse in sign relative to the charge on the rest of the compound. When the tag is attached, the charge on the overall compound may be neutral. Release of the tag may result in two molecules, a charged tag and a charged nucleotide. The charged tag passes through a nanopore and is detected in some cases.

Figure 7:
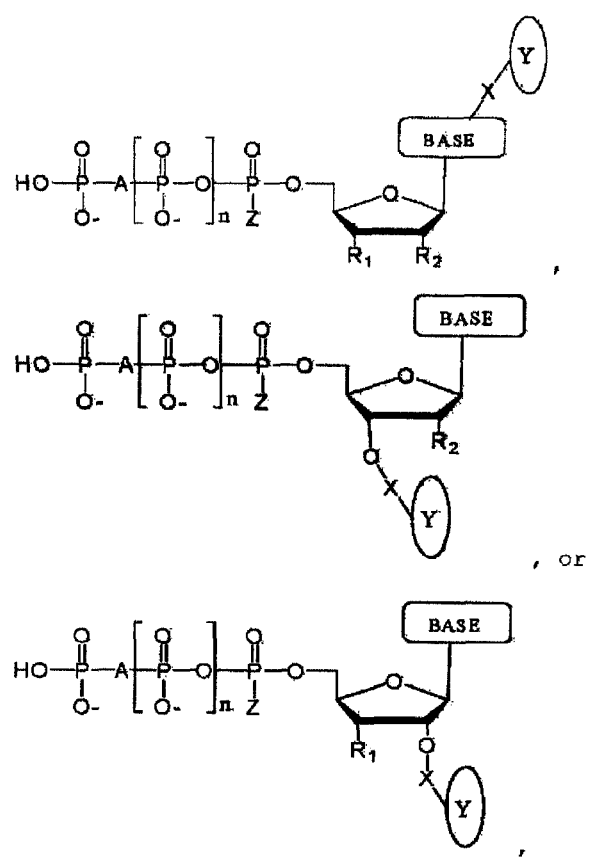
FIG. 7 shows examples of alternate tag locations.

More examples of suitable tagged nucleotides are shown in FIG. 7. The tag may be attached to the sugar molecule, the base molecule, or any combination thereof. With reference to FIG. 7, Y is a tag and X is a cleavable linker. Furthermore, $R_1$, if present, is generally OH, —$OCH_2N_3$ or —O-2-nitrobenzyl, and $R_2$, if present, is generally H. Also, Z is generally O, S or $BH_3$, and n is any integer including 1, 2, 3, or 4. In some cases, the A is O, S, CH2, CHF, CFF, or NH.

With continued reference to FIG. 7, the type of base on each dNPP analogue is generally different from the type of base on each of the other three dNPP analogues, and the type of tag on each dNPP analogue is generally different from the type of tag on each of the other three dNPP analogues. Suitable bases include, but are not limited to adenine, guanine, cytosine, uracil or thymine, or a derivative of each thereof. In some cases, the base is one of 7-deazaguanine, 7-deazaadenine or 5-methylcytosine.

In cases where $R_1$ is —O—$CH_2N_3$, the methods optionally further comprise treating the incorporated dNPP analogue so as to remove the —$CH_2N_3$ and result in an OH group attached to the 3' position thereby permitting incorporation of a further dNPP analogue.

In cases where $R_1$ is —O-2-nitrobenzyl, the methods optionally further comprise treating the incorporated nucleotide analogue so as to remove the -2-nitrobenzyl and result in an OH group attached to the 3' position thereby permitting incorporation of a further dNPP analogue.

Exemplary Tags

A tag may be any chemical group or molecule that is capable of being detected in a nanopore. In some cases, a tag comprises one or more of ethylene glycol, an amino acid, a carbohydrate, a peptide, a dye, a chemilluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

It is also contemplated that the tag further comprises appropriate number of lysines or ar balance the number of phosphates in the compound.

In some cases, the tag is a polymer. Polyethylene glycol (PEG) is an example of a polymer and has the structure as follows:

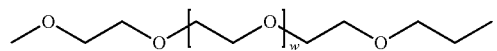

Any number of ethylene glycol units (W) may be used. In some instances, W is an integer between 0 and 100. In some cases, the number of ethylene glycol units is different for each type of nucleotide. In an embodiment, the four types of nucleotides comprise tags having 16, 20, 24 or 36 ethylene glycol units. In some cases, the tag further comprises an additional identifiable moiety, such as a coumarin based dye.

In some cases, a tag comprises multiple PEG chains. In an example, a tag has the structure as follows:

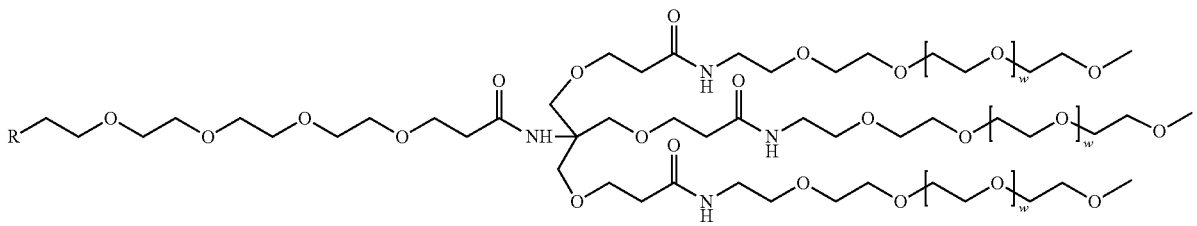

wherein R is $NH_2$, OH, COOH, CHO, SH, or $N_3$, and W is an integer from 0 to 100.

Figure 8:
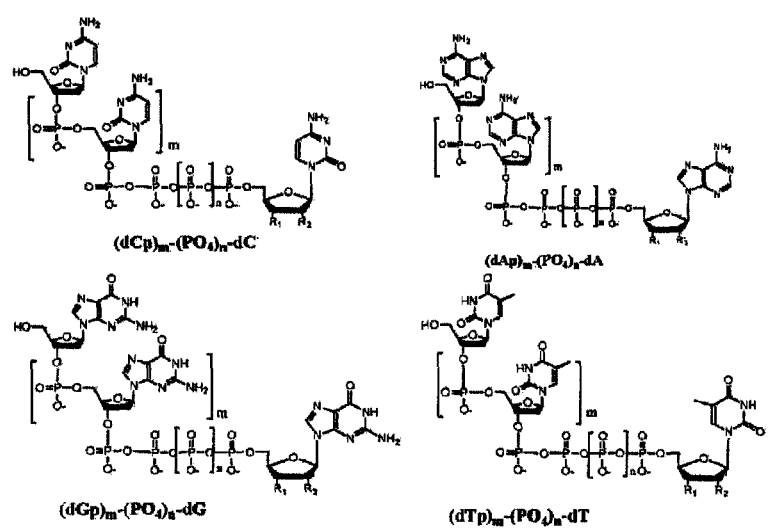
FIG. 8 shows an example of tagged nucleotides.

In some instances a tag is chosen from the molecules (dCp)m, (dGp)m, (dAp)m, and (dTp)m. FIG. 8 shows these molecules attached to a nucleotide. Here, 'm' is, independently, an integer from 0 to 100, and wherein when m is 0 the terminal phosphate of the dNPP is bonded directly to the 3' O atom of the nucleoside shown on the left hand side of the structure. In some cases, the value of n is different for each type of base.

In some instances, a tag is a hydrocarbyl, substituted or unsubstituted, such as an alkyl, alkenyl, alkynyl, and having a mass of 3000 daltons or less.

As used herein, the term "alkyl" includes both branched and straight-chain saturated aliphatic hydrocarbon groups having the specified number of carbon atoms and may be unsubstituted or substituted. As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom.

Non-limiting examples of tagged nucleotides include compounds having the structure:

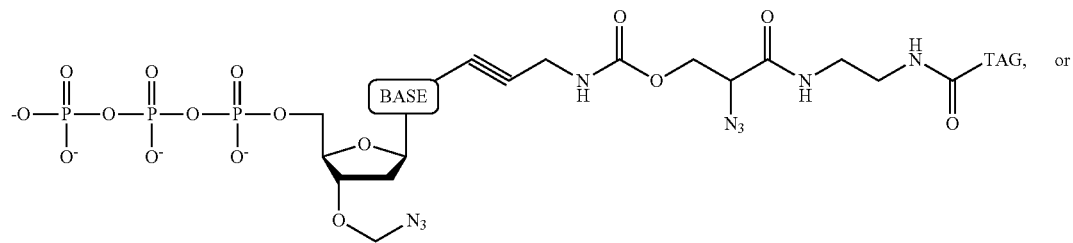

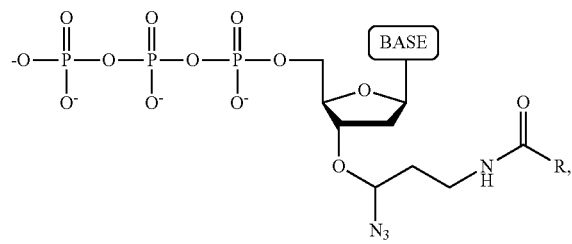

wherein 'R' is a substituted or unsubstituted hydrocarbyl, up to 3000 daltons, and wherein the base is adenine, guanine, cytosine, thymine, uracil, a 7-deazapurine or a 5-methylpyrimidine.

Further non-limiting examples of tagged nucleotides include compounds having the structure:

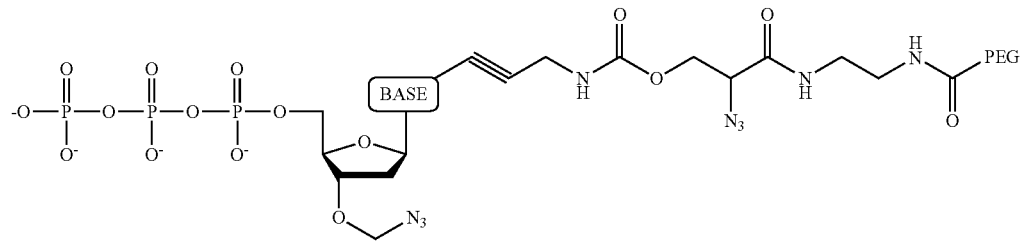

wherein the base is adenine, guanine, cytosine, thymine, uracil, a 7-deazapurine or a 5-methylpyrimidine.

Further non-limiting examples of tagged nucleotides include compounds having the structure:

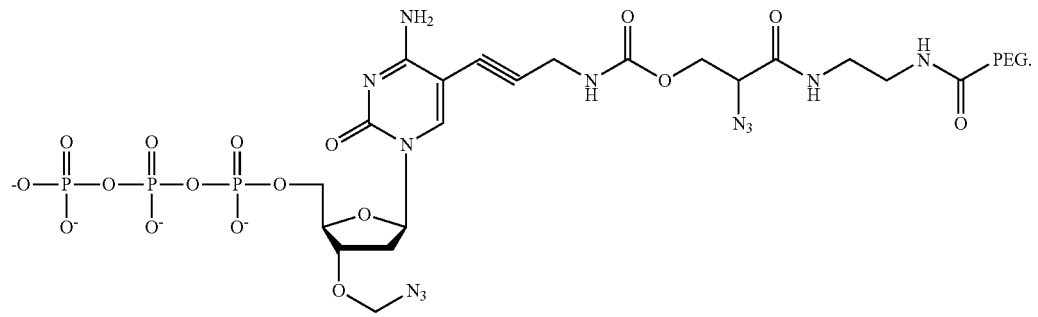

Further non limiting examples of tagged nucleotides include compounds having the structure:

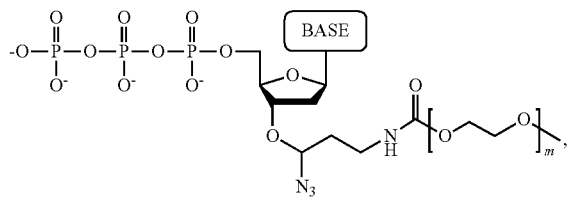

wherein m is an integer from 1-50, and wherein the base is adenine, guanine, cytosine, thymine, uracil, a 7-deazapurine or a 5-methylpyrimidine.

Methods for Attaching Tags

Any suitable method for attaching the tags may be used. In an example, tags may be attached to the terminal phosphate by (a) contacting a nucleotide triphosphate with dicyclohexylcarbodiimide/dimethylformamide under conditions permitting production of a cyclic trimetaphosphate; (b) contacting the product resulting from step a) with a nucleophile so as to form an —OH or —NH$_2$ functionalized compound; and (c) reacting the product of step b) with a tag having a —COR group attached thereto under conditions permitting the tag to bond indirectly to a terminal phosphate thereby forming the nucleotide triphosphate analogue, In some cases, the nucleophile is H$_2$N—R—OH, H$_2$N—R—NH$_2$, R'S—R—OH, R'S—R—NH$_2$, or

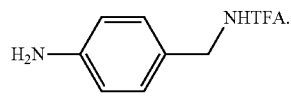

In some instances, the method comprises, in step b), contacting the product resulting from step a) with a compound having the structure:

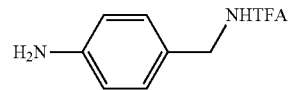

and subsequently or concurrently contacting the product with NH$_4$OH so as to form a compound having the structure:

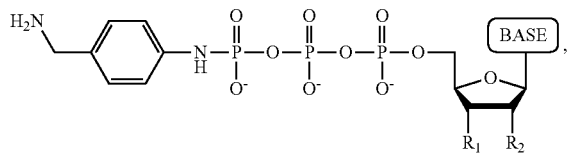

The product of step b) may then be reacted with a tag having a —COR group attached thereto under conditions permitting the tag to bond indirectly to a terminal phosphate thereby forming the nucleotide triphosphate analogue having the structure:

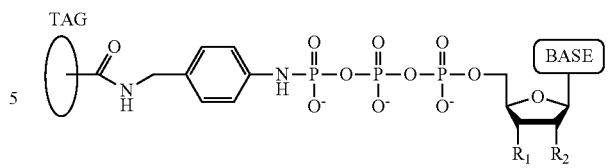

wherein R$_1$ is OH, wherein R$_2$ is H or OH, wherein the base is adenine, guanine, cytosine, thymine, uracil, a 7-deazapurine or a 5-methylpyrimidine.

Release of Tags

A tag may be released in any manner. In some cases, the tag is attached to polyphosphate (e.g., FIG. 6) and incorporation of the nucleotide into a nucleic acid molecule results in release of a polyphosphate having the tag attached thereto. The incorporation may be catalyzed by at least one polymerase, optionally attached to the nanopore. In some instances, at least one phosphatase enzyme is also attached to the pore. The phosphatase enzyme may cleave the tag from the polyphosphate to release the tag. In some cases, the phosphatase enzymes are positioned such that pyrophosphate produced by the polymerase in a polymerase reaction interacts with the phosphatase enzymes before entering the pore.

In some cases, the tag is not attached to polyphosphate (see, e.g., FIG. 7). In these cases, the tag is attached by a cleavable linker (X). Methods for production of cleavably capped and/or cleavably linked nucleotide analogues are disclosed in U.S. Pat. No. 6,664,079, which is entirely incorporated herein by reference.

The linker may be any suitable linker and cleaved in any suitable manner. The linkers may be photocleavable. In an embodiment UV light is used to photochemically cleave the photochemically cleavable linkers and moieties. In an embodiment, the photocleavable linker is a 2-nitrobenzyl moiety.

The —CH$_2$N$_3$ group may be treated with TCEP (tris(2-carboxyethyl)phosphine) so as to remove it from the 3'O atom of a dNPP analogue, or rNPP analogue, thereby creating a 3' OH group.

Detection of Tags

Tags may flow through a nanopore after they are released from the nucleotide. In some instances, a voltage is applied to pull the tags through the nanopore. At least about 85%, at least 90%, at least 95%, at least 99%, at least 99.9 or at least 99.99% of the released tags may translocate through the nanopore.

In some instances of the method, a polymerase draws from a pool of tagged nucleotides comprising a plurality of different bases (e.g., A, C, G, T, and/or U). It is also possible to iteratively contact the polymerase with the various types of tagged bases. In this case, it may not be necessary that each type of nucleotide have a unique base, but the cycling between different base types adds cost and complexity to the process in some cases, nevertheless this embodiment is encompassed in the present invention.

Figure 9:
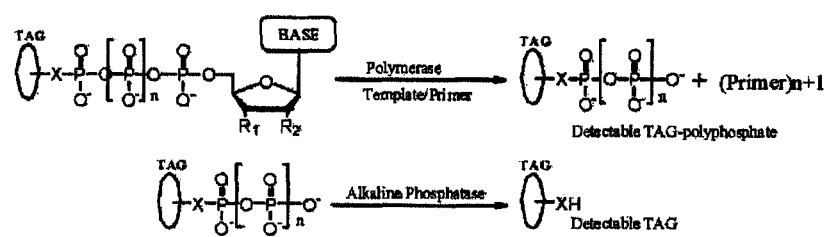
FIG. 9 shows detectable TAG-polyphosphate and detectable TAG.

FIG. 9 shows that incorporation of the tagged nucleotide into a nucleic acid molecule (e.g., using a polymerase to extend a primer base paired to a template) releases a detectable TAG-polyphosphate. In some cases, the TAG-polyphosphate is detected as it passes through the nanopore. It is even possible to distinguish the nucleotide based on the number of phosphates comprising the polyphosphate (e.g., even when the TAGs are identical). Nevertheless, each type of nucleotide generally has a unique tag.

With reference to FIG. 9, the TAG-polyphosphate compound may be treated with phosphatase (e.g., alkaline phosphatase) before passing the tag through a nanopore and measuring the ionic current.

The tag may be detected in the nanopore (at least in part) because of its charge. In some instances, the tag compound is an alternatively charged compound which has a first net charge and, after a chemical, physical or biological reaction, a different second net charge. In some instance, the magnitude of the charge on the tag is the same as the magnitude of the charge on the rest of the compound. In an embodiment, the tag has a positive charge and removal of the tag changes the charge of the compound.

In some cases, as the tag passes through the nanopore, it may generate an electronic change. In some cases the electronic change is a change in current amplitude, a change in conductance of the nanopore, or any combination thereof.

The nanopore may be biological or synthetic. It is also contemplated that the pore is proteinaceous, for example wherein the pore is an alpha hemolysin protein. An example of a synthetic nanopore is a solid-state pore or graphene.

In some cases, polymerase enzymes and/or phosphatase enzymes are attached to the nanopore. Fusion proteins or disulfide crosslinks are example of methods for attaching to a proteinaceous nanopore. In the case of a solid state nanopore, the attachment to the surface near the nanopore may be via biotin-streptavidin linkages. In an example the DNA polymerase is attached to a solid surface via gold surface modified with an alkanethiol self-assembled monolayer functionalized with amino groups, wherein the amino groups are modified to NHS esters for attachment to amino groups on the DNA polymerase.

An aspect of the present disclosure provides a method for sequencing a nucleic acid molecule. In some embodiments, said computer processor is in a workstation that is in proximity to said chip. In some cases, the tag passes through the nanopore. In some embodiments, the tag passes adjacent to the nanopore. In some embodiments, the rate of polymerization is less than the rate of tag passage through or adjacent to the nanopore. In some cases, said electrode is adapted to supply an electrical stimulus across said membrane. The chip can have features and properties disclosed in, for example, U.S. Pat. No. 8,324,914, which is entirely incorporated herein by reference.

In some embodiments, said membrane has a capacitance greater than about 5 fF/$\mu$m$^2$ as measured across said membrane. In some cases, said membrane has a resistance greater than or equal to about 500 M$\Omega$ as measured across said membrane. In some embodiments, said membrane has a resistance less than or equal to about 1 G$\Omega$ across said membrane. In some cases, said resistance is measured with the aid of opposing electrodes disposed adjacent to said membrane. In some embodiments, said resistance is measured with the aid of opposing electrodes disposed adjacent to said membrane.

In some cases, each individually addressable nanopore is adapted to regulate molecular flow. In some cases, said individually addressable nanopore is adapted to detect said tag upon molecular flow of said tag thereof through or adjacent to said nanopore. In some cases, said electrode is individually addressable. In some cases, said electrode is coupled to an integrated circuit that processes a signal detected with the aid of said electrode.

In some cases, said integrated circuit comprises a logic controller. In some cases, said electrode is part of an integrated circuit that processes a signal detected with the aid of said electrode.

In some cases, said membrane is a lipid bilayer. In some cases, the membrane is a diphytanoylphosphatidylcholine (DPhPC) lipid bilayer. In some cases, the nanopore is an alpha-hemolysin nanopore. In some cases, said membrane exhibits (i) a capacitance greater than about 5 fF/$\mu$m$^2$ or a resistance less than or equal to about 1 G$\Omega$ across said membrane, or (ii) a capacitance greater than about 5 fF/$\mu$m$^2$ and a resistance less than or equal to about 1 G$\Omega$ across said membrane. In some cases, said membrane is disposed adjacent to a membrane compatible surface. In some cases, said plurality of individually addressable nanopores are at a density of at least about 500, 600, 700, 800, 900, 1000, 10,000, 100,000, or 1,000,000 individually addressable nanopores per mm$^2$.

In some cases, each type of nucleotide comprises a unique tag. In some cases, the tag is initially attached to the 5'-phosphate of the individual nucleotide. In some cases, the primer is annealed to a specific position on the single stranded nucleic acid template.

Another aspect of the present disclosure provides a method for nucleic acid sequencing, comprising detecting, with the aid of a nanopore, the incorporation of a nucleotide into a nucleic acid molecule, wherein the nucleic acid molecule does not pass through the nanopore. In some cases, tags associated with the nucleotides are released upon incorporation, and wherein subsequent to being released the tags pass through the nanopore.

In some cases, nucleotide incorporation events are detected with an accuracy of at least 4$\sigma$. In some cases, nucleotide incorporation events are detected with an accuracy of at least 5$\sigma$. In some cases, nucleotide incorporation events are detected with an accuracy of at least 6$\sigma$.

Another aspect of the present disclosure provides a method for nucleic acid sequencing, comprising detecting a byproduct of an individual nucleotide incorporation event with the aid of a nanopore. In some cases, the nucleotide is not directly detected by said nanopore. In some cases, the byproduct of the nucleotide incorporation event is a tag molecule that is released upon said individual nucleotide incorporation event. In some cases, the tag molecule passes through the nanopore. A method for sequencing a nucleic acid molecule, comprising distinguishing between individual nucleotide incorporation events with an accuracy of greater than 4$\sigma$. In some cases, the accuracy is greater than 5$\sigma$. In some cases, the accuracy is greater than 6$\sigma$. In some cases, the nucleotide incorporation events are detected with aid of a nanopore. In some cases, said nanopore is an individually addressable nanopore. In some cases, said nanopore is in a membrane that is disposed adjacent to an electrode. In some cases, said electrode is in an array of electrodes at a density of at least about 500 electrodes per mm$^2$. In some cases, said individual nucleotide incorporation events comprise the incorporation of a nucleotide in a nucleic acid strand that is complementary to said nucleic acid molecule, wherein said nucleotide comprises a tag that is released upon the incorporation of said nucleotide in said nucleic acid strand, and wherein said tag passes through or adjacent to said nanopore subsequent to being released from said nucleotide. In some cases, said tag is detected with the aid of said electrode subsequent to being released from said nucleotide.

Another aspect of the present disclosure provides a method for nucleic acid sequencing, the method comprising: (a) providing an array of nanopores, wherein an individual nanopore in said array is coupled to a nucleic acid polymerase; and (b) polymerizing tagged nucleotides with the polymerase, wherein an individual tagged nucleotide comprises a tag, and wherein the tag is released and detected with the aid of the nanopore. In some cases, the tag passes adjacent to the nanopore subsequent to being released. In some cases, the tag passes through the nanopore subsequent to being released. In some cases, the rate of polymerization is less than the rate of tag passage through the nanopore. In some cases, the nanopores are individually addressable.

Another aspect of the present disclosure provides a tagged nucleotide, wherein the nucleotide comprises a tag capable of being cleaved in a nucleotide polymerization event and detected with the aid of a nanopore in a chip comprising an array of nanopores. In some cases, the tag is attached to the 5'-phosphate of the nucleotide. In some cases, the tag is not a fluorophore. In some cases, the tag is detectable by its charge, shape, size, or any combination thereof.

Another aspect of the present disclosure provides a system for sequencing a nucleic acid molecule. In some cases, said electrode is adapted to supply an electrical stimulus across said membrane. In some cases, said membrane has a capacitance greater than about 5 fF/µm$^2$ as measured across said membrane. In some cases, said membrane has a resistance greater than or equal to about 500 MΩ as measured across said membrane. In some cases, said membrane has a resistance less than or equal to about 1 GΩ across said membrane. In some cases, said resistance is as measured by opposing electrodes disposed adjacent to said membrane. In some cases, each individually addressable nanopore is adapted to regulate molecular flow. In some cases, each individually addressable nanopore is adapted to regulate molecular flow with the aid of an electrical stimulus applied to said nanopore. In some cases, said computer processor is in a workstation that is in proximity to said chip. In some cases, said computer processer is comprised in said chip. In some cases, said individually addressable nanopore is adapted to detect said tag upon molecular flow of said tag thereof through or adjacent to said nanopore. In some cases, said electrode is individually addressable. In some cases, said electrode is coupled to an integrated circuit that processes a signal detected with the aid of said electrode. In some cases, said integrated circuit comprises a logic controller. In some cases, said electrode is part of an integrated circuit that processes a signal detected with the aid of said electrode.

In some cases, said membrane is a lipid bilayer. In some cases, the nanopore is an alpha-hemolysin nanopore. In some cases, the membrane is a diphytanoylphosphatidylcholine (DPhPC) lipid bilayer. In some cases, said membrane is disposed adjacent to a membrane compatible surface. In some cases, said plurality of individually addressable nanopores are at a density of at least about 500 individually addressable nanopores per mm$^2$. In some cases, said density is at least about 1000 individually addressable nanopores per mm$^2$.

Another aspect of the present disclosure provides a method for sequencing a nucleic acid molecule, the method comprising providing an array of individually addressable sites at a density of at least about 500 sites per mm$^2$, each site having a nanopore attached to a nucleic acid polymerase, and, at a given site of the array, polymerizing tagged nucleotides with a polymerase, wherein upon polymerization a tag is released and detected by a nanopore at the given site. In some cases, the method further comprises directing generating, with the aid of a processor, a nucleic acid sequence of the nucleic acid molecule based upon the detected tags. In some cases, the tag passes through the nanopore. In some cases, the tag passes adjacent to the nanopore. In some cases, the rate of polymerization is less than the rate of tag passage through or adjacent to the nanopore.

Methods and Systems for Tan Sequencing

Another aspect of the present disclosure provides a conductance measurement system comprising a first and a second compartment with a first and a second electrolyte solution separated by a physical barrier, which barrier has at least one pore with diameter on nanometer scale. The system can further include a means for applying an electric field across the barrier, a means for measuring change in the electric field, at least one polymerase attached to the pore, and one or more phosphatase enzymes attached to the pore.

In an embodiment of the system, the pore has a diameter of from about 1 to 10 nm. In another embodiment, the polymerase and the phosphatase enzymes are covalently attached to the pore. In a further embodiment, more phosphatase enzymes than polymerases are attached to the pore.

In one embodiment of the system, the phosphatase enzymes are positioned such that polyphosphate produced by the polymerase in a polymerase reaction interacts with the phosphatase enzymes before entering the pore.

In another embodiment, the rate of interaction between the phosphatase enzymes and the polyphosphate is faster than, or equal to, the rate of the polymerase producing the polyphosphate.

In another embodiment, each of the first and the second compartments has an electrical charge. It is also contemplated that the interior of the pore has a negative charge.

In yet another embodiment of the system, the pore is biological or synthetic. It is also contemplated that the pore is proteinaceous, for example wherein the pore is an alpha hemolysin protein.

In a further embodiment of the system, the pore is a solid-state pore or graphene.

It is also contemplated that the system comprising an array of pores each having substantially identical features, or an array of pores of different diameters, or an array of pores wherein different electrical fields are applied across the barrier.

Figure 46:
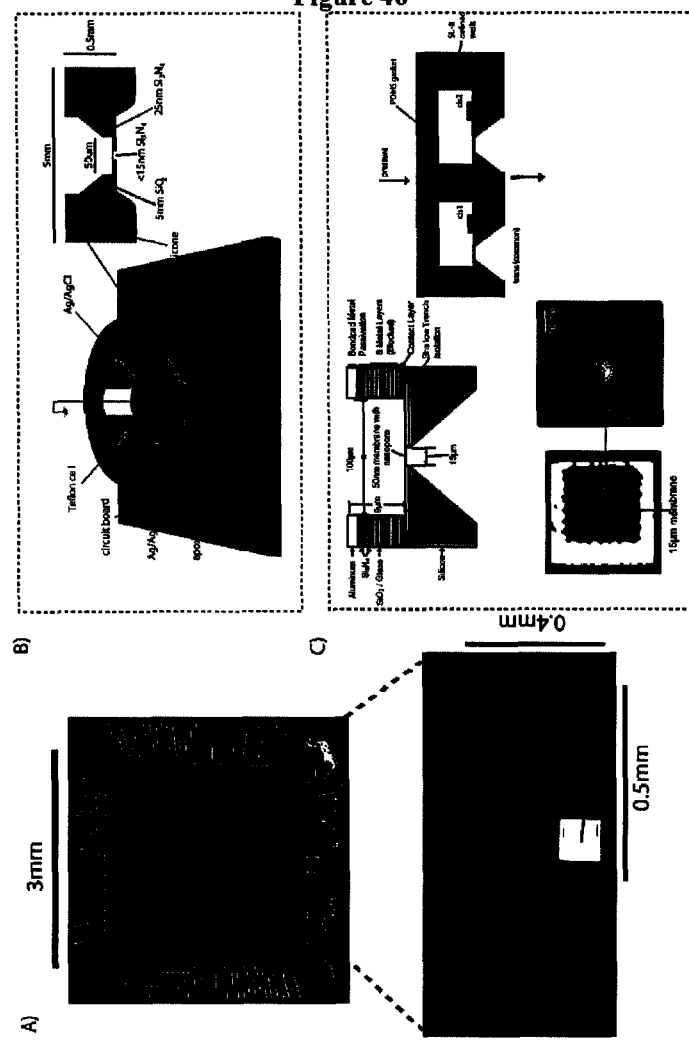
FIG. 46 shows CMOS-integrated nanopore measurement platform: (A) a micrograph of the eight-channel CMOS preamplifier chip with an image of one amplifier channel with the integrated cis-side electrode; (B) diagram showing the two-chip integration with a solid-state nanopore; (C) diagram showing the cross section of the chip and how the nanopore is etched directly into the chip in the one-chip implementation; packaging occurs with an independent well on the cis side; and a TEM image of a 3.5-nm-diameter nanopore.

It is further contemplated that the conductance measurement system is integrated with CMOS electronics, or that the pore or array of pores is integrated directly into a CMOS die as shown in FIG. 46.

A compound having the structure:

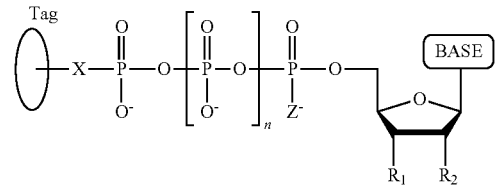

wherein the tag comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or $BH_3$, wherein the base is adenine, guanine, cytosine, thymine, uracil, or a derivative of one of these bases, wherein n is 1, 2, 3, or 4, and wherein the tag has a charge which is reverse in sign relative to the charge on the rest of the compound.

In one embodiment of the compound, the magnitude of the charge on the tag is the same as the magnitude of the charge on the remainder of the compound.

In another embodiment of the compound, the tag comprising multiple ethylene glycol units, perferably, 16, 20, 24, or 36 ethylene glycol units.

In a further embodiment of the compound, the tag further comprises an additional identifiable moiety, such as a coumarin based dye.

In one embodiment, the tag has a positive charge. In another embodiment, oval of the tag changes the charge of the compound.

It is also contemplated that the tag further comprises appropriate number of lysines or arginines to balance the number of phosphates in the compound.

A composition comprising four different types of a compound having the structure:

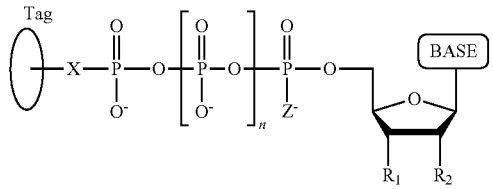

wherein the tag comprises one or more of ethylene glycol, an amino acid, a carbohydrate, a peptide, a dye, a chemilluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an allcynyl group, an azido group, or a combination thereof, wherein $R_1$ is OH, wherein $R_2$ is H or OH, wherein X is O, NH, S, or $CH_2$, wherein Z is O, S, or $BH_3$, wherein n is 1, 2, 3, or 4, wherein the tag has a charge which is reverse in sign relative to the charge on the rest of the compound, wherein the base of a first type of compound is adenine or a derivative thereof, the base of a second type of compound is guanine or a derivative thereof, the base of a third type of compound is cytosine or a derivative thereof, and the base of a fourth type of compound is thymine or a derivative thereof or uracil or a derivative thereof, and wherein the tag on each type of compound is different from the tag on each of the other three types of compound While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

A method for nucleic acid sequencing, the method comprising providing an array of individually addressable sites, each site having a nanopore attached to a nucleic acid polymerase, and, at a given site of said array, polymerizing tagged nucleotides with a polymerase, wherein a tag is released and detected by a nanopore at said given site.

In one embodiment, the tags passes through the nanopore. In another embodiment, the rate of polymerization is slower than the rate of tag passage through the nanopore.

A method for nucleic acid sequencing, the method comprising: (a) polymerizing tagged nucleotides at a first rate, wherein a tag associated with an individual nucleotide is released upon polymerization; and (b) detecting the released tag by passing it through a nanopore at a second rate, where the second rate is faster than or equal to the Lust rate.

In one embodiment, each type of nucleotide comprises a unique tag. In another embodiment, the tag is initially attached to the 5'-phosphate of the individual nucleotide.

A method for nucleic acid sequencing, the method comprising: (a) polymerizing tagged nucleotides, wherein a tag associated with an individual nucleotide is released upon polymerization; and (b) detecting the released tag with the aid of a nanopore.

In one embodiment, the method further comprises directing the tag released from an individual nucleotide through the nanopore. In another embodiment, each type of nucleotide comprises a unique tag. In a further embodiment, the tag is initially attached to the 5'-phosphate of the individual nucleotide.

A method for nucleic acid sequencing, comprising detecting, with the aid of a nanopore, the incorporation of a nucleotide into a nucleic acid molecule, wherein said nucleic acid molecule does not pass through the nanopore.

In one embodiment, tags associated with the nucleotides are released upon incorporation and the tags pass through the nanopore. In another embodiment, nucleotide incorporation events are detected with an accuracy of at least $4\sigma$.

A method for nucleic acid sequencing, comprising detecting a byproduct of an individual nucleotide incorporation event with the aid of a nanopore.

In one embodiment, the nucleotide is not detected directly. In another embodiment, the byproduct of the nucleotide incorporation event is a released tag molecule. In a further embodiment, the tag molecule passes through the nanopore.

A method for nucleic acid sequencing, comprising distinguishing between individual nucleotide incorporation events with an accuracy of greater than $4\sigma$, $5\sigma$, or $6\sigma$.

In one embodiment, the nucleotide incorporation events are detected with aid of a nanopore. In another embodiment, tags associated with the nucleotides are released upon incorporation and the tags pass through the nanopore.

A method for nucleic acid sequencing, the method comprising providing an array of nanopores attached to a nucleic acid polymerase and polymerizing tagged nucleotides with the polymerase, wherein the tag is released and detected by the nanopore.

In one embodiment, the tag passes through the nanopore. In another embodiment, the rate of polymerization is slower than the rate of tag passage through the nanopore.

A tagged nucleotide, wherein the nucleotide comprises a tag capable of being cleaved in a nucleotide polymerization event and detected with the aid of a nanopore.

In one embodiment, the tag is attached to the 5'-phosphate of the nucleotide. In another embodiment, the tag is not a fluorophore. In a further embodiment, the tag is detectable by its charge, shape, size, or any combination thereof.

A method for determining the identity of a compound comprising: (a) contacting the compound with a conductance measurement system comprising: (i) a first and a second compartment with a first and a second electrolyte solution separated by a physical barrier, which barrier has at least one pore with diameter on nanometer scale; (ii) a means for applying an electric field across the barrier, (iii) a means for measuring change in the electric field; (b) recording the change in the electric field when the compound translocates through the pore wherein the change in the electric field is the result of interaction between the compound, the electrolyte, and the pore, and is indicative of the size, charge, and composition of the compound, thereby allowing correlation between the change and predetermined values to determine the identity of the compound.

In one embodiment, the method further comprising a step of treating the compound with a phosphatase enzyme before step (a).

A method for determining whether a compound is a tag or a precursor of the tag comprising: (a) contacting the compound with a conductance measurement system comprising: (i) a first and a second compartment with a first and a second electrolyte solution separated by a physical barrier, which barrier has at least one pore with diameter on nanometer scale; (ii) a means for applying an electric field across the bather; (iii) a means for measuring change in the electric field; recording the change in the electric field when the compound translocates through the pore; and comparing the change in the electric field with pre-determined values corresponding to the tag and the precursor of the tag, thereby determining whether the compound is the tag or the precursor thereof.

In one embodiment, the method further comprising a step of adjusting current bias of the electric field in step (a).

A method for determining the nucleotide sequence of a single-stranded DNA, which method comprising:

(a) contacting the single-stranded DNA with a conductance measurement system comprising: (i) a first and a second compartment with a first and a second electrolyte solution separated by a physical barrier, which barrier has at least one pore with diameter on nanometer scale; (ii) a means for applying an electric field across the barrier; (iii) a means for measuring change in the electric field; (iv) at least one polymerase attached to the pore; and (v) more than one phosphatase enzyme attached to the pore, and a composition comprising four different types of a compound having the structure:

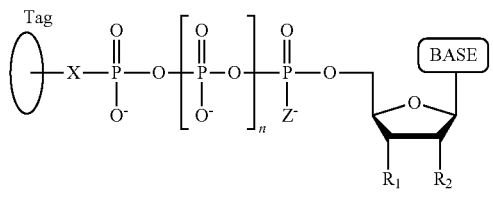

wherein the tag comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or $BH_3$, wherein n is 1, 2, 3, or 4, wherein the tag has a charge which is reverse in sign relative to the charge on the rest of the compound, wherein the base of a first type of compound is adenine or a derivative thereof, the base of a second type of compound is guanine or a derivative thereof, the base of a third type of compound is cytosine or a derivative thereof, and the base of a fourth type of compound is thymine or a derivative thereof, and wherein the tag on each type of compound is different from the tag on each of the other three types of compound, wherein the single-stranded DNA is in an electrolyte solution in contact with the polymerase attached to the pore and wherein the single-stranded DNA has a primer hybridized to a portion thereof, under conditions permitting the polymerase to catalyze incorporation of one of the compounds into the primer if the compound is complementary to the nucleotide residue of the single-stranded DNA immediately 5' to a nucleotide residue of the single-stranded DNA hybridized to the 3' terminal nucleotide residue of the primer, so as to form a DNA extension product, wherein incorporation of the compound results in release of a polyphosphate having the tag attached thereto, wherein the phosphatase enzyme attached to the pore cleaves the tag from the polyphosphate to release the tag;

(b) determining which compound has been incorporated into the primer to form the DNA extension product in step (a) by applying an electric field across the barrier and measuring an electronic change across the pore resulting from the tag generated in step (a) translocating through the pore, wherein the electronic change is different for each type of tag, thereby identifying the nucleotide residue in the single-stranded DNA complementary to the incorporated compound; and (c) repeatedly performing step (b) for each nucleotide residue of the single-stranded DNA being sequenced, thereby determining the nucleotide sequence of the single-stranded DNA.

A method for determining the nucleotide sequence of a single-stranded DNA, the method comprising:

(a) contacting the single-stranded DNA with a conductance measurement system comprising: (i) a lust and a second compartment with a first and a second electrolyte solution separated by a physical barrier, which barrier has at least one pore with diameter on nanometer scale; (ii) a means for applying an electric field across the barrier; (iii) a means for measuring change in the electric field; (iv) at least one polymerase attached to the pore; and (v) more than one phosphatase enzyme attached to the pore, and a compound having the structure:

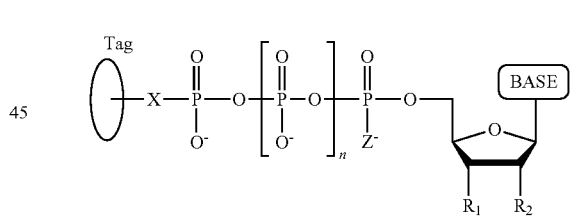

wherein the tag comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or $BH_3$, wherein the base is adenine, guanine, cytosine, thymine, or a derivative of one of these bases, wherein n is 1, 2, 3, or 4, and wherein the tag has a charge which is reverse in sign relative to the charge on the rest of the compound, wherein the single-stranded DNA is in an electrolyte solution in contact with the polymerase attached to the pore and wherein the single-stranded DNA has a primer hybridized to a portion thereof, under conditions permitting the polymerase to catalyze incorporation of the compound into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein if the compound is not incorporated, iteratively repeating the contacting with different compounds until a compound is incorporated, with the proviso that (1) the type of base on the compound is different from the type of base on each of the previous compounds, and (2) the type of tag on the compound is different from the type of tag on each of the previous compounds, wherein incorporation of the compound results in release of a polyphosphate having the tag attached thereto, wherein the phosphatase enzyme attached to the pore cleaves the tag from the polyphosphate to release the tag;

(b) determining which compound has been incorporated into the primer to form the DNA extension product in step (a) by applying an electric field across the barrier and measuring an electronic change across the pore resulting from the tag generated in step (a) translocating through the pore, wherein the electronic change is different for each type of tag, thereby identifying the nucleotide residue in the single-stranded DNA complementary to the incorporated compound; and (c) iteratively performing steps (a) and (b) for each nucleotide residue of the single-stranded DNA being sequenced, thereby determining the nucleotide sequence of the single-stranded DNA.

A method for determining the nucleotide sequence of a single-stranded RNA, which method comprising:

(a) contacting the single-stranded RNA with a conductance measurement system comprising: (i) a first and a second compartment with a first and a second electrolyte solution separated by a physical barrier, which barrier has at least one pore with diameter on nanometer scale; (ii) a means for applying an electric field across the barrier; (iii) a means for measuring change in the electric field; (iv) at least one polymerase attached to the pore; and (v) more than one phosphatase enzyme attached to the pore, and a composition comprising four different types of a compound having the structure:

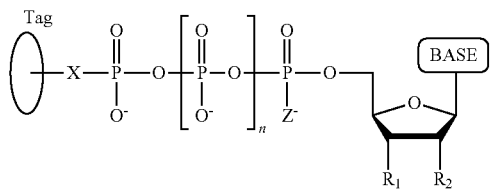

wherein the tag comprises one or more of ethylene glycol, an amino acid, a carbohydrate, a peptide, a dye, a chemiluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an allcynyl group, an azido group, or a combination thereof, wherein $R_1$ is OH, wherein $R_2$ is H or OH, wherein X is O, NH, S, or $CH_2$, wherein Z is O, S, or $BH_3$, wherein n is 1, 2, 3, or 4, wherein the tag has a charge which is reverse in sign relative to the charge on the rest of the compound, wherein the base of a first type of compound is adenine or a derivative thereof, the base of a second type of compound is guanine or a derivative thereof, the base of a third type of compound is cytosine or a derivative thereof, and the base of a fourth type of the compound is uracil or a derivative thereof, and wherein the tag on each type of compound is different from the tag on each of the other three types of compound, wherein the single-stranded RNA is in an electrolyte solution in contact with the polymerase attached to the pore and wherein the single-stranded RNA has a primer hybridized to a portion thereof, under conditions permitting the polymerase to catalyze incorporation of one of the compounds into the primer if the compound is complementary to the nucleotide residue of the single-stranded RNA immediately 5' to a nucleotide residue of the single-stranded RNA hybridized to the 3' terminal al nucleotide residue of the primer, so as to form an RNA extension product, wherein incorporation of the compound results in release of a polyphosphate having the tag attached thereto, wherein the phosphatase enzyme attached to the pore cleaves the tag from the polyphosphate to release the tag;

(b) determining which compound has been incorporated into the primer to form the RNA extension product in step (a) by applying an electric field across the barrier and measuring an electronic change across the pore resulting from the tag generated in step (a) translocating through the pore, wherein the electronic change is different for each type of tag, thereby identifying the nucleotide residue in the single-stranded RNA complementary to the incorporated compound; and (c) repeatedly performing step (b) for each nucleotide residue of the single-stranded RNA being sequenced, thereby determining the nucleotide sequence of the single-stranded RNA.

A method for determining the nucleotide sequence of a single-stranded RNA, the method comprising:

(a) contacting the single-stranded RNA with a conductance measurement system comprising: (i) a first and a second compartment with a first and a second electrolyte solution separated by a physical barrier, which barrier has at least one pore with diameter on nanometer scale; (ii) a means for applying an electric field across the barrier; (iii) a means for measuring change in the electric field; (iv) at least one polymerase attached to the pore; and (v) more than one phosphatase enzyme attached to the pore, and a compound having the structure:

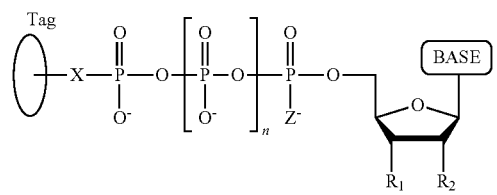

wherein the tag comprises one or more of ethylene glycol, an amino acid, a carbohydrate, a peptide, a dye, a chemiluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an allcynyl group, an azido group, or a combination thereof, wherein $R_1$ is OH, wherein $R_2$ is H or OH, wherein X is O, NH, S, or $CH_2$, wherein Z is O, S, or $BH_3$, wherein the base is adenine, guanine, cytosine, uracil, or a derivative of one of these bases, wherein n is 1, 2, 3, or 4, and wherein the tag has a charge which is reverse in sign relative to the charge on the rest of the compound, wherein the single-stranded RNA is in an electrolyte solution in contact with the polymerase attached to the pore and wherein the single-stranded RNA has a primer hybridized to a portion thereof, under conditions permitting the polymerase to catalyze incorporation of the compound into the primer if it is complementary to the nucleotide residue of the single-stranded RNA which is immediately 5' to a nucleotide residue of the single-stranded DNA hybridized to the 3' terminal nucleotide residue of the primer, so as to form an RNA extension product, wherein if the compound is not incorporated, iteratively repeating the contacting with different compounds until a compound is incorporated, with the proviso that (1) the type of base on the compound is different from the type of base on each of the previous compounds, and (2) the type of tag on the compound is different from the type of tag on each of the previous compounds, wherein incorporation of the compound results in release of a polyphosphate having the tag attached thereto, wherein the phosphatase enzyme attached to the pore cleaves the tag from the polyphosphate to release the tag;

(b) determining which compound has been incorporated into the primer to form the RNA extension product in step (a) by applying an electric field across the barrier and measuring an electronic change across the pore resulting from the tag generated in step (a) translocating through the pore, wherein the electronic change is different for each type of tag, thereby identifying the nucleotide residue in the single-stranded RNA complementary to the incorporated compound; and (c) iteratively performing steps (a) and (b) for each nucleotide residue of the single-stranded RNA being sequenced, thereby determining the nucleotide sequence of the single-stranded RNA.

In one embodiment of the method, more phosphatase enzymes than polymerases are attached to the pore. In an embodiment, the single-stranded DNA or RNA is obtained by denaturing a double-stranded DNA or RNA, whichever is applicable. In another embodiment, multiple copies of the same single-stranded DNA or RNA are immobilized on a bead. It is also contemplated that the nucleotide sequence of the single-stranded DNA or RNA is determined using multiple copies of the same single-stranded DNA or RNA.

In another embodiment, a washing step after each iteration of step (b) to remove unincoporated compound from contact with the single-stranded DNA or RNA is performed. In a further embodiment, a step after each iteration of step (b) to determine the identity of an additional identifiable moiety attached to the tag is contemplated.

In one embodiment of the method, at least 85%, 90%, 95%, or 99% of the released tags translocate through the nanopore.

In one embodiment, the compound further comprises a reversible terminator, optionally, the method further comprises a step of removing the reversible terminator after each iteration of step (b), wherein the reversible terminator is removed by biological means, chemical means, physical means, or by light irradiation.

In another embodiment, the interior of the pore has a charge which is reverse in sign relative to the charge of the tag or of the polyphosphate having the tag attached thereto.

In yet another embodiment, each of the first and the second compartments of the conductance measurement system has a charge, optionally, the charges of the first and the second compartments are opposite in polarity. It is also contemplated that the charges of the first and the second compartments are adjustable.

In a further embodiment, the rate of the tag translocating through the pore in step (b) is determined based on the charge of tag and the charges of the first and the second compartments.

In yet a further embodiment, each of the first and the second compartments has a charge such that in step (b) the tag translocates through the pore at a rate which is faster than, or equal to, the rate at which the tag or the polyphosphate having the tag attached thereto is being released in step (a).

A conductance measurement system comprising:

an electrically resistive barrier separating at least a first and a second electrolyte solution;

said electrically resistive barrier comprises at least one pore with a diameter on nanometer scale;

at least one compound with a tag in at least one of said first and second electrolyte solutions;

said at least one pore being configured to allow an ionic current to be driven across said first and second electrolyte solutions by an applied potential;

said at least one pore comprising a feature configured to cleave the tag from the compound to release the tag; and a means of measuring the ionic current and a means of recording its time course as a time series, including time periods when the at least one pore is unobstructed by the tag and also time periods when the tag causes pulses of reduced-conductance.

In one embodiment of the system, the tag has a residence time in the pore which is greater than limitations of ionic current bandwidth and current shot noise of said means of measuring the ionic current.

A method to delineate segments of a conductance time series into regions statistically consistent with the unobstructed pore conductance level, and pulses of reduced-conductance, and also statistically stationary segments within individual pulses of reduced-conductance, said conductance time series being generated with a conductance measurement system comprising:

an electrically resistive barrier separating at least a first and a second electrolyte solution;

said electrically resistive barrier comprises at least one pore with a diameter on nanometer scale;

at least one compound with a tag in at least one of said first and second electrolyte solutions;

said at least one pore being configured to allow an ionic current to be driven across said first and second electrolyte solutions by an applied potential;

said at least one pore comprising a feature configured to cleave the tag from the compound to release the tag; and a means of measuring the ionic current and a means of recording said conductance time series, including time periods when the at least one pore is unobstructed by said tag and also time periods when said tag causes pulses of reduced-conductance;

said method to delineate segments of a conductance time series being selected from the group consisting of:

(a) a Viterbi decoding of the maximum likelihood state sequence of a Continuous Density of a Hidden Markov Model estimated from the raw conductance time series;

(b) a delineation of the regions of pulses of reduced-conductance via comparison to a threshold for deviation from the open-pore conductance level; and (c) a means to characterize pulses of reduced-conductance by estimating the central tendencies of the ionic current levels for each segment, or by measure of central tendencies and segment duration together, the measure of segment central tendency being selected from the group consisting of: (i) a mean parameter of a Gaussian component of a first GMM estimated from the conductance time series as part of a Continuous Density Hidden Markov Model; (ii) an arithmetic mean; (iii) a trimmed mean; (iv) a median; and (v) a Maximum A Posteriori estimator of sample location, or a maximum likelihood estimator of sample location.

In another embodiment, the method further comprising at least one: (a) a maximum likelihood estimate of a second Gaussian Mixture Model based upon the measures of central tendency of conductance segments; (b) a peak finding by means of interpolation and smoothing of the empirical probability density of the estimates of central tendencies of segments of the conductance times series and finding roots of the derivatives of the interpolating functions; and (c) another means of locating the modes of multimodal distribution estimator.

A method for determining at least one parameter of a compound in a solution comprising the steps of:

placing a first fluid in a first reservoir;

placing a second fluid in a second reservoir; at least one of said first and said second fluid comprising at least one compound, wherein the compound is a tagged nucleotide or a tag cleaved from a tagged nucleotide; said first fluid in said first reservoir being separated from said second fluid in said second reservoir with an electrically resistive barrier; said electrically resistive barrier comprising at least one pore;

passing an ionic current through said first fluid, said at least one pore, and said second fluid with an electrical potential between said first and said second fluid;

measuring the ionic current passing through said at least one pore and the duration of changes in the ionic current; the measuring of the ionic current being carried out for a period of time sufficient to measure a reduction in the ionic current caused by the compound interacting with said at least one pore; and determining at least one parameter of the compound by mathematically analyzing the changes in the ionic current and the duration of the changes in the ionic current over the period of time; said mathematical analysis comprising at least one step selected from the group consisting of: (a) a mean parameter of a Gaussian component of a first GMM estimated from the conductance time series as part of a Continuous Density Hidden Markov Model; (b) an Event-Mean Extraction; (c) Maximum Likelihood Event State Assignment; (d) threshold detection and averaging; (e) sliding window analysis; (f) an arithmetic mean; (g) a trimmed mean; (h) a median; and (i) a Maximum A Posteriori estimator of sample location, or a maximum likelihood estimator of sample location.

In one embodiment of the method, the compound is treated with phosphatase before measuring the reduction in the ionic current. In another embodiment, the compound is an alternatively charged compound which has a first net charge and, after a chemical, physical or biological reaction, a different second net charge.

In another embodiment, the mathematical analysis is selected from the group consisting of GMM, threshold detection and averaging, and sliding window analysis.

In a further embodiment, the at least one parameter is selected from the group consisting of the concentration, size, charge, and composition of the compound.

It is contemplated that an embodiment of the method comprising a step of calibrating the conductance measurement system.

In one embodiment, the accuracy of the method is greater than 4σ, 5σ, or 6σ.

A tagged nucleotide, wherein the nucleotide comprises a tag capable of being cleaved in a nucleotide polymerization event and detected with the aid of a nanopore.

In one embodiment, the tag is attached to the 5'-phosphate of the nucleotide. In another embodiment, the tag is not a fluorophore. In a further embodiment, the tag is detectable by its charge, shape, size, or any combination thereof.

In one embodiment of the conductance measurement system, the first and second electrolyte solutions are the same.

In one embodiment of the method, the first and the second electrolyte solutions are the same.

A tagged nucleotide, wherein the nucleotide comprises a tag capable of being cleaved in a nucleotide polymerization event and detected with the aid of a nanopore.

In one embodiment, the tag is attached to the 5'-phosphate of the nucleotide. In another embodiment, the tag is not a fluorophore. In a further embodiment, the tag is detectable by its charge, shape, size, or any combination thereof.

A method for nucleic acid sequencing, the method comprising providing an array of individually addressable sites, each site having a nanopore attached to a nucleic acid polymerase, and, at a given site of said array, polymerizing tagged nucleotides with a polymerase, wherein a tag is released and detected by a nanopore at said given site.

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, with a DNA polymerase and four deoxyribonucleotide polyphosphate (dNPP) analogues at least one of which can hybridize with each of an A, T, G, or C nucleotide in the DNA being sequenced under conditions permitting the DNA polymerase to catalyze incorporation of one of the dNPP analogues into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein each of the four dNPP analogues has the structure:

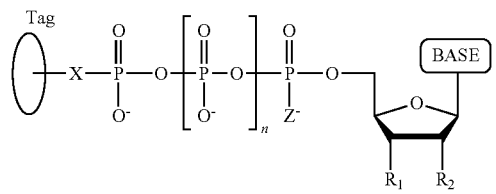

wherein the base is adenine, guanine, cytosine, thymine or uracil, or a derivative of one or more of these bases, wherein $R_1$ is OH, wherein $R_2$ is H, wherein X is O, NH, S, or $CH_2$, wherein n is 1, 2, 3, or 4, wherein Z is O, S, or $BH_3$, and with the proviso that (i) the type of base on each dNPP analogue is different from the type of base on each of the other three dNPP analogues, and (ii) either the value of n of each dNPP analogue is different from the value of n of each of the other three dNPP analogues, or the value of n of each of the four dNPP analogues is the same and the type of tag on each dNPP analogue is different from the type of tag on each of the other three dNPP analogues, wherein incorporation of the dNPP analogue results in release of a polyphosphate having the tag attached thereto; and (b) identifying which dNPP analogue has been incorporated into the primer to form the DNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, whichever is applicable, thereby permitting identifying the nucleotide residue in the single-stranded DNA complementary to the incorporated dNPP analogue; and (c) repeatedly performing step (b) for each nucleotide residue of the single-stranded DNA being sequenced, wherein in each iteration of step (b) identify which dNPP analogue has been incorporated into the DNA extension product in step (a), wherein the dNPP analogue is located immediately 5' to a nucleotide residue of the single-stranded DNA hybridized to the 3' terminal nucleotide residue of the DNA extension product, thereby determining the nucleotide sequence of the single-stranded DNA.

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, with a DNA polymerase and a deoxyribonucleotide polyphosphate (dNPP) analogue which can hybridize with an A, T, G, or C nucleotide in the DNA being sequenced under conditions permitting the DNA polymerase to catalyze incorporation of the dNPP analogue into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein the dNPP analogue has the structure:

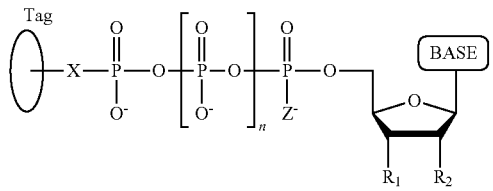

wherein the base is adenine, guanine, cytosine, uracil or thymine, or a derivative of one of these bases, wherein $R_1$ is —OH, —O—$CH_2N_3$, or —O-2-nitrobenzyl, wherein $R_2$ is H, wherein X is O, NH, S, or $CH_2$, wherein n is 1, 2, 3, or 4, wherein Z is O, S, or $BH_3$, and wherein if the dNPP analogue is not incorporated, iteratively repeating the contacting with a different dNPP analogue until a dNPP analogue is incorporated, with the proviso that (i) the type of base on each dNPP analogue is different from the type of base on each of the other dNPP analogues, and (ii) either the value of n of each dNPP analogue is different from the value of n of each of the other dNPP analogues, or the value of n of each of the dNPP analogues is the same and the type of tag on each dNPP analogue is different from the type of tag on each of the other dNPP analogues, wherein incorporation of the dNPP analogue results in release of a polyphosphate having the tag attached thereto;

(b) identifying which dNPP analogue has been incorporated into the primer to form the DNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, whichever is applicable, thereby permitting identifying the nucleotide residue in the single-stranded DNA complementary to the incorporated dNPP analogue;

(c) repeatedly performing steps (a) and (b) for each nucleotide residue of the single-stranded DNA being sequenced, wherein in each iteration of step (a) the dNPP analogue is incorporated into the DNA extension product if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, with a DNA polymerase and four deoxyribonucleotide polyphosphate (dNPP) analogues at least one of which can hybridize with each of an A, T, G, or C nucleotide in the DNA being sequenced under conditions permitting the DNA polymerase to catalyze incorporation of one of the dNPP analogues into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein each of the four dNPP analogues has a structure chosen from the following:

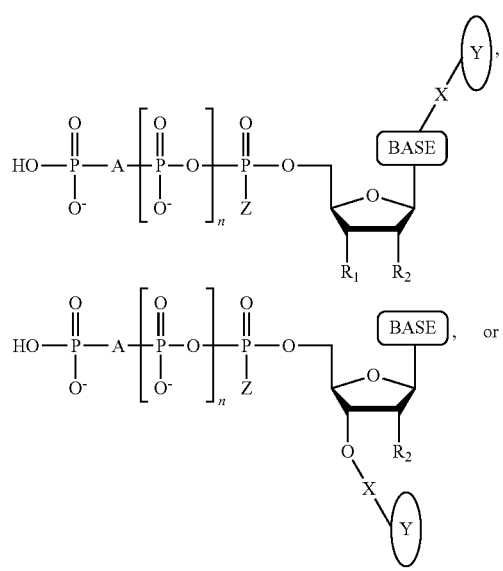

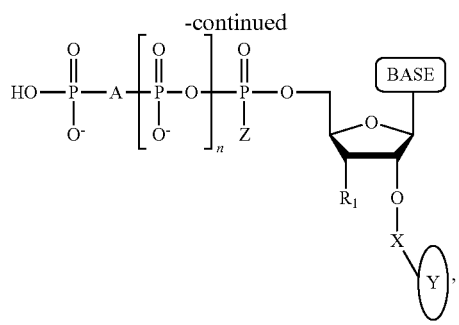

wherein the base is adenine, guanine, cytosine, uracil or thymine, or a derivative of one or more of these bases, wherein Y is a tag, wherein $R_1$, if present, is OH, wherein $R_2$, if present, is H, wherein X is a cleavable linker, wherein Z is O, S, or $BH_3$, wherein n is 1, 2, 3, or 4, wherein A is O, S, CH2, CHF, CFF, or NH, and with the proviso that (i) the type of base on each dNPP analogue is different from the type of base on each of the other three dNPP analogues, and (ii) the type of tag on each dNPP analogue is different from the type of tag on each of the other three dNPP analogues;

(b) cleaving the tag from the dNPP analogue incorporated in step (a);

(c) identifying which dNPP analogue has been incorporated into the primer to form the DNA extension product in step (a) by applying a voltage across the membrane and measuring an electronic change across the nanopore resulting from tag cleaved off in step (b) translocating through the nanopore, wherein the electronic change is different for each different type of tag, thereby permitting identifying the nucleotide residue in the single-stranded DNA complementary to the incorporated dNPP analogue; and (d) repeatedly performing steps (b) and (c) for each nucleotide residue of the single-stranded DNA being sequenced, wherein in each iteration of step (c) identify which dNPP analogue has been incorporated into the DNA extension product in step (a) immediately 5' to a nucleotide residue of the single-stranded DNA hybridized to the 3' terminal nucleotide residue of the DNA extension product, thereby determining the nucleotide sequence of the single-stranded DNA.

A method for determining the nucleotide sequence of a single-stranded DNA comprising:

(a) contacting the single-stranded DNA, wherein the single-stranded DNA is in an electrolyte solution in contact with a nanopore in a membrane and wherein the single-stranded DNA has a primer hybridized to a portion thereof, with a DNA polymerase and a deoxyribonucleotide polyphosphate (dNPP) analogue which can hybridize with an A, T, G, or C nucleotide in the DNA being sequenced under conditions permitting the DNA polymerase to catalyze incorporation of the dNPP analogue into the primer if it is complementary to the nucleotide residue of the single-stranded DNA which is immediately 5' to a nucleotide residue of the single-stranded DNA hybridized to the 3' terminal nucleotide residue of the primer, so as to form a DNA extension product, wherein the dNPP analogue has the structure:

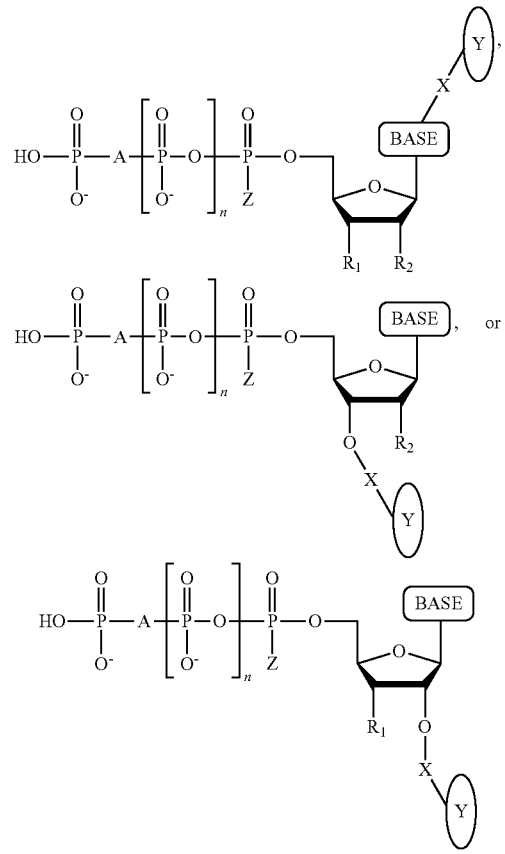

wherein the base is adenine, guanine, cytosine, uracil or thymine, or derivative of one of these bases, wherein Y is a tag, and wherein $R_1$, if present, is OH, $-OCH_2N_3$, or $-O$-2-nitrobenzyl, wherein $R_3$, if present, is H, wherein X is a cleavable linker, wherein Z is O, S, or $BH_3$, wherein n is 1, 2, 3, or 4, wherein A is O, S, CH2, CHF, CFF, or NH, and wherein if the dNPP analogue is not incorporated, iteratively repeating the contacting with a different dNPP analogue until a dNPP analogue is incorporated, with the proviso that (i) the type of base on each dNPP analogue is different from the type of base on each of the other dNPP analogues, and (ii) the type of tag on each dNPP analogue is different from the type of tag on each of the other dNPP analogues;

(b) cleaving the tag from the dNPP analogue incorporated in step (a); and (c) identifying which dNPP analogue has been incorporated into the primer to form the DNA extension product in step (a) by applying a voltage across the membrane and measuring an electronic change across the nanopore resulting from the tag cleaved off in step (b) translocating through the nanopore, wherein the electronic change is different for each type of tag, thereby permitting identifying the nucleotide residue in the single-stranded DNA complementary to the incorporated dNPP analogue;

(d) repeatedly performing steps (a) through (c) for each nucleotide residue of the single-stranded DNA being sequenced, wherein in each iteration of step (a) the dNPP analogue is incorporated into the DNA extension product if it is complementary to the nucleotide residue of the single-stranded DNA which is immediately 5' to a nucleotide residue of the single-stranded DNA hybridized to the 3' terminal nucleotide residue of the DNA extension product, thereby determining the nucleotide sequence of the single-stranded DNA.

In some cases a tagged nucleotide comprises a tag capable of being cleaved in a nucleotide polymerization event and detected with the aid of a nanopore. The tag may be attached to the 5'-phosphate of the nucleotide. In some instances, the tag is not a fluorophore. The tag may be detectable by its charge, shape, size, or any combination thereof. Exemplary tags include various polymers. Each type of nucleotide (i.e., A, C, G, T) generally comprises a unique tag.

Figure 34:
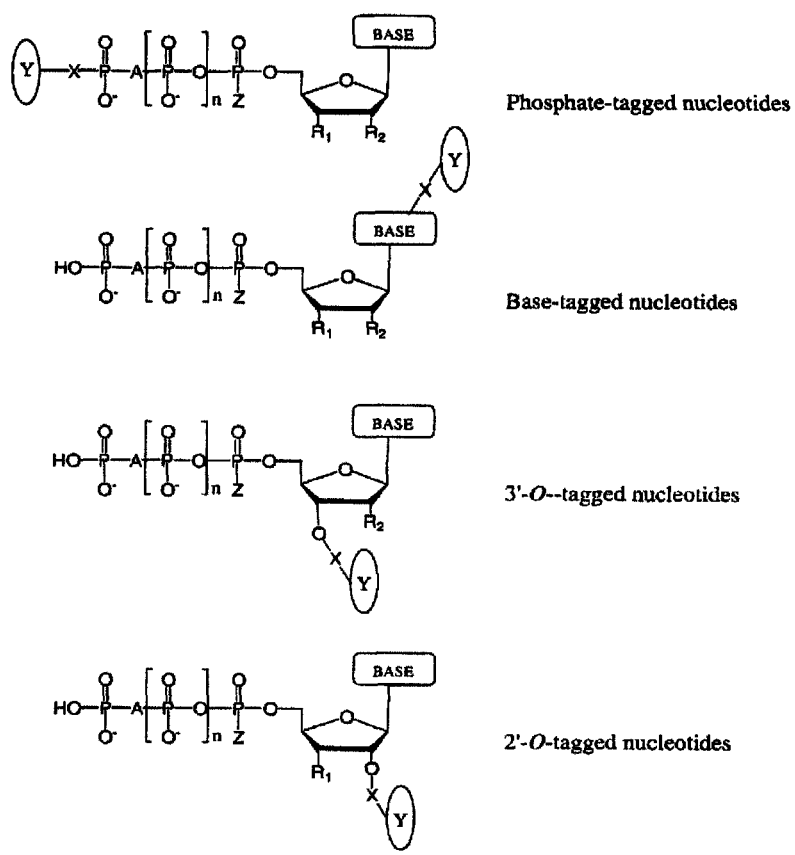
FIG. 34 shows phosphate, base, 2'- and 3'-modified nucleoside phosphates with possible linkers and tags; BASE=adenine, guanine, thymine, cytosine, uracil, 5-methyl C, 7-deaza-A, 7-deaza-G or their derivatives thereof; and $R_2$=H, OH, F, $NH_2$, $N_3$, or OR'; n=1-5; A=O, S, $CH_2$, CHF, CFF, NH; Z=O, S, $BH_3$, X=linker which links phosphate or the 2'-O or 3'-O or the base to the detectable moiety and may contain O, N or S, P atoms (the linker can also be a detectable moiety, directly or indirectly, such as amino acids, peptides, proteins, carbohydrates, PEGs of different length and molecular weights, organic or inorganic dyes, fluorescent and fluorogenic dyes, drugs, oligonucleotides, mass tags, chemiluminiscent tags and may contain positive or negative charges.); Y=tags or detectable moiety, such as aliphatic or organic aromatic compounds with one or more rings, dyes, proteins, carbohydrates, PEGs of different length and molecular weights, drugs, oligonucleotides, mass tags, fluorescent tags, chemiluminiscent tags and may contain positive or negative charge.

Tags may be located on any suitable position on the nucleotide. FIG. 34 provides some non-limiting examples of a tagged nucleotide. In the first diagram, $R_1$ is generally OH and $R_2$ is H (i.e., for DNA) or OH (i.e., for RNA), although other modifications are acceptable. In FIG. 34, X is any suitable linker. In some cases, the linker is cleavable. Examples of linkers include without limitation, O, NH, S, or $CH_2$. Examples of suitable chemical groups for the position Z include O, S, or $BH_3$. The base is any base suitable for incorporation into a nucleic acid including adenine, guanine, cytosine, thymine, uracil, or a derivative thereof. Universal bases are also acceptable in some cases.

The number of phosphates (n) is any suitable integer value (e.g., a number of phosphates such that the nucleotide may be incorporated into a nucleic acid molecule). In some instances, all types of tagged nucleotides have the same number of phosphates, but this is not required. In some applications, there is a different tag for each type of nucleotide and the number of phosphates is not necessarily used to distinguish the various tags. However, in some cases more than one type of nucleotide (e.g., A, C, T, G or U) have the same tag molecule and the ability to distinguish one nucleotide from another is determined at least in part by the number of phosphates (with various types of nucleotides having a different value for n). In various embodiments, the value for n is 1, 2, 3, 4, 5, 6, 7, 8, 9, 10, or greater.

Suitable tags are described below. In some instances, the tag has a charge which is reverse in sign relative to the charge on the rest of the compound. When the tag is attached, the charge on the overall compound may be neutral. Release of the tag may result in two molecules, a charged tag and a charged nucleotide. The charged tag passes through a nanopore and is detected in some cases.

Additional examples of suitable tagged nucleotides also are shown in FIG. 34. As shown in the second through the fourth diagrams, the tag also may be attached to the sugar molecule, the base molecule, or any combination thereof. With reference to FIG. 34, Y is a tag and X is a cleavable linker. Furthermore, $R_1$, if present, is generally OH, $—OCH_2N_3$ or —O-2-nitrobenzyl, and $R_2$, if present, is generally H. Also, Z is generally O, S, or $BH_3$, and n is any integer including 1, 2, 3, or 4. In some cases, the A is O, S, CH2, CHF, CFF, or NH.

With continued reference to FIG. 34, the type of base on each dNPP analogue is generally different from the type of base on each of the other three dNPP analogues, and the type of tag on each dNPP analogue is generally different from the type of tag on each of the other three dNPP analogues. Suitable bases include, but are not limited to adenine, guanine, cytosine, uracil or thymine, or a derivative of each thereof. In some cases, the base is one of 7-deazaguanine, 7-deazaadenine or 5-methylcytosine.

In cases where $R_1$ is $—O—CH_2N_3$, the methods optionally further comprise treating the incorporated dNPP analogue so as to remove the $—CH_2N_3$ and result in an —OH group attached to the 3' position thereby permitting incorporation of a further dNPP analogue.

In cases where $R_1$ is —O-2-nitrobenzyl, the methods optionally further comprise treating the incorporated nucleotide analogue so as to remove the -2-nitrobenzyl and result in an —OH group attached to the 3' position thereby permitting incorporation of a further dNPP analogue A tag may be any chemical group or molecule that is capable of being detected in a nanopore. In an embodiment of the methods the tag comprises one or more of ethylene glycol, an amino acid, a carbohydrate, a dye, a mononucleotide, a dinucleotide, a trinucleotide, a tetranucleotide, a pentanucleotide, a hexanucleotide, a fluorescent dyes, a chemiluminiscent compound, an amino acid, a peptide, a carbohydrate, a nucleotide monophopshate, a nucleotide diphosphate, an aliphatic acid, an aromatic acid, an alcohol, a thiol unsubstituted or substituted with one or more halogens, a cyano group, a nitro group, an alkyl group, an alkenyl group, an alkynyl group, an azido group, or a combination thereof.

In an embodiment of the methods the base is selected from the group consisting of adenine, guanine, cytosine, thymine, 7-deazaguanine, 7-deazaadenine, or 5-methylcytosine.

In an embodiment the methods further comprise a washing step after each iteration of step (b) to remove unincoporated dNPP analogues from contact with the single-stranded DNA.

In an embodiment the methods further comprise a washing step after each iteration of step (c) to remove unincoporated dNPP analogues from contact with the single-stranded DNA.

In an embodiment the methods the single-stranded DNA, electrolyte solution, and nanopore in the membrane are located within a single container.

In an embodiment of the methods wherein $R_1$ is $—O—CH_2N_3$, the methods optionally further comprise treating the incorporated dNPP analogue so as to remove the $—CH_2N_3$ and result in an —OH group attached to the 3' position thereby permitting incorporation of a further dNPP analogue.

In an embodiment of the methods wherein $R_1$ is —O-2-nitrobenzyl, the methods optionally further comprise treating the incorporated nucleotide analogue so as to remove the -2-nitrobenzyl and result in an —OH group attached to the 3' position thereby permitting incorporation of a further dNPP analogue.

In an embodiment of the methods the dNPP analogues have the following structures:

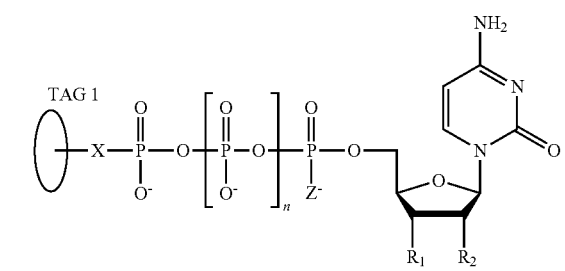

wherein $R_1$ is OH, wherein $R_2$ is H or OH, wherein Z is O, S, or $BH_3$, and wherein the base is adenine, guanine, cytosine, thymine, uracil, a 7-deazapurine, or a 5-methylpyrimidine.

In an embodiment of the methods the tag is a mononucleotide, a dinucleotide, a trinucleotide, a tetranucleotide, a pentanucleotide, or a hexanucleotide, wherein the base of the mononucleotide, the dinucleotide, the trinucleotide, the tetranucleotide, the pentanucleotide, or the hexanucleotide is the same type of base as the base of the dNPP analogue.

In an embodiment of the methods the tag is chosen from the following:

$(dCp)_m\text{-}(PO_4)_n\text{-}dC$

-continued
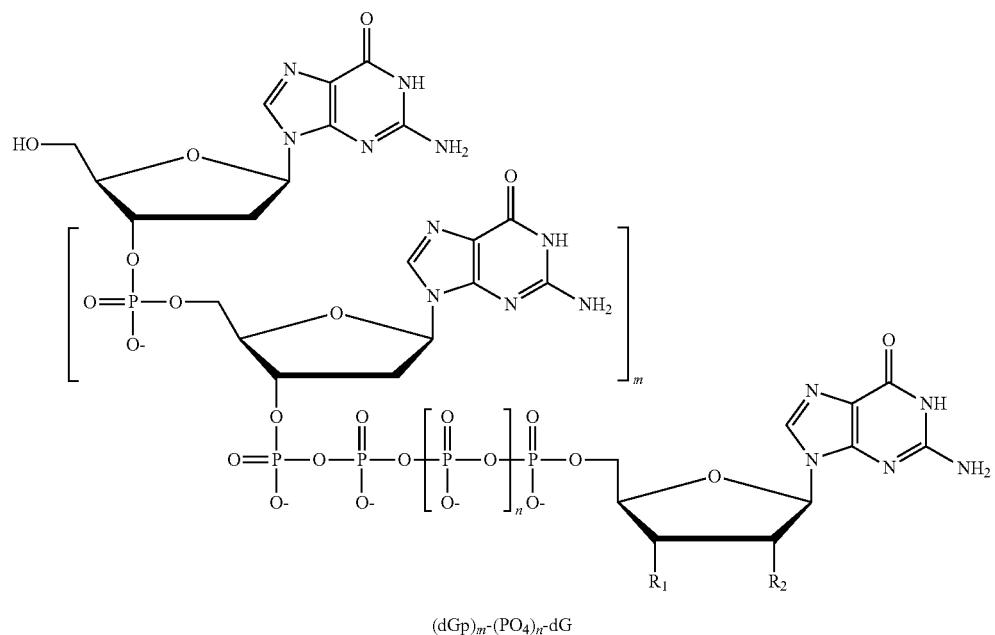
(dGp)$_m$-(PO$_4$)$_n$-dG
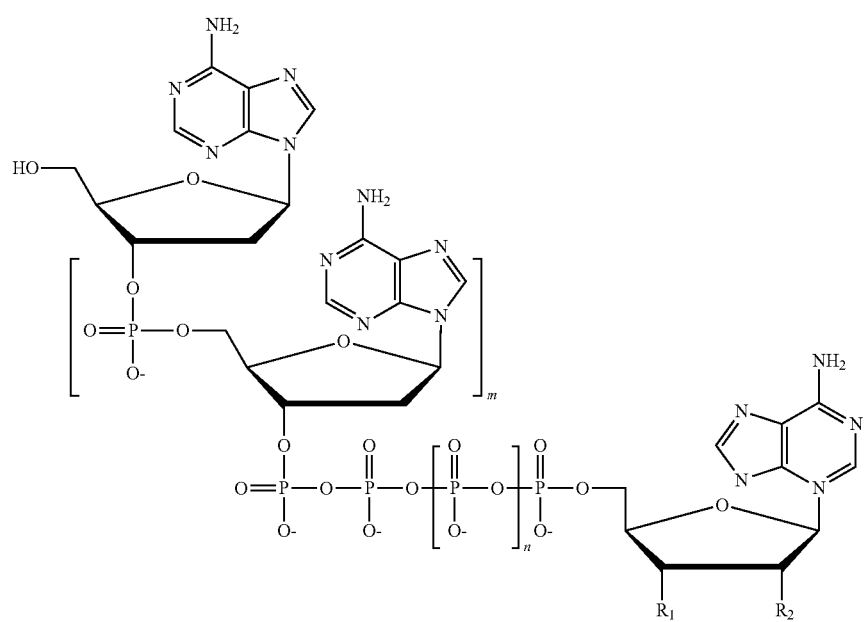
(dAp)$_m$-(PO$_4$)$_n$-dA

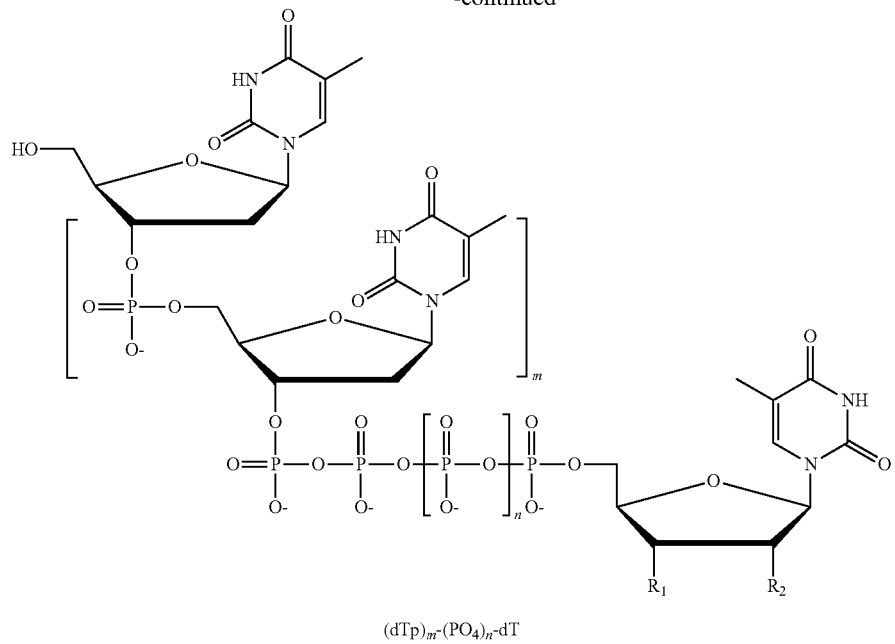

(dTp)$_m$-(PO$_4$)$_n$-dT wherein in each structure n is, independently, 1, 2, 3, or 4, and m is, independently, an integer from 0 to 100, and wherein when m is 0 the terminal phosphate of the dNPP is bonded directly to the 3' O atom of the nucleoside shown on the left hand side of the structure, and wherein the value of n is different for each type of base.

In an embodiment of the methods m is an integer from 0 to 50. In an embodiment of the methods m is an integer from 0 to 10.

Various non-limiting examples of tagged nucleotides are provided. In an embodiment of the methods the dNPP analogue has the structure:

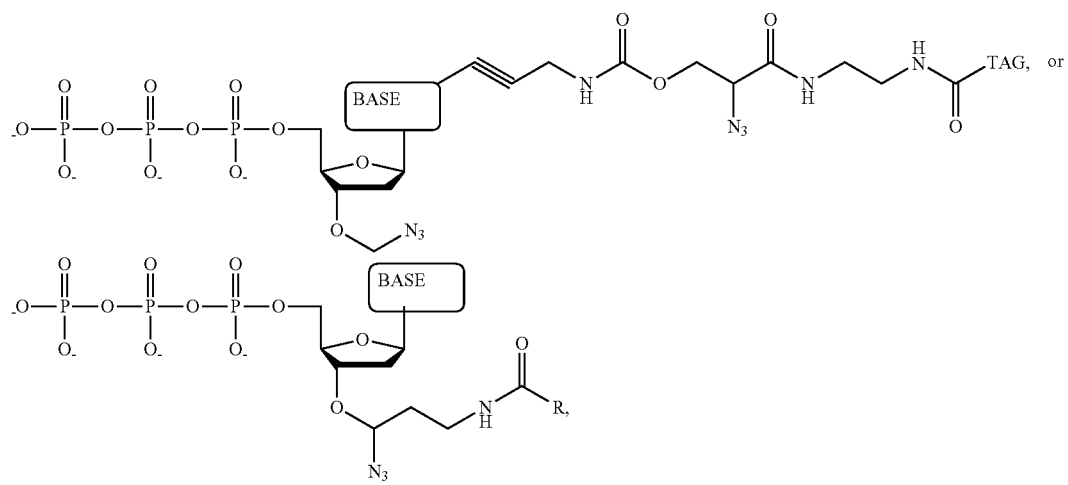

wherein R is a substituted or unsubstituted hydrocarbyl, up to 3000 daltons, and wherein the base is adenine, guanine, cytosine, thymine, uracil, a 7-deazapurine, or a 5-methylpyrimidine.

In an embodiment of the methods the dNPP analogue has the structure:

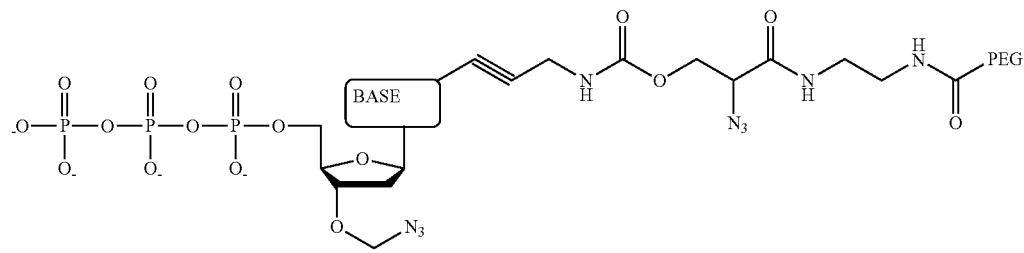

wherein the base is adenine, guanine, cytosine, thymine, uracil, a 7-deazapurine, or a 5-methylpyrimidine.

In an embodiment of the methods the dNPP analogue has the structure:

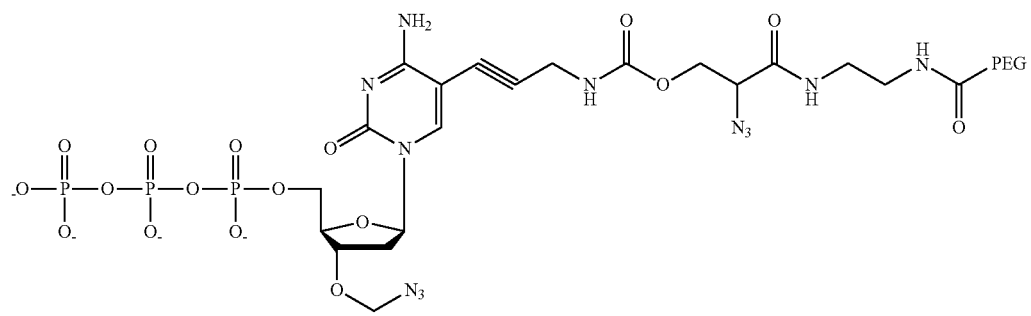

In an embodiment of the methods the dNPP analogue has the structure:

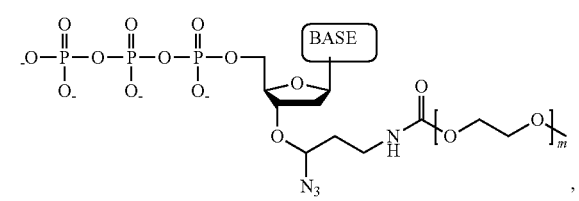

wherein m is an integer from 1-50, and wherein the base is adenine, guanine, cytosine, thymine, uracil, a 7-deazapurine, or a 5-methylpyrimidine.

In an embodiment of the methods the electronic change is a change in current amplitude.

In an embodiment of the methods the electronic change is a change in conductance of the nanopore.

In an embodiment of the methods the nanopore is biological. In an embodiment of the methods the nanopore is proteinaceous. In an embodiment of the methods the nanopore comprises alpha hemolysin. In an embodiment of the methods the nanopore is graphene. In an embodiment of the methods the nanopore is a solid-state nanopore. In an embodiment of the methods the nanopore is in a solid-state membrane.

In an embodiment of the methods the single stranded DNA, the primer, or the DNA polymerase is attached to a solid surface.

In another embodiment of the methods the nanopore is part of an array of nanopores.

Any suitable method for attaching the tags may be used. In an example, tags may be attached to the terminal phosphate by (a) contacting a nucleotide triphosphate with dicyclohexylcarbodiimide/dimethylformamide under conditions permitting production of a cyclic trimetaphosphate; (b) contacting the product resulting from step a) with a nucleophile so as to form an —OH or —NH$_2$ functionalized compound; and (c) reacting the product of step b) with a tag having a —COR group attached thereto under conditions permitting the tag to bond indirectly to a terminal phosphate thereby forming the nucleotide triphosphate analogue.

In some cases, the nucleophile is H$_2$N—R—OH, H$_2$N—R—NH$_2$, R'S—R—OH, R'S—R—NH$_2$, or

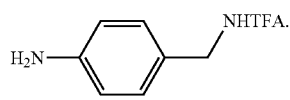

In some instances, the method comprises, in step b), contacting the product resulting from step a) with a compound having the structure:

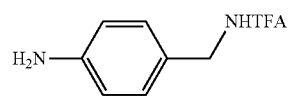

and subsequently or concurrently contacting the product with NH$_4$OH so as to form a compound having the structure:

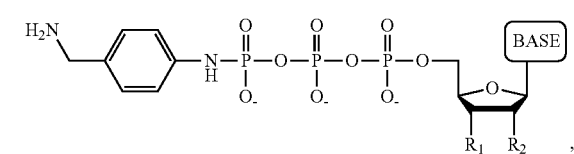

The product of step b) may then be reacted with a tag having a —COR group attached thereto under conditions permitting the tag to bond indirectly to a terminal phosphate thereby forming the nucleotide triphosphate analogue having the structure:

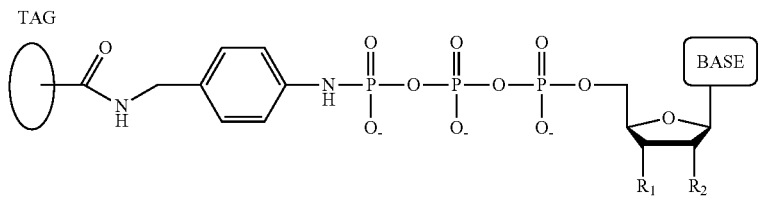

wherein $R_1$ is OH, wherein $R_2$ is H or OH, wherein the base is adenine, guanine, cytosine, thymine, uracil, a 7-deazapurine or a 5-methylpyrimidine.

In particular is a process for producing a nucleotide triphosphate analogue, wherein the nucleotide triphosphate analogue differs from a nucleotide triphosphate by having a tag attached to the terminal phosphate thereof, comprising: (a) contacting a nucleotide triphosphate with dicyclohexylcarbodiimide/dimethylformamide under conditions permitting production of a cyclic trimetaphosphate; and (b) contacting the product resulting from step a) with a tag having a hydroxyl or amino group attached thereto under conditions permitting nucleophilic opening of the cyclic trimetaphosphate so as to bond the tag to a terminal phosphate thereby forming the nucleotide triphosphate analogue.

A process for producing a nucleotide triphosphate analogue, wherein the nucleotide triphosphate analogue differs from a nucleotide triphosphate by having a tag attached to the terminal phosphate thereof, comprising: (a) contacting a nucleotide triphosphate with dicyclohexylcarbodiimide/dimethylformamide under conditions permitting production of a cyclic trimetaphosphate; (b) contacting the product resulting from step a) with a nucleophile so as to form an —OH or —NH$_2$ functionalized compound; and (c) reacting the product of step b) with a tag having a —COR group attached thereto under conditions permitting the tag to bond indirectly to a terminal phosphate thereby forming the nucleotide triphosphate analogue.

In an embodiment of the instant process the nucleophile is H$_2$N—R—OH, H$_2$N—R—NH$_2$, R'S—R—OH, R'S—R—NH$_2$, or

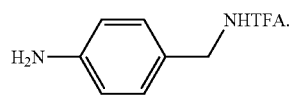

In an embodiment the instant process comprises in step b) contacting the product resulting from step a) with a compound having the structure:

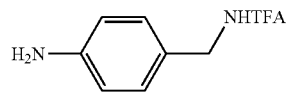

and then NH$_4$OH so as to form a compound having the structure:

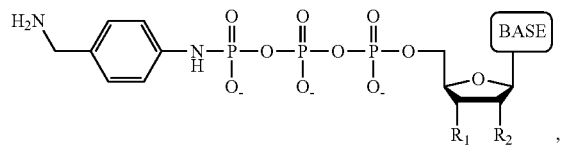

and reacting the product of step b) with a tag having a —COR group attached thereto under conditions permitting the tag to bond indirectly to a terminal phosphate thereby forming the nucleotide triphosphate analogue having the structure:

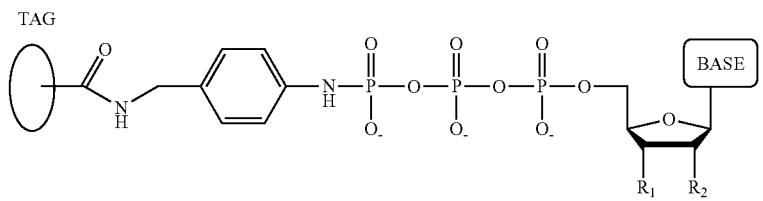

wherein $R_1$ is OH, wherein $R_2$ is H or OH, wherein the base is adenine, guanine, cytosine, thymine, uracil, a 7-deazapurine, or a 5-methylpyrimidine.

A process for producing a nucleotide tetraphosphate analogue, wherein the nucleotide tetraphosphate analogue differs from a nucleotide tetraphosphate by having a tag attached to the terminal phosphate thereof, comprising:

(a) contacting a nucleotide triphosphate with 1,1'-carbonyldiimidazole/dimethylformamide under conditions permitting formation of the following structure:

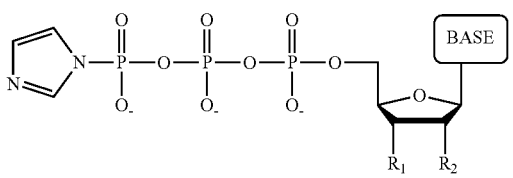

wherein $R_1$ is OH, wherein $R_2$ is H or OH, wherein the base is adenine, guanine, cytosine, thymine, uracil, a 7-deazapurine, or a 5-methylpyrimidine; and (b) contacting the product resulting from step a) with a tag having a monophosphate group attached thereto under conditions permitting formation of the nucleotide tetraphosphate analogue.

A process for producing a nucleotide tetraphosphate analogue, wherein the nucleotide tetraphosphate analogue differs from a nucleotide tetraphosphate by having a tag attached to the terminal phosphate thereof, comprising:

(a) contacting a nucleotide triphosphate with 1,1'-carbonyldiimidazole/dimethylformamide under conditions permitting formation of the following structure:

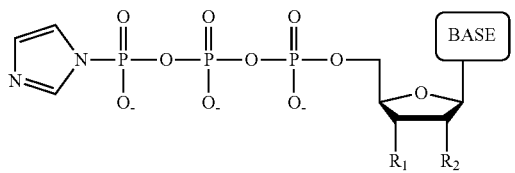

wherein $R_1$ is OH, wherein $R_2$ is H or OH, wherein the base is adenine, guanine, cytosine, thymine, uracil, a 7-deazapurine, or a 5-methylpyrimidine;

(b) contacting the product resulting from step a) with phosphoric acid under conditions permitting formation of a nucleotide tetraphosphate;

(c) contacting the nucleotide tetraphosphate with 1) carbonyldiimidazole/dimethylformanide; 2) a nucleophile and then 3) NH$_4$OH so as to form an —OH or —NH$_2$ functionalized compound; and (d) contacting the product of step c) with a tag having a —COR group attached thereto under conditions permitting the tag to bond indirectly to a terminal phosphate thereby forming the nucleotide tetraphosphate analogue.

In an embodiment of the instant process the nucleophile is H$_2$N—R—OH, H$_2$N—R—NH$_2$, R'S—R—OH, R'S—R—NH$_2$, or

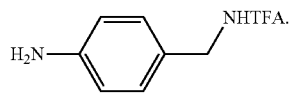

In an embodiment the instant process comprises in step b) contacting the nucleotide tetraphosphate with 1) carbonyldiimidazole/dimethylformamide; 2) a compound having the structure:

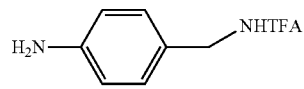

and then 3) NH$_4$OH so as to form a compound having the structure:

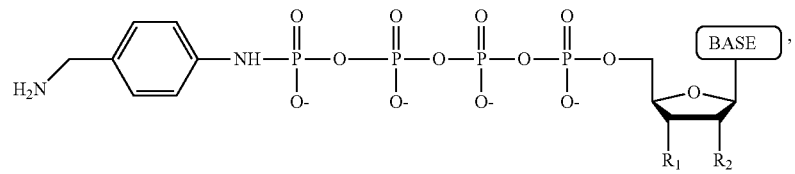

and contacting the product of step b) with a tag having a —COR group attached thereto under conditions permitting the tag to bond indirectly to a terminal phosphate thereby forming the nucleotide triphosphate analogue having the structure:

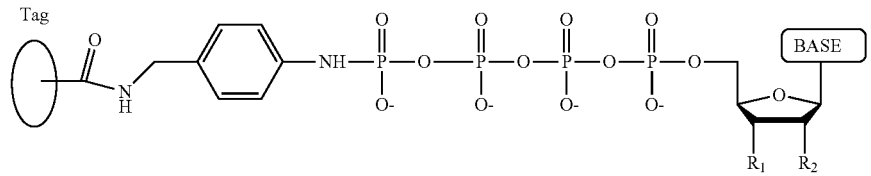

wherein $R_1$ is OH, wherein $R_2$ is H or OH, wherein the base is adenine, guanine, cytosine, thymine, uracil, a 7-deazapurine, or a 5-methylpyrimidine.

A process for producing a nucleotide tetraphosphate analogue, wherein the nucleotide tetraphosphate analogue differs from a nucleotide tetraphosphate by having a tag attached to the terminal phosphate thereof, comprising:

(a) contacting a nucleotide triphosphate with 1,1'-carbonyldiimidazole/dimethylformamide under conditions permitting formation of the following structure:

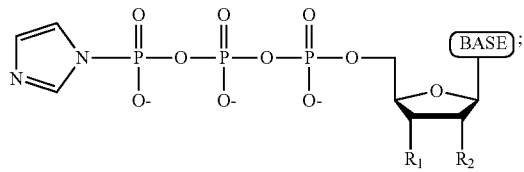

(b) contacting the product resulting from step a) with phosphoric acid under conditions permitting formation of a nucleotide tetraphosphate; and (c) contacting the nucleotide tetraphosphate with carbonyldiimidazoleldimethylfonnamide and a tag having a hydroxyl or amino group attached thereto so as to form a compound having the structure:

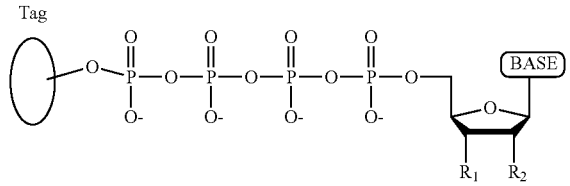

wherein $R_1$ is OH, wherein $R_2$ is H or OH, wherein the base is adenine, guanine, cytosine, thymine, uracil, a 7-deazapurine, or a 5-methylpyrimidine.

A process for producing a nucleotide pentaphosphate analogue, wherein the nucleotide pentaphosphate analogue differs from a nucleotide pentaphosphate by having a tag attached to the terminal phosphate thereof, comprising:

(a) contacting a nucleotide triphosphate with 1,1'-carbonyldiimidazole/dimethylfomamide under conditions permitting formation of the following structure:

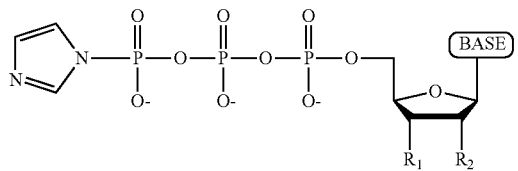

wherein $R_1$ is OH, wherein $R_2$ is H or OH, wherein the base is adenine, guanine, cytosine, thymine, uracil, a 7-deazapurine, or a 5-methylpyrimidine; and (b) contacting the product resulting from step a) with a tag having a pyrophosphate group attached thereto under conditions permitting formation of the nucleotide pentaphosphate analogue.

A process for producing a nucleotide pentaphosphate analogue, wherein the nucleotide pentaphosphate analogue differs from a nucleotide pentaphosphate by having a tag attached to the terminal phosphate thereof, comprising:

(a) contacting a nucleotide triphosphate with 1,1'-carbonyldiimidazole/dimethylformamide under conditions permitting formation of the following structure:

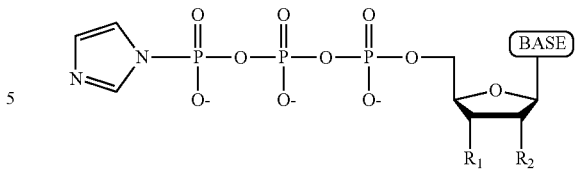

wherein $R_1$ is OH, wherein $R_2$ is H or OH, wherein the base is adenine, guanine, cytosine, thymine, uracil, a 7-deazapurine, or a 5-methylpyrimidine;

(b) contacting the product resulting from step a) with a pyrophosphate group under conditions permitting formation of a nucleotide pentaphosphate; and (c) contacting the nucleotide pentaphosphate with carbonyldiimidazole/dimethylformamide and a tag having a hydroxyl or amino group attached thereto so as to form the nucleotide pentaphosphate analogue.

A process for producing a nucleotide hexaphosphate analogue, wherein the nucleotide hexaphosphate analogue differs from a nucleotide hexaphosphate by having a tag attached to the terminal phosphate thereof, comprising:

(a) contacting a nucleotide triphosphate with 1,1'-carbonyldiimidazole/dimethylformamide under conditions permitting formation of the following structure:

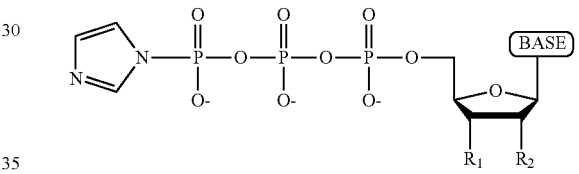

wherein $R_1$ is OH, wherein $R_2$ is H or OH, wherein the base is adenine, guanine, cytosine, thymine, uracil, a 7-deazapurine, or a 5-methylpyrimidine; and (b) contacting the product resulting from step a) with a tag having a triphosphate group attached thereto under conditions permitting formation of the nucleotide hexaphosphate analogue.

A process for producing a nucleotide hexaphosphate analogue, wherein the nucleotide hexaphosphate analogue differs from a nucleotide hexaphosphate by having a tag attached to the terminal phosphate thereof, comprising:

(a) contacting a nucleotide triphosphate with 1,1'-carbonyldiimidazole/dimethylformamide under conditions permitting formation of the following structure:

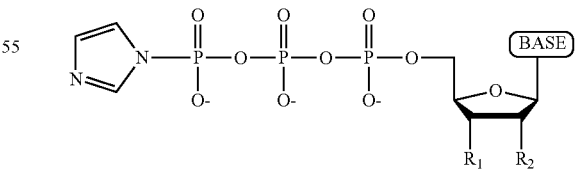

wherein $R_1$ is OH, wherein $R_2$ is H or OH, wherein the base is adenine, guanine, cytosine, thymine, uracil, a 7-deazapurine, or a 5-methylpyrimidine;

(b) contacting the product resulting from step a) with a triphosphate group under conditions permitting formation of a nucleotide hexaphosphate; and (c) contacting the nucleotide hexaphosphate with carbonyldiimidazole/dimethylfortnamide and a tag having a hydroxyl or amino group attached thereto so as to form the nucleotide hexaphosphate analogue.

A compound having the structure:

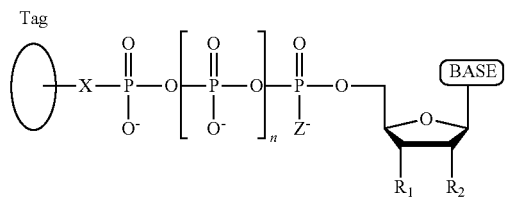

wherein the tag is ethylene glycol, an amino acid, a carbohydrate, a dye, mononucleotide, dinucleotide, trinucleotide, tetranucleotide, pentanucleotide or hexanucleotide, wherein $R_1$ is OH, wherein $R_2$ is H or OH, wherein X is O, NH, S or $CH_2$, wherein Z is O, S, or $BH_3$, wherein the base is adenine, guanine, cytosine, thymine, uracil, a 7-deazapurine, or a 5-methylpyrimidine, and wherein n is 1, 2, 3, or 4.

In an embodiment $R_2$ is H. In an embodiment $R_2$ is OH.

Figure 27:
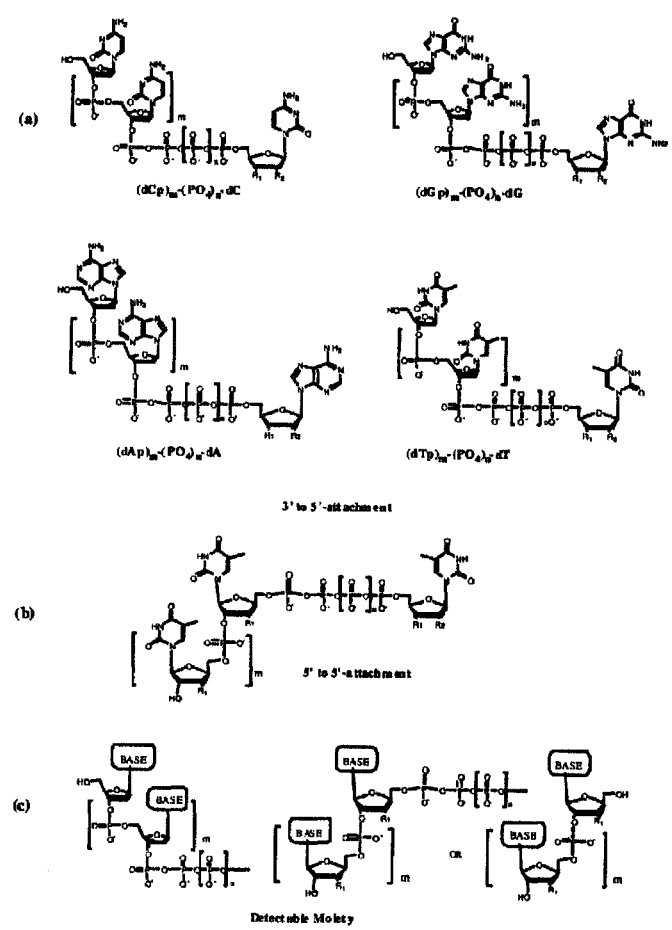
FIG. 27 shows a) oligo-3' to 5'-phosphate attachment, b) oligo-5' to 5'-phosphate attachment, c) detectable moiety after polymerase reaction.

In some instances a tag is chosen from the molecules (dCp)m, (dGp)m, (dAp)m, and (dTp)m. FIG. 27(a) shows some examples of these molecules attached to a nucleotide. For instance, a compound having the structure:

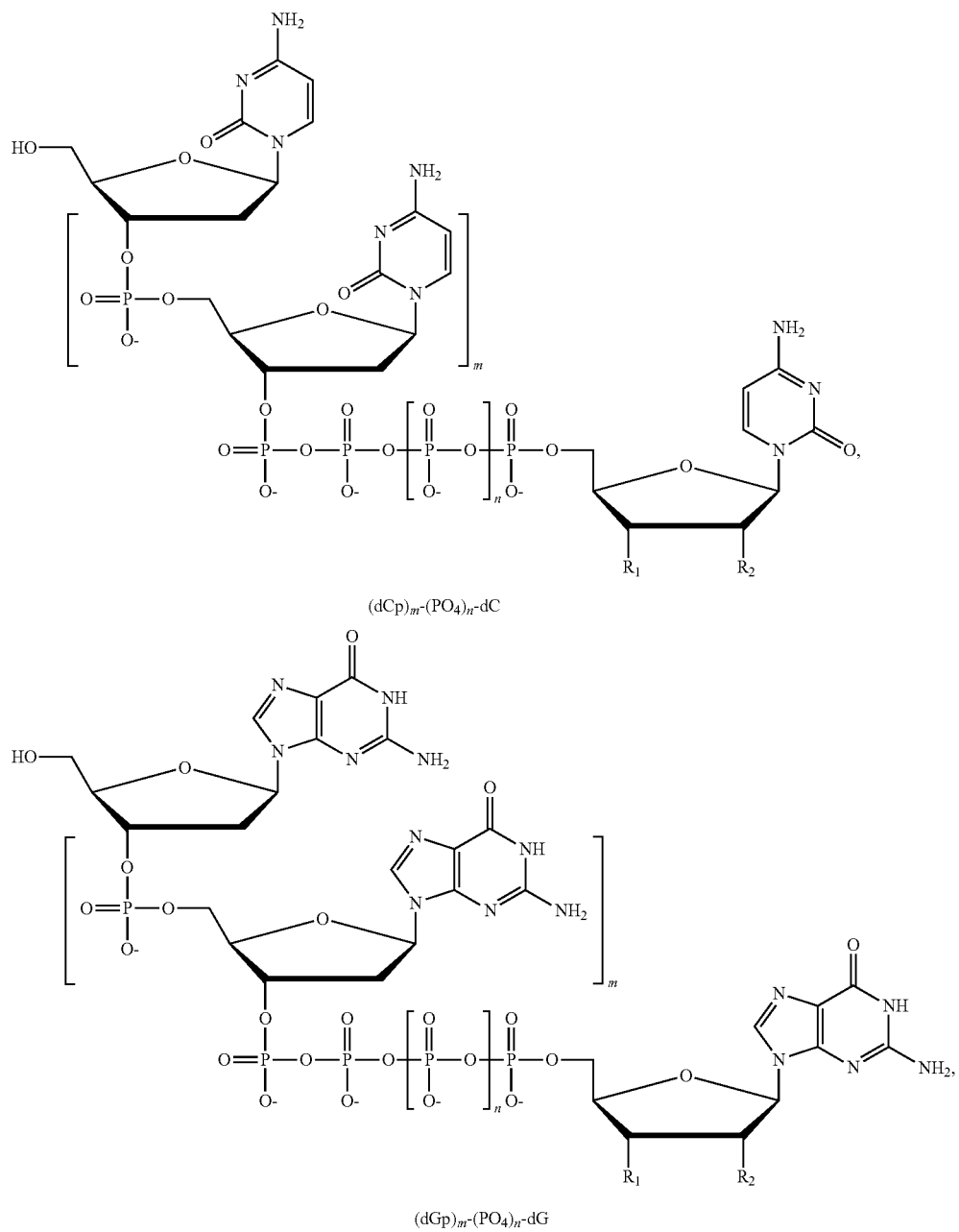

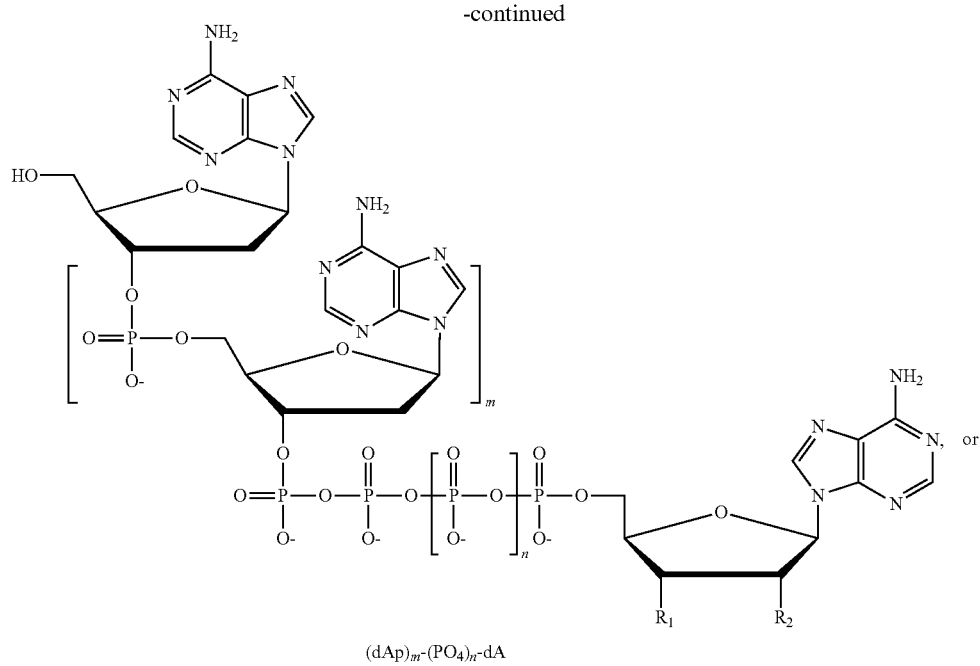

(dAp)$_m$-(PO$_4$)$_n$-dA

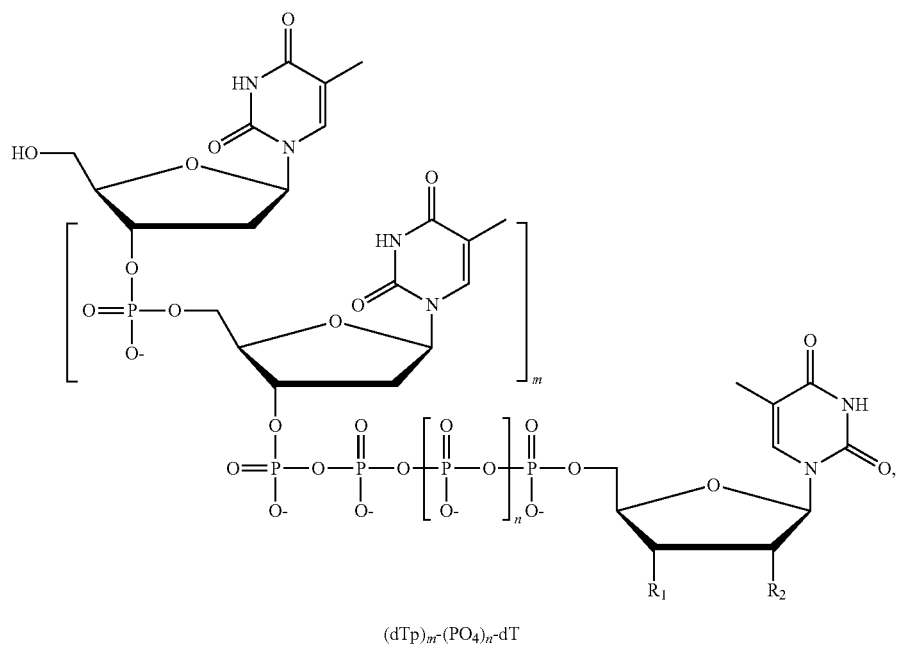

(dTp)$_m$-(PO$_4$)$_n$-dT wherein in each structure n is, independently, 1, 2, 3, or 4, and m is, independently, an integer from 0 to 100, and wherein when m is 0 the terminal phosphate of the dNTP is bonded directly to the 3' O atom of the nucleoside shown on the left hand side of the structure, wherein R$_1$ is —OH or —O—CH$_2$N$_3$, and R$_2$ is H or OH. In some cases, the value of n is different for each type of base.

In an embodiment m is from 0 to 50. In an embodiment m is from 0 to 10. In an embodiment R$_1$ is —OH. In an embodiment R$_2$ is —H. In an embodiment R$_2$ is —OH.

A compound having the structure:

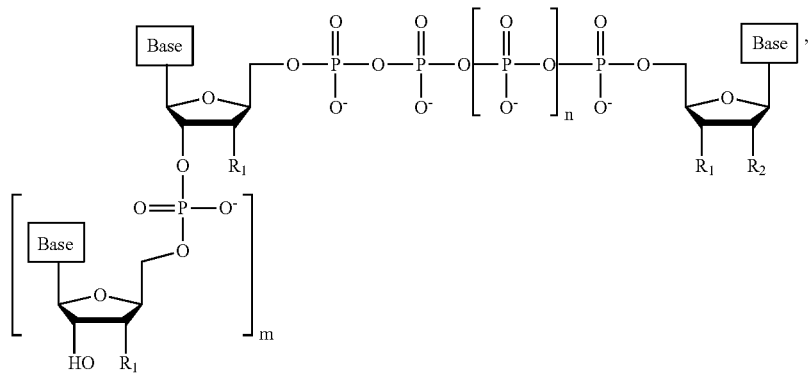

wherein m an integer from 0 to 100, and wherein the compound comprises a single type of base, and wherein the base is adenine, guanine, cytosine, uracil or thymine, or a derivative of one of these bases.

In an embodiment m is from 0 to 50. In an embodiment m is from 0 to 10.

In an embodiment the compound has the structure:

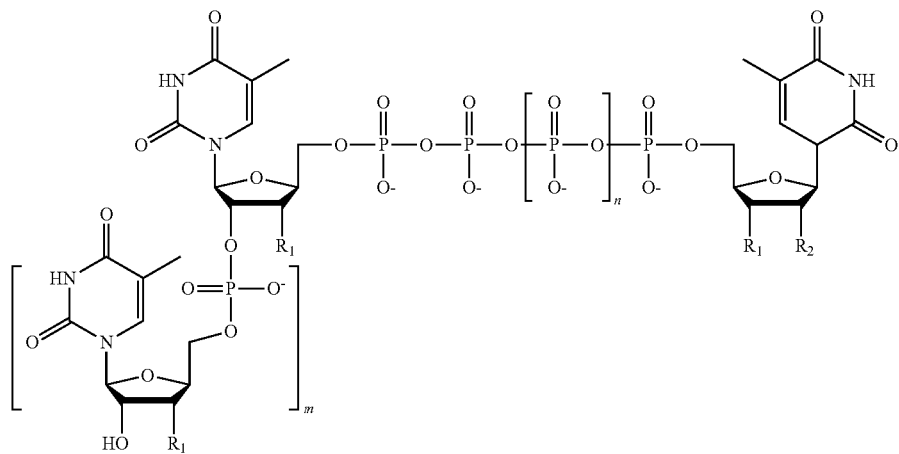

wherein m is an integer from 0 to 100.

A compound having the structure:

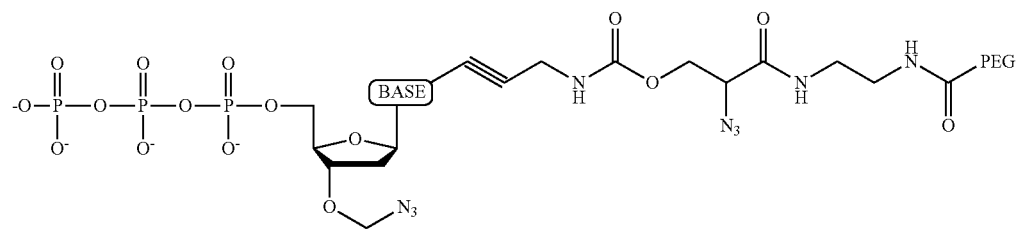

wherein the base is adenine, guanine, cytosine, thymine, uracil, a 7-deazapurine or a 5-methylpyrimidine.

A compound having the structure:

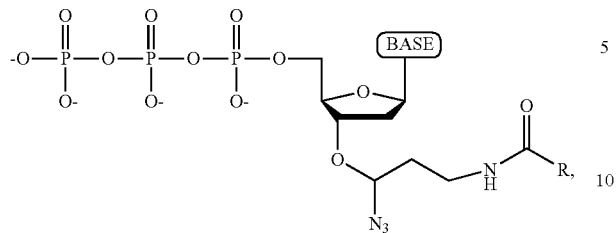

wherein the base is adenine, guanine, cytosine, thymine, uracil, a 7-deazapurine or a 5-methylpyrimidine, and R is a substituted or unsubstituted hydrocarbyl, up to 3000 daltons.

A compound having the structure:

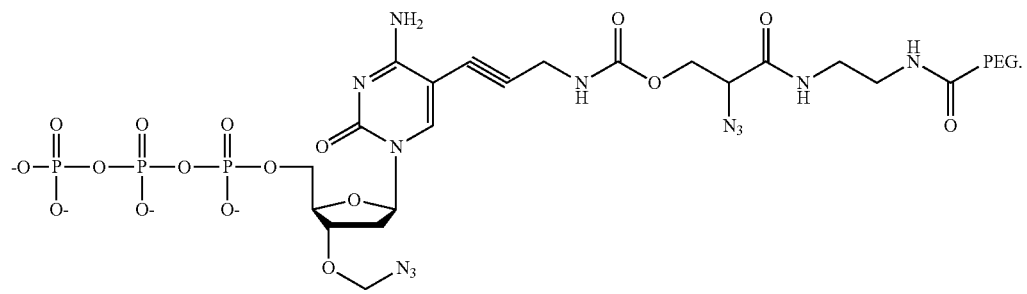

A compound having the structure:

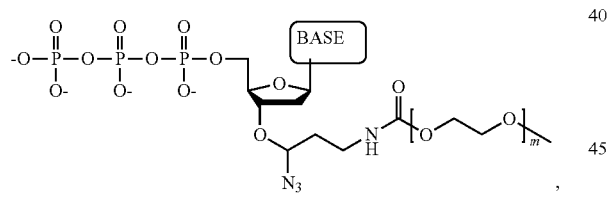

wherein the base is adenine, guanine, cytosine, thymine, uracil, a 7-deazapurine, or a 5-methylpyrimidine, and m is an integer from 1-50.

A compound having the structure:

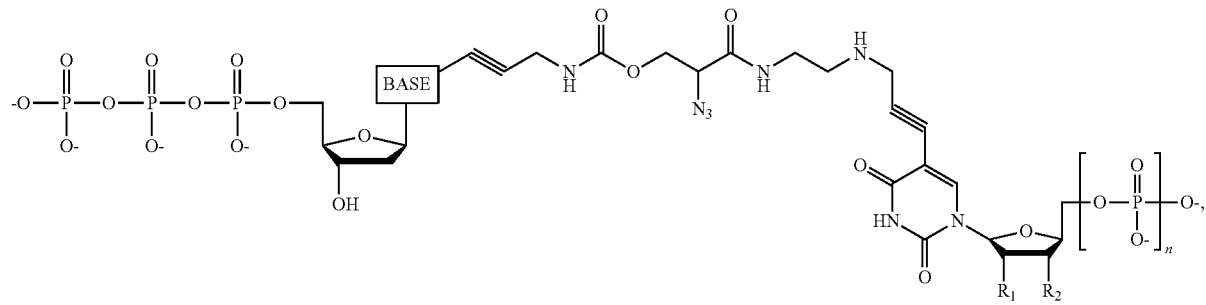

wherein n is 1 or 2 and the base is adenine, guanine, cytosine, thymine, uracil, a 7-deazapurine, or a 5-methylpyrimidine.

A compound having the structure:

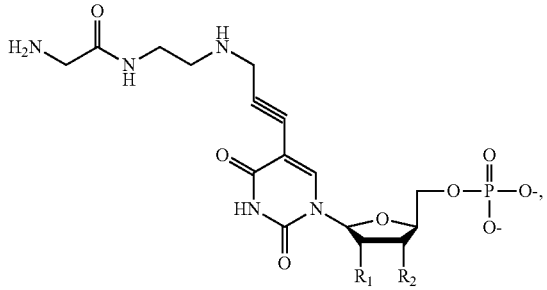

-continued

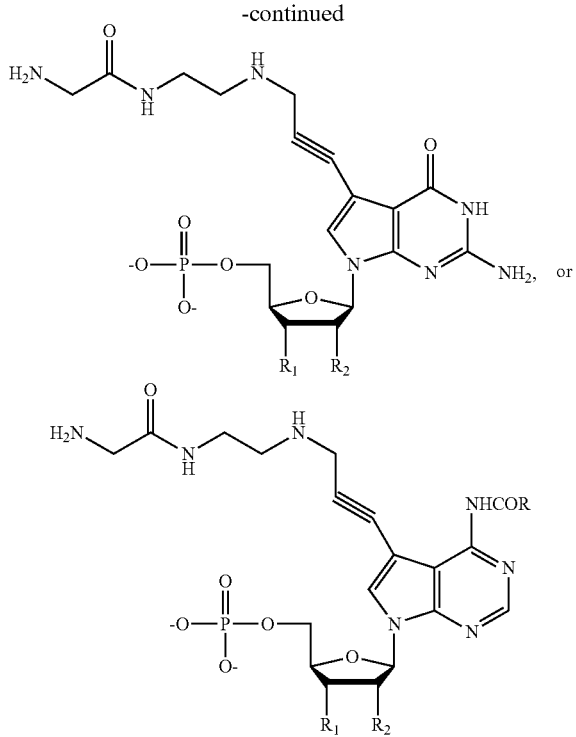

wherein $R_1$ is —OH or —O—$CH_2N_3$, and $R_2$ is H or OH.

A method for determining the nucleotide sequence of a single-stranded RNA comprising:

(a) contacting the single-stranded RNA, wherein the single-stranded RNA is in an electrolyte solution in contact with a nanopore in a membrane and wherein the single-stranded RNA has a primer hybridized to a portion thereof, with a RNA polymerase and four ribonucleotide polyphosphate (rNPP) analogues at least one of which can hybridize with each of an A, U, G, or C nucleotide in the RNA being sequenced under conditions permitting the RNA polymerase to catalyze incorporation of one of the rNPP analogues into the primer if it is complementary to the nucleotide residue of the single-stranded RNA which is immediately 5' to a nucleotide residue of the single-stranded RNA hybridized to the 3' terminal nucleotide residue of the primer, so as to form a RNA extension product, wherein each of the four rNPP analogues has the structure:

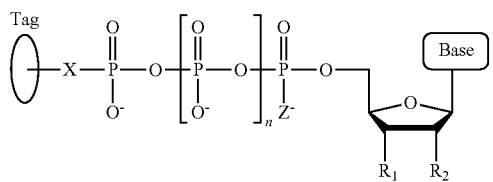

wherein the base is adenine, guanine, cytosine, thymine or uracil, or a derivative of one or more of these bases, wherein $R_1$ is OH, wherein $R_2$ is OH, wherein X is O, NH, S, or $CH_2$, wherein n is 1, 2, 3, or 4, wherein Z is O, S, or $BH_3$, and with the proviso that (i) the type of base on each rNPP analogue is different from the type of base on each of the other three rNPP analogues, and (ii) either the value of n of each rNPP analogue is different from the value of n of each of the other three rNPP analogues, or the value of n of each of the four rNPP analogues is the same and the type of tag on each rNPP analogue is different from the type of tag on each of the other three rNPP analogues, wherein incorporation of the rNPP analogue results in release of a polyphosphate having the tag attached thereto; and (b) identifying which rNPP analogue has been incorporated into the primer to form the RNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or for each different type of tag, whichever is applicable, thereby permitting identifying the nucleotide residue in the single-stranded RNA complementary to the incorporated rNPP analogue; and (c) repeatedly performing step (b) for each nucleotide residue of the single-stranded RNA being sequenced, wherein in each iteration of step (b) identify which rNPP analogue has been incorporated into the RNA extension product in step (a), wherein the rNPP analogue is located immediately 5' to a nucleotide residue of the single-stranded RNA hybridized to the 3' terminal nucleotide residue of the RNA extension product, thereby determining the nucleotide sequence of the single-stranded RNA.

A method for determining the nucleotide sequence of a single-stranded RNA comprising:

(a) contacting the single-stranded RNA, wherein the single-stranded RNA is in an electrolyte solution in contact with a nanopore in a membrane and wherein the single-stranded RNA has a primer hybridized to a portion thereof, with a RNA polymerase and a ribonucleotide polyphosphate (rNPP) analogue which can hybridize to an A, U, G, or C nucleotide in the RNA being sequenced under conditions permitting the RNA polymerase to catalyze incorporation of the rNPP analogue into the primer if it is complementary to the nucleotide residue of the single-stranded RNA which is immediately 5' to a nucleotide residue of the single-stranded RNA hybridized to the 3' terminal nucleotide residue of the primer, so as to form a RNA extension product, wherein the rNPP analogue has the structure:

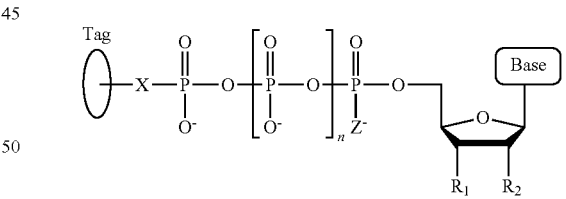

wherein the base is adenine, guanine, cytosine, uracil, or a derivative of one of these bases, wherein $R_1$ is —OH, —O—$CH_2N_3$, or —O-2-nitrobenzyl, wherein $R_2$ is —OH, wherein X is O, NH, S, or $CH_2$, wherein n is 1, 2, 3, or 4, wherein Z is O, S, or $BH_3$, and wherein if the rNPP analogue is not incorporated, iteratively repeating the contacting with a different rNPP analogue until a rNPP analogue is incorporated, with the proviso that (i) the type of base on each rNPP analogue is different from the type of base on each of the other rNPP analogues, and (ii) either the value of n of each rNPP analogue is different from the value of n of each of the other rNPP analogues, or the value of n of each of the rNPP analogues is the same and the type of tag on each rNPP analogue is different from the type of tag on each of the three rNPP analogues, wherein incorporation of the rNPP analogue results in release of a polyphosphate having the tag attached thereto;

(b) identifying which rNPP analogue has been incorporated into the primer to form the RNA extension product in step (a) by applying a voltage across the membrane and measuring an electronic change across the nanopore resulting from the polyphosphate having the tag attached thereto generated in step (a) translocating through the nanopore, wherein the electronic change is different for each value of n, or different for each type of tag, whichever is applicable, thereby permitting identifying the nucleotide residue in the single-stranded RNA complementary to the incorporated rNPP analogue;

(c) repeatedly performing steps (a) and (b) for each nucleotide residue of the single-stranded RNA being sequenced, wherein in each iteration of step (a) the rNPP analogue is incorporated into the RNA extension product if it is complementary to the nucleotide residue of the single-stranded RNA which is immediately 5' to a nucleotide residue of the single-stranded RNA hybridized to the 3' terminal nucleotide residue of the RNA extension product, thereby determining the nucleotide sequence of the single-stranded RNA.

In an embodiment the dNPP analogue has the structure:

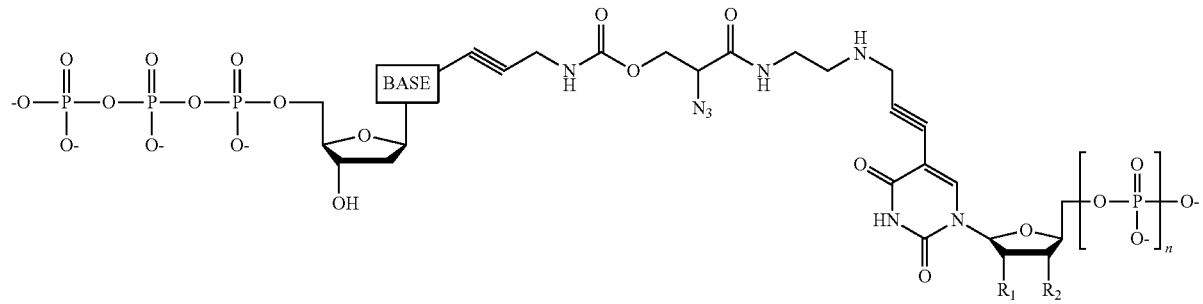

wherein n is 1 or 2 and the base is adenine, guanine, cytosine, thymine, uracil, a 7-deazapurine, or a 5-methylpyrimidine.

In an embodiment the biological nanopore is integrated with CMOS electronics. In another embodiment the solid-state nanopore is integrated with CMOS electronics.

In an embodiment the attachment to the solid surface is via biotin-streptavidin linkages. In another embodiment the DNA polymerase is attached to the solid surface via gold surface modified with an alkanethiol self-assembled monolayer functionalized with amino groups, wherein the amino groups are modified to NHS esters for attachment to amino groups on the DNA polymerase.

In one embodiment the dNPP analogue is a terminal-phosphate-tagged nucleoside-polyphosphate. In a further embodiment each type of dNPP analogue has a polyethylene glycol tag which differs in size from the polyethylene glycol tags of each of the other three types of dNPP analogues.

In some cases, the tag is a polymer. Polyethylene glycol (PEG) is an example of a polymer. In one embodiment the tag has the structure as follows:

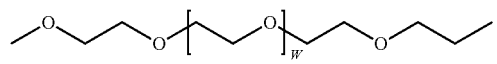

wherein W is an integer between 0 and 100. Any number of ethylene glycol units (W) may be used. In some instances, W is an integer between 0 and 100. In some cases, the number of ethylene glycol units is different for each type of nucleotide. In an embodiment, the four types of nucleotides comprise tags having 16, 20, 24, or 36 ethylene glycol units. In some cases, the tag further comprises an additional identifiable moiety, such as a coumarin based dye.

In some cases, a tag comprises multiple PEG chains. An example of such tag has the structure as follows:

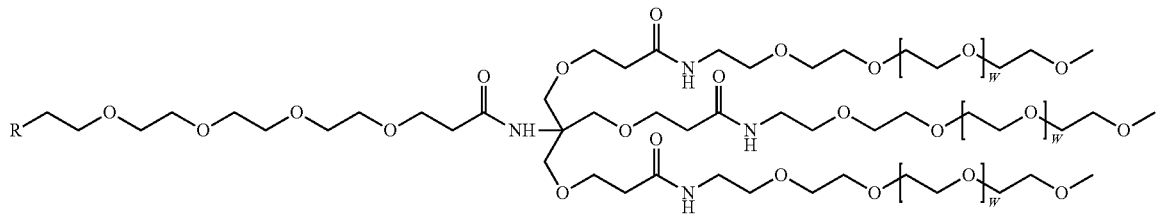

wherein R is $NH_2$, OH, COOH, CHO, SH, or $N_3$, and W is an integer from 0 to 100.

A composition comprising at least four deoxynucleotide polyphosphate (dNPP) analogues, each having a structure selected from the structures set forth in claims 74 and 75, wherein each of the four dNPP analogues comprises a type of base which is different from the type of base of the other three dNPP analogues.

In one embodiment, each of the four dNPP analogues has a polyethylene glycol tag which is different in size from the polyetheylene glycol tags of each of the other three dNPP analogues.

In an embodiment, the net charge on the tagged nucleoside polyphosphate is neutral. In another embodiment, the released tag has a positive charge.

In one embodiment, the method further comprising a step of treating with alkaline phosphatase after step b), wherein the alkaline phosphatase hydrolyzes free phosphate groups on the released tag-pyrophosphate.

In one embodiment multiple copies of the single-stranded DNA are immobilized on a bead.

Figure 51:
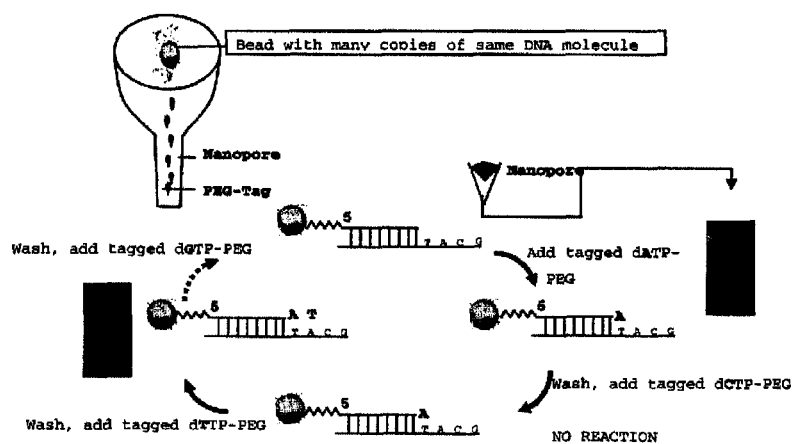
FIG. 51 shows sequencing by synthesis with PEG-nucleotides and nanopore detection (many copies of the same DNA molecule immobilized on a bead and addition of one PEG-nucleotide at a time); use same PEG attached to the all four nucleotides; add one PEG-nucleotide at a time, reads at least one base per cycle if correct nucleotide is incorporated.

A method as shown in FIG. 51 for determining the nucleotide sequence of multiple copies of the same single-stranded DNA molecule comprising:

(a) treating the single-stranded DNA in an electrolyte solution in contact with a nanopore in a membrane and wherein the DNA has a primer hybridized to a portion thereof, with a DNA polymerase and successively which each of four tagged deoxyribonucleotide analogues which can hybridize with an A, T, G, or C nucleotide in the DNA being sequenced under conditions permitting the DNA polymerase to catalyze incorporation of the analogue onto the end of an extension product of the primer if it is complementary to the nucleotide residue of the DNA being sequenced immediately 5' to a nucleotide residue of the single-stranded DNA being sequenced hybridized to 3' terminal nucleotide residue of the primer, wherein if the analogue is not incorporated, iteratively repeating the contacting with a different analogue until an analogue is incorporated, with the proviso that (i) the type of base on each analogue is different from the type of base on each of the other analogues, and (ii) the type of tag on each analogue is different from the type of tag on each of the other analogues, wherein incorporation of the analogue results in release of the tag;

(b) identifying the analogue which has been incorporated into the extension product in step (a) by applying a voltage across the membrane and measuring an electric change across the nanopore resulting from the tag attached to the analogue; and (c) repeatedly performing steps (a) and (b), thereby obtain the nucleotide sequence of the single-stranded DNA.

Figure 52:
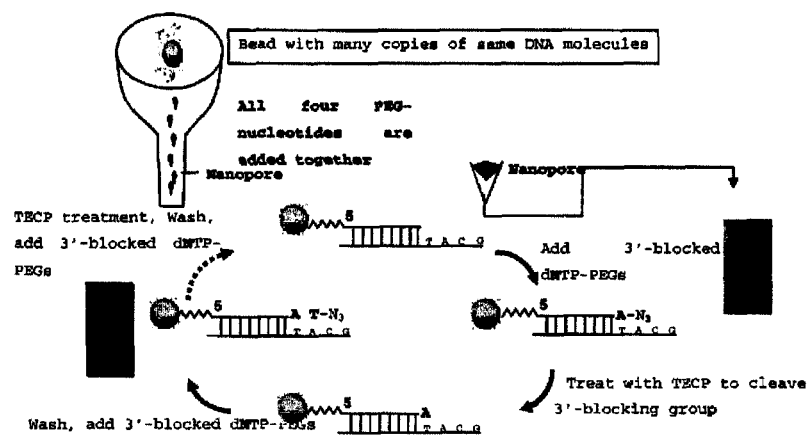
FIG. 52 shows sequencing by synthesis with 3'-O-blocked-PEG-nucleotides and nanopore detection (many copies of same DNA molecule immobilized on a bead and addition of all four 3'-O-blocked-PEG-nucleotides at same time); add all four 3'-blocked, different size PEG attached nucleotides (3'-blocked dNTP-PEGs) together; detection of the incorporated nucleotide based on the blockade signal of the released PEGs; the 3'-blocking group is removed by TECP treatment and continued cycle for correctly sequencing the template including homopolymeric regions.

A method as shown in FIG. 52 for determining the nucleotide sequence of multiple copies of the same single-stranded DNA molecule comprising:

(a) treating the single-stranded DNA in an electrolyte solution in contact with a nanopore in a membrane and wherein the DNA has a primer hybridized to a portion thereof, with a DNA polymerase and four 3'-blocked doxyribonucleotide analogues at least one of which can hybridize with each of an A, T, G, or C nucleotide in the DNA being sequenced under conditions permitting the DNA polymerase to catalyze incorporation of the analogue onto the end of an extension product of the primer if it is complementary to the nucleotide residue of the DNA being sequenced immediately 5' to a nucleotide residue of the single-stranded DNA being sequenced hybridized to 3' terminal nucleotide residue of the primer, wherein each analogue comprises a reversible terminator, with the proviso that (i) the type of base on each analogue is different from the type of base on each of the other three analogues, and (ii) the tag on each analogue is different from the tag on each of the other three analogues, wherein incorporation of the analogue results in release of the tag;

(b) identifying the analogue which has been incorporated into the extension product in step (a) by applying a voltage across the membrane and measuring an electric change across the nanopore resulting from the tag attached to the analogue;

(c) remove the reversible terminator from the analogue which has been incorporated into the extension product in step (a); and (d) repeatedly performing steps (b) and (c), thereby obtain the nucleotide sequence of the single-stranded DNA.

In one embodiment, the nanopore is integrated directly into a CMOS die as shown in FIG. 46.

It is contemplated that the nanopore has a negative charge or alternatively, has a charge which is opposite in sign to the charge of the tag or of the polyphosphate having the tag attached thereto.

In one embodiment, the rate of incorporation of the nucleotide analogue by the polymerase is less than, or alternatively, is the same as, the rate of translocation of the tag or the polyphosphate having the tag attached thereto through the nanopore, The invention further comprises obtaining the single-stranded DNA or RNA to be sequenced from a double-stranded DNA or RNA prior to step (a).

In one embodiment, the polymerase is attached to the nanopore.

It is contemplated that the tag is detectable based on size, length, shape, mass, charge, or any combinations thereof.

It is contemplated that various embodiments of the conductance measurement system also are applicable to the method for determining nucleotide sequence, and vice versa.

The present invention also provides a compound having the structure of any of the compounds set forth in the figures and/or schemes of the present application.

The present invention also provides a dNPP analogue comprising a tag having the structure of any of the tags set forth in the figures and/or schemes of the present application.

In an embodiment, the tag is a hydrocarbyl, substituted or unsubstituted, such as an alkyl, alkenyl, alkynyl, and having a mass of 3000 daltons or less.

In an embodiment the single-stranded DNA, RNA, primer or probe is bound to a solid substrate via 1,3-dipolar azide-alkyne cycloaddition chemistry. In an embodiment the DNA, RNA, primer or probe is bound to a solid substrate via a polyethylene glycol molecule. In an embodiment the DNA, RNA, primer or probe is alkyne-labeled. In an embodiment the DNA, RNA, primer or probe is bound to a solid substrate via a polyethylene glycol molecule and a solid substrate is azide-functionalized in an embodiment the DNA, RNA, primer or probe is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. In an embodiment the DNA is single-stranded DNA. In an embodiment the RNA is single-stranded RNA.

In an embodiment the solid substrate is in the form of a chip, a bead, a well, a capillary tube, a slide, a wafer, a filter, a fiber, a porous media, a porous nanotube, or a column. This invention also provides the instant method, wherein the solid substrate is a metal, gold, silver, quartz, silica, a plastic, polypropylene, a glass, or diamond. This invention also provides the instant method, wherein the solid substrate is a porous non-metal substance to which is attached or impregnated a metal or combination of metals. The solid surface may be in different forms including the non-limiting examples of a chip, a bead, a tube, a matrix, a nanotube. The solid surface may be made from materials common for DNA microarrays, including the non-limiting examples of glass or nylon. The solid surface, for example beads/micro-beads, may be in turn immobilized to another solid surface such as a chip.

In an embodiment nucleic acid samples, DNA, RNA, primer or probe are separated in discrete compartments, wells or depressions on a surface or in a container.

This invention also provides the instant method, wherein about 1000 or fewer copies of the nucleic acid sample, DNA, RNA, primer or probe, are bound to the solid surface. This invention also provides the instant invention wherein $2 \times 10^7$, $1 \times 10^7$, $1 \times 10^6$ or $1 \times 10^4$ or fewer copies of the nucleic acid sample, DNA, RNA, primer or probe are bound to the solid surface.

In an embodiment the immobilized nucleic acid sample, DNA, RNA, primer or probe is immobilized at a high density. This invention also provides the instant invention wherein over or up to $1 \times 10^7$, $1 \times 10^8$, $1 \times 10^9$ copies of the nucleic acid sample, DNA, RNA, primer or probe, are bound to the solid substrate.

In an embodiment the DNA polymerase is 9° N polymerase or a variant thereof, *E. Coli* DNA polymerase I, Bacteriophage T4 DNA polymerase, Sequenase, Taq DNA polymerase or 9° N polymerase (exo-)A485UY409V.

In an embodiment of the methods or of the compositions described herein, the DNA is single-stranded. In an embodiment of the methods or of the compositions described herein, the RNA is single-stranded, Phi29, or variants thereof.

In an embodiment of the methods described for RNA sequencing, the polymerase is an RNA polymerase, reverse transcriptase or appropriate polymerase for RNA polymerization.

The linkers may be photocleavable. In an embodiment UV light is used to photochemically cleave the photochemically cleavable linkers and moieties. In an embodiment, the photocleavable linker is a 2-nitrobenzyl moiety.

The —CH$_2$N$_3$ group can be treated with TCEP (tris(2-carboxyethyl)phosphine) so as to remove it from the 3' O atom of a dNPP analogue, or rNPP analogue, thereby creating a 3' OH group.

A tag may be released in any manner. In some cases, the tag is attached to polyphosphate (e.g., FIG. 34) and incorporation of the nucleotide into a nucleic acid molecule results in release of a polyphosphate having the tag attached thereto. The incorporation may be catalyzed by at least one polymerase, optionally attached to the nanopore. In some instances, at least one phosphatase enzyme is also attached to the pore. The phosphatase enzyme may cleave the tag from the polyphosphate to release the tag. In some cases, the phosphatase enzymes are positioned such that pyrophosphate produced by the polymerase in a polymerase reaction interacts with the phosphatase enzymes before entering the pore.

In some cases, the tag is not attached to polyphosphate (see, e.g., FIG. 34). In these cases, the tag is attached by a cleavable linker (X). Methods for production of cleavably capped and/or cleavably linked nucleotide analogues are disclosed in U.S. Pat. No. 6,664,079, which is hereby incorporated by reference.

The linker may be any suitable linker and cleaved in any suitable manner. For example, the linkers may be photocleavable. In an embodiment light that is not damaging DNA is used to photochemically cleave the photochemically cleavable linkers and moieties. In an embodiment, the photocleavable linker is a 2-nitrobenzyl moiety. In another embodiment, the —CH$_2$N$_3$ group may be treated with TCEP (tris(2-carboxyethyl)phosphine) so as to remove it from the 3' O atom of a dNPP analogue, or rNPP analogue, thereby creating a 3' OH group.

A "nucleotide residue" is a single nucleotide in the state it exists after being incorporated into, and thereby becoming a monomer of, a polynucleotide. Thus, a nucleotide residue is a nucleotide monomer of a polynucleotide, e.g. DNA, which is bound to an adjacent nucleotide monomer of the polynucleotide through a phosphodiester bond at the 3' position of its sugar and is bound to a second adjacent nucleotide monomer through its phosphate group, with the exceptions that (i) a 3' terminal nucleotide residue is only bound to one adjacent nucleotide monomer of the polynucleotide by a phosphodiester bond from its phosphate group, and (ii) a 5' terminal nucleotide residue is only bound to one adjacent nucleotide monomer of the polynucleotide by a phosphodiester bond from the 3' position of its sugar.

Because of well-understood base-pairing rules, determining the identity (of the base) of dNPP analogue (or rNPP analogue) incorporated into a primer or DNA extension product (or RNA extension product) by measuring the unique electrical signal of the tag translocating through the nanopore, and thereby the identity of the dNPP analogue (or rNPP analogue) that was incorporated, permits identification of the complementary nucleotide residue in the single stranded polynucleotide that the primer or DNA extension product (or RNA extension product) is hybridized to. Thus, if the dNPP analogue that was incorporated comprises an adenine, a thymine, a cytosine, or a guanine, then the complementary nucleotide residue in the single stranded DNA is identified as a thymine, an adenine, a guanine or a cytosine, respectively. The purine adenine (A) pairs with the pyrimidine thymine (T). The pyrimidine cytosine (C) pairs with the purine guanine (G). Similarly, with regard to RNA, if the rNPP analogue that was incorporated comprises an adenine, an uracil, a cytosine, or a guanine, then the complementary nucleotide residue in the single stranded RNA is identified as an uracil, an adenine, a guanine or a cytosine, respectively.

Incorporation into an oligonucleotide or polynucleotide (such as a primer or DNA extension strand) of a dNPP or rNPP analogue means the formation of a phosphodiester bond between the 3' carbon atom of the 3' terminal nucleotide residue of the polynucleotide and the 5' carbon atom of the dNPP analogue or rNPP analogue, respectively.

As used herein, unless otherwise specified, a base (e.g. of a nucleotide polyphosphate analogue) which is different from the type of base of a referenced molecule, e.g. another nucleotide polyphosphate analogue, means that the base has a different chemical structure from the other/reference base or bases. For example, a base that is different from adenine can include a base that is guanine, a base that is uracil, a base that is cytosine, and a base that is thymine. For example, a base that is different from adenine, thymine, and cytosine can include a base that is guanine and a base that is uracil.

As used herein, unless otherwise specified, a tag (e.g. of a nucleotide polyphosphate analogue) which is different from the type of tag of a referenced molecule, e.g. another nucleotide polyphosphate analogue, means that the tag has a different chemical structure from the chemical structure of the other/referenced tag or tags.

Tags may flow through a nanopore after they are released from the nucleotide. In some instances, a voltage is applied to pull the tags through the nanopore. At least about 85%, at least 90%, at least 95%, at least 99%, at least 99.9 or at least 99.99% of the released tags may translocate through the nanopore.

In some instances of the method, a polymerase draws from a pool of tagged nucleotides comprising a plurality of different bases (e.g., A, C, G, T, and/or U). It is also possible to iteratively contact the polymerase with the various types of tagged bases. In this case, it may not be necessary that each type of nucleotide have a unique base, but the cycling between different base types adds cost and complexity to the process in some cases, nevertheless this embodiment is encompassed in the present invention.

FIG. 9 shows that incorporation of the tagged nucleotide into a nucleic acid molecule (e.g., using a polymerase to extend a primer base paired to a template) releases a detectable TAG-polyphosphate. In some cases, the TAG-polyphosphate is detected as it passes through the nanopore. It is even possible to distinguish the nucleotide based on the number of phosphates comprising the polyphosphate (e.g., even when the TAGs are identical). Nevertheless, each type of nucleotide generally has a unique tag.

With reference to FIG. 28, the TAG-polyphosphate compound may be treated with phosphatase (e.g., alkaline phosphatase) before passing the tag through a nanopore and measuring the ionic current.

The tag may be detected in the nanopore (at least in part) because of its charge. In some instances, the tag compound is an alternatively charged compound which has a first net charge and, after a chemical, physical or biological reaction, a different second net charge. In some instance, the magnitude of the charge on the tag is the same as the magnitude of the charge on the rest of the compound. In an embodiment, the tag has a positive charge and removal of the tag changes the charge of the compound.

In some cases, as the tag passes through the nanopore, it may generate an electronic change. In some cases the electronic change is a change in current amplitude, a change in conductance of the nanopore, or any combination thereof.

"Nanopore" as used herein, generally refers to a pore, channel or passage formed or otherwise provided in a barrier/membrane. "Nanopore" includes, for example, a structure comprising (a) a first and a second compartment separated by a physical barrier, which barrier has at least one pore with a diameter, for example, of from about 1 to 10 nm, and (b) a means for applying an electric field across the barrier so that a charged molecule such as DNA, nucleotide, nucleotide analogue, or tag, can pass from the first compartment through the pore to the second compartment. The nanopore ideally further comprises a means for measuring the electronic signature of a molecule passing through its barrier. The nanopore barrier may be synthetic or naturally occurring in part. A barrier/membrane may be an organic membrane, such as a lipid bilayer, or a synthetic membrane, such as a membrane formed of a polymeric material. Barriers can include, for example, lipid bilayers having therein alpha-hemolysin, oligomeric protein channels such as porins, and synthetic peptides and the like. Barriers can also include inorganic plates having one or more holes of a suitable size. The nanopore may be disposed adjacent or in proximity to a sensing circuit, such as, for example, a complementary metal-oxide semiconductor (CMOS) or field effect transistor (FET) circuit. A nanopore may have a characteristic width or diameter on the order of 0.1 nanometers (nm) to about 1000 nm. The nanopore may be biological or synthetic. It is also contemplated that the pore is proteinaceous, alpha hemolysin is an example of a protein nanopore. An example of a synthetic nanopore is a solid-state pore or graphene. Herein "nanopore", "nanopore barrier" and the "pore" in the nanopore barrier are sometimes used equivalently.

In some cases, polymerase enzymes and/or phosphatase enzymes are attached to the nanopore. Fusion proteins or disulfide crosslinks are example of methods for attaching to a proteinaceous nanopore. In the case of a solid state nanopore, the attachment to the surface near the nanopore may be via biotin-streptavidin linkages. In an example the DNA polymerase is attached to a solid surface via gold surface modified with an alkanethiol self-assembled monolayer functionalized with amino groups, wherein the amino groups are modified to NHS esters for attachment to amino groups on the DNA polymerase.

Described herein are methods, devices and systems for sequencing nucleic acids using a nanopore. The methods may accurately detect individual nucleotide incorporation events, such as upon the incorporation of a nucleotide into a growing strand that is complementary to a template. An enzyme (e.g., DNA polymerase) may incorporate nucleotides to a growing polynucleotide chain, wherein the added nucleotide is complimentary to the corresponding template nucleic acid strand which is hybridized to the growing strand (e.g., polymerase chain reaction (PCR)). These nucleotide incorporation events release tags from the nucleotides which pass through a nanopore and are detected. In this way, the incorporated base may be identified (i.e., A, C, G, T or U) because a unique tag is released from each type of nucleotide (i.e., A, C, G, T or U).

Nucleotide incorporation events may be detected in real-time (i.e., as they occur) and with the aid of a nanopore. In some instances, an enzyme (e.g., DNA polymerase) attached to or in proximity to the nanopore may facilitate the flow of a nucleic acid molecule through a nanopore. A nucleotide incorporation event, or the incorporation of a plurality of nucleotides, may release one or more tag molecules (also "tags" herein), which may be detected by a nanopore as the tags flow through the nanopore. In some cases, an enzyme attached to or in proximity to the nanopore may aid in detecting tags or other by-products released upon the incorporation of one or more nucleotides.

Methods described herein may be single-molecule methods. That is, the signal that is detected is generated by a single molecule (i.e., single nucleotide incorporation) and is not generated from a plurality of clonal molecules. The method may not require DNA amplification.

Nucleotide incorporation events may occur from a mixture comprising a plurality of nucleotides (e.g., deoxyribonucleotide triphosphate (dNTP where N is adenosine (A), cytidine (C), thymidine (T), guanosine (G), or uridine (U)). Nucleotide incorporation events do not necessarily occur from a solution comprising a single type of nucleotide (e.g., dATP). Nucleotide incorporation events do not necessarily occur from alternating solutions of a plurality of nucleotides (e.g., dATP, followed by dCTP, followed by dGTP, followed by dTTP, followed by dATP).

Nanopore devices and systems of the present disclosure may be combined with or modified by other nanopore devices, such as those described in U.S. Pat. Nos. 7,005,264 B2; 7,846,738; 6,617,113; 6,746,594; 6,673,615; 6,627,067; 6,464,842; 6,362,002; 6,267,872; 6,015,714; 5,795,782; and U.S. Publication Nos. 2004/0121525, 2003/0104428, and 2003/0104428, each of which is entirely incorporated herein by reference.

In an embodiment of the molecules and the methods disclosed herein the tag is attached to the remainder of the molecule by a chemical linker which is cleavable.

In an embodiment the nanpore is in a solid-state membrane. In an embodiment the membrane is a silicon nitride membrane. In an embodiment the nanopore is a biopore. In an embodiment the pore is proteinaceous. In an embodiment the pore is an alpha-hemolysin pore. In an embodiment the pore is a graphene pore.

In an embodiment the DNA, RNA or single stranded nucleic acid is located on one side of the membrane in which the nanopore is located and the membrane is located in a conducting electrolyte solution.

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

All combinations of the various elements described herein are within the scope of the invention. All sub-combinations of the various elements described herein are also within the scope of the invention.

Methods for sequencing nucleic acids may include retrieving a biological sample having the nucleic acid to be sequenced, extracting or otherwise isolating the nucleic acid sample from the biological sample, and in some cases preparing the nucleic acid sample for sequencing.

Provided herein are systems and methods for sequencing a nucleic acid molecule with the aid of a nanopore. The nanopore may be formed or otherwise embedded in a membrane disposed adjacent to a sensing circuit, such as a field effect transistor or a complementary metal-oxide semiconductor (CMOS). In some cases, as a nucleic acid or tag flows through the nanopore, the sensing circuit detects an electrical signal associated with the nucleic acid or tag. The nucleic acid may be a subunit of a larger strand. The tag may be a byproduct of a nucleotide incorporation event or other interaction between a tagged nucleic acid and the nanopore or a species adjacent to the nanopore, such as an enzyme that cleaves a tag from a nucleic acid.

Byproducts of nucleotide incorporation events may be detected by the nanopore. "Nucleotide incorporation events" are the incorporation of a nucleotide into a growing polynucleotide chain. A byproduct may be correlated with the incorporation of a given type nucleotide. The nucleotide incorporation events are generally catalyzed by an enzyme, such as DNA polymerase, and use base pair interactions with a template molecule to choose amongst the available nucleotides for incorporation at each location.

In some cases, the DNA polymerase is 9° N polymerase or a variant thereof, E. Coli DNA polymerase Bacteriophage T4 DNA polymerase, Sequenase, Taq DNA polymerase, 9° N polymerase (exo-)A485L/Y409V or Phi29 DNA Polymerase (φ29 DNA Polymerase).

A nucleic acid sample may be sequenced using tagged nucleotides or nucleotide analogs. In some examples, a method for sequencing a nucleic acid molecule comprises (a) polymerizing tagged nucleotides, wherein a tag associated with an individual nucleotide is released upon polymerization, and (b) detecting the released tag with the aid of a nanopore.

The rate of nucleotide incorporation events is generally slower than (or equal to) the rate at which tags molecules released during the nucleotide incorporation events pass through and/or are detected by the nanopore. Generally, the rate of nucleotide incorporation events is not greater than the rate at which tags molecules released during the nucleotide incorporation events pass through and/or are detected by the nanopore (i.e., otherwise the nucleotide incorporation events are not detected accurately and/or in the correct sequence).

In some cases, a single tag is released upon incorporation of a single nucleotide and detected by a nanopore. In other cases, a plurality of tags is released upon incorporation of a plurality of nucleotides. A nanopore sensor adjacent to a nanopore may detect an individual released tag, or a plurality of released tag. One or more signals associated with plurality of released tags may be detected and processed to yield an averaged signal.

Methods provided herein may accurately distinguish between individual nucleotide incorporation events (e.g., single-molecule events). The methods may accurately distinguish between individual nucleotide incorporation events in a single pass—i.e., without having to re-sequence a given nucleic acid molecule.

A method for nucleic acid sequencing comprises distinguishing between individual nucleotide incorporation events with an accuracy of greater than about $4\sigma$. In some cases, the nucleotide incorporation events are detected with aid of a nanopore. Tags associated with the nucleotides may be released upon incorporation and the tags pass through the nanopore. A different tag may be associated with and/or released from each type of nucleotide (e.g., A, C, T, G) and is detected as it passes through the nanopore. Errors include, but are not limited to, (a) failing to detect a tag, (b) mis-identifying a tag, (c) detecting a tag where there is no tag, (d) detecting tags in the incorrect order (e.g., two tags are released in a first order, but pass each other and are detected in a second order), (e) a tag that has not been released from a nucleotide is detected as being released, or any combination thereof. In some embodiments, the accuracy of distinguishing between individual nucleotide incorporation events is 100% subtracted by the rate at which errors occur (i.e., error rate).

The accuracy of distinguishing between individual nucleotide incorporation events is any suitable percentage. In some instances, the accuracy of distinguishing between individual nucleotide incorporation events is reported in sigma ($\sigma$) units. Sigma is a statistical variable that is sometimes used in business management and manufacturing strategy to report error rates such as the percentage of defect-free products. Here, sigma values may be used interchangeably with accuracy according to the relationship as follows: $4\sigma$ is 99.38% accuracy, $5\sigma$ is 99.977% accuracy, and $6\sigma$ is 99.99966% accuracy.

The method may involve sequencing a template nucleic acid strand by adding tagged nucleotides to a strand complimentary to the template strand and detecting released tag molecules in a nanopore. The methods disclosed herein may be combined with other sequencing methods, such as, for example, those described in U.S. Pat. No. 5,470,724, which is entirely incorporated herein by reference.

This invention will be better understood by reference to the Experimental Details which follow, but those skilled in the art will readily appreciate that the specific experiments detailed are only illustrative of the invention as described more fully in the claims which follow thereafter.

Another aspect of the present disclosure provides a conductance measurement system comprising: (a) a first and a second compartment with a first and a second electrolyte solution separated by a physical barrier, which barrier has at least one pore with diameter on nanometer scale; (b) a means for applying an electric field across the barrier; (c) a means for measuring change in the electric field; (d) at least one polymerase attached to the pore; and (e) more than one phosphatase enzyme attached to the pore.

In some cases, the pore has a diameter of from about 1 to 10 nm. In some cases, the polymerase and the phosphatase enzymes are covalently attached to the pore. In some cases, more phosphatase enzymes than polymerases are attached to the pore. In some cases, the phosphatase enzymes are positioned such that polyphosphate produced by the polymerase in a polymerase reaction interacts with the phosphatase enzymes before entering the pore. In some cases, the rate of interaction between the phosphatase enzymes and the polyphosphate is faster than, or equal to, the rate of the polymerase producing the polyphosphate.

In some cases, each of the first and the second compartments has an electrical charge. In some cases, the interior of the pore has a negative charge. In some cases, the pore is biological or synthetic. In some cases, the pore is proteinaceous. In some cases, the pore is an alpha hemolysin protein. In some cases, the pore is a solid-state pore. In some cases, the pore is formed of graphene.

In some cases, the conductance measurement system further comprises an array of pores each having substantially identical features. In some cases, the conductance measurement system further comprises an array of pores of different diameters. In some cases, the conductance measurement system further comprises an array of pores, wherein the pores are configured to apply different electrical fields across the barrier.

In some cases, the conductance measurement system is integrated with CMOS electronics. In some cases, the pore or array of pores is integrated directly into a CMOS die as shown in FIG. 46.

Another aspect of the present disclosure provides a compound having the structure:

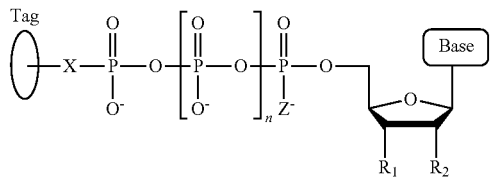

wherein the tag comprises one or more of ethylene glycol, an amino acid, a carbohydrate, a peptide, a dye, a chemilluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof, wherein $R_1$ is OH, wherein $R_2$ is H or OH, wherein X is O, NH, S, or $CH_2$, wherein Z is O, S, or $BH_3$, wherein the base is adenine, guanine, cytosine, thymine, uracil, or a derivative of one of these bases, wherein n is 1, 2, 3, or 4, and wherein the tag has a charge which is reverse in sign relative to the charge on the rest of the compound.

In some cases, the magnitude of the charge on the tag is the same as the magnitude of the charge on the remainder of the compound. In some cases, the tag comprising multiple ethylene glycol units. In some cases, the tag comprises 16, 20, 24, or 36 ethylene glycol units. In some cases, the tag comprises an additional identifiable moiety. In some cases, the additional identifiable moiety is a coumarin based dye. In some cases, the tag has a positive charge. In some cases, removal of the tag changes the charge of the compound. In some cases, the tag further comprises appropriate number of lysines or arginines to balance the number of phosphates.

Another aspect of the present disclosure provides a method for determining the nucleotide sequence of a single-stranded DNA or RNA. In some cases, more phosphatase enzymes than polymerases are attached to the pore. In some cases, the single-stranded DNA or RNA is obtained by denaturing a double-stranded DNA or RNA, whichever is applicable. In some cases, multiple copies of the same single-stranded DNA or RNA are immobilized on a bead. In some cases, the nucleotide sequence of the single-stranded DNA or RNA is determined using multiple copies of the same single-stranded DNA or RNA. In some cases, the method further comprises a washing step after each iteration of step (b) to remove unincoporated compound from contact with the single-stranded DNA or RNA. In some cases, the method further comprises a step after each iteration of step (b) to determine the identity of an additional identifiable moiety attached to the tag. In some cases, at least 85-99% of the released tags translocate through the pore. In some cases, the compound further comprises a reversible terminator. In some cases, the method further comprises a step of removing the reversible terminator after each iteration of step (b). In some cases, the reversible terminator is removed by biological means, chemical means, physical means, or by light irradiation. In some cases, the interior of the pore has a charge which is reverse in sign relative to the charge of the tag or of the polyphosphate having the tag attached thereto. In some cases, each of the first and the second compartments of the conductance measurement system has a charge. In some cases, the charges of the first and the second compartments are opposite in polarity. In some cases, the charges of the first and the second compartments are adjustable. In some cases, the rate of the tag translocating through the pore in step (b) is determined based on the charge of tag and the charges of the first and the second compartments. In some cases, each of the first and the second compartments has a charge such that in step (b) the tag translocates through the pore at a rate which is faster than, or equal to, the rate at which the tag or the polyphosphate having the tag attached thereto is being released in step (a).

Another aspect of the present disclosure provides a method for determining at least one parameter of a compound in a solution. In some cases, the compound is treated with phosphatase before measuring the reduction in the ionic current. In some eases, the compound is an alternatively charged compound which has a fust net charge and, after a chemical, physical or biological reaction, a different second net charge. In some cases, the mathematical analysis is selected from the group consisting of GMM, threshold detection and averaging, and sliding window analysis. In some cases, the at least one parameter is selected from the group consisting of the concentration, size, charge, and composition of the compound.

In some cases, the method further comprises a step of calibrating the conductance measurement system. In some cases, the accuracy is greater than 4σ. In some cases, the accuracy is greater than 5σ. In some cases, the accuracy is greater than 6σ.

Aspects describe methods and conductance measurement systems involving first and second electrolyte solutions and/or first and second fluids. In some cases, the first and second electrolyte solutions are the same. In some cases, the first fluid and the second fluid are the same.

Nanopore Detection and Tags

The invention disclosed herein pertains to modified nucleotides for single molecule analysis of DNA (or RNA, *mutatis mutandis*) using nanopores. Modifications can be made at various positions of a nucleotide, i.e. the terminal phosphate, the base, and/or the 2', or 3'-OH to form a nucleotide analogue. After a polymerase extension reaction on a template-primer complex, the released tag-attached pyrophosphate passes through a nanopore and the resulting current blockage is monitored to determine the nucleotide base added. If the modification or tag is at the base moiety, or the 2'/3'-OH of the sugar moiety of the nucleotide, then after incorporation by DNA/RNA polymerase, the linker-tag is cleaved from the base/sugar by chemical or photochemical means and released linker-tag passes through a nanopore to identify the added nucleotide.

Nucleoside-5'-polyphosphates carrying different number of phosphate groups as linkers and modified with tags attached to the terminal phosphate of the nucleotides are designed and synthesized. After incorporation by DNA/RNA polymerase in a template-primer extension reaction, the released tag-attached polyphosphate (di-, tri-, tetra-, penta-, etc.) can be detected using a nanopore to produce sequence data. Optionally, the released tag-polyphosphates can also be treated with alkaline phosphatase to provide free tags. Using four different tags which are distinct and specific for each nucleotide base, the sequence of the template DNA or RNA can be determined.

Nucleotides carrying different number of phosphate groups or tags for the synthesis of modified nucleotides, which are efficient substrates in polymerase reactions, are provided. The released tag-attached polyphosphate is detected using a nanopore to determine conditions for design and modification of the nucleotides to achieve distinct blockade signals.

Also provided are nucleotides carrying linker-tag attached at the nucleotide base moiety, and/or the 2'/3'-OH of the sugar moiety, for DNA polymerase reaction to generate linker-tag labeled single base DNA extension product. These nucleotides are good substrates for commonly used DNA/RNA polymerases. The linker-tag attached at the extended DNA product is cleaved by chemical or photochemical means to generate the primer ready for further extension using the modified nucleotides. The released linker-tag is passed through nanopore and identified based on the difference in size, shape, and charge on the tag to produce sequence data.

As disclosed herein, these molecular tools facilitate single molecule sequencing using nanopore at single base resolution.

Here are disclosed several improvements to the nanopore approach: 1) to achieve accurate and obvious discrimination of the four bases (A, C, G and T) that make up the nucleic acid molecules; 2) to enhance and differentiate the strength of the detection signals; 3) to develop an effective method for discerning and processing the electronic blockade signals generated; 4) to control the translocation rate of nucleic acids through the pore, such as slowing down the movement of tags to improve the ability of base-to-base discrimination; and 5) to design and make new and more effective synthetic nanopores for differentiating the four different nucleotides in DNA.

Figure 22:
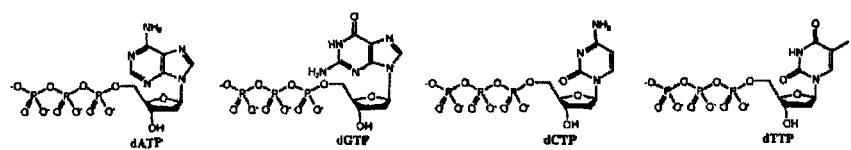
FIG. 22 shows structures of nucleotides deoxyribonucleotide adenosine triphosphate, deoxyribonucleotide guanosine triphosphate, deoxyribonucleotide cytosine triphosphate, and deoxyribonucleotide thymidine triphosphate.

The structures of four nucleotides are shown in FIG. 22. A and G are purines, while C and T are pyrimidines. The overall molecular size of A and G is very similar, while the size of C and T is similar. Nanopores have been shown to be able to differentiate between purines and pyrimidines (Akeson et al. 1999 and Meller et al. 2000), but not be able to distinguish between individual purines, A and G, or between individual pyrimidines, C and T.

Previous studies have shown modifications of nucleoside-5'-triphosphates, including introducing more phosphate groups to produce tetra-, penta-, or hexa-phosphates, introducing dye directly to the terminal phosphate, or attaching a linker between the terminal phosphate and the dye (Kumar et al., 2006 and 2008). Tetra- and penta-phosphates are better DNA polymerase substrates, and dye-labeled hexa-phosphate nucleotides have been developed (Kumar et al, 2005; Sood et al. 2005; Eid et al. 2009).

Nucleotide analogues which are designed to enhance discrimination of each nucleotide by modification of the nucleotides at the terminal phosphate moiety are disclosed herein. Nucleoside-5'-polyphosphates are synthesized and different tags (such as, different length/mass poly(ethylene glycol)s (PEGs), amino acids, carbohydrates, oligonucleotides, dyes or organic/inorganic molecules) are attached to the terminal phosphate group. After polymerase extension reactions, tag-attached polyphosphate moieties are generated (FIG. 9) and different signal specific to each base is produced when the tag-attached polyphosphate moieties pass through the nanopore. These modifications enlarge the discrimination of the bases by nanopore due to the increased size, mass or charge differences of released tagged-polyphosphate units between the four nucleotides (A, G, C and T).

The DNA translocation rate through the nanopore is reduced due to the bulkiness of the released tag-attached polyphosphates, although the translocation rate of the tags through the nanopore does not need to be reduced as long as the tags can be differentiated. Thus, the accuracy and reliability required for the base-to-base sequencing becomes achievable. Other analytical parameters in nanopore sequencing, such as concentration of the polynucleotide, magnitude of the applied voltage, temperature and pH value of the solution, are optimized in order to get the most accurate and reliable results for the detection and analysis of DNA chain.

Single-molecule approaches to sequencing allow for the possibility of deriving haplotypes for genetic studies and permitting direct sequencing of mRNAs. Among the potential single-molecule approaches for decoding the sequence of DNA or RNA molecules is the use of biological or synthetic nanopores as detectors of the individual DNA bases.

Existing sequencing-by-synthesis (SBS) approach uses cleavable fluorescent nucleotide reversible terminators (CF-NRTs) (Guo et al. 2010). SBS method is based on the ability to pause after each nucleotide addition during the polymerase reaction and the use of specific fluorophores to discriminate among the 4 bases. However, a major limitation of SBS for single molecule sequencing is the requirement for expensive fluorescence detectors and rapid imaging software. The method and process disclosed herein harness the advantages of SBS, especially its high accuracy, with the speed and sensitivity of the nanopore as an ionic current impedance detector.

While much research has gone into threading DNA through nanopores, with the hope of discriminating each base as it passes through due to its variable effect on the ion current, this has been very hard to achieve, both due to the speed of transmission and the effect of surrounding bases which may contribute their own effects on ions and counter ions passing through the pores (Timp et al. 2010). The use of cyclodextrins or other ring-shaped structures in the lumen of protein pores help provide a ratcheting mechanism to slow down transit time (Astier et al. 2006), but the ability to absolutely recognize each base for sequencing as it passes remains a challenge. An alternative strategy which uses exonuclease to allow one nucleotide at a time to traverse the pore has led to single base discrimination (Clarke et al. 2009). However, there is still difficulty in controlling the reaction time of the exonuclease for different lengths of DNA and nucleotide and the speed at which the released ions arrive at the pore with this approach.

Polymerase reaction itself displays high processivity and stable rates of base incorporation. Indeed, polymerase reactions have been used to control the movement of DNA strands through nanopores for direct base discrimination (Benner et al. 2007, Cockroft et al. 2008, Hurt et al. 2009). During the polymerase reaction, there is release of a pyrophosphate (PPi) moiety. Therefore, if one attaches a different tag to the triphosphate for each of the four nucleotides, these can be discriminated as they are released and pass through an appropriate nanopore for DNA sequence determination. These relatively small pyrophosphate analogs, or equivalent molecules with additional positively charged groups, can reach the pore extremely rapidly. The rate of nucleotide incorporation by polymerases is approximately 1000 nucleotides per second, i.e. a millisecond per base addition, while the transport rate through the nanopore is 1 molecule per microsecond. Thus, with proper fluidics and engineering, there are no de-phasing issues to sequence DNA with our approach, nor are there difficulties with the decoding of homopolymer stretches. It has been shown that one can discriminate among a wide size range of polyethylene glycols differing by as little as one or two carbon units by the effect they have on blocking currents in nanopores (Reiner et al. 2010, Robertson et al. 2007), a resolution essentially equivalent to that obtained by a mass spectrometer. Therefore, as described below, different length PEG chains are attached to the terminal phosphate of dATP, dCTP, dGTP and dTTP. As each nucleotide is incorporated during the polymerase reaction, a specifically tagged phosphate group is released into the nanopore, yielding a distinct current blockade signal to indicate which nucleotide is incorporated. The speed of sequencing is extremely fast, limited only by the rate of the polymerase reaction. As an alternative approach for tagging the nucleotides, we also utilize different phosphate chain lengths (e.g., tri-, tetra-, and penta-phosphates).

Additionally, we also use solid-state nanopores which have advantages in terms of better control over and flexibility of fabrication, thus ensure rapid vectorial transport of tagged polyphosphates but not the nucleotide precursors or the DNA toward and through the nanopores or nanochannels. To achieve this, two important design features are incorporated. First, the precursors (tagged nucleotide polyphosphates) are synthesized with an overall neutral charge, while the cleaved tagged phosphates have an overall positive charge. By utilizing a current that attracts positive ions, the nanopores only need to discriminate the four alternative released tagged molecules. Differential charge on precursors and products are achieved by incorporate into the tags a number of lysines or arginines (positively charged) exactly balancing the number of phosphates (negatively charged). After incorporation of the a-phosphate into the growing primer, there is one more lysine than phosphate in the released product. Optionally, alkaline phosphatase can be used to cleave off all the phosphates to produce a PEG tag with a stronger positive charge. Second, to assure that the released phosphates move immediately through the nearest pore, the DNA polymerase is immobilized to the inlet of the pore, for example via a biotin-streptavidin linkage. As the DNA chain threads through the polymerase, the released tagged products only have to diffuse the same short distance to reach the nanopore.

It is also important to recognize the advantages of the bioelectronic transduction mechanism over optical approaches. For single-molecule optical transduction techniques, the signal from a single-fluorophore is typically <2500 photons/sec (corresponding to detected current levels on the order of 50 fA) at high short noise levels, requiring complex optics to try to collect every photon emitted, making scaling of the platforms to higher densities difficult. Synthesis reactions must be slowed to 1 Hz to allow sufficient integration times for these weak, noisy optical signals. The challenges to optical techniques have opened up the possibility for bioelectronic detection approaches, which have significantly higher signal levels (typically more than three orders of magnitude higher), allowing for the possibility for high-bandwidth detection with the appropriate co-design of transducer, detector, and amplifier. Signal levels for nanopores can be as high as 100 pA from alpha-hemolysin (Kasianowicz et al. 1996), 300 pA for MspA (Derrington et al. 2010), and upwards of 4 nA from solid-state nanopores (Wanunu at al. 2010).

Significant effort has been directed toward the development of nanopore technology as a bioelectronic transduction mechanism (Benner at al. 2007, Deamer at al. 2002, Kasianowicz at al. 1996, Branton 2008, Branton at al. 2008, Chen 2004, Gershow at al. 2007, Nealy 2007, Matysiak at al. 2006). Two essential attributes of this electronic sensor give it single-molecule sensitivity. The first is the very localized (nanoscale) geometry of charge sensitivity in the pore itself. The diameter of a pore may be 2-3 nm, and due to electrolyte charge screening the measured current is highly insensitive to charge sources more than a few nanometers from the pore. Second, the nanopore sensor provides a gain through the effect the comparatively slow-moving charge a biopolymer has on a nearby concentration of higher-mobility salt ions. Nanopores, however, are extremely limited by the relatively short time biomolecules spend in the charge-sensitive region of the pore. This is directly addressed by the use of tags, which can be optimized to produce high signal levels and longer translocation events. At the same time, CMOS co-integration of these pores is exploited to dramatically improve the noise-limited bandwidths for detection in a nanopore device. Both solid-state and biological pores are supported by this platform. This solid-state integration, along with associated microfluidics, also uniquely enables the scale-up of this design to large arrays with integrated electronics for detection.

Computer Systems

Figure 18:
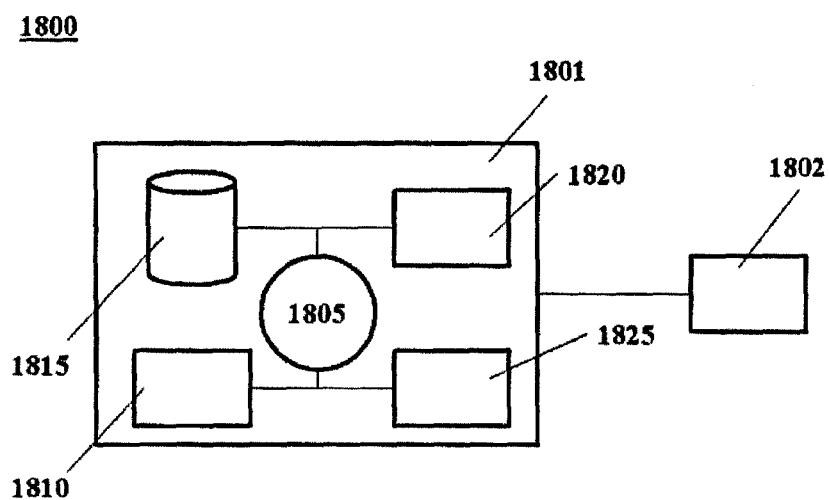
FIG. 18 shows a computer system configured to control a sequencer.

Nucleic acid sequencing systems and methods of the disclosure may be regulated with the aid of computer systems. FIG. 18 shows a system 1800 comprising a computer system 1801 coupled to a nucleic acid sequencing system 1802. The computer system 1801 may be a server or a plurality of servers. The computer system 1801 may be programmed to regulate sample preparation and processing, and nucleic acid sequencing by the sequencing system 1802. The sequencing system 1802 may be a nanopore-based sequencer (or detector), as described elsewhere herein.

The computer system may be programmed to implement the methods of the invention. The computer system 1801 includes a central processing unit (CPU, also "processor" herein) 1805, which can be a single core or multi core processor, or a plurality of processors for parallel processing. The computer system 1801 also includes memory 1810 (e.g., random-access memory, read-only memory, flash memory), electronic storage unit 1815 (e.g., hard disk), communications interface 1820 (e.g., network adapter) for communicating with one or more other systems, and peripheral devices 1825, such as cache, other memory, data storage and/or electronic display adapters. The memory 1810, storage unit 1815, interface 1820 and peripheral devices 1825 are in communication with the CPU 1805 through a communications bus (solid lines), such as a motherboard. The storage unit 1815 can be a data storage unit (or data repository) for storing data. The computer system 1801 may be operatively coupled to a computer network ("network") with the aid of the communications interface 1820. The network can be the Internet, an internet and/or extranet, or an intranet and/or extranet that is in communication with the Internet. The network can include one or more computer servers, which can enable distributed computing.

Methods of the invention can be implemented by way of machine (or computer processor) executable code (or software) stored on an electronic storage location of the computer system 1801, such as, for example, on the memory 1810 or electronic storage unit 1815. During use, the code can be executed by the processor 1805. In some cases, the code can be retrieved from the storage unit 1815 and stored on the memory 1810 for ready access by the processor 1805. In some situations, the electronic storage unit 1815 can be precluded, and machine-executable instructions are stored on memory 1810.

The code can be pre-compiled and configured for use with a machine have a processer adapted to execute the code, or can be compiled during runtime. The code can be supplied in a programming language that can be selected to enable the code to execute in a pre-compiled or as-compiled fashion.

The computer system 1801 can be adapted to store user profile information, such as, for example, a name, physical address, email address, telephone number, instant messaging (IM) handle, educational information, work information, social likes and/or dislikes, and other information of potential relevance to the user or other users. Such profile information can be stored on the storage unit 1815 of the computer system 1801.

Aspects of the systems and methods provided herein, such as the computer system 1801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., ROM, RAM) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Systems and methods provided herein may be combined with, or modified by, other systems and methods, such as, for example, systems and methods described in PCT Patent Publication No. WO/2012/083249, which application is entirely incorporated herein by reference

EXAMPLES

Example 1

I. Design and Synthesis of Modified Nucleotides

Figure 23:
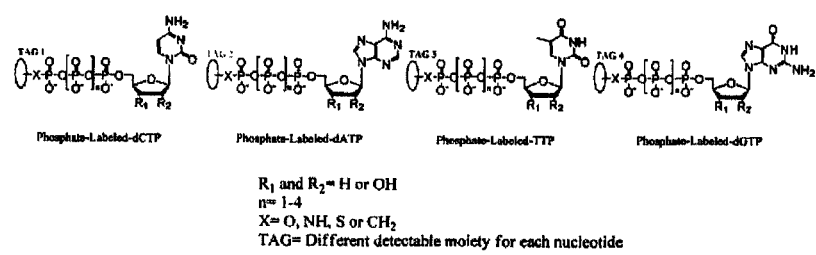
FIG. 23 shows structures of four phosphate-tagged nucleoside-5'-polyphosphates.

Effect of bulkiness of the tagged-polyphosphate on electronic blockade signals generated by a nanopore is determined using various phosphate-linked-nucleotides with different size tags or groups attached to the terminal phosphate of the nucleotide. Structures of four phosphate-tagged nucleoside-5'-polyphosphates are shown in FIG. 23. First, a series of nucleoside-5'-tri-, tetra-, penta-, and hexa-phosphates is synthesized. In these nucleotides, the terminal phosphate is attached with a linker through which different tags, e.g. different length and mass ethylene glycols or other molecules which increases the bulkiness or charge of the released polyphosphate, are attached. These nucleotides are tested with nanopore to determine which tags or bulky groups attached to the terminal phosphate correlate to more dramatic difference in electronic blockade signal between the different bases.

Figure 24:
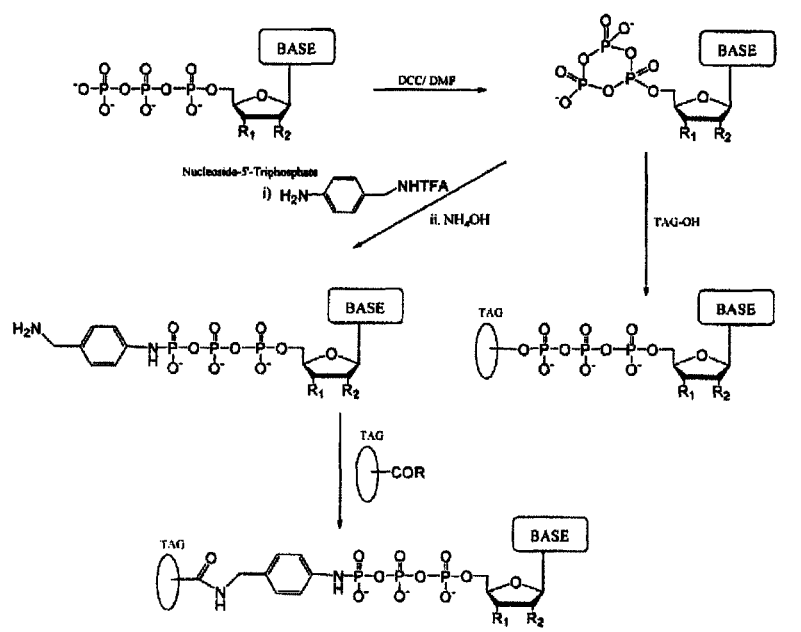
FIG. 24 shows synthesis of phosphate-tagged nucleoside-5'-triphosphates.

1) Terminal Phosphate-modified Nucleoside-Polyphosphates a. Terminal Phosphate-tagged Nucleoside-5'-triphosphates As shown in FIG. 24, terminal phosphate tagged-nucleoside-5'-triphosphates can be synthesized by reacting the corresponding dNTP with DCC/DMF to give cyclic trimetaphosphate which can be opened with appropriate nucleophiles to give tag or linker attached nucleoside-5'-triphosphate. This can be used in a template-primer extension reaction and the released tag-attached pyrophosphate can be read using nanopore. Alternatively, the linker attached to the phosphate can be reacted with tag-NHS ester to provide alternate tag-attached nucleoside-5'-triphosphate.

b. Terminal Phosphate-tagged Nucleoside-5'-tetraphosphates

Figure 25:
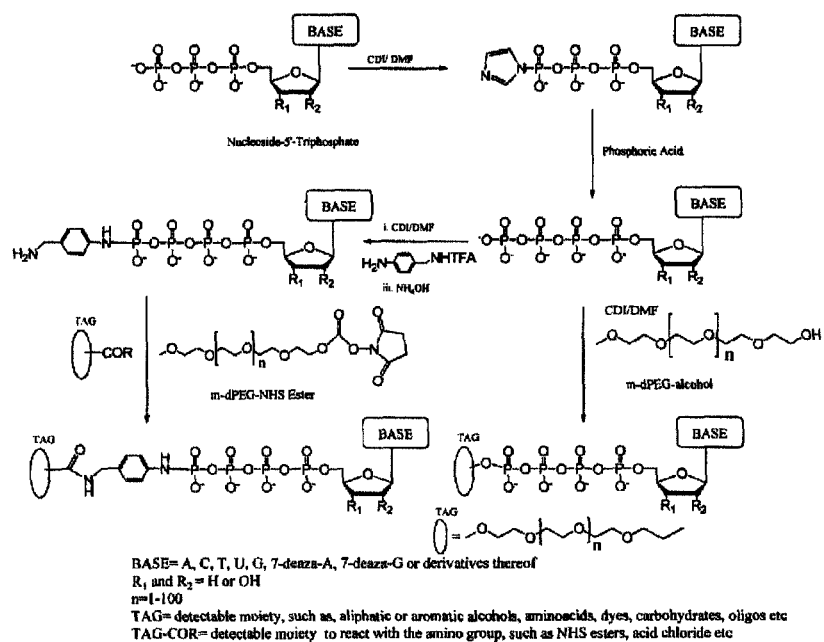
FIG. 25 shows synthesis of phosphate-tagged nucleoside-5'-tetraphosphates.

For the synthesis of terminal phosphate tagged nucleoside-5'-tetraphosphates, the corresponding triphosphate is first reacted with CDI in DMF to activate the terminal phosphate group which is then reacted with phosphoric acid or tag-monophosphate to give the tetraphosphate (FIG. 25). The terminal phosphate on the tetraphosphate can be further activated with CDI followed by reaction with appropriate nucleophiles to provide a linker attached tertraphosphate which can further be used to attach tags of different mass, length or bulk, such as m-dPEG-NHS ester, also shown in FIG. 25.

c. Terminal Phosphate-tagged Nucleoside-5'-penta- and Hexaphosphates

Figure 26:
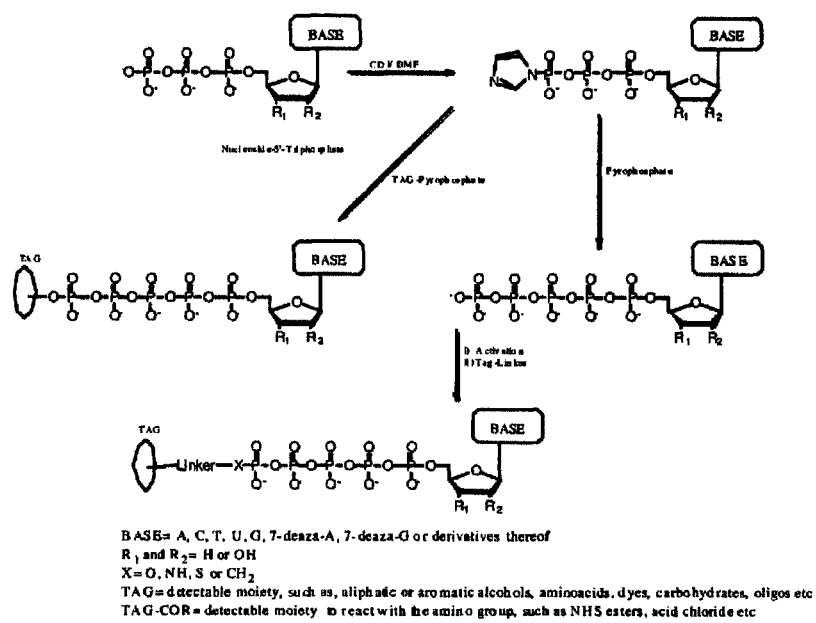
FIG. 26 shows synthesis of terminal phosphate-tagged nucleoside-5'-pentaphosphates.

Synthesis of terminal phosphate tagged nucleoside-5'-penta- and hexaphosphates follows the same principle as shown in FIG. 26. They can be prepared either from activated triphosphates or the tetraphosphates by reacting with phosphoric acid, pyrophosphate or tag-attached phosphates. Alternatively, a linker can be attached to penta- or hexaphosphate followed by reaction with activated NHS esters.

d. Oligo-tag Attached Nucleoside-Polyphosphates

There are a number of issues with current approach to nanopore sequencing such as recognition of the bases as they pass through the nanopore and the speed or rate of transport to allow recognition of the nucleobase be registered. DNA passes through a alpha-hemolysin nanopore at a rate of 1-5 μs, which is too fast to record for single molecule sequencing experiments. Some progress has been made to overcome these issues by a variety of protein engineering strategies including the use of molecular brakes (short covalently attached oligonucleotides) (Bayley, H. 2006).

As disclosed herein, short oligonucleotides can be attached to the terminal-phosphate of a nucleoside polyphosphate by reaction of the activated terminal phosphate with the 3'-OH or the 5'-OH of the oligonucleotide. Alternatively, the 3'- or 5'-phosphate of the oligonucleotide can be activated with CDI or Imidazole/DCC and reacted with nucleoside-5'-polyphosphates. Structures of oligo-attached nucleoside phosphates (oligo-3' to 5'-phosphate; oligo-5' to 5'-phosphate) are shown in FIGS. 27(a) and 27(b), respectively. The polymerase reaction by-product which is monitored by passing through the nanopore is shown in FIG. 27(c).

The rate of migration through the nanopore of the polymerase reaction by-product can be controlled by attaching oligonucleotides of different length to different nucleoside-5'-polyphosphates. For example, if nucleoside dA has 1 or 2 oligo-dA units attached, dT may have 3 oligo-dT units, dC may have 4 oligo-dC units, and dG may have 5 oligo-dG units. Different combinations of the number of oligos for each nucleotide can be used to control the transport and retention time in a nanopore.

The transport and retention time in a nanopore also can be controlled by adding different number of phosphate groups to the nucleotides. Thus the charge and mass can vary for each nucleotide polyphosphate.

Examples of Linker Tag Structure

Specific examples of reactive groups on the terminal phosphates or the nucleoside base moiety and groups with which groups can react are provided in Table 1. The reactive groups with which they can react can be present either on the linker or on the tag.

TABLE 1

Possible Reactive Substituents and Functional Groups Reactive Therewith

| Reactive Groups | Functional Groups |
|---|---|
| Succinimidyl esters | Primary amino, secondary amino |
| Anhydrides, acid halides | Amino and Hydroxyl groups |
| Carboxyl | Amino, Hydroxy, Thiols |
| Aldehyde, Isothiocyanate & Isocyanates | Amino groups |
| Vinyl sulphone & Dichlorotriazine | Amino groups |
| Haloacetamides | Thiols, Imidazoles |
| Maleimides | Thiols, Hydroxy, Amino |
| Thiols | Thiols, Maleimide, Haloacetamide |
| Phosphoramidites, Activated P. | Hydroxy, Amino, Thiol groups |
| Azido | Alkyne |

Tags which can be detected by nanopore are included herewith but by no means are they limited to these group of compounds. One skilled in the art may change the functional group(s) to come up with a suitable tag.

Figure 35:
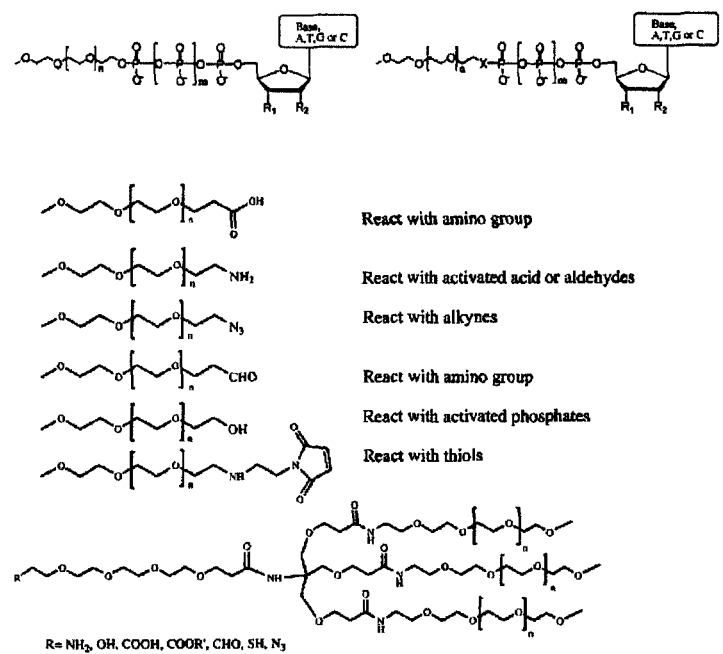
FIG. 35 shows structures of PEG-phosphate-labeled nucleotides and examples of possible PEGs with different reactive groups to react with functional groups.

The tags include aliphatic, aromatic, aryl, heteroaryl compounds with one or more 4-8 membered rings and may optionally be substituted with halo, hydroxy, amino, nitro, alkoxy, cyano, alkyl, aryl, heteroaryl, acid, aldehyde, Azido, alkenyl, alkynyl, or other groups. These includes, polyethylene glycols (PEGs), carbohydrates, aminoacids, peptides, fluorescent, fluorogenic (non-fluorescent but become fluorescent after removal of protecting group) chromogenic (colorless but become colored after removal of protecting group) dyes, chemiluminescent compounds, nucleosides, nucleoside-mono, di or polyphosphates, oligonucleotides, aryl, heteroaryl or aliphatic compounds. Some examples are given in FIG. 35.

Figure 36:
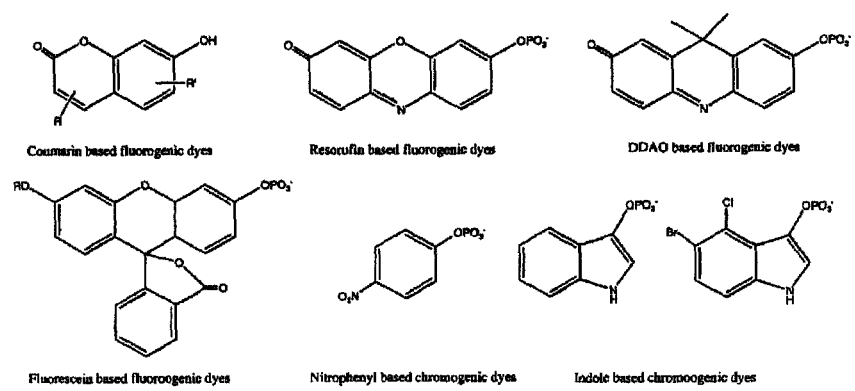
FIG. 36 shows non-limiting, specific examples of reactive groups on the terminal phosphates, which can also be attached with appropriate changes to a nucleoside base moiety, and groups with which groups can react to form tags.

Structure of PEG-phosphate-labeled nucleotides and some examples of possible PEGS with different reactive groups to react with functional groups are exemplified in FIG. 36.

Some other examples of the dyes or compounds which can be used to attach to the terminal phosphate or the base moiety of the nucleotides are provided here. By no means, these are the only compounds which can be used. These are listed here as examples and one skilled in the art can easily come up with a suitable linker-tag which can be attached to the nucleotide and detected by nanopore.

Other examples of suitable tags are:

Fluorescent dyes: Xanthine dyes, Bodipy dyes, Cyanine dyes Chemiluminiscent compounds: 1,2-dioxetane compounds (Tropix Inc., Bedford, Mass.). Amino acids & Peptides: naturally occurring or modified aminoacids and polymers thereof. Carbohydrates: glucose, fructose, galactose, mannose, etc. NMPs & NDPs: nucleoside-monophosphates, nucleoside-diphosphates. Aliphatic or aromatic acids, alcohols, thiols, substituted with halogens, cyano, nitro, alkyl, alkenyl, alkynyl, azido or other such groups.

2) Base-modified Nucleoside-5'-Triphosphates

A variety of nucleotide reversible terminators (NRTs) for DNA sequencing by synthesis (SBS) are synthesized wherein a cleavable linker attaches a fluorescent dye to the nucleotide base and the 3'-OH of the nucleotide is blocked with a small reversible terminating group (Ju et al. 2006, Guo et al. 2008 & 2010). Using these NRTs, DNA synthesis is reversibly stopped at each position. After recording the fluorescent signal from the incorporated base, the cleavable moieties of the incorporated nucleotides are removed and the cycle is repeated.

Figure 28A:
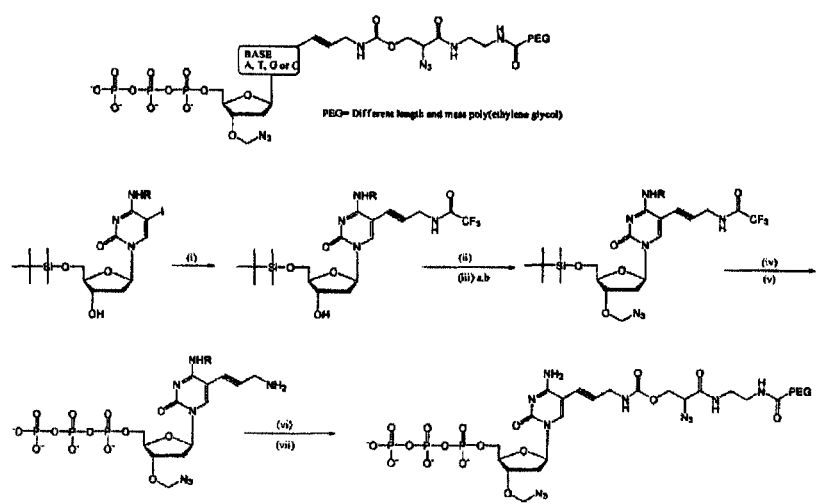
FIG. 28(A) shows synthesis of base-modified nucleoside-5'-triphosphates.

The same type of nucleotides can also be used for nanopore DNA sequencing. As shown in FIG. 28(A), a small blocking group at 3'-OH and a tag-attached at the base linked through a cleavable linker can be synthesized. After polymerase extension reaction, both the 3'-O-blocking group and the tag from the base are cleaved and the released tag can be used to pass through the nanopore and the blockage signal monitored. Four different tags (e.g. different length and molecular weight poly-ethylene glycols (PEGs), as shown in FIG. 28(A)) can be used, one for each of the four bases, thus differentiating the blockage signals.

Figure 28B:
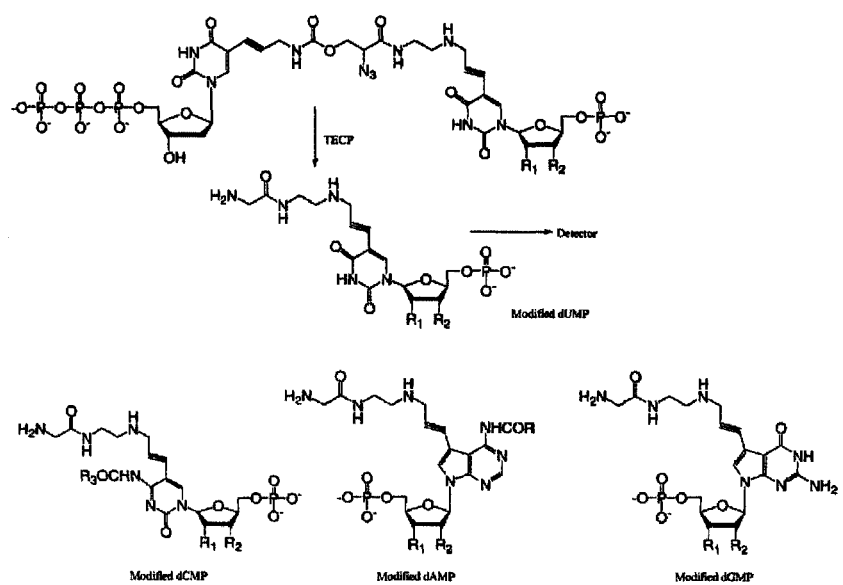
FIG. 28(B) shows cleavage of base-modified nucleoside-5'-triphosphate with TCEP.

Alternatively, the 3'-O-blocking group is not used because it has been shown that a bulky group or nucleotide base can prevent the DNA polymerase from adding more than one nucleotide at a time (Harris et al. 2008). As shown in FIG. 28(B), a bulky dNMP is introduced through a cleavable linker. Thus, different dNMPs are introduced through a linker according to the original dNTP. For example, with dTTP nucleotide, a dTMP is introduced (for dATP, a dAMP; for dGTP, a dGMP and for dCTP, a dCMP is introduced). After polymerase incorporation and cleavage with TCEP, modified dNMPs are generated which are passed through the nanopore channel and detected by appropriate methods.

3) 2'-or 3'-OH Modified Nucleoside-5'-Triphosphates

Figure 29:
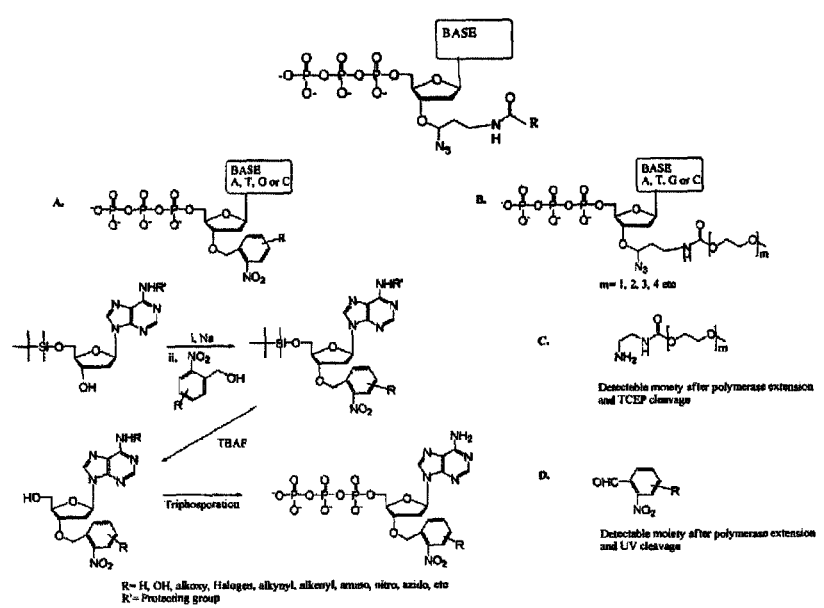
FIG. 29 shows synthesis of 3'-O-modified nucleoside-5'-triphosphates; (A) 3'-O-2-nitrobenzyl attached dNTPs; (B) 3'-O-azidomethyl attached dNTPs; (C) detectable moiety after polymerase extension and TCEP cleavage; and (D) detectable moiety after polymerase extension and UV cleavage.

Synthesis of all four 3'-modified nucleoside-5'-triphosphates can be carried out (Guo et al. 2008, Li et al. 2003, Seo et al. 2004). 3'-O-2-nitrobenzyl and 3'-O-azidomethyl attached dNTPs (FIGS. 29A and 29B, respectively) are good substrates for DNA polymerases. After incorporation by DNA/RNA polymerase in a sequencing reaction, these 3'-O-tagged nucleotides terminate the synthesis after single base extension because of the blocking group at the 3'-OH. Further extension is possible only after cleavage of the blocking group from the 3'-O position. The 3'-O-2-nitrobenzyl group can be efficiently cleaved by LW light and 2'-O—azidomethyl by treatment with TCEP to generate the free OH group for further extension. The cleaved product from the reaction (FIG. 29C or 29D) is monitored for electronic blockage by passing through the nanopore and recording the signal. Four different substituted nitrobenzyl protected dNTPs and four different azidomethyl substituted dNTPs, one for each of the four bases of DNA, are synthesized.

II. DNA-extension Using Modified Nucleotides

1) Phosphate-Tagged Nucleotides

Figure 30:
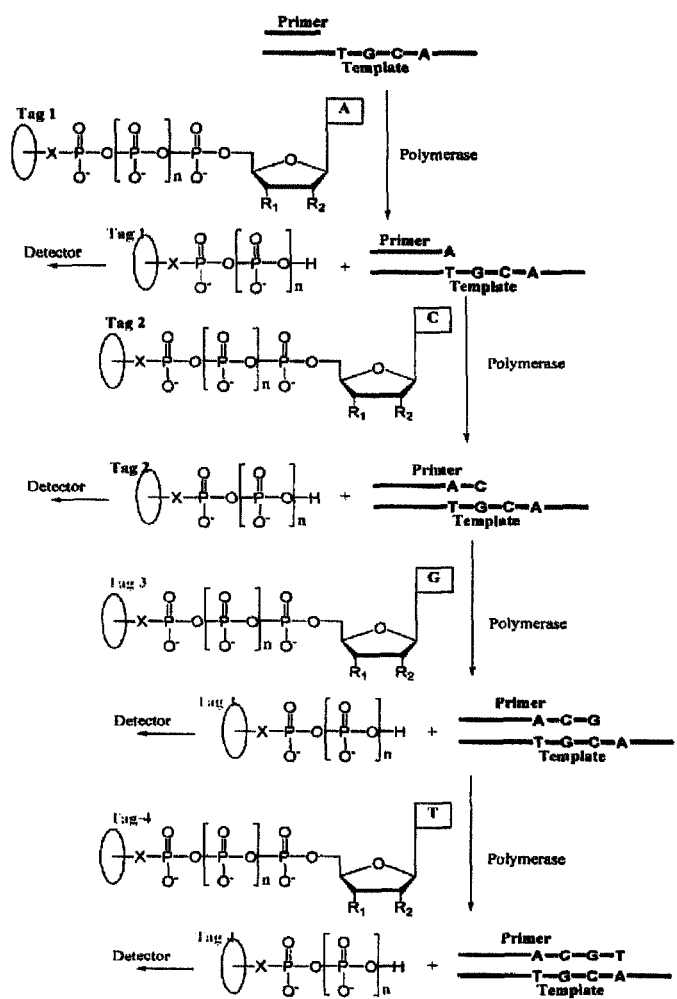
FIG. 30 shows DNA extension reaction using phosphate modified nucleotide analogues.

Terminal phosphate-tagged nucleoside polyphosphates described above are used in polymerase reactions to generate extension products. As shown in FIG. 30, after a polymerase reaction, the released by-product of the phosphate-tagged nucleotide, tag-polyphosphate, is obtained and the extended DNA is free of any modifications. The released tag-polyphosphate is then used in an engineered nanopore by single-channel recording techniques for sequencing analysis. The released tag-polyphosphates can also be treated with alkaline phosphatase to provide free tags which can also be detected. Using four different tags for the four nucleotides (A, T, G & C) to generate four different tagged-polyphosphates which differ by mass, charge or bulk, the sequence of the DNA can be determined.

2) Base-Tagged Nucleotides with Cleavable Linkers

Figure 31:
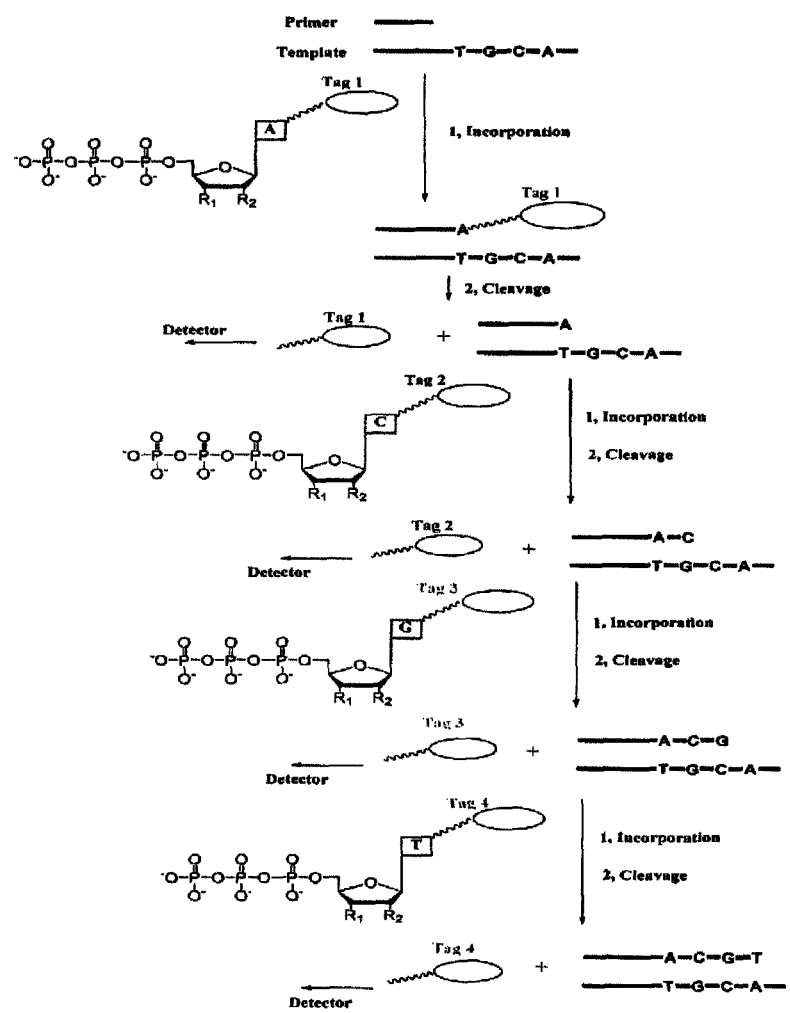
FIG. 31 shows DNA extension reaction using base-tagged nucleotide analogues.

Base-tagged nucleotide triphosphates for DNA sequencing by synthesis (SBS) and single molecule sequencing are synthesized (Guo et al. 2008 and 2010). The addition of large bulky groups at the 5-position of pyrimidines (C & T) and 7-position of 7-deazapurines (G & A) can block the addition of more than one nucleotide in a DNA polymerase reaction. Modified nucleotides with a cleavable linker, a bulky group, and different charges attached to the nucleotide base are synthesized. The modified nucleotides may also have a small blocking group at the 3'-OH of the nucleotides. These modified nucleotides are used in a polymerase extension reaction. As shown in FIG. 31, after extension with the appropriate nucleotide, the linker and tag from the nucleotide base and from sugar 3'-O, if blocked, are cleaved by chemical or photochemical means and the released linker-tag is used in an engineered nanopore by single-channel recording techniques for sequencing analysis.

3) 2'-or 3'-Tagged Nucleotides with Cleavable Linkers

Figure 32:
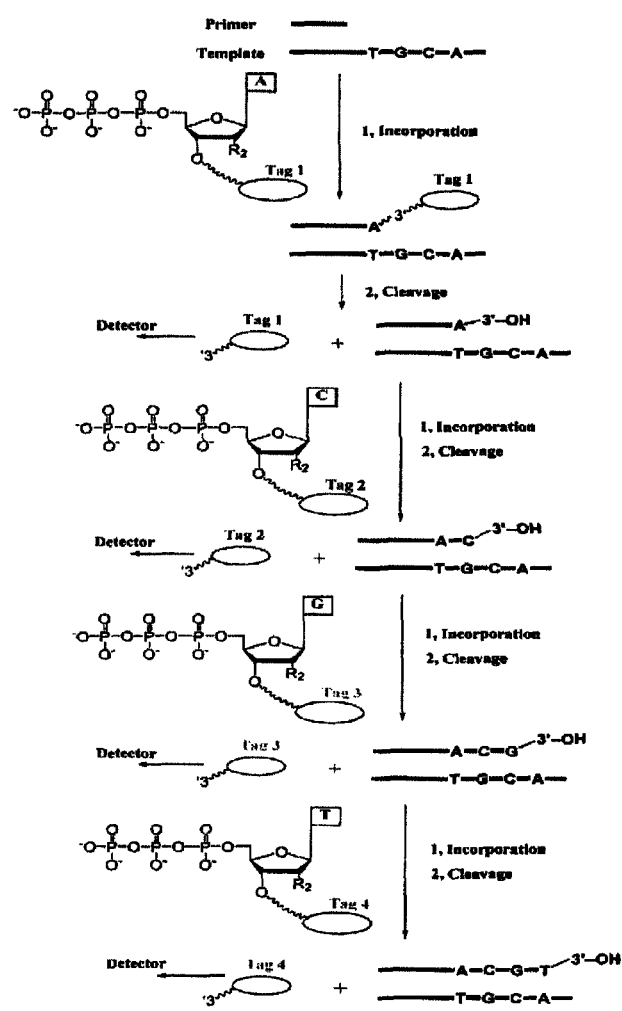
FIG. 32 shows DNA extension reaction using 2'- or 3'-OH labeled nucleotide analogues.

A linker and tag can also be attached to the 2'-or 3'-OH of nucleotides. After a polymerase extension reaction, the linker-tag is cleaved from the extended product by chemical, photochemical or enzymatic reaction to release the free 3'-OH for further extension. As shown in FIG. 32, the released linker-tag is then used in an engineered nanopore by single-channel recording techniques for sequencing analysis.

III. DNA-sequencing Study Using Nanopore

Figure 33:
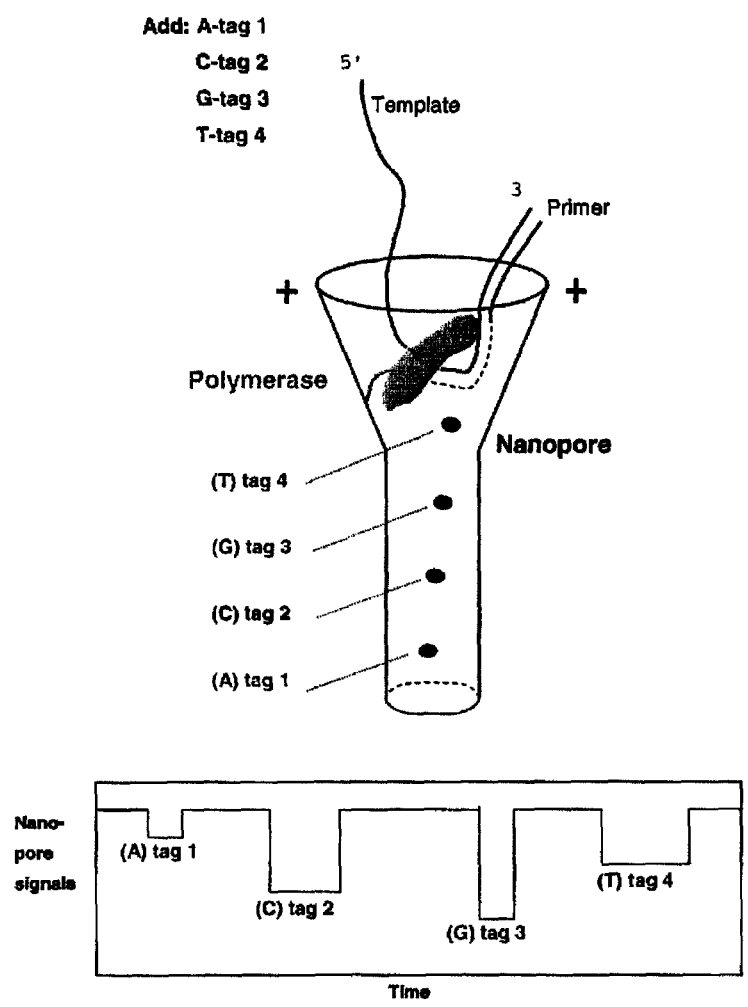
FIG. 33 shows schematic of DNA sequencing by nanopore with modified nucleotides, particularly applicable to single molecule real time sequencing involving addition of all 4 nucleotides and polymerase at same time to contact a single template molecule.

Discrimination of different nucleotides in DNA sequencing using nanopore is evaluated following the strategy shown in FIGS. 30-32. To validate a nanopore's ability to distinguish the four different linker-tags in DNA, a series of experiments as shown in FIG. 33 is performed. The DNA/RNA polymerase can be bound to the nanopore and a template to be sequenced is added along with the primer. Either DNA template or primer can also be immobilized on top of the nanopore and then subsequently form a template-primer complex upon addition of a DNA polymerase. To this template-primer complex, four differently tagged nucleotides are added together or sequentially. After polymerase catalyzed incorporation of the correct nucleotide, the added nucleotide releases the tag-attached polyphosphate (in case of terminal-phosphate-labeled nucleotides) which then pass through the nanopore to generate the electric signal to be recorded and used to identify the added base. Optionally, the released tag-polyphosphate can also be treated with alkaline phosphatase to provide free tag which can also be detected by passing through the nanopore. Each tag generates a different electronic blockade signature due to the difference in size, mass or charge. In the case of base-modified or 2'/3'-modified nucleotides, after the DNA/RNA polymerase extension, the tag from the extended primer is cleaved by chemical, photochemical or enzymatic means and the electronic signature of the released tag is monitored. The shape, size, mass, charge or other properties of the tag can be adjusted according to the requirements.

As disclosed herein, signals from each of the nucleotides (FIG. 34) and the transitions between nucleotides of different identities are distinguished and characterized. The magnitude and duration of the blockade signatures on the event diagram are analyzed and compared with known diagrams. Thus, with these rational chemical designs and modifications of the building blocks of DNA, the use of nanopore is optimized to decipher DNA sequence at single molecule level with single base resolution.

Figure 37:
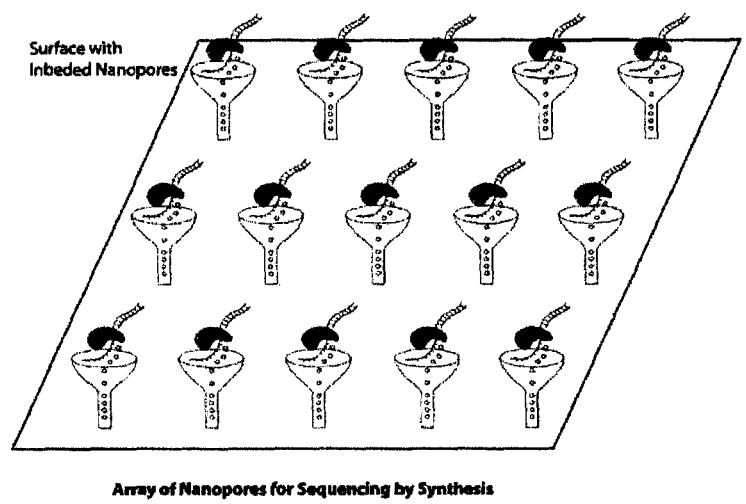
FIG. 37 shows a schematic of array of nanopores for massive parallel DNA sequencing by synthesis.

To implement this novel strategy for DNA sequencing, an array of nanopores can be constructed on a planar surface to conduct massive parallel DNA sequencing as shown in FIG. 37. The array of nanopores can also be constructed on a silicon chip or other such surfaces. The nanopore can be constructed from the protein with lipid bilayers or other such layers (alpha-hemolysin pore, *Mycobacterium smegnatis* porin A, MspA) (Derrington et al. 2010) or they can be synthetic solid-state nanopores fabricated in silicon nitride, silicon oxide or metal oxides (Storm et. al. 2005; Wanunu et al. 2008) or a hybrid between a solid-state pore and □-hemolysin (Hall et al. 2010).

FIG. 37 shows a schematic of array of nanopores for massive parallel DNA sequencing by synthesis. The nanopores can sense each DNA/RNA polymerase catalyzed nucleotide addition by-product (Tag-attached to the phosphate or the base and/or 2',3'-OH of the sugar moiety) as it passes through the nanopore. The electrical properties of different tags will distinguish the bases based on their blockade property in the nanopores. The array of nanopores shown in FIG. 37 can each read the same sequence or different sequence. Increasing the number of times each sequence is read will result in better quality of the resulting sequence data.

Example 2

I. Synthesis of PEG-labeled-deoxyguanosine-5'-tetra-phosphates (dG4P-PEG)

Figure 38:
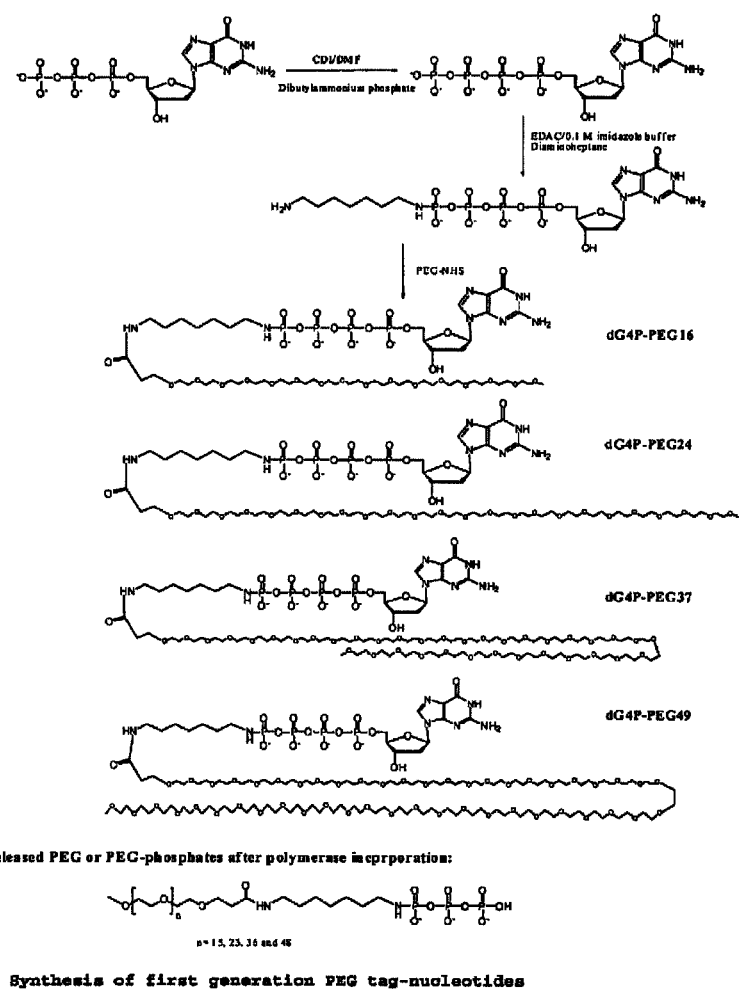
FIG. 38 shows synthesis of PEG—phosphate-labeled nucleotides.

PEG-labeled-deoxyguanosine-5'-tetraphosphates (dG4P-PEGs) is synthesized according to FIG. 38. First, 2'-deoxyguanosine triphosphate (dGTP) reacts with CDI in DMF to activate the terminal phosphate group which is then reacted with dibutylammonium phosphate to give the tetraphosphate. The terminal phosphate on this tetraphosphate is further activated with EDAC in 0.1M imidazole buffer followed by reaction with diaminoheptane to provide an amino attached tetraphosphate which is further reacted with mPEG-NHS esters to provide the required four PEG-dG4Ps. After polymerase incorporation, the net charge on the released PEG is -3 (PEG-NH-triphosphate).

II. Testing of Modified Nucleotides in Single Base Extension Reactions

The dG4P-PEGs are characterized by MALDI-TOF mass spectroscopy as shown in Table II.

TABLE II

MALDI-TOF MS Results for dG4P-PEG

| | Calculated M.W. | Measured M.W. |
|---|---|---|
| dG4P-PEG24 | 1798 | 1798 |
| dG4P-PEG37 | 2371 | 2374 |

Figure 39:
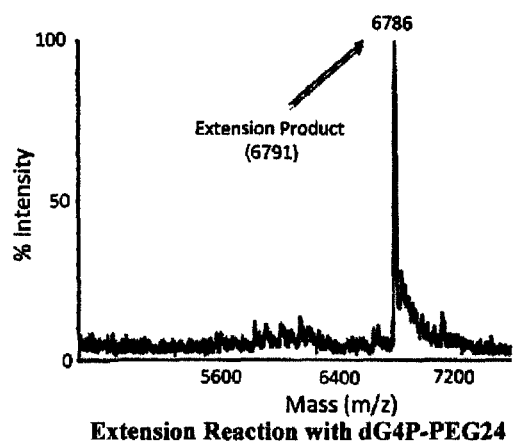
FIG. 39 shows MALDI-TOF mass spectra of the DNA extension products generated by incorporation of PEG-phosphate-labeled nucleotide analogues (dG4P-PEG); the single products shown in the spectra indicate that the dG4P-PEG24 and dG4P-PEG37 are incorporated at nearly 100% efficiency.
Figure 39:
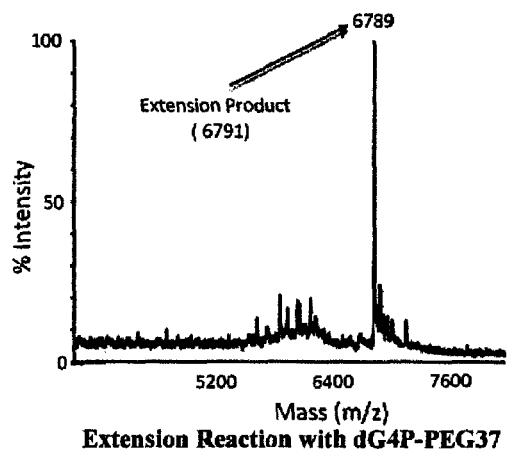

The dG4P-PEGs are excellent substrates for DNA polymerase in primer extension. The MALDI-TOF mass spectra of the DNA extension products are shown in FIG. 39.

Example 3

Single Molecule Detection by Nanopore of the Pegs Used to Label the Nucleotides

Figure 40:
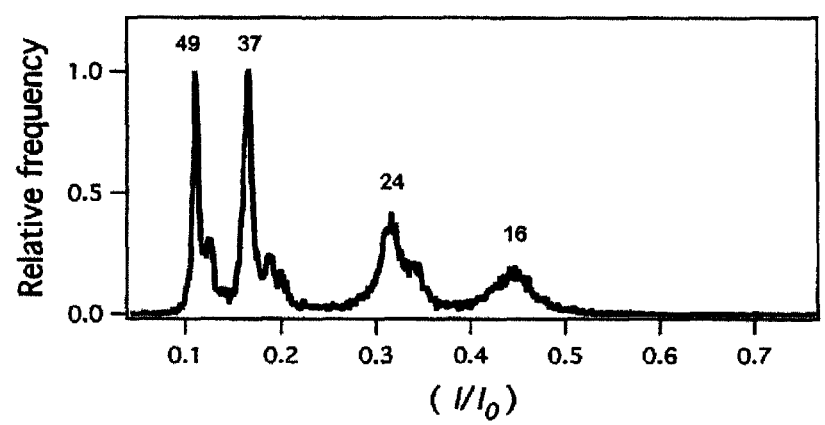
FIG. 40 shows the relative blockade depth distributions for a-hemolysin nanopore in the presence of PEGs that contain either 49, 37, 24, or 16 ethylene oxide monomers at +40 mV applied potential; the four species are easily identified.

Poly(ethylene glycol) is a nonelectrolyte polymer that weakly binds cations (e.g., it binds $K^+$ ions at $K_d$~2 M). Thus, the net charge on the polymer depends on the mobile cation concentration and on the presence of other moieties that are chemically linked to it. It has been demonstrated that a single e-hemolysin nanopore can easily distinguish between differently-sized PEG polymers at better than monomer resolution, i.e., better than 44 g/mol (Reiner et al. 2010; Robertson et al. 2007). That level of discrimination is made possible because the polymer reduces the pore's conductance due to volume exclusion (the pore conductance decreases with increasing polymer size) and by binding mobile cations that can otherwise flow freely through the pore (Reiner et al. 2010). In addition, the residence time of the polymer in the pore is highly senstive to the polymer's charge, which for PEG, scales in proportion to the polymer's length. A nanopore should be able to distinguish between differently-sized PEGs that are chemically linked to other moieties. PEGs (PEG 16, 24, 37 and 49) for labeling nucleotides are tested on nanopore and generate distinct electronic blockade signatures at the single molecule level as shown in FIG. 40.

To investigate the effect of bulkiness of the variously tagged polyphosphates on electronic blockade signals generated in the nanopore, various phosphate-linked-nucleotides are synthesized with different size polyethylene glycol (PEG) tags attached to the terminal phosphate of the nucleotide. First, as shown in FIG. 23, we synthesize a series of nucleoside-5'-tri-, tetra-, and penta-phosphates with the terminal phosphate attached via a linker to which different tags, e.g. different length and mass PEGs or other molecules to increase the molecular size or modify the charge of the released polyphosphate, can be attached. We then test these nucleotides in polymerase reactions coupled with detection by nanopore to see which tags or bulky groups attached to the terminal phosphate produce more dramatic differences in electronic blockade signals among different bases.

I. Screen and Select 4 PEG Tags with Distinct Nanopore Blockade Signals

Recently, it has been shown that when a polyethylene glycol (PEG) molecule enters a single a-hemolysin pore, it elicits distinct mass-dependent conductance states with characteristic mean residence times (Robertson et al. 2007). FIG. 41A shows that the conductance based mass spectrum clearly resolves the repeat units of ethylene glycol, and the residence time increases with the mass of PEG.

I.a Testing PEG for Nanopore Blockade Signatures.

Figure 41:
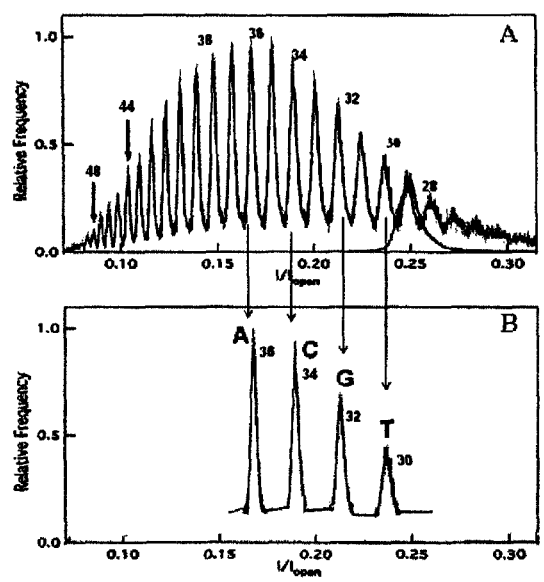
FIG. 41 shows (A) separation and mass distribution of mixed poly (ethylene glycol) (PEG) units through a single nanopore; and (B) selection of 4 distinct PEG units with base line separation as tags for the 4 bases, A, C, G, and T; the structures of linear and branched PEGs are also shown.
Figure 41:
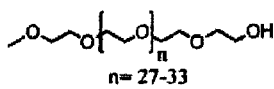
Figure 41:
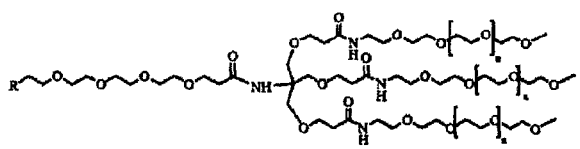

Different length and molecular weight PEGs (commercially available from Quanta Biodesign Ltd or other suppliers) are selected and the nanopore blockade signals monitored, as described in Example 2. As shown in FIG. 41A PEGs of 28-48 ethylene glycol units are clearly distinguished by nanopore. Therefore, PEGs with a broad range of ethylene glycol units displaying very distinct nanopore blockade signals are selected as tags to label the nucleotides A, C, G and T. Examples are shown in FIG. 41B. Branched PEGs as tags are also evaluated as these can be modified with positive charges in a more straightforward fashion. Structures of some linear and branched PEGs are shown at the bottom of FIG. 41.

I.b Design and Synthesis of Phosphate-Labeled PEGs Selected in I.a

Figure 42:
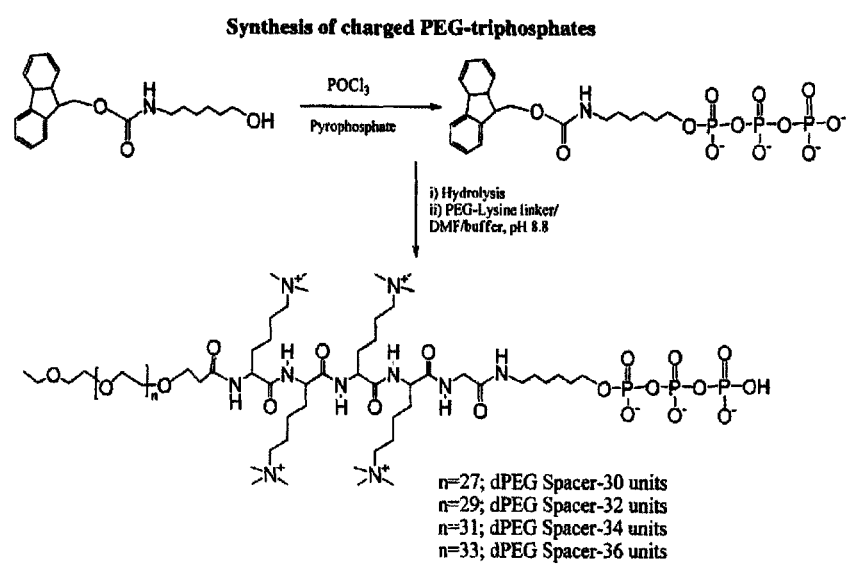
FIG. 42 shows synthesis of charged PEG-triphosphates (the charge can be adjusted based on the requirements).

In nanopore sequencing, the current blockade signals in the nanopore are generated by the PEG-phosphates released during the polymerase reaction. Thus, we design and synthesize phosphate-labeled PEGs with positively charged linkers, and test these molecules with organic (e.g., a-hemolysin) and synthetic (solid phase) nanopores to evaluate their current blockade signals. The selected PEGs are converted to their triphosphates as shown in FIG. 42. For example, Fmoc-protected amino-butanol can be converted to the corresponding triphosphate by reacting first with phosphorous oxychloride followed by reaction with tributylammonium pyrophosphate in a one pot reaction. The triphosphate after purification is activated with DCC/DMF or CDI/DMF to provide activated triphosphate which reacts with the OH-group of the PEGs to generate PEG-triphosphates. The same scheme is applicable for both linear as well as branched PEGs. These PEG phosphates are tested in nanopores to optimize the conditions for generating distinct current blockade signals.

The polyamino acid (polylysine, polyarginine, interrupted polylysine) linkers are synthesized by standard peptide synthetic strategies; if an ester linkage to the polyphosphate chain is built in, it should be possible to use alkaline phosphatase to cleave it, resulting in more strongly positive tags for nanopore interrogation. Positive charges may also be incorporated into the PEG chains.

I.c Design and Synthesis of a Library of Terminal Phosphate-Tagged Nucleoside-5'-Triphosphates.

Terminal phosphate tagged nucleoside-5'-tri-, tetra-, and penta-phosphates are designed and synthesized. These molecules are tested in the polymerase reaction and the optimal ones are selected for nanopore detection. Terminal phosphate-tagged nucleoside-5'-tri-, tetra-, and penta-phosphates with a variety of tags, including small or large polylysines, amino acids, a variety of negatively or positively charged dyes, such as Energy Transfer dyes, and ethylene glycol units, have been shown to be accepted by DNA polymerases as excellent substrates for printer extension (Kumar et al. 2006 and 2008; Sood et al. 2005; and Eid et al. 2009).

I.c.1 Design and Synthesis of Terminal Phosphate-Tagged Nucleoside-5'-Triphosphates.

Figure 43:
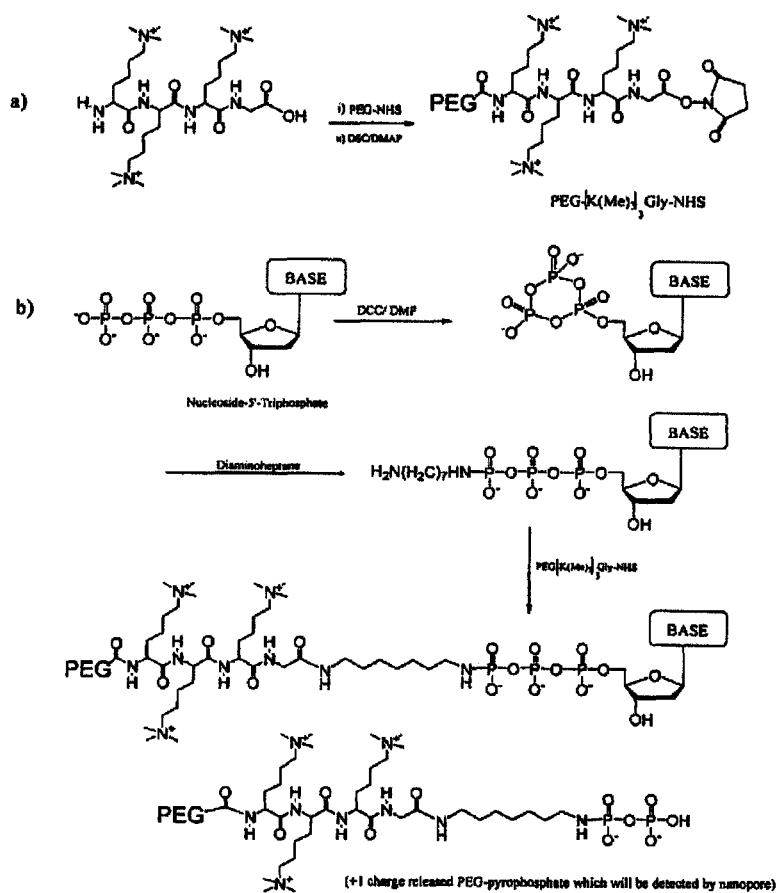
FIG. 43 shows synthesis of phosphate-tagged nucleoside-5'-triphosphates.

As shown in FIG. 43, terminal phosphate tagged-nucleoside-5'-triphosphates is synthesized by reacting the corresponding dNTP with DCC/DMF to yield a cyclic trimetaphosphate which can be opened with nucleophiles to generate a tag or linker attached nucleoside-5'-triphosphate. In addition, the linker attached to the phosphate can be reacted with PEG-NHS esters to provide alternate PEG-attached nucleoside-5'-triphosphates. The resulting terminal phosphate-tagged nucleoside-5'-triphosphate is used in the template-primer extension reaction and the released tag-attached pyrophosphate is detected and differentiated by its specific nanopore current blockade parameters.

I.c.2 Design and Synthesis of Terminal Phosphate-tagged Nucleoside-5'-tetraphosphates.

Figure 44:
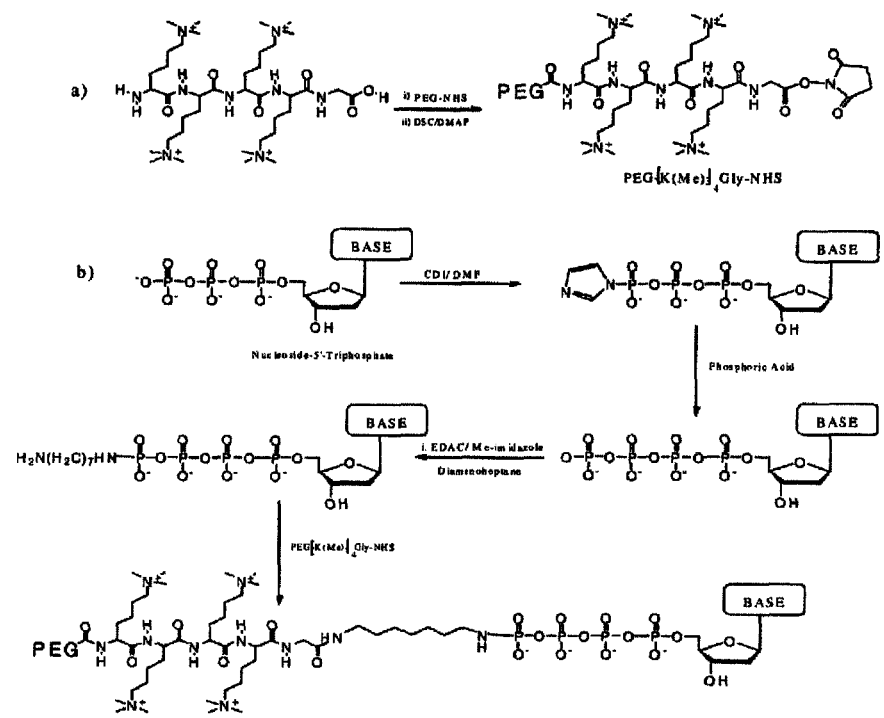
FIG. 44 shows synthesis of phosphate-tagged nucleoside-5'-tetraphosphates.

For synthesis of terminal phosphate tagged nucleoside-5'-tetraphosphates, the corresponding triphosphate is first reacted with CDI in DMF to activate the terminal phosphate group which is then reacted with phosphoric acid or tag-monophosphate to give the tetraphosphate as shown in FIG. 44. The terminal phosphate on the tetraphosphate can be further activated with EDAC in 0.1M imidazole buffer followed by reaction with an appropriate nucleophile to provide a linker attached tetraphosphate which can be used to attach tags of different mass, length or charge, such as m-PEG-NHS esters. In this case, four trimethyllysines are used to neutralize the charge of four phosphates. After polymerase incorporation, the net charge on the released PEG is +1 or, if treated with alkaline phosphatase, +4, which can be detected by the nanopore.

I.c.3 Design and Synthesis of Terminal Phosphate-tagged Nucleoside-5'-penta-phosphates.

Figure 45:
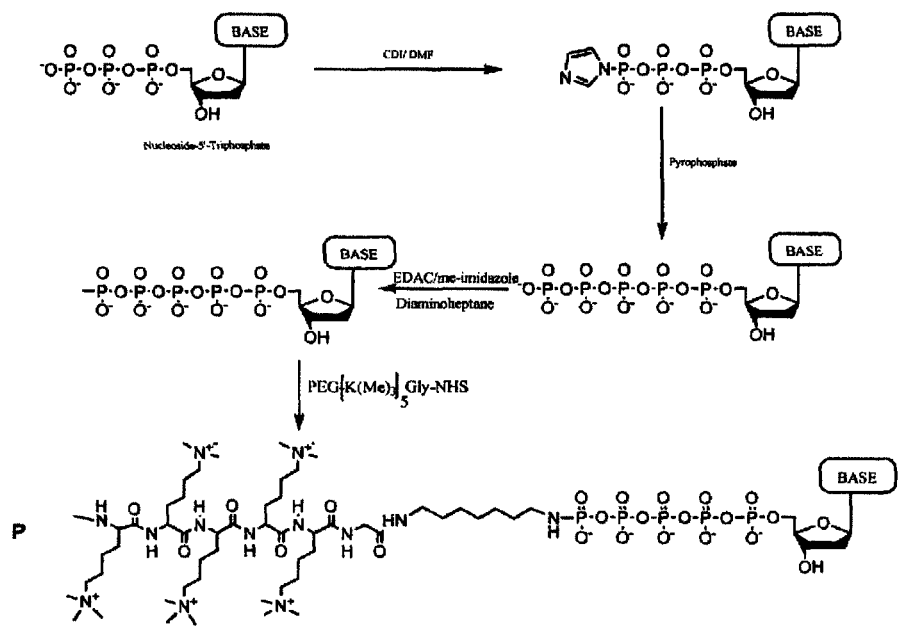
FIG. 45 shows synthesis of terminal phosphate-tagged nucleoside-5'-pentaphosphates.

Synthesis of terminal phosphate tagged nucleoside-5'-penta-phosphates follows the same principle as shown in FIG. 45. They can be prepared either from activated triphosphates or tetraphosphates by reacting with phosphoric acid, pyrophosphate or tag-attached phosphates. Alternatively, a linker can be attached to the pentaphosphate followed by reaction with activated NHS esters.

The terminal phosphate tagged nucleoside polyphosphates described above are used in the polymerase reaction to generate extension products. Following the scheme shown in FIG. 30 the performance of the terminal phosphate tagged nucleoside polyphosphates in polymerase extension are evaluated. We first perform a single base extension reaction and characterize the DNA extension product by MALDI-TOF mass spectroscopy to evaluate incorporation efficiency. After establishing optimized reaction conditions, we immobilize the template on magnetic beads and repeat the single base extension reaction, after which the released polyphosphate-tags are isolated from the solution for detection using a single nanopore. This reaction is performed continuously to evaluate all 4 nucleotides (A, C, G, and T) and their corresponding released tags detected by the nanopore. Continuous polymerase reaction with the polyphosphate-tag nucleotides and the clear distinction of the released polyphosphate-tag by nanopore establish the feasibility of the approach.

As shown in FIG. 30, after the polymerase reaction, the released by-product of the phosphate-tagged nucleotide (tag-polyphosphate) is obtained and the extended DNA strand is free of any modifications. This is advantageous because any scam remaining on growing DNA chains can affect their ability to be recognized by polymerase with increasing nucleotide additions, eventually terminating further DNA synthesis. The released tag-attached polyphosphate are assayed in the nanopore to evaluate sequencing sensitivity and accuracy. In initial experiments we test the tags for their blockade signals before running SBS reactions. DNA sequence can be determined if different tags for the four nucleotides are used to generate four different tagged-polyphosphates which differ by mass, charge or bulk, and yield 4 distinct blockade signals.

II. Detection of the Released Tagged Phosphates by Protein Nanopores

We use a single α-hemolysin nanopore to detect PEGs that are linked to nucleotides attached via a multi-phosphate linker and the same polymer after the nucleotide/ribose moiety has been cleaved by the DNA polymerase reaction. Each of the four different DNA bases is linked to a PEG polymer with a unique length. Thus, each base that is removed from the PEG by the polymerase is identified. Because the unreacted nucleotides cannot be separated from the released tagged polyphosphates, especially in real time situations, we take advantage of the method's extreme sensitivity to molecular charge to discriminate between the released reaction product and the starting material. We measure single a-hemolysin conductance using conical glass supports (White et al., 2006 and 2007) which allow data collection at 100 kHZ and ~4 pA RMS noise. We measure the blockade depth and residence time distributions of both the tagged nucleotides and tagged products over a wide range of transmembrane potentials to determine optimum conditions for nucleotide discrimination and to extend our current theoretical understanding of PEG-nanopore interactions (Robertson et al. 2007) to molecules with fixed charges. Characterization and theoretical understanding permit the unambiguous identification of the nucleotides incorporated into polynucleotides by polymerase. Thus, with these rational chemical designs and modifications of the building blocks of DNA, we optimize the use of nanopores to decipher DNA at the single molecule level with single base resolution in protein or synthetic nanopores.

Example 4

Fabrication of a Single Solid-State Nanopore for Single Molecule Sequencing

The transition from a protein nanopore to a solid state nanopore makes the fabrication of high-density nanopore arrays possible, a key step for yielding a high-throughput single molecule electronic DNA sequencer. Here, an integrated single solid state nanopore platform is developed to characterize the tagged nucleotides in the polymerase reaction based on the knowledge gained from the protein nanopore.

Integrated Nanopore Platform.

We developed specialized integrated low-noise CMOS electronics, which when integrated with solid-state nanopores, deliver significant performance advantages over "standard" measurement techniques which employ external electrophysiological amplifiers, such as the Axopatch 200B. These advantages come from exploiting capacitive (rather than resistive) feedback in a custom integrating amplifier design. DC current, which is characteristic of this and other bioelectronic interfaces, is removed with a low-noise current source operating in a DC servo loop. Reduced amplifier input capacitances and reduced parasitic capacitances associated with co-integration improve noise performance at high frequencies, enabling bandwidths approaching 1 MHz for solid-state pores. Such high temporal resolution, when combined with the tags developed, will provide high flexibility for tuning this platform for high sensitivity and real-time performance.

Use of this CMOS-integrated nanopore (CNP) integrated circuit in either a two-chip or one-chip configuration as shown in FIG. 46. In the former case, the pore is packaged together with the CNP as shown in FIG. 46B. In the latter, the pore is fabricated directly into the CNP as shown in FIG. 46C with fluidics on either side of the chip. In both cases, the cis electrode, which connects to the input of the amplifier, is integrated directly on the surface of the CNP. The one-chip configuration has the advantage of being easily scalable to a multiplexed platform at the cost of additional fabrication complexity. The ability to post-process fabricated CMOS dice (which are no more than 5 mm on a side) is a unique capability established over the last five years (Huang et al. 2011, Lei et al. 2008, and Levine et al. 2009). This approach completely leverages existing foundry process flows rather than requiring new process development.

The one-chip fabrication approach proceeds by adapting standard solid-state nanopore fabrication techniques (Rosenstein et al. 2011). In areas of the die reserved for the sensors, all metals have been blocked, leaving a thick stack of alternating glass fill and silicon nitride capping layers. The majority of the dielectric stack is etched using an inductively-coupled $CHF_3$ plasma. After depositing and patterning a PECVD $Si_3N_4$ etch mask on the back of the die, localized openings in the silicon substrate are made using an anisotropic potassium hydroxide etch. A short dip in buffered hydrofluoric acid is then used to isolate a single 50 nm layer of silicon nitride from the original dielectric stack as a suspended membrane. Finally, nanopores are drilled through these nitride membranes with a high resolution transmission electron microscope.

Figure 47:
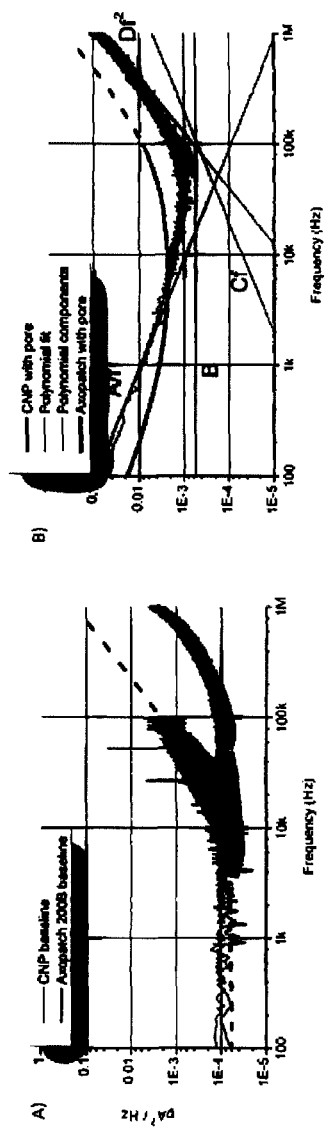
FIG. 47 shows electrical performance of the CMOS-integrated nanopore electronics (A) Input-referred baseline current noise spectrum for $C_F$=0.15 pF, 1 MHz 4-pole Bessel filter, $f_s$=4MS/s. Also shown is the measured open-headstage of an Axopatch 200B in whole-cell mode with β=1, 100 kHz 4-pole Bessel filter, $f_s$=250 kS/s (B) noise floor of the new amplifier with a nanopore attached compared with the same nanopore measured by the Axopatch 200B.

The measured noise of this system is shown in FIG. 47A, alongside a measurement of the baseline noise for a comparable configuration of the Axopatch 200B. For the highest bandwidth supported by the Axopatch (B=100 kHz), the integrated amplifier has a noise floor of 3.2 $pA_{RMS}$, compared to 9 $pA_{RMS}$ for the Axopatch. At the highest bandwidth characterized for the integrated amplifier (B=1 MHz), the noise level is 27 $pA_{RMS}$, in contrast with 247 $pA_{RMS}$ modeled by extrapolating the Axopatch response beyond its supported range (approximately a factor-of-ten lower noise). As a point of comparison, for a 1 nA signal, only about 6250 ions are transported through the pore in 1 us. An input-referred noise level of 27$pAV_{RMS}$ for integrated amplifier allows resolution of as few as 150 ions in this interval.

It is also important to note this superior electrical performance is obtained with an integrated amplifier that consumes an area of only 0.2 $mm^2$ on a CMOS chip compared with a rack-mounted Axopatch amplifier, demonstrating the significance of the innovative electronics. When a nanopore is connected to the amplifier input, the introduction of 1/f noise and membrane capacitance raises the noise spectrum above the open-headstage baseline. FIG. 47b shows a typical noise spectrum in this case, demonstrating noise floors of only 10 $pA_{RMS}$ and 163 $pA_{RMS}$ for bandwidths of 100 kHz and 1 MHz, respectively. Measured comparisons are shown with the Axopatch up to 100 kHz for the same nanopore. At 100 kHz, there is more than a factor-of-two reduction in input-referred noise power for the CNP. If the Axopatch can be measured at higher bandwidths, there can be a factor-of-six noise power difference at 1 MHz.

This platform also allows the integration of biological nanopores, providing even more flexibility. Biological nanopores are created in lipid membranes (typically 1,2-dioleoyl-sn-glycero-3-phosphocholine (DOPC)) formed over a hole in a teflon membrane between two fluid cells. The surface must be sufficiently hydrophilic for the membrane to form from unilamellar vesicles. The conductance between the two chambers of the cell is monitored while the membrane protein is added to one of the cells, which is immediately flushed once incorporation is detected. The membranes used to fabricate the nanopores can also be used as solid supports for lipid bilayers with the drilling of larger holes into the membranes, over which the lipid bilayer is formed (Clarke et al. 2009; Benner et al., 2007; Hou et al., 2009; and Wang et al. 2011). Planar bilayer lipid membranes (BLMs) have been engineered with different protein channels on patterned solid supports with nanopatterned holes (~100 nm in diameter), as well as tethering them directly on gold through a self-assembled monolayer assembly (Axelrod et al., 1976, Bultmann et al. 1991, Dutta et al. 2010, Jenkins et al. 2001, Nam et al. 2006, Palegrosdemange et al. 1991, Shen et al. 2009, Srinivasan et al. 2001, Yang et al. 2003, Yin et al. 2005). Moreover, it has been shown that formation of contiguous BLMs with a diffusion coefficient of 4 $\mu m^2$/s on nanopatterned substrates; BLMs formed on SAM-gold assemblies yielded a coefficient of 0.8 $\mu m^2$/s. Both fall within the ideal diffusion range of 0.1-10 $\mu m^2$/s representative of well-formed BLMs (Axelrod et al. 1976, Bultmann et. al. 1991). Electrical characterizations of these BLMs indicate a high impedance membrane with a 1.4GW-$mm^2$ resistance, making it amenable for further electrical analysis of biological nanopores formed in the membrane (Oliver et al. 1994, Shi et al. 2000, Wiehelman 1988).

Immobilization of Polymerase to Nanopore-Bearing Surfaces

The size of the polymerase is about 5 nm×5 nm. One polymerase is positioned near the entrance to each nanopore. To accomplish this for the solid-state nanopores, it is necessary that (1) a unique position on the surface be modified with functional groups during CMOS fabrication to bind the polymerase; (2) that the sites be small enough that only one polymerase molecule can bind; (3) that they be far enough apart that there is little possibility of diffusion of the released tagged polyphosphates to a nearby channel; and (4) that the cross-linking agent be sufficiently flexible that the enzyme is functionally intact. Polymerase tethering is accomplished by combining a patterned attachment point with the use of an appropriate concentration of polymerase solution during incubation such that at most one enzyme molecule is attached.

Establishment of the appropriate tether point for the polymerase is accomplished by exploiting existing fabrication approaches for solid-state nanopores. Typically, to maximize the transduction signals, these pores are created by thinning a supported $Si_3N_4$ membrane using e-beam lithography to define a window which is subsequently thinned with a plasma etch (e.g. $SF_6$). The nanopore is then drilled in the thinned region using e-beam ablation. The well created by this window (FIG. 48) creates a natural place to tether the polymerase, guaranteeing close proximity to the nanopore entrance. Prior to etching the thinned window, the original membrane can be augmented with a buried epitaxial layer of attachment material. Once the window is etched, this can become a selective sidewall region for polymerase attachment. Attachment materials include silicon dioxide or gold. There may be limited selectivity with silicon dioxide, however, because an oxide can also form on the silicon nitride surface under appropriate conditions.

In principle, with silicon dioxide surfaces, biotin-streptavidin linkages can be used (Korlach et al. 2008 and 2010), utilizing biotinylated PEG molecules on the silica patches and incubate biotin-end labeled polymerase in the presence of streptavidin. The remainder of the surface is passivated with polyvinylphosphonic acid. Due to the concerns raised above, it is preferable instead to modify the gold surface with an alkanethiol self-assembled monolayer (SAM) functionalized with amino groups (Love et al. 2005). These can be easily modified to NHS esters for attachment to amino groups on the polymerase. The thickness and homogeneity of the layer is determined by ellipsometry or atomic force microscopy.

Development of 5'-Modified Nucleotides with Positively Charged Linkers

A system for rapid diffusion of the released tags toward the pores while the precursor nucleotides and DNA are repelled by the pores is generated. The tagged nucleotides are engineered so that after incorporation into the DNA, the tag released from the nucleoside has a cumulative positive charge while the intact tag-nucleotides remain neutral. This allows actively gating the released tag specifically through the detection channel, if the channel is negatively charged according to methods (Wanunu et al. 2007). As all other free molecules present in the reaction mix (primers, unreacted nucleotides, template), other than the tag, are negatively charged, only the released tag carrying positive charge is attracted into the channel, increasing the specificity of detection and reducing noise. A different number of charged groups can be used on different tags, depending on the specific nucleotide base. Thus the cumulative charge of the tag along with its size can be used for base discrimination. After incorporation and release of the tag, if the polyphosphate is deemed to mask the positive charge, it can be removed using secondary reactions (for example, alkaline phosphatase immobilized at a second downstream site in the pore). The positively charged tag can be gated into the negatively charged channel for detection and recognition.

Diffusion and Drift

Figure 48:
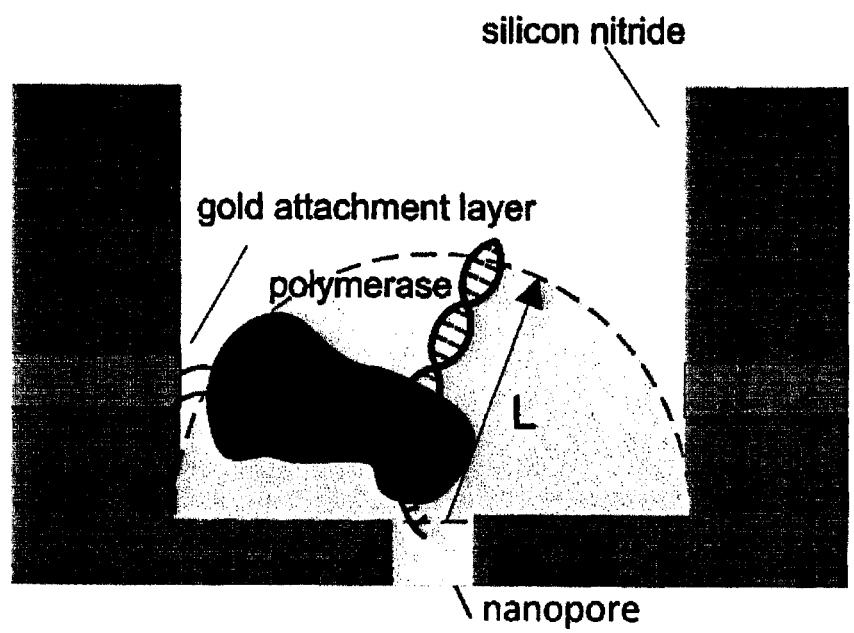
FIG. 48 shows tethering of the polymerase in the vicinity of the nanopore; a well helps to restrict diffusion; L denotes the critical distance from the pore opening at which molecular motions due to diffusion and electrophoresis are equal.

A critical aspect of this sequencing system is the reliable and timely capture of each nucleotide's released tag by the adjacent nanopore. Conditions must be engineered such that tags are captured quickly and in the correct order. Additionally, the capture rate of unincorporated tags should be minimized, and interference from adjacent channels should be negligible. Creating the well at the entrance of the pore (as shown in FIG. 48) assists this process, which also depends on close proximity of the polymerase to the nanopore opening. Analysis of nanopore capture processes generally considers a radially symmetric process surrounding the pore. Geometry dictates that in the absence of an electric field, a molecule tends to diffuse farther from a pore, opposing the electrostatic attraction. With a voltage gradient, there exists a critical distance L at which molecular motion due to diffusion and electrophoresis are equal (Gershow et al. 2007). This critical distance is a function of the ionic current (I) and electrolyte conductivity ($\sigma$), as well as the diffusion constant (D) and mobility ($\mu$) of the analyte molecule, $$L = \frac{|I|}{2\pi\sigma}\frac{\mu}{D}.$$

Capture is a statistical process, but approximately 50% of molecules at a distance L is captured. This likelihood increases for shorter distances, and exceeds 90% for d<L/3. During this process, molecules typically are captured in a timescale on the order of $$t_{capture} = \frac{L^2}{2D}.$$

By placing the polymerase within L/3 of the nanopore, nearly all molecules are captured. It also ensures that $t_{capture}$ is significantly faster than the polymerase incorporation rate, to capture bases in the correct order.

An approximate value for the diffusion coefficient of 25-unit PEG molecules in water is D=3e-10 $m^2/s$ (Shimada et al. 2005), which is on the same order of magnitude as a similar-length ssDNA fragment (Nkodo et al. 2001). Assuming validity of the Nernst-Einstein relation (although this does not always hold true for polymers), the mobility can be estimated as a function of the diffusion constant and net charge (Q), $$\mu \approx \frac{QD}{k_B T}.$$

For these estimates, then, with I=5 nA in 1M KCl—see the following Table.

|  | +1e | +4e |
| --- | --- | --- |
| 50% capture | 2.1 nm | 5.8 nm |
| 90% capture | 0.7 nm | 1.9 nm |
| $t_{capture}$ | 7.1 ns | 114 ns |

Example 5

Fabricate an Array of Solid-State Nanopores

In addition to improved performance, only with the integrated electronics is it possible to produce massively parallel nanopore arrays. This involves the one-chip topology shown in FIG. 46C in which nanopores are integrated directly into the CMOS die with fluidics on either side of the chip. The approach for integrating multiple pores is also shown in FIG. 46C. In this case, wells of SU-8 photoresist are used to isolate individual nanopores from each other. This is an approach similar to that of Rothberg et al. 2011. In Rothberg et al., however, the wells can still remain "connected" by the solution reservoir above the chip. In present case, since electrical isolation is necessary between the cis reservoirs, a PDMS cap is used to seal the wells for measurement after the introduction of reagents as shown in FIG. 46C. 64 solid-state nanopores are integrated onto the same 5-mm-by-5-mm die. The current integrating amplifier design, which can have to be duplicated at each pore site, is only 250 um by 150 um, but additional space has to be left for the fabrication of the pore itself. As fabrication techniques are further developed to reduce the chip area, this can be easily scaled to an array of 16-by-16 electrodes.

Example 6

Pyrosequencing Using Phosphate-Tagged Nucleotide and Nanopore Detection

Pyrosequencing is sequencing by synthesis (SBS) method which relies on the detection of pyrophosphate that is released when a nucleotide is incorporated into the growing DNA strand in the polymerase reaction (Ronaghi et al. 1998). In this approach, each of the four dNTPs is added sequentially with a cocktail of enzymes, substrates, and the usual polymerase reaction components. If the added nucleotide is complementary to the first available base on the template, the nucleotide will be incorporated and a pyrophosphate will be released. Through an enzyme cascade, the released pyrophosphate is converted to ATP, and then turned into a visible light signal by firefly luciferase. On the other hand, if the added nucleotide is not incorporated, no light will be produced and the nucleotide will simply be degraded by the enzyme apyrase. Pyrosequencing has been applied successfully to single nucleotide polymorphism (SNP) detection and DNA sequencing. A commercial sequencing platform was developed combining pyrosequencing and DNA template amplification on individual microbeads for high-throughput DNA sequencing (Margulies et al. 2005). However, there are inherent difficulties in pyrosequencing for determining the number of incorporated nucleotides in homopolymeric regions (e.g. a string of several T's in a row) of the template. Beside this, there are other aspects of pyrosequencing that still need improvement. For example, each of the four nucleotides has to be added and detected separately. The accumulation of undegraded nucleotides and other components can also lower the accuracy of the method when sequencing a long DNA template.

This is a modified pyrosequencing approach which relies on the detection of released tag- or tag-phosphates during polymerase reaction. In this approach, phosphate-tagged nucleotides are used in polymerase catalyzed reaction on a template-primer complex. Upon incorporation of the tagged-nucleotides, the phosphate-tag moiety is released, which can be detected by passing through a nanopore. The same tag can be used on each nucleotide or a different molecular weight and length tag (such as PEGs) can be used. It has been shown that polyethylene glycols (PEGs) of different length and mass can be resolved at single-molecule sensitivity when passed through hemolysin nanopore (Robertson et al. 2009).

An α-hemolysin channel can be used to detect nucleic acids at the single molecule level (Kasianowicz et al. 1996). The monomeric polypeptide self-assembles in a lipid bilayer to form a heptameric pore, with a 1.5 nm-diameter limiting aperture. In an aqueous ionic salt solution, the pore formed by the α-hemolysin channel conducts a strong and steady ionic current when an appropriate voltage is applied across the membrane. The limiting aperture of the nanopore allows linear single-stranded but not double-stranded nucleic acid molecules (diameter ~2.0 nm) to pass through. The polyanionic nucleic acids are driven through the pore by the applied electric field, which blocks or reduces the ionic current. This passage generates a unique electronic signature. Thus a specific event diagram, which is the plot of translocation time versus blockade current, will be obtained and used to distinguish the length and the composition of polynucleotides by single-channel recording techniques based on characteristic parameters such as translocation current, translocation duration, and their corresponding dispersion in the diagram. Four PEG tags, which have been shown to yield distinct current blockade signals in nanopores, are selected to couple with four nucleotides (A, C, G, T) at the terminal phosphate. These novel nucleotide analogs are used in a polymerase reaction and use nanopores to detect the released tags for decoding the incorporated bases as shown in FIG. 33.

There are several advantages to this approach:
1) Avoid the use of many different enzymes (saves cost and complexity).
2) Addition of single tag-attached nucleoside polyphosphate sequentially or all four nucleotides with different tags attached to each nucleotide.
3) Use of PEGs as tags which can be detected by nanopore at a single unit resolution.
4) Real time Single molecule detection sequencing as the tag passes through the nanopore.
5) Massively parallel sequencing, low cost and high throughput.

As shown in FIG. 33, DNA polymerase is immobilized to the nanopore and the template-primer along with the PEG-tagged nucleotides is added. On incorporation of the correct PEG-tagged nucleotide, the released PEG-phosphates pass through the nanopore and the electronic blockade signal is measured. Different length PEGs have different blockade signals, thus, 4 different PEGs can be used for 4 different nucleotides.

The nucleotides can be added one at a time, if the correct nucleotide is added it gives a distinct blockade signal. However, if the nucleotide is not complementary to the template nucleic acid base, it will not be incorporated and thus no signal detected. In a massive parallel way high density array of micro/nano wells to perform the biochemical process can be constructed. Each micro/nano-well holds a different DNA template and nanopore device. The released PEGs are detected at single-molecule sensitivity.

Figure 49:
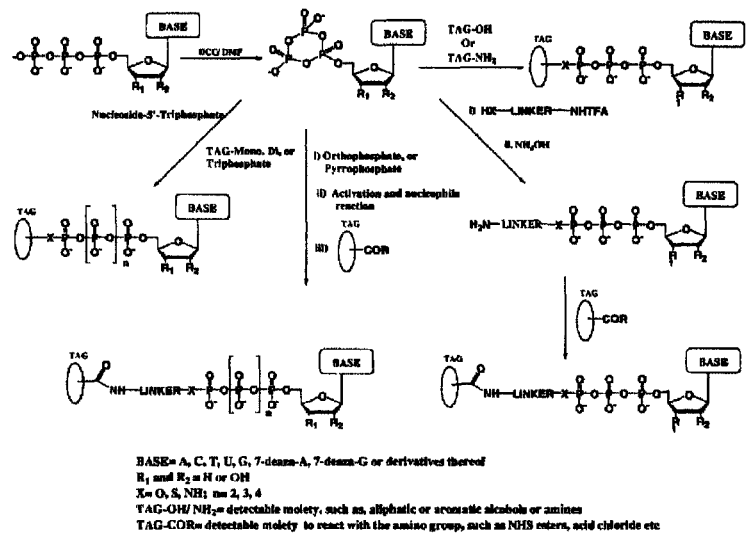
FIG. 49 shows synthesis of Tag-labeled-nucleoside-5'-polyphosphates.

General methods for synthesis of TAG-labeled-nucleoside-5'-polyphosphate is shown in FIG. 49. Terminal-phosphate-labeled-nucleoside-5'-tri, tetra-, penta-, or hexa-phosphates can be synthesized starting from the corresponding nucleoside-5'-triphosphates (NTP). Thus, triphosphate is first activated with DCC/DMF which can be directly reacted with the TAG-nucleophile to give TAG-attached-NTP or it can be reacted with a linker nucleophile to which a TAG-NHS or appropriately activated TAG can be reacted to provide TAG-linker-attached NTP. For the synthesis of TAG-attached nucleoside tetraphosphates (N4P) or pentaphosphates (N5P), the activated triphosphate is first reacted with phosphoric acid or pyrophosphate to give tetra- and penta-phosphate, respectively, which can be reacted with linker nucleophile followed by the reaction with appropriate activated TAGs.

Synthesis of PEG-labeled nucleotides are discussed above in Examples 2 and 3. The PEG-labeled nucleotides have -3, -4, -5, or -6 charges based on the use of tri, tetra-, penta-, or hexa-phosphates. After polymerase catalyzed primer-extension reaction, the net charge on the released PEG-tags will be one less (−1) than the starting PEG-nucleotide which is enough to distinguish by the nanopore ionic blockade signal (unreacted PEG-nucleotide is also bulkier than the released PEG-phosphates, thus different ionic blockade signal). Alternatively, if alkaline phosphatase is present in the reaction mixture, the released PEG will be neutral (the free phosphate groups are hydrolyzed by alkaline phosphatase). The released PEG-tags can also be made positively charged as shown below so that they can be easily detected by nanopores. Similarly, they can also be made highly negatively charge.

Synthesis of Positively Charged TAG-Attached-Nucleoside-Polyphosphates:

The positively charged TAG-attached nucleoside-polyphosphates are synthesized as shown in FIG. 44. First, a positively charged trimethyl-(lysine)$_n$-glycine amino acid (K((Me)$_3$)$_n$-Gly) is reacted with the PEG-NHS ester and then activated to form the PEG-K((Me)$_3$)$_n$-Gly-NHS ester. This activated ester is reacted with the amino-terminated nucleoside-polyphosphate as shown in FIGS. 38 and 44. The net charge on the nucleoside-tetraphosphate is neutral but after polymerase incorporation, the released PEG has a +1 positive charge and if alkaline phosphatase is added to the reaction cocktail, the net charge on the released PEG is +4. Thus the released TAG can be easily separated and identified by passing through the nanopore.

Synthesis of 3'-Blocked-PEG-Attached-Nucleoside-Polyphosphates for Sequencing by Synthesis with Nanopore Detection.

Figure 50:
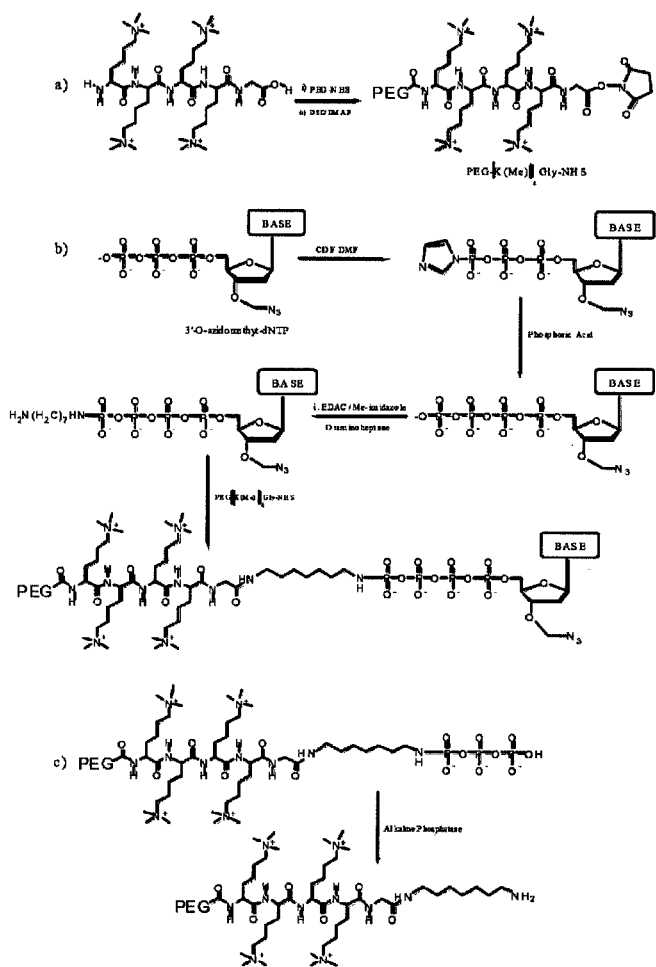
FIG. 50 shows synthesis of 3'-O-blocked-PEG-nucleotides.

The synthesis of 3'-blocked-nucleoside-polyphosphates essentially follows the same route as shown for TAG-attached nucleoside-polyphosphates, except that the starting nucleoside-5'-triphosphate is 3'-O-blocked-dNTP. As shown in FIG. 50, 3'-O-azidomethyl-dNTP (6) is first reacted with CDI or DCC/DMF followed by reaction with phosphoric acid (tetraphosphate) or pyrophosphate (pentaphosphates). This is reacted after purification with the appropriate nucleophile to provide amino-terminated phosphate which is then reacted with the appropriate PEG-NHS ester (neutral, positively charged or negatively charged) to provide required 3'-O-blockade-PEG-attached-nucleoside-polyphosphate.

Sequencing scheme with PEG-nucleotides and nanopore detection (many copies of a DNA molecule are immobilized on a bead and sequential addition of one PEG-nucleotide at a time).

As shown in FIG. 51, the DNA molecules are immobilized on a bead. Thus each bead has many copies of the same DNA molecule. The bead is added to a micro/nano-well which is attached to a nanopore. The DNA forms the complex with the DNA polymerase which is either attached to the nanopore or added to the micro/nano well along with the PEG-attached nucleotide. The nucleotides can be added one at a time, if the correct nucleotide is added it is incorporated and release a PEG-Tag which gives a distinct blockade signal when passed through a nanopore. However, if the nucleotide is not complementary to the template nucleic acid base, it will not be incorporated and thus no signal detected. In this case, the same length and molecular weight PEG can be used on all four nucleotides, or, if desired, four different PEGs can also be used. Thus, addition of nucleic acid base can be easily detected by the nanopore blockade signal at single-molecule sensitivity.

Sequencing by synthesis with 3'-O-blocked-PEG-nucleotides and nanopore detection (many copies of a DNA molecule are immobilized on a bead and simultaneous addition of all four 3'-O-blocked-PEG-nucleotides).

The homopolymeric regions of the DNA can be corrected sequenced using this approach. Thus, if the 3'-OH group of the nucleotide is blocked by a reversible moiety, the DNA synthesis will stop after addition of only one nucleotide. The synthesis can be continued after the removal of the blocking group to generate a free 3'-OH group. As shown in FIG. 52 all four different size PEG-attached-3'-O-azidomethyl-nucleotides can be added to the reaction micro/nano-well and whenever a correct nucleotide is incorporated, the released PEG-tag is read by passing through the nanopore and ionic signal detected. Because 3'-OH group is blocked only one nucleotide is added at one time. This 3'-O-blocked group can be cleaved by TECP treatment and thus free OH group is ready for further nucleotide incorporation. By repeated nucleotide addition and cleavage, homopolymeric region can be correctly and easily sequenced.

Figure 53:
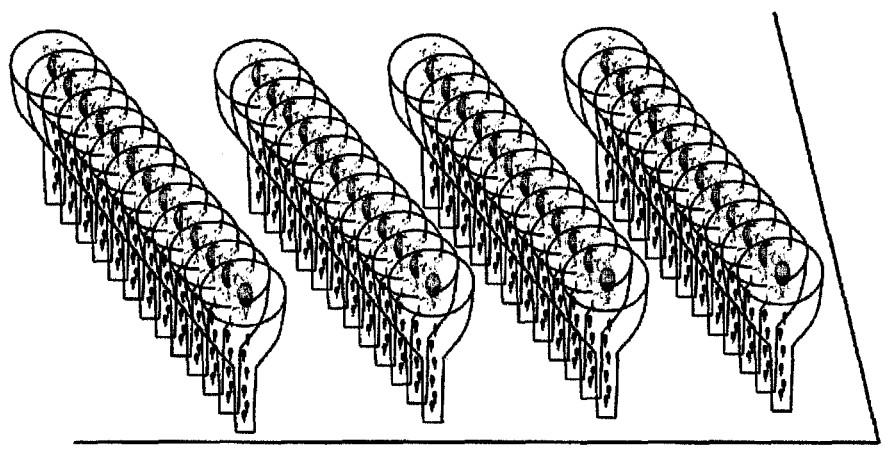
FIG. 53 shows a schematic for a massive parallel high density array of micro wells to perform the sequencing process. Each well can hold a different DNA template and nanopore device.

Massively Parallel Pyrosequencing Using Nanopores:

As shown in FIG. 53, in a massive parallel way high density array of micro wells to perform the biochemical process can be constructed. Each micro/nano-well holds a different DNA template and nanopore device. The released PEGs are detected at single-molecule sensitivity.

Summary of Experiment:
1) Any TAG of different size, length, molecular weight, charge attached to the terminal phosphate of the nucleotide which can be detected by nanopore after polymerase incorporation.
2) TAG attached to the tri-, tetra-, penta-, hexa-phosphates.
3) Electronic Detection
4) Group of DNA molecules attached to the bead or solid surface and single-molecule detection sensitivity (High density and high sensitivity).
5) Easily sequenced homopolymeric region by using TAG-attached-3'-O-blocked nucleotides.
6) Add one TAG-nucleotide per cycle.
7) Add all four reversibly tagged-nucleotides together for sequencing homopolymeric regions.
8) High sensitivity, accuracy and speed.
9) Massive parallel sequencing.

Example 7

Single Molecule Mass/Size Spectrometry in Solution Using Nanopore

Method

Solvent-free planar lipid bilayer membranes were formed from diphytanoyl phospatidylcholine (1,2-diphytanoyl-sn-glycero-3-phosphocholine; Avanti Polar Lipids, Alabaster, Ala.) in pentane (J. T. Baker, Phillipsburg, N.J.) on an ~70-μm diameter hole in a 25-μm thick Teflon partition that separates two identical Teflon chambers. The hole was pretreated with a solution of 1:400 vol/vol hexadecane (Aldrich, St. Louis, Mo.) in pentane, Both chambers contained 4 M KCl (Mallinckrodt, Paris, Ky.), 5 mM 2-amino-2-hydroxymethyl-1,3-propanediol (Tris; Schwarz/Mann Biotech, Cleveland, Ohio), adjusted to pH 7.5 with concentrated citric acid (Fluka, Buchs, Switzerland).

Single channels were formed by adding ~0.25 µg of α-hemolysin (List Biological Laboratories, Campbell, Calif.) to the solution on one side of the partition. After a single channel formed, the first chamber was rapidly flushed with fresh buffer to prevent further channel incorporation. Unless otherwise stated, the data were obtained with an applied potential of −40 mV with two Ag/AgCl electrodes separated from the bulk electrolyte by Vycor salt bridges (3 M KCl). The current was measured using an Axopatch 200B patch-clamp amplifier (Molecular Devices, Sunnyvale, Calif.) and filtered at 10 kHz with a four-pole Bessel filter before digitization at 50 kHz.

The α-hemolysin toxin may form at least two conformers that have different conductance levels and gating properties. Only the higher conductance conformer was used here, which has an approximately ohmic conductance of 3.75 nS between ±50 mV (data not shown). PEG (polydisperse PEG 1500; Fluka; or monodisperse PEG 1294; Polypure, Oslo, Norway) was added to the second chamber from stock solutions of 12 mg/ml in electrolyte to a final concentration of 0.045 mg/ml.

MALDI-TOF mass spectra of the PEG samples were obtained with a Voyager DE-STR (PerSeptive Biosystems, Framingham, Mass.) by using the reflection mode. Desorption/ionization was produced by irradiation with pulsed UV light (337 nm) from a nitrogen laser. The instrument was operated at 25 kV in the positive ion mode by using an extraction delay time set at 600 ns. The final spectra were averaged from 100 shots while moving the laser over the surface of the sample with the laser power set slightly over the threshold for the appearance of each spectrum. The samples were prepared from 1% wt/wt PEG solutions in distilled water. The matrix solution was 1:1 acetonitrile: water saturated with all-trans-retinoic acid (Sigma, St. Louis, Mo.) with 0.1% fluoroacetic acid (Matheson, Joliet, Ill.) added. The sample and matrix were mixed 1:1 to a total volume of 2 µl before drying.

Discussion

In the absence of analyte, the ionic current caused by a DC potential is well defined. The intrinsic noise in the ionic current may be caused in part by the Brownian motion of ions in the nanopore and the resistive barrier capacitance. The addition of analyte (for example, poly(ethylene glycol)) causes well-defined transient decreases in the conductance. Each pulse may correspond to the presence of a single PEG molecule in the nanopore. The current reductions cover a range of only ~50 picoamperes for a polydisperse PEG-1500 sample (average molecular mass ~1500 g/mol).

Nonelectrolyte polymers cause well-defined reductions in the ionic current as they partition into a solitary nanopore in a lipid bilayer membrane. The ionic current, through an a-hemolysin channel bathed by a polymer-free solution, is quiescent. Addition of polydisperse PEG ($M_r$=1,500 g/mol) cause persistent current reduced-conductance pulses.

A single nanopore discriminates between polymers with different molecular masses. The difference between the conductance states caused by polydisperse ($M_r$=1,500) and monodisperse (M=1,294 g/mol, n=29) PEG is readily apparent. The time series data contained ~500 and ~700 events for the poly- and monodisperse PEG samples, respectively. All-points histograms of the ionic current reflect the distinct natures of the two polymer samples. The ionic current histograms for each sample were calculated from >$10^5$ reduced-conductance pulse events. The long-lived, small ionic current reduced-conductance pulses near zero in the monodisperse PEG time series are most likely caused by impurities in the PEG samples. These events are long-lived but few in number.

Calibration of the mass or size spectrum may be accomplished by several techniques. For example, repeating the conductance-based experiment using a standard-size analyte allows assignment of the PEG 1294 g/mol peak in the polydisperse sample indicated as the polydisperse sample data. Neighboring peaks in the conductance-based histogram are caused by PEG molecules that differ by a single ethylene glycol unit (i.e., $CH_2$—$CH_2$—O). A comparison of the conductance-based size distribution to a MALDI-TOF mass spectrum of the same polydisperse PEG sample demonstrates accuracy of this method.

Example 8

Single Molecule Sequencing Using Tagged Polyphosphate Nucleotides and Nanopores

There is a significant need to accurately sequence single DNA and RNA molecules for personalized medicine. A novel nanopore-based sequencing by synthesis (SBS) strategy is described herein that accurately differentiates at single molecule level four different sized tags that are initially attached to the 5'-phosphate of each nucleotide. As each nucleotide is incorporated into the growing DNA strand during the polymerase reaction, its tag is released by phosphodiester bond formation between the a-phosphate of the tagged nucleotide and the 3'-OH group of the previous nucleotide. The released tags enter a nanopore in the order they were released, and effect a unique ionic current blockade signature due to their size, shape and charge, thereby determining the DNA sequence electronically at single molecule level with single base resolution. As a non-limiting example, four different length PEG-coumarin tags are attached to the terminal phosphate of 2'-deoxyguanosine-5'-tetraphosphate. Efficient incorporation of these modified nucleotides during the polymerase reaction is observed, and better than 6σ tag discrimination between the four tags based on the degree to which different tags reduce the nanopore ionic current. The molecular approach described here coupled with polymerase covalently attached to the nanopores in an array format yields a single-molecule nanopore-based SBS platform Methods Synthesis of Coumarin-PEG-dG4P Nucleotide Analogs All of the nucleotides are purified by reverse-phase HPLC on a 150×4.6 mm column (Supelco), mobile phase: A, 8.6 mM $Et_3N$/100 mM 1,1,1,3,3,3-hexafluoro-2-propanol in water (pH 8.1); B, methanol. Elution is performed from 100% A isocratic over 10 min followed by a linear gradient of 0-50% B for 20 min and then 50% B iscocratic over another 30 min.

A. Synthesis of Coumarin-PEGn-dG4P

Figure 15:
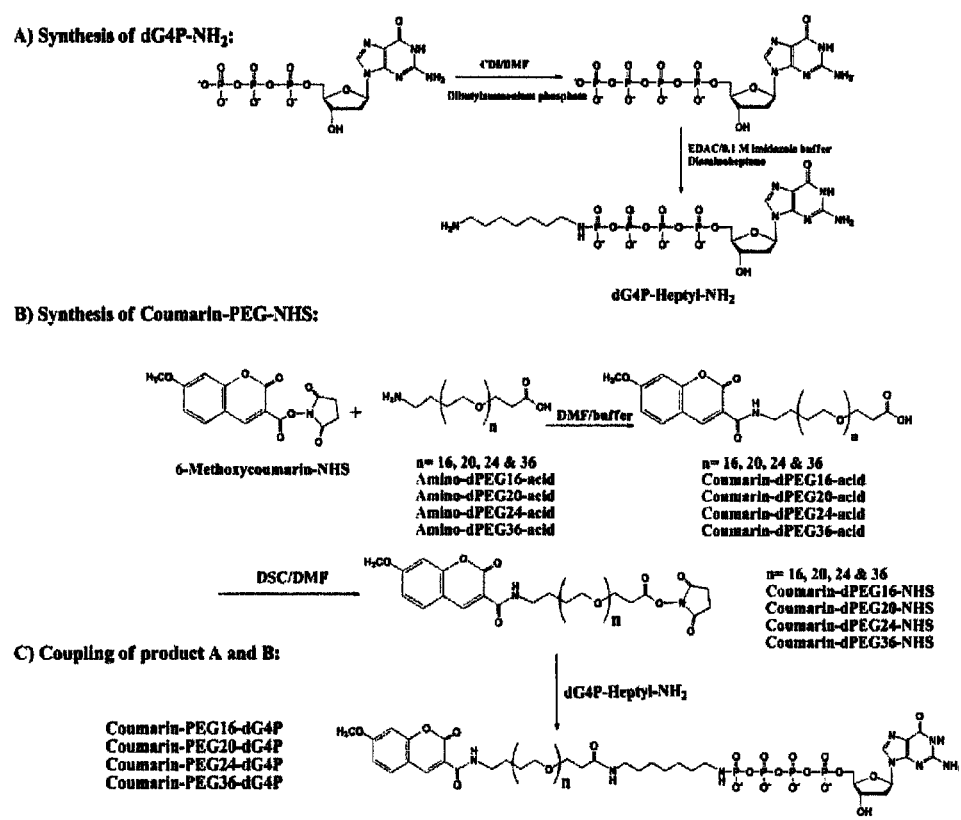
FIG. 15 shows an example of synthesis of coumarin-PEG-dG4P nucleotide analogs.

The synthesis of coumarin-$PEG_n$-dG4P involves three steps as shown in the scheme in FIG. 15.

A.1 Synthesis of 2'-deoxyguanosine-5'-tetraphosphate (dG4P)

First the synthesis of 2'-dG4P is carried out starting from 2'-dGTP. 300 umoles of 2'-dGTP (triethylammonium salt) is converted to the tributylammonium salt by using 1.5 mmol (5 eq) of tributylamine in anhydrous pyridine (5 ml). The resulting solution is concentrated to dryness and co-evaporated with 5 ml of anhydrous DMF (×2). The dGTP (tributylammonium salt) is dissolved in 5 ml anhydrous DMF, and 1.5 mmol 1,1-carbonyldiimidazole added. The reaction is stirred for 6 hr, after which 12 ul methanol added and stirring continued for 30 min. To this solution, 1.5 mmol phosphoric acid (tributylammonium salt, in DMF) added and the reaction mixture stirred overnight at room temperature.

The reaction mixture is diluted with water and purified on a Sephadex-A25 column using 0.1 M to 1M TEAB gradient (pH 7.5). The dG4P elutes at the end of the gradient. The appropriate fractions are combined and further purified by reverse-phase HPLC to provide 175 umol of the pure tetraphosphate (dG4P). $^{31}$P-NMR: δ, −10.7 (d, 1P, α-P), −11.32 (d, 1P, δ-P), −23.23 (dd, 2P, β, γ-P); ESI-MS (−ve mode): Calc. 587.2. Found 585.9 (M-2).

A.2 Synthesis of dG4P-heptyl-NH$_2$

To 80 umol dG4P in 2 ml water and 3.5 ml 0.2M 1-methylimidazole-HCl (pH 6) added 154 mg EDAC and 260 mg diaminoheptane. The pH of the resulting solution is adjusted to 6 with conc. HCl and stirred at room temperature overnight. This solution is diluted with water and purified by Sephadex-A25 ion-exchange chromatography followed by reverse-phase HPLC to give ~20 μmol dG4P-NH$_2$. This is confirmed by ESI-MS data (−ve mode): calc. 699.1. Found (698.1, M-1).

B. Synthesis of Coumarin-PEG-Acids and NHS Esters

The commercially available amino-dPEG-acids (Amino-d(PEG)16, 20, 24, 36-acids; Quanta Biodesign) are reacted with 6-methoxy coumarin-NHS ester to provide the corresponding coumarin-(PEG)$_n$-acid. Amino-PEG-acid (1 eq) is dissolved in carbonate-bicarbonate buffer (pH 8.6), followed by addition of coumarin-NHS (1 eq) in DMF, and the reaction mixture stirred overnight. The coumarin-PEG-acid is purified by silica-gel chromatography using a CH$_2$Cl$_2$-MeOH (5-15%) mixture and the appropriate fractions combined. These compounds are analyzed by $^1$H NMR and MALDI-TOF MS analysis.

MALDI-TOF MS Data:

|  | Coumarin-PEG16-acid | Coumarin-PEG20-acid | Coumarin-PEG24-acid | Coumarin-PEG36-acid |
| --- | --- | --- | --- | --- |
| Expected MW | 996 | 1,172 | 1,348 | 1,877 |
| Observed MW* | 1,016 | 1,192 | 1,368 | 1,899 |

*Difference in observed values due to presence of sodium salt.

The coumarin-PEG-acids are converted to the corresponding NHS esters by reacting with 1.5 eq. of disuccinimidyl carbonate (DSC) and 2 eq of triethylamine in anhydrous DMF for 2 h. The resulting NHS ester, which moves slightly higher than the acid on silica-gel plates, is purified by silica-gel chromatography using a CH$_2$Cl$_2$-MeOH (5-15%) mixture and used in the next step.

C. Coumarin-PEG$_n$-dG4P dG4P-heptyl-NH2 from step A above is taken up in 0.1 M carbonate-bicarbonate buffer (pH 8.6) and to this stirred solution added one of the coumarin-PEG-NHS compounds (in DMF). The resulting mixture stirred overnight at room temperature and then purified on a silica-gel cartridge (15-25% MeOH in CH$_2$C12 to remove unreacted coumarin-acid or —NHS and then 6:4:1 isopropanol/NH$_4$OH/H$_2$O). This is further purified twice by reverse-phase HPLC to provide pure coumarin-PEG-dG4P. The structure is confirmed by analysis on MALDI-TOF MS. Coumarin-PEG16-dG4P: retention time, 31.7 min; coumarin-PEG20-dG4P: retention time, 32.2 min; coumarin-PEG24-dG4P: retention time, 33.0 min; coumarin-PEG36-dG4P: retention time, 34.3 min.

MALDI-TOF MS Data:

|  | Coumarin-PEG16-dG4P | Coumarin-PEG20-dG4P | Coumarin-PEG24-dG4P | Coumarin-PEG36-dG4P |
| --- | --- | --- | --- | --- |
| Expected MW | 1,673 | 1,850 | 2,025 | 2,554 |
| Observed MW | 1,682 | 1,858 | 2,036 | 2,569 |

Figure 56:
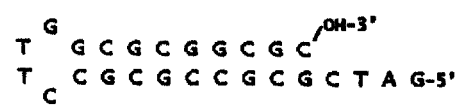
FIG. 56 shows structure of template-loop-primer used for SBS reactions; the C in the "template strand" allows addition by polymerase of dGMP to the "primer strand" and release of the coumarin-PEG-triphosphate tags from the coumarin-PEG-dG4P nucleotides.
Figure 58:
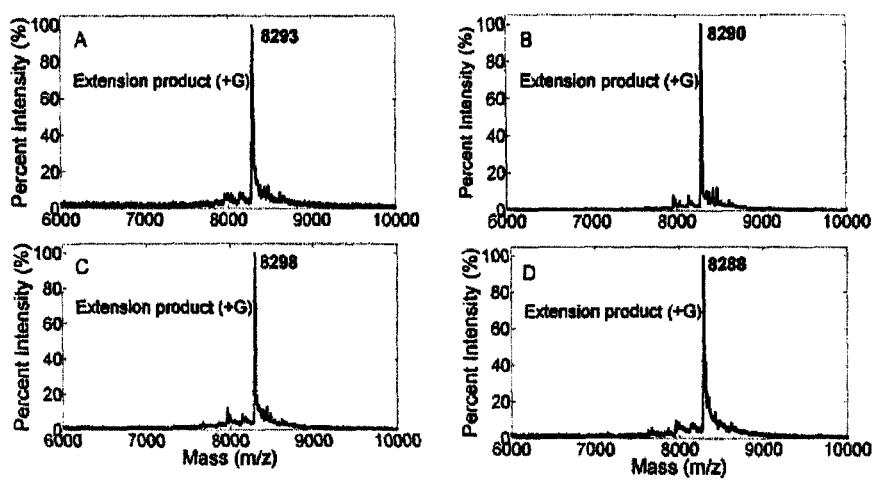
FIG. 58 shows MALDI-TOF MS measurement of the extension products obtained with the four coumarin-PEG-dG4P nucleotides; a template-loop primer, in which the template contained a C at the next position, was used along with one of the four PEG-tag-modified nucleotides for the polymerase reaction; in each case, 2'-dGMP is incorporated into the DNA, leading to a single base primer extension product.

DNA polymerase extension reactions using coumarin-PEG$_n$-dG4P:

Extension reactions are performed using a looped template-primer (5' GAT CGCGCCGCGCCTTGGCGCGGCGC-3', M.W. 7966), in which the next complementary base on the template is a C, allowing extension by a single G (FIG. 56). Each extension reaction is carried out in a GeneAmp PCR System 9700 thermal cycler (Applied Biosystems) at 65° C. for 25 minutes in 20 μl reactions consisting of 3 μM looped template-primer, 1× Therminator γ buffer (50 mM KCl, 20 mM Tris-HCl, 5 mM MgSO$_4$, 0.02% IGEPAL CA-630 (pH9.2@25° C.)), 2 units of Therminator v DNA polymerase (New England Biolabs), and 15 μM of one of the coumarin-PEG-dG4P nucleotides. The DNA extension products are precipitated with ethanol, purified through C18 ZipTip columns (Millipore), and characterized by MALDI-TOF MS using an ABI Voyager instrument. As shown in FIG. 58, four identical products (expected molecular weight 8,295) are obtained.

Polymerase extension reactions for each coumarin-PEG$_n$dG4P are repeated and the products (coumarin-PEG$_n$-triphosphate, FIG. 57) are treated with alkaline phosphatase (1U at 37° C. for 15 min) to yield the coumarin-PEG$_n$NH$_2$ tags. These are extracted into dichloromethane and characterized by MALDI-TOF-MS analysis.

Acid Hydrolysis of Coumarin-PEG-dG4P (FIG. 57):

Acetic acid is added to the coumarin-PEG-dG4P nucleotides to a final concentration of 10%, and the solution is vigorously shaken overnight to ensure the hydrolysis of the N—P bond between the 8 phosphate and the heptylamine. The solution is dried using a CentriVap and resuspended in an appropriate volume of water. A 1 μl aliquot is collected for MALDI-TOF mass spectrometry characterization, and a second aliquot is measured at 260 nm and 350 nm using a NanoDrop ND-1000 spectrophotometer.

Figure 16:
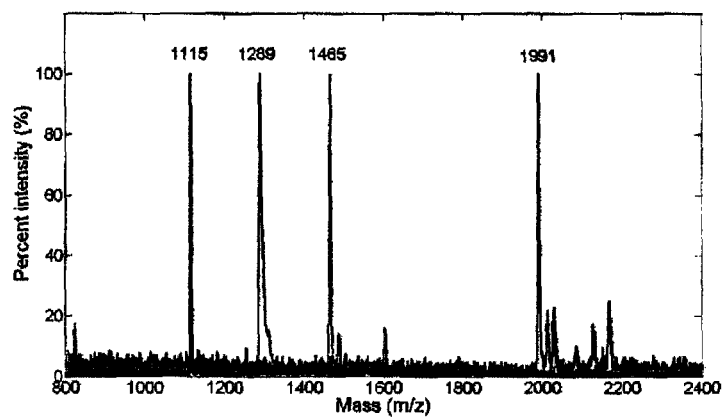
FIG. 16 shows an example of characterization of the released tags by MALDI-TOF MS; coumarin-PEG-$NH_2$ tags generated by acid hydrolysis of coumarin-PEG16-dG4P yielding coumarin-PEG16-$NH_2$ (blue), coumarin-PEG20-dG4P yielding coumarin-PEG20-$NH_2$ (green), coumarin-PEG24-dG4P yielding coumarin-PEG24-$NH_2$ (orange) and coumarin-PEG36-dG4P yielding coumarin-PEG36-$NH_2$ (red), are identical to the corresponding released tags generated in polymerase extension reactions after treatment with alkaline phosphatase, as shown by MALDI-TOF-MS analysis; a composite image of four separately obtained MS spectra is shown; the structures of the coumarin-PEG-$NH_2$ tags are shown.
Figure 16:
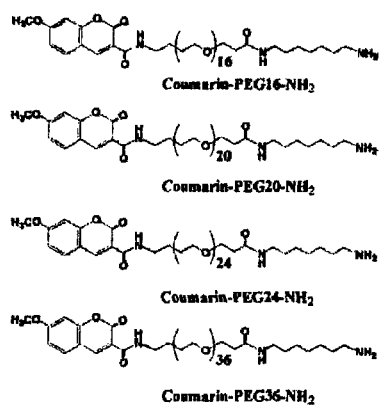

The resulting coumarin-PEG-amine compounds are the expected size as measured by MALDI-TOF MS (see FIG. 16 and following table).

|  | Coumarin-PEG16-NH$_2$ | Coumarin-PEG20-NH$_2$ | Coumarin-PEG24-NH$_2$ | Coumarin-PEG36-NH$_2$ |
| --- | --- | --- | --- | --- |
| Expected MW | 1,107 | 1,284 | 1,460 | 1,988 |
| Observed MW | 1,115 | 1,289 | 1,465 | 1,991 |

Nanopore Measurements:
Membrane and Channel Formation

Single α-hemolysin channels are inserted into solvent-free planar lipid bilayer membranes (BLMs)(Montal et al., 1972) fabricated across an ~80 μm diameter hole in a 25 μm thick Teflon partition separating two electrolyte solution wells as described previously. (Reiner et al. 2010) 4 M KCl, 10 mM Tris titrated to pH 7.2 with citric acid is used throughout the experiment. Membranes are formed by first wetting the partition with 1% v/v hexadecane/pentane. 10 mg/mL diphytanoyl phospatidylcholine (DPhyPC) in pentane is spread at both air-electrolyte solution interfaces with the solution levels well below the hole in the Teflon partition. After 10 min, the solution levels are raised above the hole spontaneously to form a membrane. Approximately 0.5 µL of 0.5 mg/mL α-hemolysin is injected into the solution immediately adjacent to the membrane and the ionic current is observed until a single channel inserted into the membrane. The cis chamber contents are then exchanged with protein-free electrolyte solution to maintain a single channel.

Coumarin-PEG$_n$-NH$_2$ molecules (n=16, 20, 24 and 36) are added to the trans side of the pore (defined as the β-barrel side of the channel) to a final concentration between 0.4 µmol/L and 1 µmol/L of each component. Ionic current is recorded between two matched Ag/AgCl (3 M KCl) at a fixed potential (−40 mV) for approximately 15 min to achieve sufficient counting statistics. Data are recorded with a 4-pole Bessel filter at 10 kHz oversampled at 50 kHz.

Data Analysis

Data are analyzed off-line with an in-house program written in LabVIEW (National Instruments) as described previously. (Rodrigues et al. 2008) In brief, blockades are located with an event detector based on a simple threshold algorithm set at 5σ of the current noise in the open state. When an event is detected, the points in the rise time and decay time are discarded (∼60 µs and 20 µs, respectively). The mean blockade depth is calculated from the remaining points and the open channel current is calculated from the mean of 0.8 ms of open channel data separated 0.2 ms from the threshold. The data are reported as a ratio of the means ($<i>/<i_{open}>$) and the nanopore spectra is calculated as a histogram of these values.

Discussion

In 1996, Kasianowicz et al. (Kasianowicz et al. 1996) first demonstrated that the α-hemolysin (αHL) channel can be used to detect nucleic acids at the single molecule level. The αHL channel has a 1.5 nm-diameter limiting aperture, (Song et al. 1996; Bezrukov et al. 1996; Krasilnikov 2002; Kasianowicz 1995) and its voltage-dependent gating can be controlled, such that the pore remains open indefinitely, (Kasianowicz 1995) which made it an ideal candidate for nanopore-based detection and discrimination. Individual single-stranded polyanionic nucleic acids are driven through the pore by the applied electric field, and the polynucleotides cause well-defined, transient reductions in the pore conductance. (Kasianowicz et al. 1996; Vercoutere et al. 2001; Deamer et al. 2002; Kasianowicz 2004) Because the residence time of the polynucleotide in the pore is proportional to the RNA or DNA contour length, it is suggested that a nanopore may be able to sequence DNA in a ticker-tape fashion if the four bases can be discriminated from each other. (Kasianowicz et al, 1996) Towards that goal, (Kasianowicz 1996; Kasianowicz et al. 2008; Kasianowicz et al. 2002) an αHL channel with a covalently linked adaptor in the pore is used to identify unlabeled nucleoside-5% monophosphates. (Clarke et al. 2009) However, a complete exonuclease-nanopore system based on this concept to sequence DNA has not been documented.

Despite the ability of nanopores to detect and characterize some physical properties of DNA at the single molecule level, the more demanding goal of accurate base-to-base sequencing by passing a single stranded DNA through the nanopore has not yet been realized. Oxford Nanopore Technologies recently announced the ability to accomplish strand sequencing in a nanopore at 3-base resolution with an error rate of 4%. (AGBT Meeting, 2012) Another group reported single base resolution strand sequencing with a nanopore, but had difficulty correctly determining homopolymer sequences. (Manrao et al. 2012)

The native αHL channel has the inherent ability for high resolution molecular discrimination. For example, it can discriminate between aqueous H$^+$ and D$^+$ ions, (Kasianowicz et al. 1995) and Robertson et al. (2007) recently demonstrated that the channel can easily separate poly(ethylene glycol) (PEG) molecules at the monomer level. In the latter study, a molecular mass or size spectrum estimated from the mean current caused by individual PEG molecules easily resolves the ethylene glycol repeat units. In addition, the mean residence time of the polymer in the pore increases with the PEG mass. (Robertson et al. 2007; Reiner et al. 2010) Based on these observations and the fact that DNA polymerase can recognize nucleotide analogs with extensive modification at the 5'-terminal phosphate group as efficient substrates, (Kumar 2005, 2006, 2008; Sood et al. 2005; Eid et al. 2009) a novel single molecule DNA sequencing approach that can identify individual bases by the detection and differentiation of a released byproduct (e.g., different length PEG tags from the DNA polymerase reaction, FIG. 9) instead of the nucleotides themselves is developed.

In this approach, during phosphodiester bond formation in the polymerase reaction, cleavage of the α-β phosphate bond in the incorporated nucleotide releases the tag. An example of a four-base reaction sequence with different tags for each base is shown in FIG. 30. An array of such nanopores, one of which is shown graphically in FIG. 33, each with a covalently attached polymerase adjacent to one of the pore entrances, allows single-molecule sequencing by synthesis (SBS). The addition of each nucleotide is determined by the effect of the released tag on the nanopore conductance.

This 5'-phosphate tag-based SBS system offers an advantage over strand sequencing through nanopores in that the speed of transit through the pore is no longer an issue, because the polymerase extension and release rate is slower than the tag transit time through the pore. This can also eliminate phasing issues inherent to strand sequencing methods. Synthesis and efficient incorporation of nucleotides with 5'-phosphate-attached tags possessing four different length PEGs and a coumarin moiety is described. Four distinct current blockade patterns of the released tags in an a-hemolysin pore at the single molecule level is demonstrated, establishing the feasibility of single molecule electronic SBS approach.

Design, synthesis and characterization of PEG-labeled nucleotides

Figure 54:
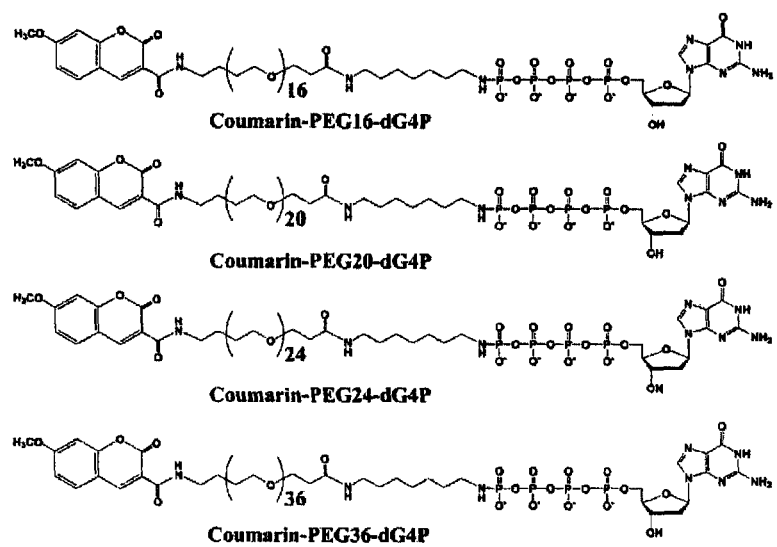
FIG. 54 shows structures of four coumarin-PEG-dG4P molecules.
Figure 55:
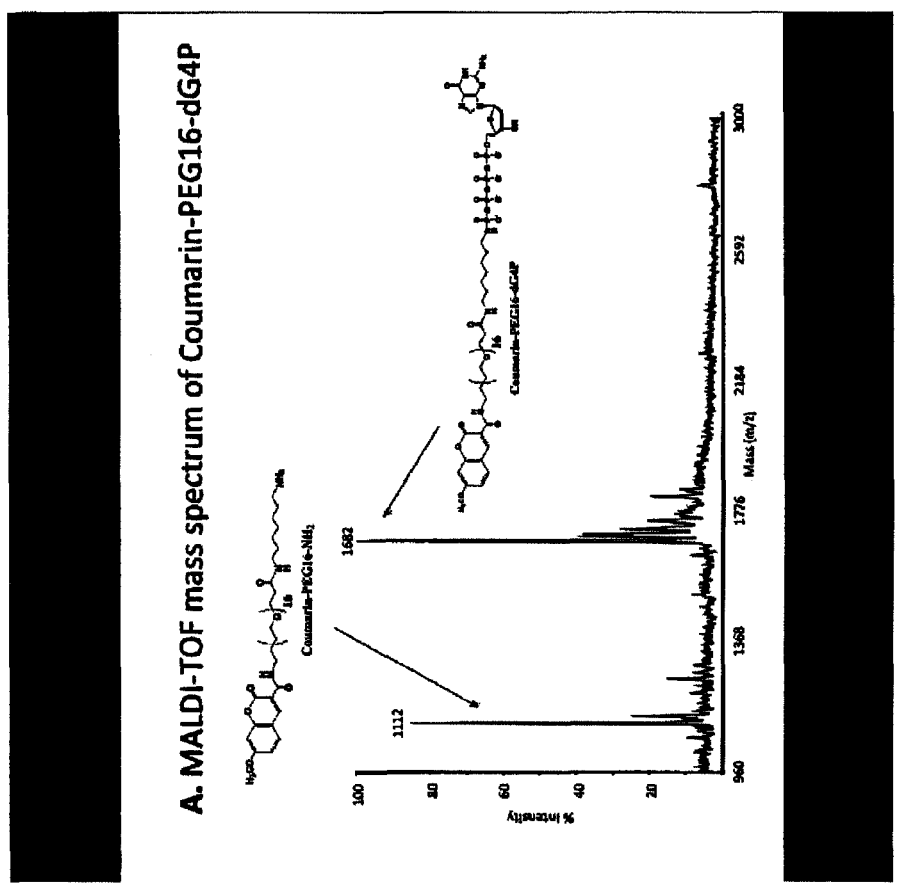
FIG. 55 shows characterization of four coumarin-$PEG_n$-dG4P nucleotides (n=16, 20, 24, 36) by MALDI-TOF MS; in addition to the full-length product peaks and related salt peaks, there is a second major peak to the left in each spectrum (coumarin-$PEG_n$-$NH_2$) representing cleavage of the N—P bond between the polyphosphate and the aminoheptane linker due to the acidic nature of the matrix used for MALDI-TOF MS analysis.
Figure 55:
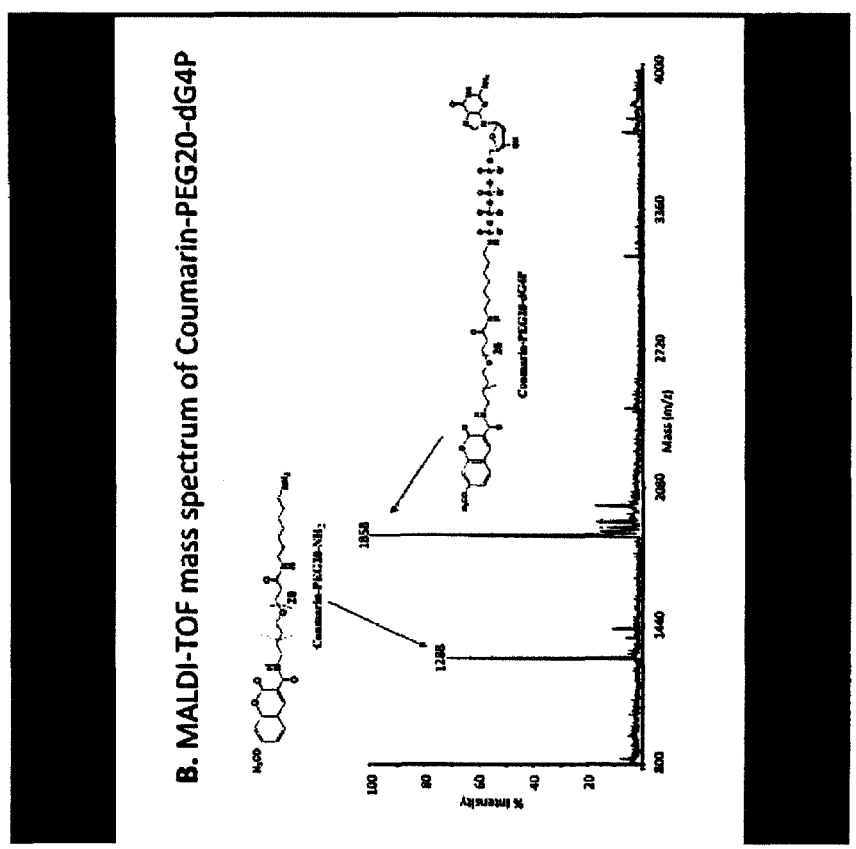
Figure 55:
Figure 55:
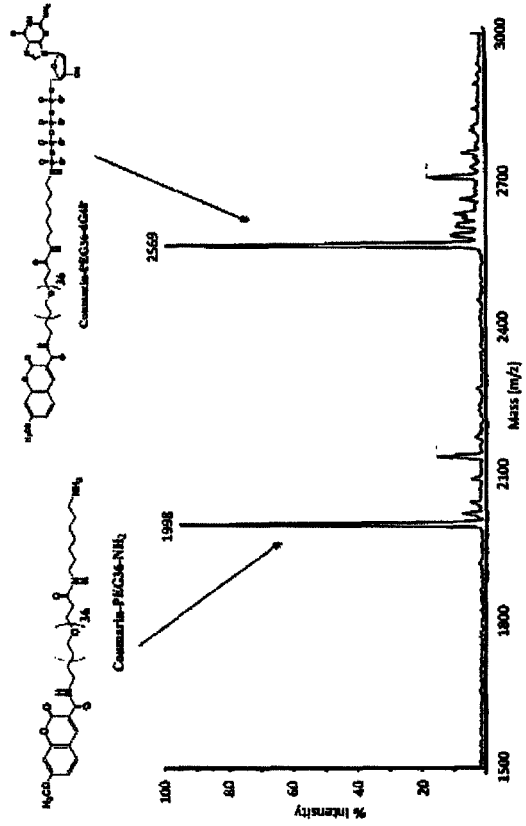

The four 5'-phosphate tagged 2'-deoxyguanosine-5'-tetraphosphates (FIG. 54) are synthesized according to the generalized synthetic scheme shown in FIG. 15 (see Methods above for details). First, 2'-deoxyguanosine-5'-triphosphate (dGTP) is converted to 2'-deoxyguanosine-5'-tetraphosphate (dG4P) and then a diaminoheptane linker is added to the terminal phosphate of the tetraphosphate, in order to attach different length PEG tags. In a separate set of reactions, 6-methoxy-coumarin N-hydroxysuccinimidyl ester is reacted with one of four amino-PEG-COOH molecules with 16, 20, 24 or 36 ethylene glycol units, to produce coumarin-PEG$_n$-COOH molecules, which are subsequently converted to the corresponding NHS-esters. These are reacted with the dG4P-heptylamine (dG4P-NH$_2$) to generate the four final nucleotide analogs, abbreviated coumarin-PEG$_n$-dG4Ps (FIG. 54). The coumarin moiety is used to track purification of intermediates and the final nucleotide analogs. Synthesis of the expected molecules is confirmed by MALDI-TOF mass spectroscopy (FIG. 55).

Figure 57:
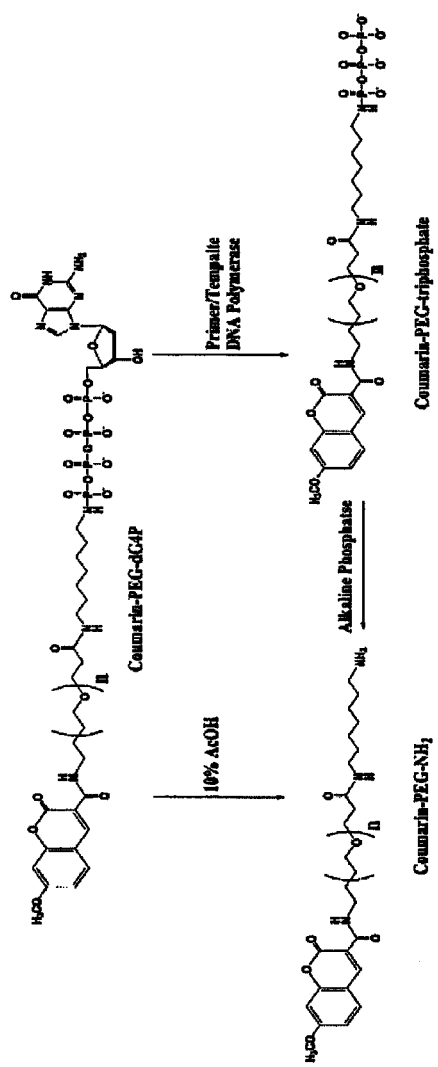
FIG. 57 shows two methods to generate coumarin-$PEG_n$-$NH_2$ tags; direct treatment of the nucleotide analogs (coumarin-$PEG_n$-dG4P, n=16, 20, 24, 36) (top) with 10% acetic acid yields the coumarin-PEG-$NH_2$ tags which are identical to the polymerase-released tags (lower right) after treatment with alkaline phosphatase; the coumarin-PEG-$NH_2$ tags (lower left) are then characterized at single molecule level by nanopore current blockade signatures.

The coumarin-PEG-dG4P nucleotides are employed in polymerase extension reactions using the Therminator γ variant of DNA polymerase. A primer-loop-template is designed where the next complementary base is a C, enabling dGMP to be added to the DNA primer (FIG. 56). Coumarin-PEG-triphosphate is released during the reaction (FIG. 57). MALDI-TOF-MS confirmed that indeed each of the four dG4P analogs gave the correct extension product with 100% incorporation efficiency, as shown by the appearance of a peak at 8,290 daltons (FIG. 58). The absence of a primer peak at 7,966 daltons suggests that the reaction proceeded essentially to completion.

All the incorporation represented the coumarin-PEG-dG4P analogs, and not potential residual dGTP or dG4P, since the molecules are purified twice in an HPLC system that separates these molecules effectively with a retention time difference of more than 10 min between the two compounds, To further exclude this possibility, the purified coumarin-PEG-dG4P analogs is treated with alkaline phosphatase, which can degrade any contaminating tri- or tetra-phosphate to the free nucleoside, and used the resulting HPLC-repurified coumarin-PEG-nucleotides in extension reactions. Importantly, the extended chains contain natural nucleotides without any modifications, allowing SBS to continue over extensive lengths.

The released tags from polymerase reactions are coumarin-PEG-triphosphate (coumarin-PEG-P$_3$, FIG. 57). To reduce the complexity of the charge on the tags, the released tags are treated with alkaline phosphatase, yielding coumarin-PEG-NH$_2$ tags, which are analyzed for their nanopore current blockade effects. In further developing the nanopore-based SBS system, the released coumarin-PEG-P$_3$ are treated with alkaline phosphatase, which like the polymerase, can be attached to one entrance of the nanopores, to generate coumarin-PEG-NH$_2$ tags, or optimize the conditions for using nanopores to directly detect the released charged tags. In subject study, in order to obtain large amounts of material for testing by MALDI-TOF MS and protein nanopores, synthetic versions of the expected released tags (coumarin-PEG-NH$_2$) are produced by acid hydrolysis of the four coumarin-PEG-nucleotide analogs to cleave the P—N bond between the polyphosphate and heptylamine moiety (FIG. 57).

Example 9

Characterization of the Released Tags by MALDI-TOF MS

The expected coumarin-PEG-NH$_2$ molecules are confirmed by MALDI-TOF-MS analysis, following HPLC purification (FIG. 16). MALDI-TOF-MS results indicate that the coumarin-PEG-NH$_2$ tags generated by acid hydrolysis are identical to the released tags produced during polymerase reaction after alkaline phosphatase treatment.

With reference to FIG. 16, coumarin-PEG-NH$_2$ tags generated by acid hydrolysis of coumarin-PEG16-dG4P yielding coumarin-PEG16-NH$_2$, coumarin-PEG20-dG4P yielding coumarin-PEG20-NH$_2$, coumarin-PEG24-dG4P yielding coumarin-PEG24-NH$_2$ and coumarin-PEG36-dG4P yielding coumarin-PEG36-NH$_2$, are identical to the corresponding released tags generated in polymerase extension reactions after treatment with alkaline phosphatase, as shown by MALDI-TOF-MS analysis. A composite image of four separately obtained MS spectra is shown. The structures of the coumarin-PEG-NH$_2$ tags are shown below.

Example 10

Discrimination of Released Tags in Protein Nanopores at Single Molecule

Figure 17:
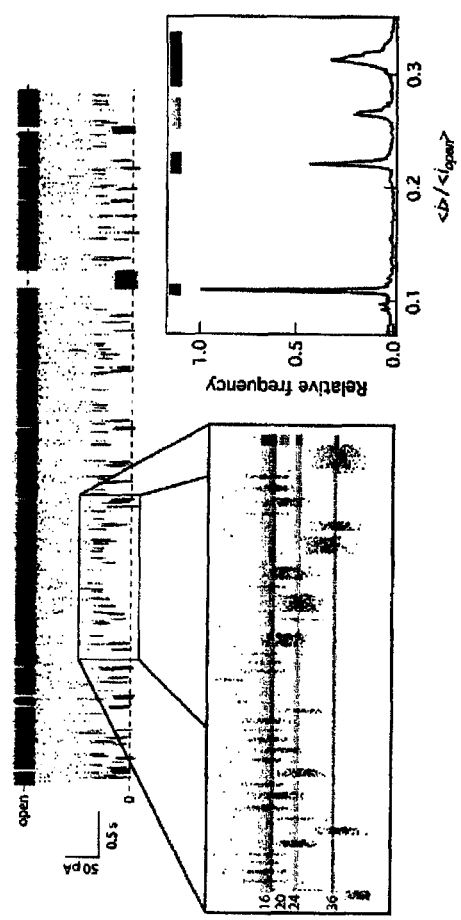
FIG. 17 shows an example of discrimination of released tags in protein nanopores at single molecule detection level; four coumarin-$PEG_n NH_2$ compounds (n=16, 20, 24 and 36), derived from the four comparable nucleotides by acid hydrolysis, were pooled and diluted in 4 M KCl, 10 mM Tris, pH 7.2 for nanopore measurement; (Left) the time series data indicates that when these PEG tags enter a single α-hemolysin ion channel, they cause current blockades that are characteristic of their size; right a histogram of the mean current blockade caused by individual molecules shows baseline resolution with a 10 kHz measurement bandwidth; the colored bars at the top represent the 6σ distribution of the data (assuming Gaussian distributions for each of four PEG tags that can represent each of the four DNA nucleotides), which suggests that a single base can be discriminated with an accuracy better than 1 in 300,000 events, represented in this figure by using A, C, G and T designations, which can occur when four different nucleotides with four different length PEGs are used for DNA sequencing.

With reference to FIG. 17, four coumarin-PEG$_n$NH$_2$ compounds (n=16, 20, 24 and 36), derived from the four comparable nucleotides by acid hydrolysis, were pooled and diluted in 4 M KCl, 10 mM Tris, pH 7.2 for nanopore measurement. The time series data on the left indicates that when these PEG tags enter a single a-hemolysin ion channel, they cause current blockades that are characteristic of their size. A histogram on the right show the mean current blockade caused by individual molecules shows baseline resolution with a 10 kHz measurement bandwidth. The colored bars at the top represent the 6σ distribution of the data (assuming Gaussian distributions for each of four PEG tags that can represent each of the four DNA nucleotides), which suggests that a single base can be discriminated with an accuracy better than 1 in 300,000 events, represented in this figure by using A, C, G and T designations, which may occur when four different nucleotides with four different length PEGs are used for DNA sequencing.

To demonstrate the electronic single molecule SBS approach, four released coumarin-PEG$_n$-NH$_2$ tags are tested for their current blockade effects on an αHL nanopore the (FIG. 17). The relative frequency distribution of the histogram of blockade events ($<i>/<i_{open}>$), shows four well separated and distinct peaks for the four coumarin-PEG$_n$-NH$_2$ tags (n=36, 24, 20, and 16 from left to right respectively in FIG. 17, lower right).

To highlight the wide separation of the peaks, and offer clear evidence that detection of a specific nucleotide may be accomplished by the unique blockade signal afforded by its released PEG, the peaks are fit with single Gaussian functions and the corresponding 6σ error distributions are shown (colored rectangles at top in FIG. 17, lower right). Separately applied coumarin-PEG-NH$_2$ molecules are characterized with the pore (data not shown), which confirmed the identity of the PEG-related peaks shown in this figure.

As described here, a single αHL ion channel may separate single molecules based on their size, and easily resolves a mixture of PEGs to better than the size of a single monomer unit (i.e., <44 g/mol). This high resolution arises from the interactions between the PEG polymer, the electrolyte (mobile cations) and amino acid side chains that line the αHL channel's lumen. These interactions allow the pore to be used as a nanometer-scale sensor that is specific to the size, charge and chemical property of an analyte.

Here, such analysis is extended to PEGs with different chemical groups on either terminus. The single channel ionic current recording in FIG. 17, top and lower left, illustrates the blockades caused by the four different sized coumarin-PEG$_n$-NH$_2$ molecules, one at a time. As with unmodified PEG, each of the current blockades is unimodal (i.e., described well with Gaussian distributions and well-defined mean values).

To accurately discriminate between the four bases (A, C, G and T) for nanopore sequencing, one or more of the following strategies need to be adopted: 1) enhance and differentiate the strength of the detection signals; 2) develop an effective method to discern and process the electronic blockade signals generated; 3) control the translocation rate of nucleic acids through the pore, e.g., by slowing down DNA movement for strand sequencing; and 4) design and make new and more effective synthetic nanopores. As demonstrated here, transforming the problem of resolving the individual bases to that of discriminating between four unique tags essentially solves the first three problems.

Here, a novel approach to enhance discrimination of four nucleotides by modifying them at the terminal phosphate moiety is demonstrated. Kumar et al. first reported on the modification of nucleoside-5% triphosphates, either by introducing more phosphate groups to produce tetra- and penta-phosphates and introducing dye directly to the terminal phosphate or attaching a linker between the terminal phosphate and the dye. (Kumar et al. 2006, 2008) Tetra- and penta-phosphates were shown to be better DNA polymerase substrates, and fluorophore-labeled phosphate nucleotides have been used widely for DNA sequencing. (Kumar et al. 2005; Sood et al. 2005; Eid et al. 2009; Sims et al. 2011)

The single molecule nanopore SBS system, which is shown schematically in FIG. 33, depicts the DNA polymerase bound in close proximity to the nanopore entrance and a template to be sequenced is added along with the primer. To this template-primer complex, four differently tagged nucleotides are added together. After polymerase catalyzes incorporation of the correct nucleotide, the tag-attached polyphosphate is released and passes through the nanopore to generate a current blockade signal, thereby identifying the added base. Each tag generates a different electronic blockade signature due to different size, mass or charge.

The physical and chemical properties of the tag can be further adjusted to optimize the capture efficiency and measurement accuracy. For instance, the insertion of a positively charged linker consisting of four lysines or arginines between the polyphosphate and the PEG produces precursors with a neutral charge and released tags with a net positive charge. Using the appropriate magnitude and sign of the potential, the released tags, but not nucleotide substrates, is transported through the pore.

Further discrimination of substrate and product can be achieved by the inclusion of several ovalently attached alkaline phosphatase molecules adjacent to the polymerase at the rim of each nanopore, which ensure an even higher positive charge on the tags. It is important that every tag released in a polymerase reaction is maintained in the proper order. Therefore, several phosphatase enzymes are needed for each polymerase molecule due to the similar turnover rates for the two enzymes.

Despite all these precautions, some unreacted nucleotides may enter the pore. Thus, the ability to discriminate between cleaved tags and unreacted nucleotides is important; they should be easily differentiated due to their significant size and charge differences, an inherent ability of the nanopore system.

The method described herein can be applied to either protein nanopores (e.g. αHL, *Mycobacterium smegmatis* porin A, MspA), (Derrington et al. 2010) or solid-state nanopores. (Garaj et al. 2010; Hall et al. 2010; Merchant et al. 2010; Schneider et al. 2010; Storm et al. 2005; Wanunu et al. 2008) These strategies provide nanopores with different properties that are appropriate for detecting a library of tags. To implement this novel strategy for DNA sequencing, an array of nanopores[37] can be constructed on a planar surface to facilitate massively parallel DNA sequencing.

In conclusion, a SBS- and nanopore-based single molecule DNA sequencing platform that takes advantage of novel releasable tags on the nucleotide substrates for the polymerase reaction is demonstrated. Such a platform is capable of long, accurate reads, and very high throughput electronic single molecule DNA sequencing.

Example 11

Synthesis of Coumarin-PEG-dG4P Nucleotide Analogs

All of the nucleotides are purified by reverse-phase HPLC on a 150×4.6 mm column (Supelco), mobile phase: A, 8.6 mM $Et_3N$/100 mM 1,1,1,3,3,3-hexafluoro-2-propanol in water (pH 8.1); B, methanol. Elution is performed from 100% A isocratic over 10 min followed by a linear gradient of 0-50% B for 20 min and then 50% B isocratic over another 30 min.

Synthesis of Coumarin-PEGn-dG4P

The synthesis of coumarin-$PEG_n$-dG4P involves three steps as shown in the scheme in FIG. 15.

A.1 Synthesis of 2'-deoxyguanosine-5'-tetraphosphate (dG4P)

First the synthesis of 2'-dG4P is carried out starting from 2'-dGTP. 300 umoles of 2'-dGTP (triethylammonium salt) is converted to the tributylammonium salt by using 1.5 mmol (5 eq) of tributylamine in anhydrous pyridine (5 ml). The resulting solution is concentrated to dryness and co-evaporated with 5 ml of anhydrous DMF (×2). The dGTP (tributylammonium salt) is dissolved in 5 ml anhydrous DMF, and 1.5 mmol 1,1-carbonyldiimidazole added. The reaction is stirred for 6 hr, after which 12 ul methanol added and stirring continued for 30 min. To this solution, 1.5 mmol phosphoric acid (tributylammonium salt, in DMF) added and the reaction mixture stirred overnight at room temperature.

The reaction mixture is diluted with water and purified on a Sephadex-A25 column using 0.1 M to 1M TEAB gradient (pH 7.5). The dG4P elutes at the end of the gradient. The appropriate fractions are combined and further purified by reverse-phase HPLC to provide 175 umol of the pure tetraphosphate (dG4P). $^{31}$P-NMR: δ, −10.7 (d, 1P, α-P), −11.32 (d, 1P, δ-P), −23.23 (dd, 2P, β, γ-P); ESI-MS (−ve mode): Calc. 587.2. Found 585.9 (M-2).

A.2 Synthesis of dG4P-heptyl-$NH_2$

To 80 umol dG4P in 2 ml water and 3.5 ml 0.2M 1-methylimidazole-HCl (pH 6) added 154 mg EDAC and 260 mg diaminoheptane. The pH of the resulting solution is adjusted to 6 with conc. HCl and stirred at room temperature overnight. This solution is diluted with water and purified by Sephadex-A25 ion-exchange chromatography followed by reverse-phase HPLC to give ~20 μmol dG4P-$NH_2$. This is confirmed by ESI-MS data (−ve mode): calc. 699.1. Found (698.1, M-1).

B) Synthesis of Coumarin-PEG-Acids and NHS Esters

The commercially available amino-dPEG-acids (Amino-d(PEG)16, 20, 24, 36-acids; Quanta Biodesign) are reacted with 6-methoxy coumarin-NHS ester to provide the corresponding coumarin-$(PEG)_n$-acid. Amino-PEG-acid (1 eq) is dissolved in carbonate-bicarbonate buffer (pH 8.6), followed by addition of coumarin-NHS (1 eq) in DMF, and the reaction mixture stirred overnight. The coumarin-PEG-acid is purified by silica-gel chromatography using a $CH_2Cl_2$-MeOH (5-15%) mixture and the appropriate fractions combined. These compounds are analyzed by $^1$H NMR and MALDI-TOF MS analysis.

MALDI-TOF MS Data:

|  | Coumarin-PEG16-acid | Coumarin-PEG20-acid | Coumarin-PEG24-acid | Coumarin-PEG36-acid |
|---|---|---|---|---|
| Expected MW | 996 | 1,172 | 1,348 | 1,877 |
| Observed MW* | 1,016 | 1,192 | 1,368 | 1,899 |

*Difference in observed values due to presence of sodium salt.

The coumarin-PEG-acids are converted to the corresponding NHS esters by reacting with 1.5 eq. of disuccinimidyl carbonate (DSC) and 2 eq of triethylamine in anhydrous DMF for 2 h. The resulting NHS ester, which moves slightly higher than the acid on silica-gel plates, is purified by silica-gel chromatography using a $CH_2Cl_2$-MeOH (5-15%) mixture and used in the next step.

C) Coumarin-$PEG_n$-dG4P:

dG4P-heptyl-NH2 from step A) above is taken up in 0.1 M carbonate-bicarbonate buffer (pH 8.6) and to this stirred solution added one of the coumarin-PEG-NHS compounds (in DMF). The resulting mixture stirred overnight at room temperature and then purified on a silica-gel cartridge (15-25% MeOH in $CH_2Cl_2$ to remove unreacted coumarin-acid or —NHS and then 6:4:1 isopropanol/$NH_4OH/H_2O$). This is further purified twice by reverse-phase HPLC to provide pure coumarin-PEG-dG4P. The structure is confirmed by analysis on MALDI-TOF MS. Coumarin-PEG16-dG4P: retention time, 31.7 min; coumarin-PEG20-dG4P: retention time, 32.2 min; coumarin-PEG24-dG4P: retention time, 33.0 min; coumarin-PEG36-dG4P: retention time, 34.3 min.

MALDI-TOF MS Data:

|  | Coumarin-PEG16-dG4P | Coumarin-PEG20-dG4P | Coumarin-PEG24-dG4P | Coumarin-PEG36-dG4P |
|---|---|---|---|---|
| Expected MW | 1,673 | 1,850 | 2,025 | 2,554 |
| Observed MW | 1,682 | 1,858 | 2,036 | 2,569 |

Example 12

Characterization of the Released Tags by MALDI-TOF MS

The expected coumarin-PEG-$NH_2$ molecules are confirmed by MALDI-TOF-MS analysis, following HPLC purification (FIG. 16). MALDI-TOF-MS results indicate that the coumarin-PEG-$NH_2$ tags generated by acid hydrolysis are identical to the released tags produced during polymerase reaction after alkaline phosphatase treatment.

With reference to FIG. 16, coumarin-PEG-$NH_2$ tags generated by acid hydrolysis of coumarin-PEG16-dG4P yielding coumarin-PEG16-$NH_2$, coumarin-PEG20-dG4P yielding coumarin-PEG20-$NH_2$, coumarin-PEG24-dG4P yielding coumarin-PEG24-$NH_2$ and coumarin-PEG36-dG4P yielding coumarin-PEG36-$NH_2$, are identical to the corresponding released tags generated in polymerase extension reactions after treatment with alkaline phosphatase, as shown by MALDI-TOF-MS analysis. A composite image of four separately obtained MS spectra is shown. The structures of the coumarin-PEG-$NH_2$ tags are shown to the right.

Example 13

Discrimination of Released Tags in Protein Nanopores at Single Molecule

With reference to FIG. 17, four coumarin-$PEG_n$-$NH_2$ compounds (n=16, 20, 24 and 36), derived from the four comparable nucleotides by acid hydrolysis, were pooled and diluted in 4 M KCl, 10 mM Tris, pH 7.2 for nanopore measurement. The time series data on the left indicates that when these PEG tags enter a single α-hemolysin ion channel, they cause current blockades that are characteristic of their size. A histogram on the right show the mean current blockade caused by individual molecules shows baseline resolution with a 10 kHz measurement bandwidth. The colored bars at the top represent the 6 σ distribution of the data (assuming Gaussian distributions for each of four PEG tags that can represent each of the four DNA nucleotides), which suggests that a single base can be discriminated with an accuracy better than 1 in 300,000 events, represented in this figure by using A, C, G and T designations, which may occur when four different nucleotides with four different length PEGs are used for DNA sequencing.

To demonstrate the electronic single molecule SBS approach, four released coumarin-$PEG_n$-$NH_2$ tags are tested for their current blockade effects on an αHL nanopore (FIG. 17). The relative frequency distribution of the histogram of blockade events ($<i>/<i_{open}>$), shows four well separated and distinct peaks for the four coumarin-$PEG_n$-$NH_2$ tags (n=36, 24, 20, and 16 from left to right respectively in FIG. 17, lower right).

To highlight the wide separation of the peaks, and offer clear evidence that detection of a specific nucleotide may be accomplished by the unique blockade signal afforded by its released PEG, the peaks are fit with single Gaussian functions and the corresponding 6σ error distributions are shown (colored rectangles at top in FIG. 17, lower right). Separately applied coumarin-PEG-$NH_2$ molecules are characterized with the pore (data not shown), which confirmed the identity of the PEG-related peaks shown in this figure.

As described here, a single αHL ion channel may separate single molecules based on their size, and easily resolves a mixture of PEGs to better than the size of a single monomer unit (i.e., <44 g/mol). This high resolution arises from the interactions between the PEG polymer, the electrolyte (mobile cations) and amino acid side chains that line the αHL channel's lumen. These interactions allow the pore to be used as a nanometer-scale sensor that is specific to the size, charge and chemical property of an analyte.

Here, such analysis is extended to PEGs with different chemical groups on either terminus. The single channel ionic current recording in FIG. 17, top and lower left, illustrates the blockades caused by the four different sized coumarin-$PEG_n$-$NH_2$ molecules, one at a time. As with unmodified PEG, each of the current blockades is unimodal (i.e., described well with Gaussian distributions and well-defined mean values).

Example 14

Detection of Tags

Figure 19:
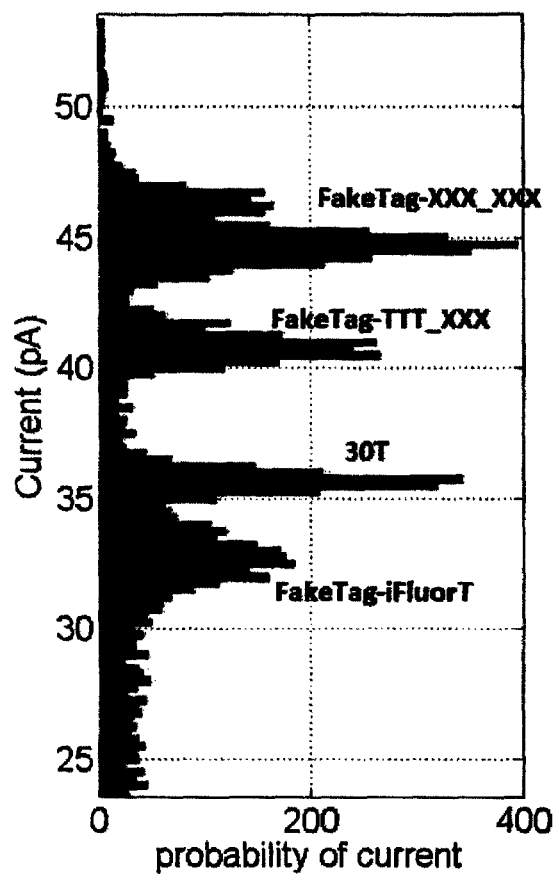
FIG. 19 shows a histogram of cell current readings.

The device is used to detect 4 distinct current levels for 4 different tag molecules. As seen in FIG. 19, each of the tags can be distinguished from any of the other three (i.e., the histogram shows four distinct peaks labeled in the graphic with the corresponding tag).

Each tag molecule is a homopolymer "T" approximately 30 bases in length, biotinylated on the 3' end with 2 regions in the strand potentially modified. In each 30 base long molecule, the regions modified are; from the 3'end, base positions 11, 12, and 13 and positions 17, 18, and 19. As used here "x" is an abasic site (no base) and "T" is thymine. The four tags are:

(a) Fake tag XXX-XXX having a sequence; Streptavidin-Biotin-10T-xxx-3T-xxx-11T (b) Fake tag TTT-XXX having a sequence; Streptavidin-Biotin-10T-TTT-3T-xxx-11T (c) 30T tag having a sequence; Streptavidin-Biotin-30T (d) Fake tag iFluorT having a sequence; Streptavidin-Biotin-10T-TTT-3T-T-IfluorT-T-11T, where the T at position 18 which is labeled with Fluoroscene The results are for one pore in an array capturing multiple molecules from solution over time. The detection conditions are 1M KCl, buffered with 20 mM HEPES, pH7.5 at room temperature. Each molecule is captured and held in the pore while a voltage is applied. The applied voltage is increased to +160 mV, a new molecule is captured, and the voltage is reduced below 0V and the tagged molecule falls out of the pore. The cycle is then repeated. Four different tag molecules are in the sample mix at once.

Figure 20:
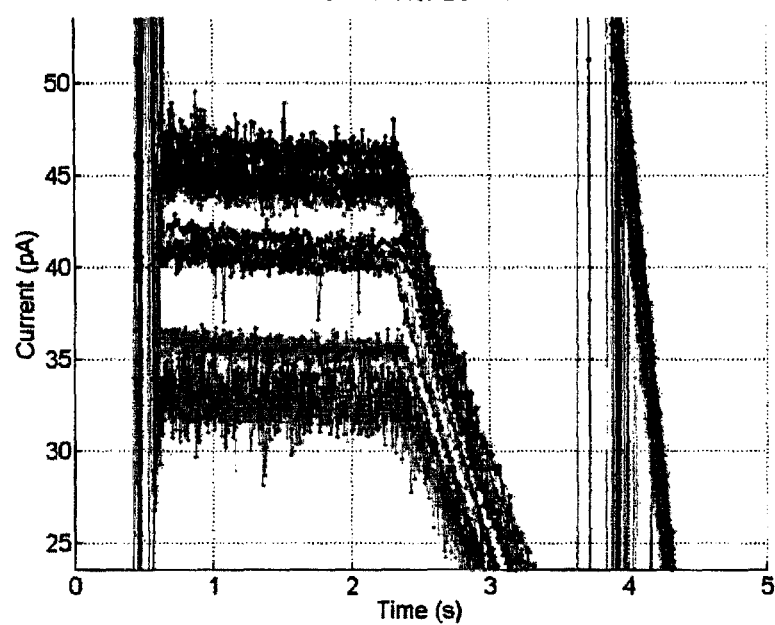
FIG. 20 shows a plot of current measured in pico-amps versus time measured in seconds for 4 different tags.

As shown in FIG. 20, the horizontal axis of the plot is time (measured in seconds) vs. current (measured in pico amps (pA)) on the vertical axis. The applied voltage waveform is not shown. The applied voltage waveform starts below 0V and quickly increases to +160 mV and is held there for approximately 2.3 seconds. The voltage is then ramped down to below 0V. The current readings follow the applied voltage with a captured molecule's current being flat while the applied voltage is at +160 mV and then ramps down as the voltage ramps down.

As shown in FIG. 19, the clear bands seen during the application of 160 mV become connected or slightly smeared in the histogram because the current during the ramp down is also plotted. Despite this, distinct, repeatable capture bands can be seen for each tag molecule.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in fonn and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

REFERENCES

1. AGBT Meeting, Marco Island, Fla., 2012 and Feb. 17 press release from Oxford Nanopore Technologies (http://www.nanoporetech.com/news/press-releases/view/39)
2. Akeson, M., Branton, D., Kasianowicz, J. J., Brandin, E. and Deamer, D. W. Microsecond time-scale discrimination between polycytidylic acid and polyadenylic acid segments within single RNA molecules. *Biophys. J.* 1999, 77, 3227-3233.
3. Aksimentiev, A. et al., Microscopic Kinetics of DNA Translocation through Synthetic Nanopores. *Biophysical Journal* 2004 87, 2086-2097.
4. Astier, Y., Braha, O. & Bayley, H. Toward single molecule DNA sequencing: direct identification of ribonucleoside and deoxyribonucleoside 5'-monophosphates by using an engineered protein nanopore equipped with a molecular adapter. *J Am Chem Soc* 128, 1705-10 (2006).
5. Axelrod, D., Koppel, D. E., Schlessinger, J., Elson, E. & Webb, W. W. Mobility measurement by analysis of fluorescence photobleaching recovery kinetics. *Biophysical Journal* 16, 1055-1069 (1976).
6. Bailey, H. Sequencing single molecules of DNA. *Curr. Opinion Chem Biol.* 2006, 10, 628-637.
7. Benner, S. et al. Sequence-specific detection of individual DNA polymerase complexes in real time using a nanopore. *Nat Nanotechnol* 2, 718-24 (2007).
8. Bezrukov S. M., Vodyanoy, L, Brutyan, R. A. & Kasianowicz, J. J. Dynamics and free energy of polymers partitioning into a nanoscale pore. *Macromolecules* 29, 8517-22 (1996)
9. Bezrukov, S. M., and Kasianowicz, J. J. Neutral polymers in the nanopore of alamethicin and alpha-hemolysin. *Biologicheskie Membrany* 2001, 18, 453-457.
10. Bokhari, S. H. and Sauer, J. R., A Parallel Graph Decomposition Algorithm for DNA Sequencing with Nanopores. *Bioinformatics* 2005 21(7), 889-896.
11. Branton, D. Nanopore sequencing. *Nat. Biotechnol.* 26, 1146-1153 (2008).
12. Branton, D. et al. The potential and challenges of nanopore sequencing. *Nat Biotechnol* 26, 1146-53 (2008).
13. Bultmann, T., Vaz, W. L., Melo, E. C., Sisk, R. B. & Thompson, T. E. Fluid-phase connectivity and translational diffusion in a eutectic, two-component, two-phase phosphatidylcholine bilayer. *Biochemistry* 30, 5573-9 (1991).
14. Chandler, E. L., Smith, A L., Burden, L. M., Kasianowicz and Burden, D. L. Membrane Surface Dynamics of DNA-Threaded Nanopores Revealed by Simultaneous Single-Molecule Optical and Ensemble Electrical Recording. *Langmuir* 2004, 20, 898-905.
15. Chen, P. Probing single DNA molecule transport using fabricated nanopores. *Nano Lett.* 4, 2293-2298 (2004).
16. Clarke, J., Wu, H., Jayasinghe, L., Patel, A., Reid, S. and Bayley, H. Continuous base identification for single-molecule nanopore DNA sequencing. *Nat. Biotech.* 2009, 1-6.
17. Cockroft, S. L., Chu, J., Amorin, M. & Ghadiri, M. R. A single-molecule nanopore device detects DNA polymerase activity with single-nucleotide resolution. *J Am Chem Soc* 130, 818-20 (2008).
18. Deamer, D. W. and Branton, D. Characterization of nucleic acids by nanopore analysis. *Acc. Chem. Res.* 2002, 35(10), 817-825.
19. Deamer, D. W. Nanopore Analysis of Nucleic Acids Bound to Exonucleases and Polymerases, *Annual Review of Biophysics*, Vol. 39: 79-90 (Volume publication date June 2010).
20. Derrington, I. M. et al. Nanopore DNA sequencing with MspA. *Proc Natl Acad Sci USA* 107, 16060-5 (2010),
21. Dutta, D., Pulsipher, A. & Yousaf, M. N. Selective Tethering of Ligands and Proteins to a Microfluidically Patterned Electroactive Fluid Lipid Bilayer Array. *Langmuir* 26, 9835-9841 (2010).

22. Eid, J., Fehr, A., Gray, J., Luong, K., Lyle, J., Otto, G. et al. Real-time DNA sequencing from single polymerase molecules. *Science* 2009, 323, 133-138.
23. Fologea, D. et al., Slowing DNA Translocation in a Solid State Nanopore. *Nano Letters* 2005 5(9), 1734-1737.
24. Fologea, D. et al., Detecting Single Stranded DNA with a Solid State Nanopore. *Nano Letters* 2005 5(10), 1905-1909.
25. Garaj, S. et al. Graphene as a subnanometre transelectrode membrane. *Nature* 467, 190-3 (2010).
26. Gershow, M. & Golovchenko, J. A. Recapturing and trapping single molecules with a solid state nanopore. *Nature Nanotechnology* 2, 775-779 (2007),
27. Guo, J; Xu, N., Li, Z., Mang, S.; Wu, J., Kim, D. H., Manna, M. S., Meng, Q., Cao, H., Li, X., Shi, S., Yu, L., Kalachikov, S., Russo, J. J., Turro, N. J., Ju, J. Four-color DNA sequencing with 3'-O-modified nucleotide reversible terminators and chemically cleavable fluorescent dideoxynucleotides. *Proc. Natl, Acad. Sci. USA* 2008, 105(27), 9145-9150
28. Guo, J., Yu, L., Turro, N. J., and Ju, J. An integrated system for DNA sequencing by synthesis using novel nucleotide analogues. Accounts of Chemical Research 2010, 43(4), 551-563.
29. Hall, A. R. et al. Hybrid pore formation by directed insertion of alpha-haemolysin into solid-state nanopores. *Nat Nanotechnol* 5, 874-7 (2010).
30. Hams, T. D., Buzby, P. J. et al. Single-molecule DNA sequencing of a viral genome. *Science* 2008, 320, 106-109.
31. Healy, K. Nanopore-based single-molecule DNA analysis. *Nanomedicine* (Lond) 2, 459-81 (2007).
32. Heng, J. B. et al., Stretching DNA Using the Electric Field in a Synthetic Nanopore. *Nano Letters* 2005 5(10), 1883-1888.
33. Heng, J. B. et al., The Electromechanics of DNA in a synthetic Nanopore. *Biophysical Journal* 2006, 90, 1098-1106.
34. Henrickson, S. E., Misakian, M., Robertson, B. and Kasianowicz, J. J. Driven asymmetric DNA transport in a nanometer-scale pore. *Physical Review Letters* 2000, 85, 3057-3060.
35. Hou, X. et al. A biomimetic potassium responsive nanochannel: G-quadruplex DNA conformational switching in a synthetic nanopore. *J Am Chem Sac* 131, 7800-5 (2009).
36. Huang, T. C. et al. Gene expression analysis with an integrated CMOS microarray by time-resolved fluorescence detection. *Biosens Bioelectron* 26, 2660-5 (2011).
37. Hurt, N., Wang, H., Akeson, M. & Lieberman, K. R. Specific nucleotide binding and rebinding to individual DNA polymerase complexes captured on a nanopore. *J Am Chem Soc* 131, 3772-8 (2009).
38. Jenkins, A. T. A., Neumann, T. & Offenhausser, A. Surface plasmon microscopy measurements of lipid vesicle adsorption on a micropatterned self-assembled monolayer. *Langmuir* 17, 265-267 (2001).
39. Ju, J., Kim, D. H., Bi, L., Meng, Q., Bi, X., Li, Z., Li, X., Manna, M. S., Shundi, S., Wu, J., Edwards, J. R., Romu, A., and Turro, N. J. Four-color DNA sequencing by synthesis using cleavable fluorescent nucleotide reversible terminators. *Proc. Natl. Acad. Sci. USA* 2006, 103(52), 19635-19640
40. Kasianowicz, J. J. & Bezrukov, S. M. Protonation dynamics of the alpha-toxin ion channel from spectral analysis of pH-dependent current fluctuations. *Biophys J* 69, 94-105 (1995).
41. Kasianowicz, J. J., Brandin, E., Branton, D. and Deamer, D. W. Characterization of individual polynucleotide molecules using a membrane channel. *Proc. Natl. Acad. Sci. USA* 1996, 93, 13770-13773.
42. Kasianowicz, Henrickson, S. E., Weetall, H. H. & Robertson, B. Simultaneous multianalyte detection with a nanometer-scale pore. *Anal Chem* 73, 2268-72 (2001).
43. Kasianowicz, J. J., et al. Physics of DNA threading through a nanometer pore and applications to simultaneous multianalyte sensing in *Structure and Dynamics of Confined Polymers*, ed. Kasianowicz, J. J., Kellemayer, M. S. Z. & Deamer, D. W., Nato Science Series, Kluwer Academic Publishers, The Netherlands 87, 141-64 (2002)
44. Kasianowicz, J. J. Nanometer-scale pores: potential applications for DNA characterization and analyte detection. *Disease Markers* 2003, 18, 185-191.
45. Kasianowicz, J. J. Nanopore. Flossing with DNA. *Nature Materials* 2004, 3, 355-356.
46. Korlach, J. et al. Selective aluminum passivation for targeted immobilization of single DNA polymerase molecules in zero-mode waveguide nanostructures. *Proc Nati Acad Sci USA* 105, 1176-81 (2008).
47. Korlach, J. et al. Real-time DNA sequencing from single polymerase molecules. *Methods Enzymol* 472, 431-55 (2010).
48. Krasilnikov, O. V. Sizing channels with neutral polymers in *Structure and Dynamics of Confined Polymers*, ed. Kasianowicz, J. J., Kellemayer, M. S. Z. & Deamer, D. W., Nato Science Series, Kluwer Academic Publishers, The Netherlands 87, 97-116 (2002)
49. Kumar, 5, and Sood, A. Labeled Nucleoside Polyphosphates. U. S. Pat. No. 7,041,812 (2006)
50. Kumar, S., McDougall, M., Sood, A., Nelson, J., Fuller, C., Macklin, J. and Mitsis, P. Terminal-Phosphate-Labeled Nucleotides with New Linkers. U. S. Pat. No. 7,393,640 (2008)
51. Kumar, S., Sood, A., Wegener, J., Finn, P., Nampalli, S., Nelson, J., Sekher, A., Mitsis, P., Macklin, J. and Fuller, C. W. Terminal Phosphate Labeled Nucleotides: Synthesis, Applications and Linker effect on incorporation by DNA Polymerases. Nucleosides, *Nucleotides & Nucleic Acids* (2005) 24 (5-7), 401-408
52. Lee S. E., Sidorov A., Gourlain T., Mignet N., Thorpe S. J., Brazier J. A., Dickman M. J., Hornby D. P., Grasby, J. A. and Williams, D. M. Enhancing the catalytic repertoire of nucleic acids: a systematic study of linker length and rigidity. *Nucleic Acids Research* 2001, 29(7), 1565-1573.
53. Lei, N., Watson, B. O., MacLean, J. N., Yuste, R. & Shepard, K. L. A 256-by-56 CMOS Microelectrode Array for Extracellular Neural Stimulation of Acute Brain Slices. in *Solid-State Circuits Conference*, 2008. ISSCC 2008. Digest of Technical Papers. IEEE International 148-603 (2008).
54. Levine, P. M., Gong, P., Levicky, R. & Shepard, K. L. Real-time, multiplexed electrochemical DNA detection using an active complementary metal-oxide-semiconductor biosensor array with integrated sensor electronics. *Biosens Bioelectron* 24, 1995-2001 (2009).
55. Li, Z., Bai, X., Ruparel, H., Kim, S., Turro, N.J. and Ju, J. A photocleavable fluorescent nucleotide for DNA sequencing and analysis. *Proc. Natl. Acad. Sci. USA* 2003, 100, 414-419.
56. Love, J. C., Estroff, L. A., Kriebel, J. K., Nuzzo, R. G. & Whitesides, G. M. Self-assembled monolayers of thiolates on metals as a form of nanotechnology. *Chem Rev* 105, 1103-69 (2005).

57. Manrao, E. A., et al. Reading DNA at single-nucleotide resolution with a mutant MspA nanopore and phi29 DNA polymerase. *Nat Biotechnol*, Advance Online Publication (2012)
58. Margulies, M. et al. Genome Sequencing in Open Microfabricated High Density Picoliter Reactors. Nature 437: 376-380 (2005).
59. Mathe, J. et al., Nanopore Unzipping of Individual Hairpin Molecules. *Biophysical Journal* 2004 87, 3205-3212.
60. Matysiak, S., Montesi, A., Pasquali, M., Kolomeisky, A. B. & Clementi, C. Dynamics of polymer translocation through nanopores: theory meets experiment. *Phys Rev Lett* 96, 118103 (2006).
61. McNally, B. et al. Optical recognition of converted DNA nucleotides for single-molecule DNA sequencing using nanopore arrays. *Nano Lett* 10, 2237-44 (2010).
62. Meller, A., Nivon, L., Brandin, E., Goloychenko, J. and Branton, D. Rapid nanopore discrimination between single polynucleotide molecules. *Proc. Natl. Acad. Sci. USA* 2000, 97, 1079-1084.
63. Meller, A. et al., Single Molecule Measurements of DNA Transport Through a Nanopore. *Electrophoresis* 2002 23, 2583-2591.
64. Merchant, C. A. et al. DNA translocation through graphene nanopores. *Nano Lett* 10, 2915-21 (2010).
65. Montal, M. & Mueller, P. Formation of bimolecular membranes from lipid monolayers and a study of their electrical properties. *Proc Natl Acad Sci USA* 69, 3561-3566 (1972)
66. Nam, J. M., Nair, P. M., Neve, R. M., Gray, J. W. & Groves, J. T. A fluid membrane-based soluble ligand-display system for live-cell assays. *ChemBioChem* 7, 436-440 (2006).
67. Nkodo, A. E. et al. Diffusion coefficient of DNA molecules during free solution electrophoresis. *ELECTROPHORESIS* 22, 2424-2432 (2001).
68. Oliver, A. E. & Deamer, D. W. Alpha-Helical Hydrophobic Polypeptides Form Proton-Selective Channels in Lipid Bilayers. *Biophysical Journal* 66, 1364-1379 (1994).
69. Palegrosdemange, C., Simon, E. S., Prime, K. L. & Whitesides, G. M. Formation of Self-Assembled Monolayers by Chemisorption of Derivatives of Oligo(Ethylene Glycol) of Structure Hs(Ch2)11(Och2ch2)Meta-Oh on Gold. *Journal of the American Chemical Society* 113, 12-20 (1991).
70. Perkins, T. T., Quake, S R., Smith, D. E. and Chu, S. Relaxation of a single DNA molecule observed by optical microscopy. *Science* 1994, 264, 822-826.
71. Reiner, J. E., Kasianowicz, J. J., Nablo, B. J. & Robertson, J. W. Theory for polymer analysis using nanopore-based single-molecule mass spectrometry. *Proc Natl Acad Sci USA* 107, 12080-5 (2010).
72. Rief, M., Clausen-Schaumann, H. and Gaub, H. E. Sequence-dependent mechanics of single DNA molecules. *Nat. Struct. Biol.* 1999, 6, 346-349.
73. Robertson, J. W. F., Rodrigues, C. W., Stanford, V. M., Rubinson, K. A., Krasilnikov, O. V. and Kasianowicz, J. J. Single-molecule mass spectrometry in solution using a solitary nanopore. Proc. *Natl. Acad. Sci. USA* 2007, 104, 8207-8211.
74. Rodrigues, C. G. et al. Mechanism of KCl enhancement in detection of nonionic polymers by nanopore sensors, *Biophys J* 95, 5186-5192 (2008)
75. Ronaghi M., Uhlen, M. & Nyren, P. A sequencing method based on real-time pyrophosphate. *Science* 281, 363-365 (1998),
76. Rosenstein, J., V. Ray, M. Dmdic, and K. L. Shepard. Solid-state nanopores integrated with low-noise preamplifiers for high-bandwidth DNA analysis. in *Life Science Systems and Applications Workshop (LiSSA)*, 2011 *IEEE/NIH* (2011).
77. Rosenstein, J., Ray, V., Dmdic, M. & Shepard, K. L. Nanopore DNA sensors in CMOS with on-chip low-noise preamplifiers. in *Solid-State Sensors, Actuators and Microsystems Conference (TRANSDUCERS)*, 2011 16*th International* 874-877 (2011).
78. Rothberg, J. M. et al. An integrated semiconductor device enabling non-optical genome sequencing. *Nature* 475, 348-352 (2011).
79. Sauer-Budge, A. F. et al., Unzipping Kinetics of Doubel Stranded DNA in a Nanopore. *Physical Review Letters* 2003 90(23), 238101-1-238101-4.
80. Schneider, G. F. et al. DNA translocation through graphene nanopores. *Nano Lett* 10, 3163-7 (2010).
81. Seo, T. S., Bai, X., Ruparel, H., Li, Z., Turro, N. J. and Ju, J. Photocleavable fluorescent nucleotides for DNA sequencing on a chip constructed by site-specific coupling chemistry. *Proc. Natl. Acad. Sci. USA* 2004, 101, 5488-5493.
82. Shapovalov, G. and Lester, H. A. Getting transitions in bacterial ion channels measured at 3 microseconds resolution. *J. Gen. Physiol.* 2004, 124, 151-161.
83. Shen, K., Tsai, J., Shi, P. & Kam, L. C. Self-aligned supported lipid bilayers for patterning the cell-substrate interface. *J Am Chem Soc* 131, 13204-5 (2009).
84. Shi, H. & Ratner, B. D. Template recognition of protein-imprinted polymer surfaces. *Journal of Biomedical Materials Research* 49, 1-11 (2000).
85. Shimada, K., Kato, H., Saito, T., Matsuyama, S. & Kinugasa, S. Precise measurement of the self-diffusion coefficient for poly(ethylene glycol) in aqueous solution using uniform oligomers. *Journal of Chemical Physics* 122(2005).
86. Sims, P. A., Greenleaf, W. J., Duan, H. & Xie, X. S. Fluorogenic DNA sequencing in PDMS microreactors. *Nat Methods* 8, 575-80 (2011)
87. Smith, S. B., Cui, Y. and Bustamante, C. Overstretching B-DNA: the elastic response of individual double-stranded and single-stranded DNA molecules. *Science* 1996, 271, 795-799.
88. Song, L., et al. Structure of staphylococcal alpha-hemolysin, a heptameric transmembrane pore. *Science* 274, 1859-66 (1996)
89. Sood, A., Kumar, S., Wegener, J., Nampalli, S., Nelson, J., Macklin, J. and Fuller, C. W. Terminal Phosphate Labeled Nucleotides with improved substrate properties for Nucleic Acid Assays. *J. Am. Chem. Soc.* 2005, 127(8), 2394-2395.
90. Srinivasan, M. P., Ratto, T. V., Stroeve, P. & Longo, M. L. Patterned supported bilayers on self-assembled monolayers: Confinement of adjacent mobile bilayers. *Langmuir* 17, 7951-7954 (2001).
91. Storm, A. J. et al. Fast DNA translocation through a solid-state nanopore. *Nano Lett* 5, 1193-1197 (2005).
92. Timp, W. et al. Nanopore Sequencing: Electrical Measurements of the Code of Life. *IEEE Trans Nanotechnol* 9, 281-294 (2010).
93. Wang, H. et al., DNA heterogeneity and Phosphorylation unveiled by Single-*Molecule* Electrophoresis. PNAS 2004 101(37), 13472-13477.

94. Wang, Y., Zheng, D., Tan, Q., Wang, M. X. & Gu, L. Q. Nanopore-based detection of circulating microRNAs in lung cancer patients. *Nat Nanotechnol* 6, 668-74 (2011).
95. Wanunu, M. & Meller, A. Chemically modified solid-state nanopores. *Nano Lett* 7, 1580-5 (2007).
96. Wanunu, M., Sutin, J., McNally, B., Chow, A. & Meller, A. DNA translocation governed by interactions with solid-state nanopores. *Biophys J* 95, 4716-25 (2008).
97. Wanunu, M. et al. Rapid electronic detection of probe-specific microRNAs using thin nanopore sensors. *Nat Nanotechnol* 5, 807-14 (2010).
98. White, R. J. et al. Ionic conductivity of the aqueous layer separating a lipid bilayer membrane and a glass support. *Langmuir* 22, 10777-83 (2006).
99. White, R. J. et al. Single ion-channel recordings using glass nanopore membranes. *J Am Chem Soc* 129, 11766-75 (2007).
100. Wiehelman, K. Investigation of the bicinchoninic acid protein assay: identification of the groups responsible for color formation. *Analytical Biochemistry* 175(1988).
101. Yang, T. L., Baryslunkova, O. K., Mao, H. B., Holden, M. A. & Cremer, P. S. Investigations of bivalent antibody binding on fluid-supported phospholipid membranes: The effect of hapten density. *Journal of the American Chemical Society* 125, 4779-4784 (2003).
102. Yin, P. Tethered Bilayer Membrane Sensors with Small Transmembrane Peptide Ion Channels —Recent Developments, Future Research and Potential Applications. in *Advances in Planar Lipid Bilayers and Liposomes*, Vol. Volume 2 (ed. Ottova-Leitmannova, A.) 49-76 (Academic Press, 2005).
103. Vercoutere, W., Winters-Hilt, S., Olsen, H., Deamer, D., Haussler, D. and Akeson, M. Rapid discrimination among individual DNA hairpin molecules at single-nucleotide resolution using an ion channel. *Nat. Biotech* 2001, 19, 248-252.

wherein the tag comprises an oligonucleotide which comprises nucleotides having natural bases and (i) at least one abasic site or (ii) at least one nucleotide having a modified base;

wherein $R_1$ is OH, wherein $R_2$ is H or OH, wherein X is a linker and may comprise O, NH, S, or $CH_2$, wherein Z is O, S, or $BH_3$, wherein the base is adenine, guanine, cytosine, thymine, uracil, or a derivative of one of these bases, wherein n is 1, 2, 3, or 4.

2. The tagged nucleotide of claim 1, wherein the tag does not comprise a fluorophore.

3. The tagged nucleotide of claim 1, wherein the tag is detectable by its charge, shape, size, or any combination thereof.

4. The tagged nucleotide of claim 1, wherein the tag comprises an additional identifiable moiety.

5. The tagged nucleotide of claim 4, wherein the additional identifiable moiety is a coumarin-based dye.

6. A composition comprising four different types of the tagged nucleotide of claim 1, wherein the base of a first type of tagged nucleotide is adenine or a derivative thereof, the base of a second type of tagged nucleotide is guanine or a derivative thereof, the base of a third type of tagged nucleotide is cytosine or a derivative thereof, and the base of a fourth type of tagged nucleotide is thymine or a derivative thereof or uracil or a derivative thereof, and wherein the tag on each type of tagged nucleotide is different from the tag on each of the other three types of tagged nucleotide.

7. The tagged nucleotide of claim 1, wherein the tag further comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

What is claimed is:

1. A tagged nucleotide, wherein the nucleotide comprises a tag capable of being cleaved in a nucleotide polymerization event and detected with the aid of a nanopore, wherein the tagged nucleotide has the structure:

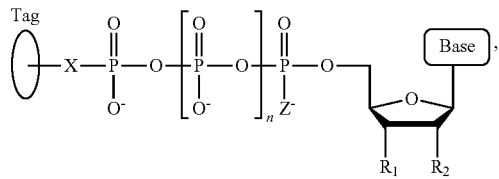

8. The tagged nucleotide of claim 1, wherein the oligonucleotide has a length of approximately 30 bases.

9. The tagged nucleotide of claim 1, wherein n is four.

10. The tagged nucleotide of claim 1, wherein the oligonucleotide comprises a 5'-OH, and the 5'-OH of said oligonucleotide is attached to the terminal phosphate of the tagged nucleotide analogue.

11. The tagged nucleotide of claim 1, wherein the oligonucleotide comprises at least one abasic site.

12. The tagged nucleotide of claim 1, wherein the oligonucleotide comprises at least one nucleotide having a modified base.

13. The tagged nucleotide of claim 1, wherein the tag has a charge which is reverse in sign relative to the charge on the rest of the tagged nucleotide.

14. The tagged nucleotide of claim 13, wherein the magnitude of the charge on the tag is the same as the magnitude of the charge on the remainder of the tagged nucleotide.

15. The tagged nucleotide of claim 13, wherein the tag has a positive charge.

16. The tagged nucleotide of claim 13, wherein the tag further comprises lysines or arginines having a positive charge, wherein the positive charge of the lysines or arginines neutralizes the negative charge of the phosphates of the tagged nucleotide.

17. The tagged nucleotide of claim 13, wherein removal of the tag changes the charge of the tagged nucleotide.

* * * * *

SEQUENCE LISTING

<160> NUMBER OF SEQ ID NOS: 1

<210> SEQ ID NO 1
<211> LENGTH: 26
<212> TYPE: DNA
<213> ORGANISM: Artificial Sequence
<220> FEATURE:
<223> OTHER INFORMATION: primer

<400> SEQUENCE: 1
gatcgcgccg cgccttggcg cggcgc                                          26